(12) United States Patent
Fueyo et al.

(10) Patent No.: US 10,080,774 B2
(45) Date of Patent: *Sep. 25, 2018

(54) ONCOLYTIC ADENOVIRUS ARMED WITH THERAPEUTIC GENES

(71) Applicant: Board of Regents, The University of Texas System, Austin, TX (US)

(72) Inventors: Juan Fueyo, Houston, TX (US); Candelaria Gomez-Manzano, Houston, TX (US); W. K. Alfred Yung, Houston, TX (US); Charles A. Conrad, Spring, TX (US); Frederick F. Lang, Jr., Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/703,876

(22) Filed: May 4, 2015

(65) Prior Publication Data

US 2015/0306160 A1    Oct. 29, 2015

Related U.S. Application Data

(63) Continuation of application No. 12/370,232, filed on Feb. 12, 2009, now Pat. No. 9,061,055, which is a continuation of application No. 11/077,513, filed on Mar. 10, 2005, now abandoned, which is a continuation-in-part of application No. 10/124,608, filed on Apr. 17, 2002, now abandoned.

(60) Provisional application No. 60/551,932, filed on Mar. 10, 2004.

(51) Int. Cl.
| | |
|---|---|
| *A61K 35/761* | (2015.01) |
| *A61K 31/513* | (2006.01) |
| *A61K 38/17* | (2006.01) |
| *A61K 38/18* | (2006.01) |
| *A61K 38/50* | (2006.01) |
| *A61K 45/06* | (2006.01) |
| *A61K 48/00* | (2006.01) |
| *C12N 15/86* | (2006.01) |
| *C07K 14/005* | (2006.01) |
| *C12N 7/00* | (2006.01) |
| *A61K 38/00* | (2006.01) |

(52) U.S. Cl.
CPC .......... *A61K 35/761* (2013.01); *A61K 31/513* (2013.01); *A61K 38/177* (2013.01); *A61K 38/1891* (2013.01); *A61K 38/50* (2013.01); *A61K 45/06* (2013.01); *A61K 48/005* (2013.01); *C07K 14/005* (2013.01); *C12N 7/00* (2013.01); *C12N 15/86* (2013.01); *A61K 38/00* (2013.01); *C12N 2710/10032* (2013.01); *C12N 2710/10043* (2013.01); *C12N 2710/10322* (2013.01); *C12N 2710/10343* (2013.01); *C12N 2710/10345* (2013.01); *C12Y 305/04001* (2013.01)

(58) Field of Classification Search
None
See application file for complete search history.

(56) References Cited

U.S. PATENT DOCUMENTS

| | | | |
|---|---|---|---|
| 4,029,663 | A | 6/1977 | Gutowski et al. |
| 5,545,548 | A | 8/1996 | Senter et al. |
| 5,670,488 | A | 9/1997 | Gregory et al. |
| 5,824,544 | A | 10/1998 | Armentano et al. |
| 5,856,181 | A | 1/1999 | McCormick |
| 5,863,904 | A | 1/1999 | Nabel et al. |
| 5,880,102 | A | 3/1999 | George et al. |
| 5,962,527 | A | 10/1999 | Pezzuto et al. |
| 5,968,735 | A | 10/1999 | Stein et al. |
| 5,997,859 | A | 12/1999 | Barber et al. |
| 6,013,638 | A | 1/2000 | Crystal et al. |
| 6,057,155 | A | 5/2000 | Wickham et al. |
| 6,063,622 | A | 5/2000 | Chamberlain et al. |
| 6,080,578 | A | 6/2000 | Bischoff et al. |
| 6,083,750 | A | 7/2000 | Chamberlain et al. |
| 6,100,243 | A | 8/2000 | Frisch |
| 6,251,886 | B1 | 6/2001 | Friedman |
| 6,455,314 | B1 | 9/2002 | Wickham et al. |
| 6,464,976 | B1 | 10/2002 | LaFace et al. |
| 6,489,305 | B1 | 12/2002 | Demers |
| 6,586,411 | B1 | 7/2003 | Russell et al. |
| 6,627,190 | B2 | 9/2003 | Wold et al. |
| 6,689,600 | B1 * | 2/2004 | Wu .......................... A01N 1/02 435/235.1 |
| 6,824,771 | B1 | 11/2004 | Curiel et al. |

(Continued)

FOREIGN PATENT DOCUMENTS

| | | |
|---|---|---|
| WO | WO 1996/012406 | 5/1996 |
| WO | WO 2000/067576 | 11/2000 |

OTHER PUBLICATIONS

Hermiston (2000) "Gene delivery from replication-selective viruses: arming guided missles in the war against cancer", Journal of Clinical Investigation, 105(9): 1169-72.*

(Continued)

*Primary Examiner* — Robert M Kelly
(74) *Attorney, Agent, or Firm* — Parker Highlander PLLC

(57) ABSTRACT

The present invention involves compositions and methods for treating cancer using a mutant adenovirus comprising a polynucleotide encoding a therapeutic polypeptide that is targeted to cells with a mutant retinoblastoma pathway. The mutant adenovirus is able to kill the tumor cells without harming cells with a wild type retinoblastoma pathway.

13 Claims, 30 Drawing Sheets
Specification includes a Sequence Listing.

(56) References Cited

U.S. PATENT DOCUMENTS 8,168,168 B2 * 5/2012 Fueyo .................. A61K 45/06
424/93.2
2003/0138405 A1 7/2003 Fueyo et al.

OTHER PUBLICATIONS

Ahmad et al., "The effects of angiopoietin-1 and -2 on tumor growth and angiogenesis in human colon cancer," Cancer Research, 61:1255-1259, 2001.
Aiello et al., "Suppression of retinal neovascularization in vivo by inhibition of vascular endothelial growth factor (VEGF) using soluble VEGF-receptor chimeric proteins," Proc. Natl. Acad. Sci. USA, 92:10457-10461, 1995.
Alemany et al., "Complementary adenoviral vectors for oncolysis," Cancer Gene Ther., 6:21-5, 1999.
Arai et al., "Tie2/angiopoietin-1 signaling regulates hematopoietic stem cell quiescence in the bone marrow niche," Cell, 118:149-161, 2004.
Barton et al., "GENIS: gene expression of sodium iodide symporter for non-invasive imaging of gene therapy vectors and quantification of gene expression in vivo," Molecular Therapy, 8:508-518, 2003.
Bernt et al., "A New Type of Adenovirus Vector That Utilizes Homologous Recombination to Achieve Tumor-Specific Replication," J. Virology, 76:10994-11002, 2002.
Bigner et al., "Brain tumors," Chapter 40, pp. 661-667, In: The Genetic Basis of Human Cancer, Vogelstein and Kinzler (eds.), 1998.
Bigner et al., "Characterization of the epidermal growth factor receptor in human glioma cell lines and xenografts," Cancer Res., 50:8017-8022, 1990.
Bischoff et al., "An adenovirus mutant that replicates selectively in p53-deficient human tumor cells," Science, 274:373-376, 1996.
Campo et al., "Design of a novel small peptide targeted against a tumor-specific receptor," Biochem. Biophys. Res. Commun., 275:631-636, 2000.
Carlson et al., "Direct Cell Adhesion to the Angiopoietins Mediated by Integrins," J. Biol. Chem., 276:26516-26525, 2001.
Carlson et al., "Restoration of a functional open reading frame by homologous recombination between two adenoviral vectors," Mol. Ther., 6:99-105, 2002.
Carmeliet et al., "Angiogenesis in cancer and other diseases," Nature, 407 249-57, 2000.
Cheng et al., "Suppression of glioblastoma angiogenicity and tumorigenicity by inhibition of endogenous expression of vascular endothelial growth factor," Proc. Natl. Acad. Sci. USA, 93:8502-8507, 1996.
Chintala et al., "Adenovirus-mediated p16/CDKN2 gene transfer suppresses glioma invasion in vitro," Oncogene, 15:2049-2057, 1997.
Cho et al., "Expression and activity of human Na+/I− symporter in human glioma cells by adenovirus-mediated gene delivery," Gene Ther., 7:740-749, 2000.
Cho et al., "In vivo imaging and radioiodine therapy following sodium iodide symporter gene transfer in animal model of intracerebral gliomas," Gene Ther., 9:1139-1145, 2002.
Conrad et al., "Genome modifications and chemotherapy enhancement of D24 antiglioma effect," American Academy of Neurology 53rd Annual Meeting Program, Supplemental to Neurology, 56, Suppl. 3:A407-A408, Abstract #P06.020, 2001.
Conrad, "Improved glioma therapy using Delta-24 replication-competent adenovirus containing a humanized form of yeast cytosine deaminase," Proceedings of the American Association for Cancer Research, vol. 44, p. 549, Abstract 2794 [abstract], 2003.
Costello et al., "Cyclin-dependent kinase 6 (CDK6) amplification in human gliomas identified using two-dimensional separation of genomic DNA," Cancer Res., 57:1250-1254, 1997.

Costello et al., "Silencing of p16/CDKN2 expression in human gliomas by methylation and chromatin condensation," Cancer Res., 56:2405-2410, 1996.
Dai et al., "Cloning and characterization of the thyroid iodide transporter," Nature, 379:458-460, 1996.
Davis et al., "Isolation of angiopoietin-1, a ligand for the TIE2 receptor, by secretion-trap expression cloning," Cell, 87:1161-116, 1996.
Drapkin et al., "Targeting the urokinase plasminogen activator receptor enhances gene transfer to human airway epithelia," J. Clin. Invest., 105:589-596, 2000.
Ekstrand et al., "Amplified and rearranged epidermal growth factor receptor genes in human glioblastomas reveal deletions of sequences encoding portions of the N- and/or C-terminal tails," Proc. Natl. Acad. Sci. USA, 89:4309-4313, 1992.
Eskandar et al., "Rapid determination of cancellous bone mineral loss in ovariectomized rats by a subtraction technique," Anat. Rec., 230:169-174, 1991.
Ferrara, "VEGF and the quest for tumour angiogenesis factors," Nat. Rev. Cancer, 2:795-803, 2002.
Frederick et al., "Analysis of genomic rearrangements associated with EGRFvIII expression suggests involvement of Alu repeat elements," Neuro-oncol., 2:159-163, 2000.
Freytag et al., "A novel three-pronged approach to kill cancer cells selectively: concomitant viral, double suicide gene, and radiotherapy," Humn. Gene Ther., 9:1323-1333, 1998.
Fueyo et al., "Preclinical Characterization of the Antiglioma Activity of a Tropism-Enhanced Adenovirus Targeted to the Retinoblastoma Pathway," J. Natl. Cancer Inst., 95:652-660, 2003.
Fueyo et al., "A mutant oncolytic adenovirus targeting the Rb pathway produces anti-glioma effect in vivo," Oncogene, 19:2-12, 2000.
Fueyo et al., "Adenovirus-mediated p16/CDKN2 gene transfer induces growth arrest and modifies the transformed phenotype of glioma cells," Oncogene, 12:103-110, 1996.
Fueyo et al., "Characterization of the anti-glioma effect of a second-generation conditionally replicating adenovirus unable to bind Rb and P53," Neuro-Oncology, Abstracts of the First Quadrennial World Federation of Neuro-Oncology Meeting, 290: Abstract #99, 2001.
Fueyo et al., "Chemotherapy enhancement of the antiglioma effect of the delta-24 adenovirus," Neuro-Oncology, Abstracts of the First Quadrennial World Federation of Neuro-Oncology Meeting, 289: Abstract #98, 2001.
Fueyo et al., "Hypermethylation of the CpG island of p16/CDKN2 correlates with gene inactivation in gliomas," Oncogene, 13:1615-1619, 1996.
Fueyo et al., "Overexpression of E2F-1 in glioma triggers apoptosis and suppresses tumor growth in vitro and in vivo," Nat. Med., 4 685-690, 1998.
Fueyo et al., "Redirecting adenoviruses to glioma: RGD-D24 infects glioma cells by adenovirus receptor-independent system," American Academy of Neurology 52nd Annual Meeting Program, Supplement to Neurology, 54(7), Supp.3: A35, Abstract #P01.025, 2000.
Fueyo et al., "Suppression of human glioma growth by adenovirus-mediated Rb gene transfer," Neurology, 50:1307-1315, 1998.
Fueyo et al., "Targeting in gene therapy for gliomas," Archives of Neurology, 56:445-448, 1999.
Fueyo et al., "The functional role of tumor suppressor genes in gliomas: clues for future therapeutic strategies," Neurology, 51:1250-1255, 1998.
Fueyo et al., "Treatment of gliomas Xenografts with D24 oncolytic adenovirus: a pathological study," American Academy of Neurology 53rd Annual Meeting Program, Supplement to Neurology, 56(8), Suppl 3:A407, Abstract #P06.017, 2001.
Fueyo et al., "Treatment of intracranial gliomas with D24-RGD," Neuro-Oncology, Abstracts for the 5th Annual Meeting of the Society for Neuro-Oncology, 263: Abstract #73, 2000.
Fueyo et al., "Treatment of intracranial gliomas with delta-24 adenovirus," Journal of Neurology, 247 (Suppl. 3):Abstract # 209, 2000.

(56) References Cited

OTHER PUBLICATIONS

Galli et al., "Isolation and Characterization of Tumorigenic, Stem-like Neural Precursors from Human Glioblastoma," *Cancer Res.*, 64:7011-7021, 2004.
GenBank Accession No. AC_000008, Human adenovirus type 5, complete genome, 2005.
GenBank Accession No. AC005796, Homo sapiens chromosome 19, cosmid R31408, complete sequence, 1998.
GenBank Accession No. U60282, Rattus norvegicus thyroid sodium/iodide symporter NIS mRNA, complete cds, 1996.
GenBank Accession No. NC_001406, Human adenovirus type 5, complete genome, 2002.
Georerger et al., "Oncolytic Activity of the E1B-55 kDa-deleted Adenovirus ONYX-015 Is Independent of Cellular p53 Status in Human Malignant Glioma Xenografts," *Cancer Res.*, 62:764-772, 2002.
Gomez-Manzano et al., "Chemotherapy enhancement of the antiglioma effect of the Delta-24 adenovirus," *American Society of Gene Therapy $5^{th}$ Annual Meeting*, Abstract #450657, Jun. 2002.
Gomez-Manzano et al., "Genetically modified adenoviruses against gliomas," *Neurology*, 63:418-426, 2004.
Gomez-Manzano et al., "Increased anti-glioma effect by adenovirus containing modification in the fiber proteins," *Journal of Neurology*, 247 (Suppl. 3):Abstract # 210, 2000.
Gomez-Manzano et al., In: *Gene Transfer and Therapy for Neurological Disorders*, Chiocca and Breakefield (Eds.), Human Press Inc.: NJ, 205-229, 1998.
Haberkorn et al., "Imaging methods in gene therapy of cancer," *Curr. Gene Ther.*, 1:163-182, 2001.
Haberkorn et al., "Iodide uptake in human anaplastic thyroid carcinoma cells after transfer of the human thyroid peroxidase gene," *Eur. J. Nucl. Med.*, 28:633-638, 2001.
Haberkorn et al., "Radionuclide imaging in the post-genomic era," *J. Cell Biochem. Suppl.*, 39:1-10, 2002.
Haberkorn et al., "Transfer of the human NaI symporter gene enhances iodide uptake in hepatoma cells," *J. Nucl. Med.*, 42:317-325, 2001.
Haberkorn, "Gene therapy with sodium/iodide symporter in hepatocarcinoma," *Exp. Clin. Endocrinol. Diabetes*, 109:60-62, 2001.
Hamel et al., "Loss in expression of the retinoblastoma gene product in human gliomas is associated with advanced disease," *J. Neurooncol.*, 16:159-165, 1993.
Heise et al., "An adenovirus E1A mutant that demonstrates potent and selective systemic anti-tumoral efficacy," *Nature Medicine*, 6(10):1134-1139, 2000.
Heise et al., "ONYX-015, an E1B gene-attenuated adenovirus, causes tumor-specific cytolysis and antitumoral efficacy that can be augmented by standard chemotherapeutic agents," *Nat. Med.*, 3:639-645, 1997.
Hemminki et al., "Targeting Oncolytic Adenoviral Agents to the Epidermal Growth Factor Fusion Molecule," *Cancer Res.*, 61:6377-6381, 2001.
Henson et al., "The retinoblastoma gene is involved in malignant progression of astrocytomas," *Ann. Neurol.*, 36:714-721, 1994.
Hermiston, "Gene delivery from replication-selective viruses: arming guided missiles in the war against cancer," *J. Clin. Invest.*, 105:1169-1172, 2000.
Hirvonen et al., "Differential expression of myc, max and RB1 genes in human gliomas and glioma cell lines," *Br. J. Cancer*, 69:16-25, 1994.
Holash et al., "New model of tumor angiogenesis: dynamic balance between vessel regression and growth mediated by angiopoietins and VEGF," *Oncogene*, 18:5356-62, 1999.
Holash et al., "Vessel cooption, regression, and growth in tumors mediated by angiopoietins and VEGF," *Science*, 284:1994-8, 1999.
Im et al, "Antiangiogenesis Treatment for Gliomas: Transfer of Antisense-Vascular Endothelial Growth Factor Inhibits Tumor Growth in Vivo," *Cancer Res.*, 59:895-900, 1999.

Ipata et al., "Baker's yeast cytosine deaminase. Some enzymic properties and allosteric inhibition by nucleosides and nucleotides," *Biochemistry*, 10:4270-4276, 1971.
Ipata et al., "Cytosine and cytidine deaminase from yeast," *Methods Enzymol.*, 51:394-400, 1978.
Izbicka et al., "Effects of ONYX adenovirus preparations on human tumor colony forming units," *Proceedings of ASCO*, Abstract #1554, 1997.
Jen et al. "Deletion of p16 and p15 genes in brain tumors," *Cancer Res.*, 54:6353-6358, 1994.
Jiang et al., "CB001, a double-mutant E1A/E1B adenovirus, shows anit-cancer effect in experimental human gliomas," *American Society of Gene Therapy $5^{th}$ Annual Meeting*, Abstract #450657, Jun. 2002.
Johnson et al., "Autoregulatory control of E2F1 expression in response to positive and negative regulators of cell cycle progression," *Gene Dev.* 8:1514-25, 1994.
Jones et al., "A Unique Autophosphorylation Site on Tie2/Tek Mediates Dok-R Phosphotyrosine Binding Domain Binding and Function," *Mol. Cell. Biol.*, 23:2658-2668, 2003.
Kaelin, "Functions of the retinoblastoma protein," *Bioessays*, 21:950-8, 1999.
Katsuragi et al., "Implantable enzyme capsules for cancer chemotherapy from bakers' yeast cytosine deaminase immobilized on epoxy-acrylic resin and urethane prepolymer," *Appl. Biochem. Biotechnol.*, 16:61-69, 1987.
Katsuragi et al., "Vascular changes associated with growth of primary and transplantable pancreatic adenocarcinomas induced in Syrian golden hamsters by N-nitrosobis(2-oxopropyl)amine (BOP) and N-nitrosobis(2-hydroxypropyl)amine (BHP)," *Exp. Pathol.*, 29:129-142, 1986.
Ke et al., "A reliability test of standard-based quantitative PCR: exogenous vs endogenous standards," *Mol. Cell Probes*, 14:127-135, 2000.
Ke et al., "The Relevance of Cell Proliferation, Vascular Endothelial Growth Factor, and Basic Fibroblast Growth Factor Production to Angiogenesis and Tumorigenicity in Human Glioma Cell Lines," *Clinical Cancer Res.*, 6:2562-2572, 2000.
Khan et al., "In vivo efficacy of Rgd-Delta24, a Rb-inactivation-dependent replicative adenovirus with increased infectivity against human glioma," *Proceedings from the $92^{nd}$ Annual Meeting of the American Association for Cancer Research*, 42:703, Abstract #3781, 2001.
Kievit et al., "Superiority of Yeast over Bacterial Cytosine Deaminase for Enzyme/Prodrug Gene Therapy in Colon Cancer Xenografts," *Cancer Res.*, 59:1417-1421, 1999.
Kirn et al., "ONYX-015: clinical data are encouraging," *Nat. Med.*, 4:1341-1342, 1998.
Kirn, "Oncolytic virotherapy for cancer with the adenovirus dl1520 (Onyx-015): results of phase I and II trials," *Expert Opin. Biol. Ther.*, 1:525-538, 2001.
Koblizek et al., "Angiopoietin-1 induces sprouting angiogenesis in vitro," *Curr. Biol.*, 8:529-532, 1998.
Kontos et al., "Tyrosine 1101 of Tie2 Is the Major Site of Association of p85 and Is Required for Activation of Phosphatidylinositol 3-Kinase and Akt," *Mol. Cell. Biol.*, 18:4131-4140, 1998.
Kuan et al., "EGF mutant receptor vIII as a molecular target in cancer therapy," *Endocrine-Related Cancer*, 8:83-96, 2001.
Kyritsis et al., "Correlation of p53 immunoreactivity and sequencing in patients with glioma," *Mol. Carcinog.*, 15:1-4, 1996.
Kyritsis et al., "Molecular genetics and tumour suppressor genes in gliomas," *Baillieres Clinical Neurology*, 5:295-305, 1996.
Kyritsis et al., "Mutations of the p16 gene in gliomas," *Oncogene*, 12:63-67, 1996.
La Perle et al., "In vivo expression and function of the sodium iodide symporter following gene transfer in the MATLyLu rat model of metastatic prostate cancer," *Prostate*, 50:170-8, 2002.
Lal et al., "An implantable guide-screw system for brain tumor studies in small animals," *J. Neurosurg.*, 92:326-33, 2000.
Lamfers et al., "Potential of the conditionally replicative adenovirus Ad5-Delta24RGD in the treatment of malignant gliomas and its enhanced effect with radiotherapy," *Cancer Research*, 62:5736-5742, 2002.

(56) References Cited

OTHER PUBLICATIONS

Lang et al., "Phase I trial of adenovirus-mediated p53 gene therapy for recurrent glioma: biological and clinical results," *J. Clin. Oncol.*, 21:2508-18, 2003.
Le Gal La Salle et al., "An adenovirus vector for gene transfer into neurons and Glia in the brain," *Science*, 259:988-990, 1993.
Levy et al., "N-linked Glycosylation of the Thyroid $Na^+/I^-$ Symporter (NIS)," *J. Biol. Chem.*, 273:22657-22663, 1998.
Levy et al., "The Na+/I− symporter (NIS): recent advances," *J. Bioenerg. Biomembr.*, 30:195-206, 1998.
Lin et al., "Antiangiogenic gene therapy targeting the endothelium-specific receptor tyrosine kinase Tie2," *Proc. Natl. Acad. Sci. USA*, 95:8829-8834, 1998.
Lorimer et al., "Recombinant immunotoxins specific for a mutant epidermal growth factor receptor: Targeting with a single chain antibody variable domain isolated by phage display," *Proc. Natl. Acad. Sci. USA*, 93:14815-14820, 1996.
Maisonpierre et al., "Angiopoietin-2, a natural antagonist for Tie2 that disrupts in vivo angiogenesis," *Science*, 277:55-60, 1997.
Manley et al., "Imatinib: a selective tyrosine kinase inhibitor," *Eur. J. Cancer*, 38(suppl 5):S19-27, 2002.
Master et al., "Dok-R plays a pivotal role in angiopoietin-1-dependent cell migration through recruitment and activation of Pak," *The EMBO Journal*, 20:5919-5928, 2001.
McCarthy et al, "Preparation of Separate Astroglial and Oligodendroglial Cell Cultures From Rat Cerebral Tissue," J. Cell Biol., 85:890-902, 1980.
Millauer et al., "Gioblastoma growth inhibited in vivo by a dominant-negative Flk-1 mutant," *Nature*, 367:576-9, 1994.
Mishima et al., "Growth Suppression of Intracranial Xenografted Glioblastomas Overexpressing Mutant Epidermal Growth Factor Receptors by Systemic Administration of Monoclonal Antibody (mAb) 806, a Novel Monoclonal Antibody Directed to the Receptor," *Cancer Res.*, 61:5349-5354, 2001.
Newsham et al., "Retinoblastoma," Chapter 19, pp. 363-392, In: *The Genetic Basis of Human Cancer*, Vogelstein and Kinzler (eds.), 1998.
Nishikawa et al., "A mutant epidermal growth factor receptor common in human glioma confers enhanced tumorigenicity," *Proc. Natl. Acad. Sci. USA*, 91:7727-7731, 1994.
Nishiyama et al., "Antineoplastic effects in rats of 5-fluorocytosine in combination with cytosine deaminase capsules," *Cancer Res.*, 45:1753-61, 1985.
Niu et al., "Deletion of the Carboxyl Terminus of Tie2 Enhances Kinase Activity, Signaling, and Function," *J. Biol. Chem.*, 277:31768-31773, 2002.
Office Action issued in U.S. Appl. No. 10/124,608, dated Apr. 8, 2004.
Office Action issued in U.S. Appl. No. 10/124,608, dated Dec. 15, 2004.
Office Action issued in U.S. Appl. No. 10/124,608, dated Oct. 30, 2003.
Office Action issued in U.S. Appl. No. 11/077,513, dated Jan. 9, 2008.
Office Action issued in U.S. Appl. No. 11/077,513, dated Jun. 13, 2007.
Office Action issued in U.S. Appl. No. 11/077,513, dated Oct. 17, 2008.
Office Action issued in U.S. Appl. No. 12/370,232, dated Jul. 8, 2010.
Office Action issued in U.S. Appl. No. 12/370,232, dated Jul. 20, 2011.
Office Action issued in U.S. Appl. No. 12/370,232, dated Oct. 14, 2010.
PCT International Preliminary Report on Patentability issued in International Application No. PCT/US2005/007985, dated Sep. 13, 2006.
PCT International Search Report issued in International Application No. PCT/US2005/007985, dated Nov. 21, 2005.
Petrich et al., "Establishment of radioactive astatine and iodine uptake in cancer cell lines expressing the human sodium/iodide symporter," *Eur. J. Nucl. Med. Mol. Imaging*, 29:842-54, 2002.
Plate et al., "Vascular endothelial growth factor," *J. Neurooncol.*, 35:365-72, 1997.
Poncet et al., "Expression of Tie-2 in human peripheral and autonomic nervous system," *Neuropathol. Appl. Neurobiol.*, 29:361-9, 2003.
Puumalainen et al., "Beta-galactosidase gene transfer to human malignant glioma in vivo using replication-deficient retroviruses and adenoviruses," *Hum. Gene Ther.*, 9:1769-74, 1998.
Reynolds et al., "Clonal and population analyses demonstrate that an EGF-responsive mammalian embryonic CNS precursor is a stem cell," *Dev. Biol.*, 175:1-13, 1998.
Rouslahti et al., "An address system in the vasculature of normal tissues and tumors," *Annu. Rev. Immunol.*, 18:813-27, 2000.
Sato et al., "Characterization of TEK receptor tyrosine kinase and its ligands, Angiopoietins, in human hematopoietic progenitor cells," *International Immunology*, 10:1217-1227, 1998.
Sato et al., "Distinct roles of the receptor tyrosine kinases Tie-1 and Tie-2 in blood vessel formation," *Nature*, 376:70-4, 1995.
Schmidt et al., "CDKN2 (p16/MTS1) gene deletion or CDK4 amplification occurs in the majority of glioblastomas," *Cancer Res.*, 54:6321-4, 1994.
Senter et al., "Generation of 5-fluorouracil from 5-fluorocytosine by monoclonal antibody-cytosine deaminase conjugates," *Bioconjug. Chem.*, 2:447-51, 1991.
Singh et al., "Identification of a Cancer Stem Cell in Human Brain Tumors," *Cancer Res.*, 63:5821-5828, 2003.
Singh, "Cancer stem cells in nervous system tumors," *Oncogene*, 23:7267-73, 2004.
Smanik et al., "Cloning of the human sodium Iodide symporter," *Biochem. Biophys. Res. Commun.*, 226:339-45, 1996.
Soudais et al., "Long-term in vivo transduction of neurons throughout the rat CNS using novel helper-dependent CAV-2 vectors," *FASEB J.*, 18:391, 2004.
Steinwaerder et al., "Tumor-specific gene expression in hepatic metastases by a replication-activated adenovirus vector," *Nat. Med.*, 7:240-3, 2001.
Sugawa et al., "Identical splicing of aberrant epidermal growth factor receptor transcripts from amplified rearranged genes in human glioblastomas," *Proc. Natl. Acad. Sci. USA*, 87:8602-8606, 1990.
Suri et al., "Increased vascularization in mice overexpressing angiopoietin-1," *Science*, 282(5388): 468-71, 1998.
Suri et al., "Requisite role of angiopoietin-1, a ligand for the TIE2 receptor, during embryonic angiogenesis," *Cell*, 87:1171-80, 1996.
Suzuki et al., "A Conditionally Replicative Adenovirus with Enhanced Infectivity Shows Improved Oncolytic Potency," *Clinical Cancer Res.*, 7:120-126, 2001.
Takakura et al., "Critical role of the TIE2 endothelial cell receptor in the development of definitive hematopoiesis," *Immunity*, 9 677-86, 1998.
Thomas et al., "Vascular endothelial growth factor receptor tyrosine kinase inhibitors: PTK787/ZK 222584," *Semin. Oncol.*, 30(3 Suppl 6):32-8, 2003.
Tournaire et al., "A short synthetic peptide inhibits signal transduction, migration and angiogenesis mediated by Tie2 receptor," *EMBO reports*, 5:262-267, 2004.
Ueki et al., "CDKN2/p16 or RB alterations occur in the majority of glioblastomas and are inversely correlated," *Cancer Res.*, 56:150-3, 1996.
Valable et al., "Angiopoietin-1-induced phosphatidyl-inositol 3-kinase activation prevents neuronal apoptosis," *The FASEB Journal*, 17:443-5, 2003.
Vile et al., "The oncolytic virotherapy treatment platform for cancer: unique biological and biosafety points to consider," *Cancer Gene Ther.*, 9:1062-7, 2002.
Wang et al., "Conditional gene expression in human intracranial xenograft tumors," *Biotechniques*, 31:196-202, 2001.
Wang et al., "Analysis of the activation status of Akt, NFkappaB, and Stat3 in human diffuse gliomas," *Lab. Invest.*, 84:941-51, 2004.

(56) References Cited

OTHER PUBLICATIONS

Wei et al., "Diffusible cytotoxic metabolites contribute to the in vitro bystander effect associated with the cyclophosphamide/cytochrome P450 2B1 cancer gene therapy paradigm," *Clin. Cancer Res.*, 1:1171-7, 1995.

Whyte et al., "Cellular targets for transformation by the adenovirus E1A proteins," *Cell*, 56:67-75, 1989.

Whyte et al., "Two Regions of the Adenovirus Early Region 1A Proteins Are Required for Transformation," *J. Virology*, 62:257-265, 1988.

Wildner et al., "Therapy of Colon Cancer with Oncolytic Adenovirus Is Enhanced by the Addition of Herpes Simplex Virus—thymidine kinase," *Cancer Res.*, 59:410-413, 1999.

Witzenbichler et al., "Chemotactic Properties of Angiopoietin-1 and -2, Ligands for the Endothelial-specific Receptor Tyrosine Kinase Tie2," *J. Biol. Chem.*, 273:18514-18521, 1998.

Xu et al., "Angiopoietin-1, Unlike Angiopoietin-2, Is Incorporated into the Extracellular Matrix via Its Linker Peptide Region," *J. Biol. Chem.*, 276:34990-34998, 2001.

Yan et al., "Developing Novel Oncolytic Adenoviruses through Bioselection," *J. Virology*, 77:2640-2650, 2003.

Yancopoulos et al., "Vascular-specific growth factors and blood vessel formation," *Nature*, 407:242-8, 2000.

Yergatian et al., "Cytosine deaminase: structural modifications studies," *Experientia*, 33:1570-1, 1977.

Zadeh et al, "Targeting the Tie2/Tek Receptor in Astrocytomas," *Am. J. Pathol.*, 164:467-476, 2004.

Zagzag et al., "Vascular apoptosis and involution in gliomas precede neovascularization: a novel concept for glioma growth and angiogenesis," *Lab Invest.*, 80:837-49, 2000.

Zolotukhin et al., "A "humanized" green fluorescent protein cDNA adapted for high-level expression in mammalian cells," *J. Virol.*, 70:4646-54, 1996.

\* cited by examiner

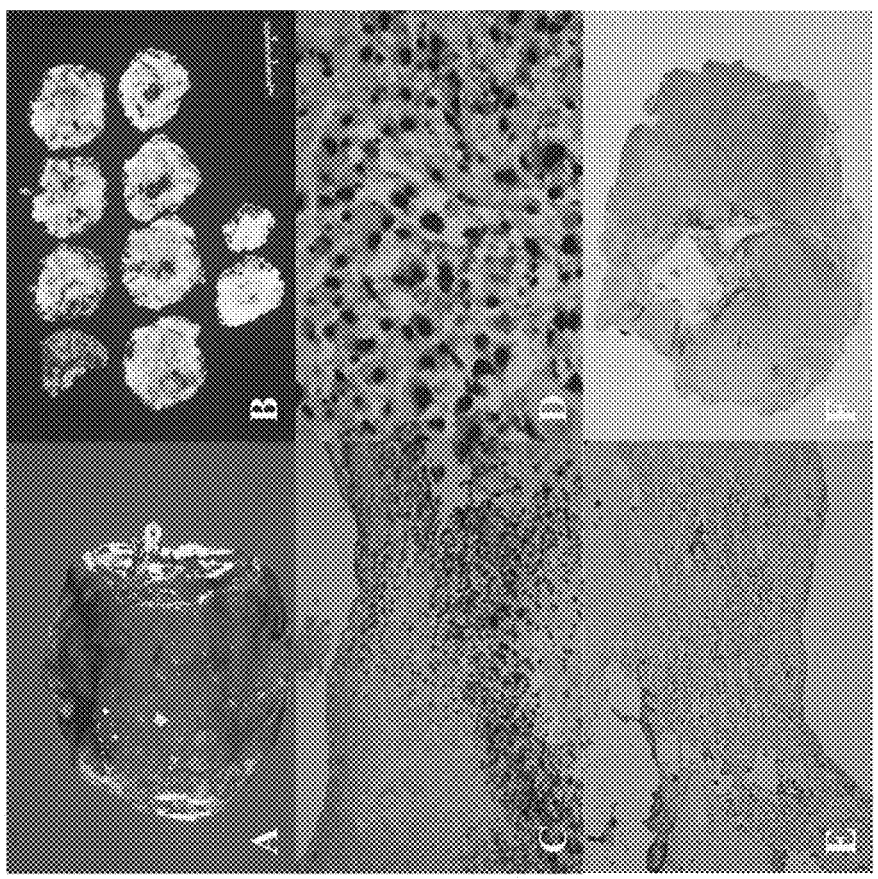
FIGS. 12A-F a

Yeast Cytosine Deaminase Humanized Codon Preference

CC GCC (AAG CTT) *CGG ACC* ATG GTG ACC GGC GGC ATG GCC TCC
AAG TGG GAT CAA AAG GGC ATG GAT ATC GCT TAC GAG GAG GCC
GCC CTG GGC TAC AAG GAG GGC GGC GTG CCT ATC GGC GGC TGT
CTG ATC AAC AAC AAG GAC GGC AGT GTG CTG GGC AGG GGC CAC
AAC ATG AGG TTC CAG AAG GGC TCC GCC ACC CTG CAC GGC GAG
ATC TCC ACC CTG GAG AAC TGT GGC AGG CTG GAG GGC AAG GTG
TAC AAG GAC ACC ACC CTG TAC ACC ACC CTG TCC CCT TGT GAC
ATG TGT ACC GGC GCT ATC ATC ATG TAC GGC ATC CCT AGG TGT
GTG GTG GGC GAG AAC GTG AAC TTC AAG TCC AAG GGC GAG AAG
TAC CTG CAA ACC AGG GGC CAC GAG GTG GTG GTT GTT GAC GAT
GAG AGG TGT AAG AAG ATC ATG AAG CAG TTC ATC GAC GAG AGG
CCT CAG GAC TGG TTC GAG GAT ATC GGC GAG TGA TAA (TCT AGA)
AGG CAA b

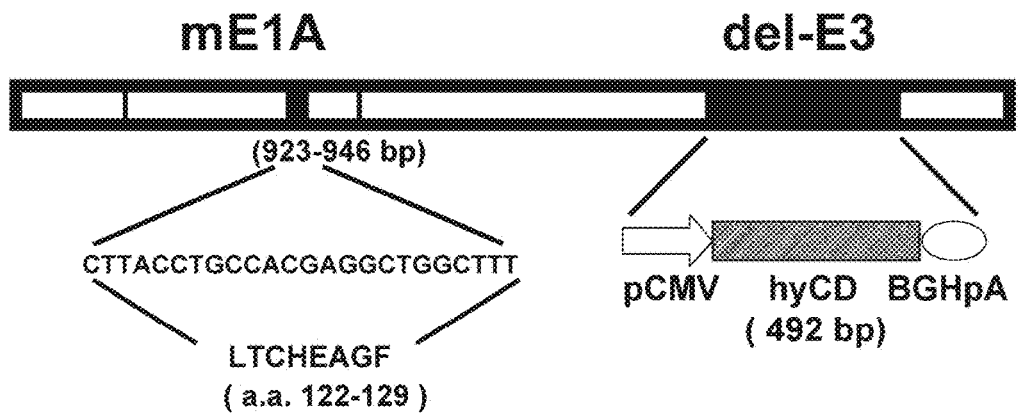

FIGS. 13A-B

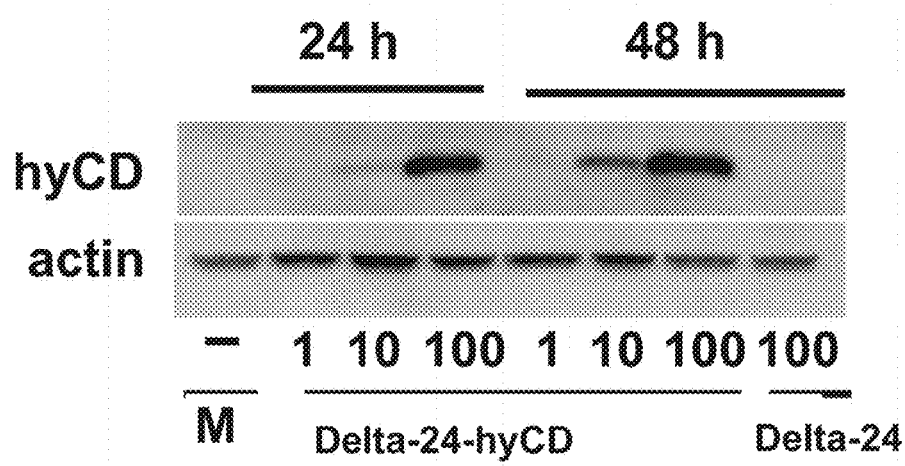
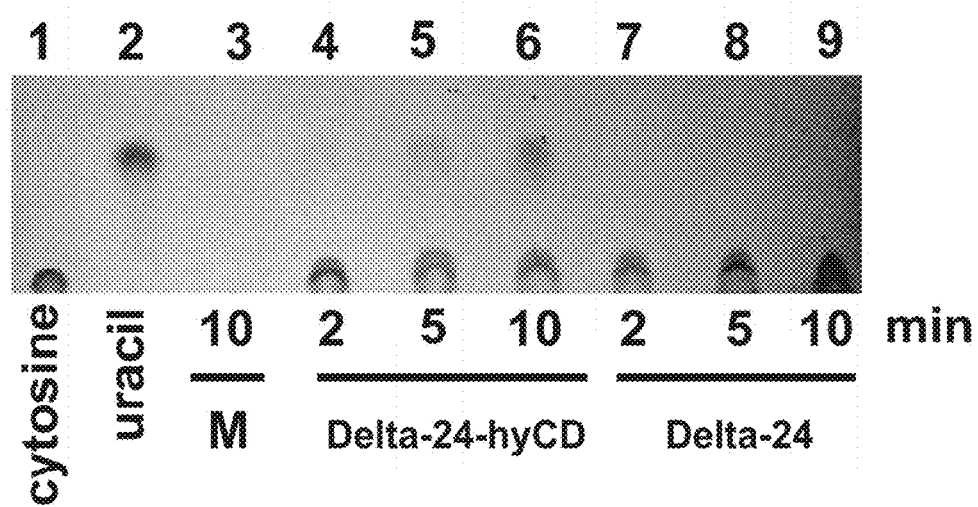
FIGS. 14A-B

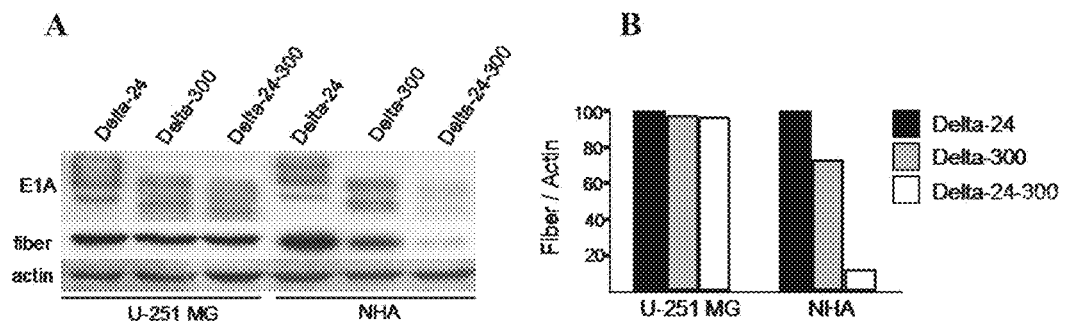
FIGS. 26A-B
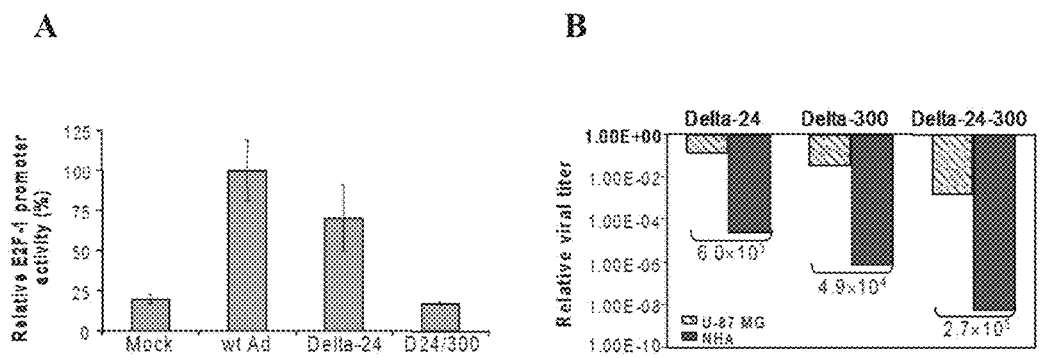
FIGS. 27A-B

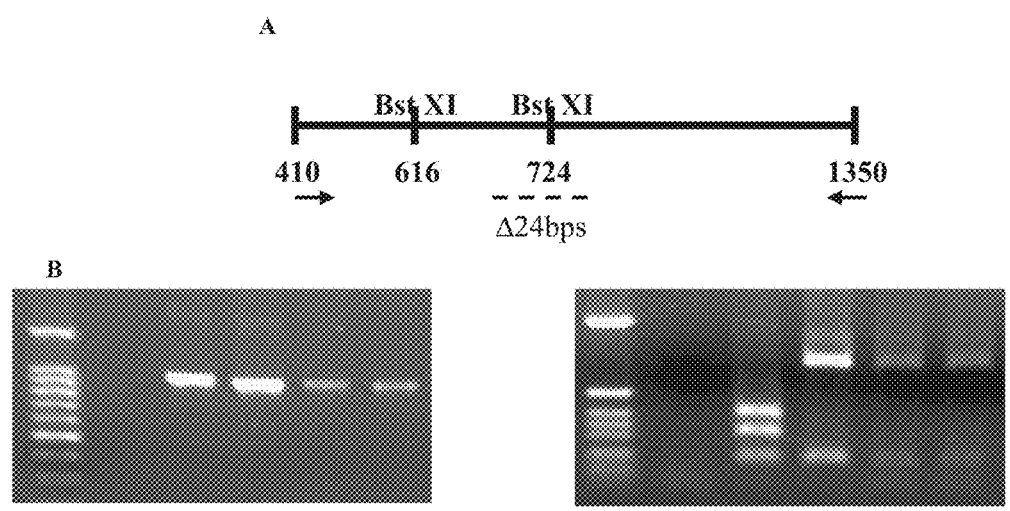
FIGS. 34A-B

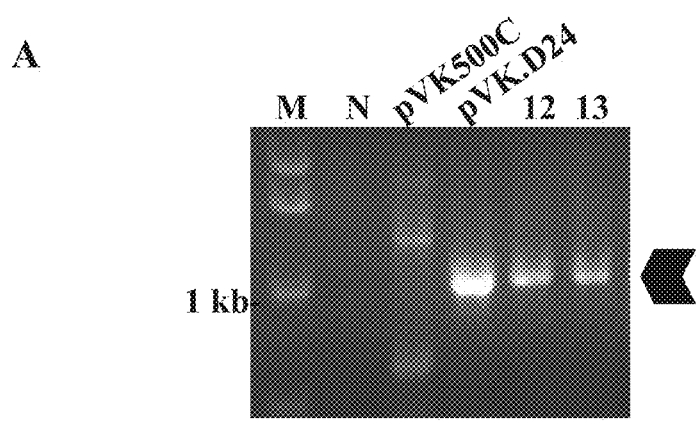
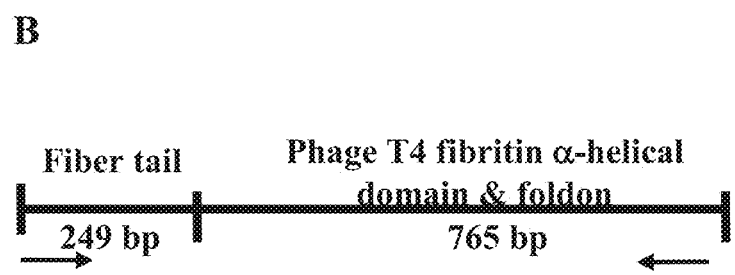
FIGS. 35A-B

SEQUENCE LISTING

```
<160> NUMBER OF SEQ ID NOS: 22

<210> SEQ ID NO 1
<211> LENGTH: 1932
<212> TYPE: DNA
<213> ORGANISM: Homo sapiens

<400> SEQUENCE: 1
atggaggccg tggagaccgg ggaacggccc accttcggag cctgggacta cggggtcttt      60
gccctcatgc tcctggtgtc cactggcatc gggctgtggg tcgggctggc tcggggcggg     120
cagcgcagcg ctgaggactt cttcaccggg ggccggcgcg tggcggccct gcccgtgggc     180
ctgtcgctgt ctgccagctt catgtcggcc gtgcaggtgc tgggcgtgcc gtcggaggcc     240
tatcgctatg gcctcaagtt cctctggatg tgcctggcc agcttctgaa ctcggtcctc      300
accgccctgc tcttcatgcc cgtcttctac cgcctgggcc tcaccagcac ctacgagtac     360
ctggagatgc gcttcagccg cgcagtgcgg ctctgcggga ctttgcagta cattgtagcc     420
acgatgctgt acaccggcat cgtaatctac gcaccggccc tcatcctgaa ccaagtgacc     480
gggctggaca tctgggcgtc gctcctgtcc accggaatta tctgcacctt ctacacggct     540
gtgggcggca tgaaggctgt ggtctggact gatgtgttcc aggtcgtggt gatgctaagt     600
ggcttctggg ttgtcctggc acgcggtgtc atgcttgtgg gcgggccccg ccaggtgctc     660
acgctggccc agaaccactc ccggatcaac ctcatggact ttaaccctga cccgaggagc     720
cgctatacat tctggacttt tgtggtgggt ggcacgttgg tgtggctctc catgtatggc     780
```

-continued

```
gtgaaccagg cgcaggtgca gcgctacgtg gcttgccgca cagagaagca ggccaagctg    840
gccctgctca tcaaccaggt cggcctgttc ctgatcgtgt ccagcgctgc ctgctgtggc    900
atcgtcatgt ttgtgttcta cactgactgc gaccctctcc tcctggggcg catctctgcc    960
ccagaccagt acatgcctct gctggtgctg acatcttcg aagatctgcc tggagtcccc   1020
gggcttttcc tggcctgtgc ttacagtggc accctcagca cagcatccac cagcatcaat   1080
gctatggctg cagtcactgt agaagacctc atcaaacctc ggctgcggag cctggcaccc   1140
aggaaactcg tgattatctc caaggggctc tcactcatct acggatcggc ctgtctcacc   1200
gtggcagccc tgtcctcact gctcggagga ggtgtccttc agggctcctt caccgtcatg   1260
ggagtcatca gcggccccct gctgggagcc ttcatcttgg aatgttcct gccggcctgc   1320
aacacaccgg gcgtcctcgc gggactaggc gcgggcttgg cgctgtcgct gtgggtggcc   1380
ttgggcgcca cgctgtaccc acccagcgag cagaccatga gggtcctgcc atcgtcggct   1440
gcccgctgcg tggctctctc agtcaacgcc tctggcctcc tggacccggc tctcctccct   1500
gctaacgact ccagcagggc ccccagctca ggaatggacg ccagccgacc cgccttagct   1560
gacagcttct atgccatctc ctatctctat tacggtgccc tgggcacgct gaccactgtg   1620
ctgtgcggag ccctcatcag ctgcctgaca ggccccacca agcgcagcac cctggccccg   1680
ggattgttgt ggtgggacct cgcacggcag acagcatcag tggcccccaa ggaagaagtg   1740
gccatcctgg atgacaactt ggtcaagggt cctgaagaac tccccactgg aaacaagaag   1800
cccctggct tcctgcccac caatgaggat cgtctgtttt cttggggca aaggagctg   1860
gaggggctg gctcttggac ccctgtgtt ggacatgatg gtggtcgaga ccagcaggag   1920
acaaacctct ga                                                      1932
```

<210> SEQ ID NO 2
<211> LENGTH: 643
<212> TYPE: PRT
<213> ORGANISM: Homo sapiens

<400> SEQUENCE: 2

```
Met Glu Ala Val Glu Thr Gly Glu Arg Pro Thr Phe Gly Ala Trp Asp
1               5                   10                  15

Tyr Gly Val Phe Ala Leu Met Leu Leu Val Ser Thr Gly Ile Gly Leu
            20                  25                  30

Trp Val Gly Leu Ala Arg Gly Gly Gln Arg Ser Ala Glu Asp Phe Phe
        35                  40                  45

Thr Gly Gly Arg Arg Leu Ala Ala Leu Pro Val Gly Leu Ser Leu Ser
    50                  55                  60

Ala Ser Phe Met Ser Ala Val Gln Val Leu Gly Val Pro Ser Glu Ala
65                  70                  75                  80

Tyr Arg Tyr Gly Leu Lys Phe Leu Trp Met Cys Leu Gly Gln Leu Leu
                85                  90                  95

Asn Ser Val Leu Thr Ala Leu Leu Phe Met Pro Val Phe Tyr Arg Leu
            100                 105                 110

Gly Leu Thr Ser Thr Tyr Glu Tyr Leu Glu Met Arg Phe Ser Arg Ala
        115                 120                 125

Val Arg Leu Cys Gly Thr Leu Gln Tyr Ile Val Ala Thr Met Leu Tyr
    130                 135                 140

Thr Gly Ile Val Ile Tyr Ala Pro Ala Leu Ile Leu Asn Gln Val Thr
145                 150                 155                 160
```

```
Gly Leu Asp Ile Trp Ala Ser Leu Leu Ser Thr Gly Ile Ile Cys Thr
            165                 170                 175

Phe Tyr Thr Ala Val Gly Gly Met Lys Ala Val Val Trp Thr Asp Val
        180                 185                 190

Phe Gln Val Val Met Leu Ser Gly Phe Trp Val Val Leu Ala Arg
        195                 200                 205

Gly Val Met Leu Val Gly Gly Pro Arg Gln Val Leu Thr Leu Ala Gln
        210                 215                 220

Asn His Ser Arg Ile Asn Leu Met Asp Phe Asn Pro Asp Pro Arg Ser
225                 230                 235                 240

Arg Tyr Thr Phe Trp Thr Phe Val Val Gly Gly Thr Leu Val Trp Leu
                245                 250                 255

Ser Met Tyr Gly Val Asn Gln Ala Gln Val Gln Arg Tyr Val Ala Cys
            260                 265                 270

Arg Thr Glu Lys Gln Ala Lys Leu Ala Leu Leu Ile Asn Gln Val Gly
            275                 280                 285

Leu Phe Leu Ile Val Ser Ala Ala Cys Cys Gly Ile Val Met Phe
    290                 295                 300

Val Phe Tyr Thr Asp Cys Asp Pro Leu Leu Gly Arg Ile Ser Ala
305                 310                 315                 320

Pro Asp Gln Tyr Met Pro Leu Val Leu Asp Ile Phe Glu Asp Leu
                325                 330                 335

Pro Gly Val Pro Gly Leu Phe Leu Ala Cys Ala Tyr Ser Gly Thr Leu
                340                 345                 350

Ser Thr Ala Ser Thr Ser Ile Asn Ala Met Ala Ala Val Thr Val Glu
            355                 360                 365

Asp Leu Ile Lys Pro Arg Leu Arg Ser Leu Ala Pro Arg Lys Leu Val
    370                 375                 380

Ile Ile Ser Lys Gly Leu Ser Leu Ile Tyr Gly Ser Ala Cys Leu Thr
385                 390                 395                 400

Val Ala Ala Leu Ser Ser Leu Leu Gly Gly Val Leu Gln Gly Ser
                405                 410                 415

Phe Thr Val Met Gly Val Ile Ser Gly Pro Leu Leu Gly Ala Phe Ile
            420                 425                 430

Leu Gly Met Phe Leu Pro Ala Cys Asn Thr Pro Gly Val Leu Ala Gly
            435                 440                 445

Leu Gly Ala Gly Leu Ala Leu Ser Leu Trp Val Ala Leu Gly Ala Thr
            450                 455                 460

Leu Tyr Pro Pro Ser Glu Gln Thr Met Arg Val Leu Pro Ser Ser Ala
465                 470                 475                 480

Ala Arg Cys Val Ala Leu Ser Val Asn Ala Ser Gly Leu Leu Asp Pro
                485                 490                 495

Ala Leu Leu Pro Ala Asn Asp Ser Ser Arg Ala Pro Ser Ser Gly Met
                500                 505                 510

Asp Ala Ser Arg Pro Ala Leu Ala Asp Ser Phe Tyr Ala Ile Ser Tyr
            515                 520                 525

Leu Tyr Tyr Gly Ala Leu Gly Thr Leu Thr Thr Val Leu Cys Gly Ala
    530                 535                 540

Leu Ile Ser Cys Leu Thr Gly Pro Thr Lys Arg Ser Thr Leu Ala Pro
545                 550                 555                 560

Gly Leu Leu Trp Trp Asp Leu Ala Arg Gln Thr Ala Ser Val Ala Pro
                565                 570                 575

Lys Glu Glu Val Ala Ile Leu Asp Asp Asn Leu Val Lys Gly Pro Glu
```

|  |  | 580 |  |  | 585 |  |  | 590 |  |  |  |
|---|---|---|---|---|---|---|---|---|---|---|---|
| Glu | Leu | Pro | Thr | Gly | Asn | Lys | Lys | Pro | Pro | Gly | Phe Leu Pro Thr Asn |
|  |  |  |  |  | 595 |  |  |  | 600 |  | 605 |

Glu Asp Arg Leu Phe Phe Leu Gly Gln Lys Glu Leu Glu Gly Ala Gly
    610                  615                620

Ser Trp Thr Pro Cys Val Gly His Asp Gly Gly Arg Asp Gln Gln Glu
625                630                635                640

Thr Asn Leu

<210> SEQ ID NO 3
<211> LENGTH: 1857
<212> TYPE: DNA
<213> ORGANISM: Rattus norvegicus

<400> SEQUENCE: 3

| | |
|---|---|
| atggaggtg cggaggccgg ggcccgggcc accttcggcg cctgggacta cggcgtgttc | 60 |
| gcgaccatgc tgctggtgtc cacgggcatc gggctatggg tcggcctggc ccgcggtggc | 120 |
| caacgcagtg ccgacgactt ctttaccggg ggccggcagt tggcagccgt tcctgtgggg | 180 |
| ctgtcgctgg ccgccagttt catgtcggct gtgcaggtgc tcgggtccc cgccgaggca | 240 |
| gcgcgctacg ggctcaagtt cctgtggatg tgcgcgggtc agttgctcaa ctcgctgctc | 300 |
| acagcgtttc tcttcttgcc gatcttctac cgcctgggcc ttaccagcac ctaccagtac | 360 |
| ctagagctgc gcttcagccg agcggtccgg ctctgcggga cgctgcagta cttggtggcc | 420 |
| acgatgctgt ataccaggcat cgtgatctac gcgcctgcgc tcatcctgaa ccaagtgacc | 480 |
| gggttggaca tctgggcatc gctcctgtcc acaggaatca tctgcacctt gtacactacc | 540 |
| gtgggtggta tgaaggccgt ggtctggaca gatgtgttcc aggttgtggt aatgctcgtt | 600 |
| ggcttctggg tgatcctggc ccgaggcgtc attctcctgg ggggtccccg gaacgtgctc | 660 |
| agcctcgctc agaaccattc ccggatcaac ctgatggact ttgaccctga tcctcggagc | 720 |
| cggtacacct tctggacttt catagtgggt ggcacactgg tgtggctctc catgtacggt | 780 |
| gtgaaccaag cccaggtaca gcgctatgtg gcctgccaca cagagggaaa ggccaaactg | 840 |
| gccctgcttg tcaaccagct gggcctcttc ctgattgtgg ccagtgcagc ttgctgtggc | 900 |
| attgtcatgt tcgtctacta caaggactgt gaccccctcc tcacaggccg tatctcagcc | 960 |
| cccgaccagt acatgccgct gcttgtgttg acattttg aggatctgcc cggggtcccc | 1020 |
| gggctcttcc tggcctgtgc ctacagtggc accctcagca ctgcatccac cagcatcaac | 1080 |
| gccatggcag ctgtgactgt ggaagacctc atcaagccga ggatgcctgg cctggcacct | 1140 |
| cggaagttgg ttttcatctc taaagggctc tcattcatct acggctctgc ctgcctcact | 1200 |
| gtggctgctc tgtcctcact gctgggaggt ggtgtcctcc agggttcctt cactgtgatg | 1260 |
| ggtgtcatca gtgggcctct actaggcgcc ttcacgcttg ggatgctgct cccagcctgc | 1320 |
| aacacgccag gcgttctctc cgggttggca gcaggcttgg ctgtatccct gtgggtggcc | 1380 |
| gtaggggcca cactgtatcc ccctggagag cagaccatgg gggtgctgcc cacctcggct | 1440 |
| gcaggctgca ccaacgattc ggtcctcctg ggcccaccctg agccaccaa cgcttccaac | 1500 |
| gggatcccca gttctggaat ggacacgggc cgccctgccc tcgctgatac cttttacgcc | 1560 |
| atctcctatc tctattacgg ggctctgggc acgctgacca ccatgctttg cggtgctctc | 1620 |
| atcagctacc ttactggtcc caccaagcgc agctccctgg gtcccggatt gctggtggg | 1680 |
| gaccttgctc gacagacagc gtctgtggcc ccaaaggaag acactgccac cctggaggag | 1740 |

```
agcctggtga aggaccgga agacatccct gctgtgacca gaagccccc tggcctcaag    1800 ccaggcgccg agaccaccc cctgtatctg gggcacgatg tggagaccaa cctctga      1857
```

<210> SEQ ID NO 4
<211> LENGTH: 618
<212> TYPE: PRT
<213> ORGANISM: Rattus norvegicus

<400> SEQUENCE: 4

```
Met Glu Gly Ala Glu Ala Gly Ala Arg Ala Thr Phe Gly Ala Trp Asp
1               5                   10                  15

Tyr Gly Val Phe Ala Thr Met Leu Leu Val Ser Thr Gly Ile Gly Leu
            20                  25                  30

Trp Val Gly Leu Ala Arg Gly Gly Gln Arg Ser Ala Asp Asp Phe Phe
        35                  40                  45

Thr Gly Gly Arg Gln Leu Ala Ala Val Pro Val Gly Leu Ser Leu Ala
    50                  55                  60

Ala Ser Phe Met Ser Ala Val Gln Val Leu Gly Val Pro Ala Glu Ala
65                  70                  75                  80

Ala Arg Tyr Gly Leu Lys Phe Leu Trp Met Cys Ala Gly Gln Leu Leu
                85                  90                  95

Asn Ser Leu Leu Thr Ala Phe Leu Phe Leu Pro Ile Phe Tyr Arg Leu
            100                 105                 110

Gly Leu Thr Ser Thr Tyr Gln Tyr Leu Glu Leu Arg Phe Ser Arg Ala
        115                 120                 125

Val Arg Leu Cys Gly Thr Leu Gln Tyr Leu Val Ala Thr Met Leu Tyr
    130                 135                 140

Thr Gly Ile Val Ile Tyr Ala Pro Ala Leu Ile Leu Asn Gln Val Thr
145                 150                 155                 160

Gly Leu Asp Ile Trp Ala Ser Leu Leu Ser Thr Gly Ile Ile Cys Thr
                165                 170                 175

Leu Tyr Thr Thr Val Gly Gly Met Lys Ala Val Val Trp Thr Asp Val
            180                 185                 190

Phe Gln Val Val Met Leu Val Gly Phe Trp Val Ile Leu Ala Arg
        195                 200                 205

Gly Val Ile Leu Leu Gly Gly Pro Arg Asn Val Leu Ser Leu Ala Gln
    210                 215                 220

Asn His Ser Arg Ile Asn Leu Met Asp Phe Asp Pro Asp Pro Arg Ser
225                 230                 235                 240

Arg Tyr Thr Phe Trp Thr Phe Ile Val Gly Gly Thr Leu Val Trp Leu
                245                 250                 255

Ser Met Tyr Gly Val Asn Gln Ala Gln Val Gln Arg Tyr Val Ala Cys
            260                 265                 270

His Thr Glu Gly Lys Ala Lys Leu Ala Leu Leu Val Asn Gln Leu Gly
        275                 280                 285

Leu Phe Leu Ile Val Ala Ser Ala Ala Cys Cys Gly Ile Val Met Phe
    290                 295                 300

Val Tyr Tyr Lys Asp Cys Asp Pro Leu Leu Thr Gly Arg Ile Ser Ala
305                 310                 315                 320

Pro Asp Gln Tyr Met Pro Leu Leu Val Leu Asp Ile Phe Glu Asp Leu
                325                 330                 335

Pro Gly Val Pro Gly Leu Phe Leu Ala Cys Ala Tyr Ser Gly Thr Leu
            340                 345                 350

Ser Thr Ala Ser Thr Ser Ile Asn Ala Met Ala Ala Val Thr Val Glu
```

```
                    355                 360                 365
Asp Leu Ile Lys Pro Arg Met Pro Gly Leu Ala Pro Arg Lys Leu Val
    370                 375                 380

Phe Ile Ser Lys Gly Leu Ser Phe Ile Tyr Gly Ser Ala Cys Leu Thr
385                 390                 395                 400

Val Ala Ala Leu Ser Ser Leu Leu Gly Gly Val Leu Gln Gly Ser
                405                 410                 415

Phe Thr Val Met Gly Val Ile Ser Gly Pro Leu Leu Gly Ala Phe Thr
                420                 425                 430

Leu Gly Met Leu Leu Pro Ala Cys Asn Thr Pro Gly Val Leu Ser Gly
            435                 440                 445

Leu Ala Ala Gly Leu Ala Val Ser Leu Trp Val Ala Val Gly Ala Thr
        450                 455                 460

Leu Tyr Pro Pro Gly Glu Gln Thr Met Gly Val Leu Pro Thr Ser Ala
465                 470                 475                 480

Ala Gly Cys Thr Asn Asp Ser Val Leu Leu Gly Pro Pro Gly Ala Thr
                485                 490                 495

Asn Ala Ser Asn Gly Ile Pro Ser Ser Gly Met Asp Thr Gly Arg Pro
                500                 505                 510

Ala Leu Ala Asp Thr Phe Tyr Ala Ile Ser Tyr Leu Tyr Gly Ala
            515                 520                 525

Leu Gly Thr Leu Thr Thr Met Leu Cys Gly Ala Leu Ile Ser Tyr Leu
        530                 535                 540

Thr Gly Pro Thr Lys Arg Ser Ser Leu Gly Pro Gly Leu Leu Trp Trp
545                 550                 555                 560

Asp Leu Ala Arg Gln Thr Ala Ser Val Ala Pro Lys Glu Asp Thr Ala
                565                 570                 575

Thr Leu Glu Glu Ser Leu Val Lys Gly Pro Gly Asp Ile Pro Ala Val
                580                 585                 590

Thr Lys Lys Pro Pro Gly Leu Lys Pro Gly Ala Glu Thr His Pro Leu
                595                 600                 605

Tyr Leu Gly His Asp Val Glu Thr Asn Leu
            610                 615

<210> SEQ ID NO 5
<211> LENGTH: 497
<212> TYPE: DNA
<213> ORGANISM: Rattus norvegicus

<400> SEQUENCE: 5
ccgccaagct tcggaccatg gtgaccggcg gcatggcctc caagtgggat caaaagggca    60
tggatatcgc ttacgaggag gccgccctgg gctacaagga gggcggcgtg cctatcggcg   120
gctgtctgat caacaacaag gacggcagtg tgctgggcag gggccacaac atcaggttcc   180
agaagggctc cgccaccctg cacggcgaga tctccaccct ggagaactgt ggcaggctgg   240
aggccaaggt gtacaaggac accacccctgt acaccaccct gtccccttgt cacatgtgta   300
ccggcgctat catcatgtac ggcatcccta ggtgtgtggt gggcgagaac gtgaacttca   360
agtccaaggg cgagaagtac ctgcaaacca ggggccacga ggtggtggtt gttgacgatg   420
agaggtgtaa gaagatcatg aagcagttca tcgacgagag gcctcaggac tggttcgagg   480
atatcggcga gtgataa                                                  497

<210> SEQ ID NO 6
<211> LENGTH: 158
```

<212> TYPE: PRT
<213> ORGANISM: Rattus norvegicus

<400> SEQUENCE: 6

```
Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Ile Arg Phe Gln Lys Gly Ser Ala Thr Leu His Gly Glu
    50                  55                  60

Ile Ser Thr Leu Glu Asn Cys Gly Arg Leu Glu Ala Lys Val Tyr Lys
65                  70                  75                  80

Asp Thr Thr Leu Tyr Thr Thr Leu Ser Pro Cys His Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155
```

<210> SEQ ID NO 7
<211> LENGTH: 19
<212> TYPE: DNA
<213> ORGANISM: Artificial Sequence
<220> FEATURE:
<223> OTHER INFORMATION: synthetic primer

<400> SEQUENCE: 7
agcctgtgca atcagggtc                                                19

<210> SEQ ID NO 8
<211> LENGTH: 16
<212> TYPE: DNA
<213> ORGANISM: Artificial Sequence
<220> FEATURE:
<223> OTHER INFORMATION: synthetic primer

<400> SEQUENCE: 8
gggtaccata tgcgct                                                   16

<210> SEQ ID NO 9
<211> LENGTH: 21
<212> TYPE: DNA
<213> ORGANISM: Artificial Sequence
<220> FEATURE:
<223> OTHER INFORMATION: synthetic primer

<400> SEQUENCE: 9
caacatgagg ttccagaagg g                                             21

<210> SEQ ID NO 10
<211> LENGTH: 22
<212> TYPE: DNA
<213> ORGANISM: Artificial Sequence
<220> FEATURE:
<223> OTHER INFORMATION: synthetic primer

```
<400> SEQUENCE: 10
cagttctcca gggtggagat ct                                              22

<210> SEQ ID NO 11
<211> LENGTH: 18
<212> TYPE: DNA
<213> ORGANISM: Artificial Sequence
<220> FEATURE:
<223> OTHER INFORMATION: synthetic primer

<400> SEQUENCE: 11
tccgccaccc tgcacggc                                                   18

<210> SEQ ID NO 12
<211> LENGTH: 21
<212> TYPE: DNA
<213> ORGANISM: Artificial Sequence
<220> FEATURE:
<223> OTHER INFORMATION: synthetic primer

<400> SEQUENCE: 12
caacatgagg ttccagaagg g                                               21

<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 13
cagttctcca gggtggagat ct                                              22

<210> SEQ ID NO 14
<211> LENGTH: 18
<212> TYPE: DNA
<213> ORGANISM: Artificial Sequence
<220> FEATURE:
<223> OTHER INFORMATION: synthetic primer

<400> SEQUENCE: 14
tccgccaccc tgcacggc                                                   18

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
tactgaagaa agaatgtgg                                                  19

<210> SEQ ID NO 16
<211> LENGTH: 19
<212> TYPE: DNA
<213> ORGANISM: Artificial Sequence
<220> FEATURE:
<223> OTHER INFORMATION: synthetic primer

<400> SEQUENCE: 16
ttagaaatct gctggtcgg                                                  19

<210> SEQ ID NO 17
<211> LENGTH: 47
```

-continued

<212> TYPE: DNA
<213> ORGANISM: Artificial Sequence
<220> FEATURE:
<223> OTHER INFORMATION: synthetic primer

<400> SEQUENCE: 17
ccacagtgca tacgtgggct ccaacaggtc ctcttccctc ccatgca      47

<210> SEQ ID NO 18
<211> LENGTH: 13
<212> TYPE: PRT
<213> ORGANISM: Artificial Sequence
<220> FEATURE:
<223> OTHER INFORMATION: synthetic peptide

<400> SEQUENCE: 18

Asp Leu Asp Val Thr Ala Pro Glu Asp Pro Asn Glu Glu
1               5                   10

<210> SEQ ID NO 19
<211> LENGTH: 15
<212> TYPE: PRT
<213> ORGANISM: Artificial Sequence
<220> FEATURE:
<223> OTHER INFORMATION: synthetic peptide

<400> SEQUENCE: 19

His Phe Leu Ile Ile Gly Phe Met Arg Arg Ala Leu Cys Gly Ala
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Asn Leu Leu Met Ala Ala Ser
1               5

<210> SEQ ID NO 21
<211> LENGTH: 186
<212> TYPE: PRT
<213> ORGANISM: Adenovirus

<400> SEQUENCE: 21

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

```
Phe Pro Pro Ser Asp Asp Glu Asp Glu Glu Gly Glu Glu Phe Val Leu
        130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165             170                 175

Arg Thr Cys Gly Met Phe Val Tyr Ser Lys
            180             185

<210> SEQ ID NO 22
<211> LENGTH: 8
<212> TYPE: PRT
<213> ORGANISM: Artificial Sequence
<220> FEATURE:
<223> OTHER INFORMATION: Adenovirus E1A segment

<400> SEQUENCE: 22

Leu Thr Cys His Glu Ala Cys Phe
1               5
```

ONCOLYTIC ADENOVIRUS ARMED WITH THERAPEUTIC GENES

This application is a continuation of U.S. patent application Ser. No. 12/370,232, filed Feb. 12, 2009, now issued as U.S. Pat. No. 9,061,055, which is a continuation of U.S. patent application Ser. No. 11/077,513, filed Mar. 10, 2005, now abandoned, which claims priority to U.S. Provisional Patent Application No. 60/551,932, filed Mar. 10, 2004. U.S. patent application Ser. No. 11/077,513 is also a continuation-in-part of U.S. patent application Ser. No. 10/124,608, filed Apr. 17, 2002, now abandoned. The entire text of each of the above referenced disclosures is specifically incorporated herein by reference

BACKGROUND OF THE INVENTION

A. Field of the Invention

The invention generally relates to the field of oncology and oncolytic adenoviruses. More particularly, it concerns compositions and methods of treating cancer of the brain in a patient using oncolytic adenoviruses armed with therapeutic transgenes.

B. Description of Related Art

The development of cancer is understood as the culmination of complex, multistep biological processes, occurring through the accumulation of genetic alterations. Many if not all of these alterations involve specific cellular growth-controlling genes. These genes typically fall into two categories: proto-oncogenes and tumor suppressor genes. Mutations in genes of both classes generally confer a growth advantage on the cell containing the altered genetic material.

The function of tumor suppressor genes, as opposed to proto-oncogenes, is to antagonize cellular proliferation. When a tumor suppressor gene is inactivated, for example by point mutation or deletion, the cell's regulatory machinery for controlling growth is upset. The studies of several laboratories have shown that the neoplastic tendencies of such mutated cells can be suppressed by the addition of a nucleic acid encoding a wild-type tumor suppressor polypeptide (a functional tumor suppressor) (Levine, 1995).

Mutations and/or loss of function in the retinoblastoma tumor suppressor gene have been associated with tumor formation. In some instances brain tumors are metastases to the brain from a primary tumor outside of the central nervous system (CNS). Brain tumors derived from metastases are typically more common than primary tumors of the brain. The most common primary tumors that metastasize to the brain are lung, breast, melanoma, and kidney. These brain metastases are usually in multiple sites, but solitary metastases may also occur.

Gene therapy is a promising treatment for brain tumors including gliomas because conventional therapies typically fail and are toxic. In addition, the identification of genetic abnormalities contributing to malignancies is providing crucial molecular genetic information to aid in the design of gene therapies. Genetic abnormalities indicated in the progression of tumors include the inactivation of tumor suppressor genes and the overexpression of numerous growth factors and oncogenes. Tumor treatment may be accomplished by supplying a polynucleotide encoding a therapeutic polypeptide or other therapeutic that target the mutations and resultant aberrant physiologies of tumors. It is these mutations and aberrant physiology that distinguishes tumor cells from normal cells. A tumor-selective virus would be a promising tool for gene therapy. Recent advances in the knowledge of how viruses replicate have been used to design tumor-selective oncolytic viruses. In gliomas, three kinds of viruses have been shown to be useful in animal models: reoviruses that can replicate selectively in tumors with an activated ras pathway (Coffey et al., 1998); genetically altered herpes simplex viruses (Martuza et al., 1991; Mineta et al., 1995; Andreanski et al., 1997), including those that can be activated by the different expression of proteins in normal and cancer cells (Chase et al., 1998); and mutant adenoviruses that are unable to express the E1B55kDa protein and are used to treat p53-mutant tumors (Bischof et al., 1996; Heise et al., 1997; Freytag et al., 1998; Kirn et al., 1998). Taken together, these reports confirm the relevance of oncolytic viruses as anti-cancer agents. In all three systems, the goal is the intratumoral spread of the virus and the ability to selectively kill cancer cells. Genetically modified adenoviruses that target cellular pathways at key points have both potent and selective anti-cancer effects in gliomas.

Targeting the Rb pathway has noted relevance for the treatment of gliomas because abnormalities of the p16/Rb/E2F pathway are present in most gliomas (Fueyo et al., 1998a; Gomez-Manzano et al., 1998). Targeting this pathway by replacement of lost tumor suppressor activity through the transfer of p16 and Rb genes has produced cytostatic effects (Fueyo et al., 1998a; Gomez-Manzano et al., 1998). Transfer of E2F-1 resulted in powerful anti-cancer effect since the exogenous wild-type E2F-1 induced apoptosis and inhibited tumor growth in vivo (Fueyo et al., 1998b). However, treating human glioma tumors with existing adenovirus constructs realistically cannot affect significant portions of the tumor, mainly because replication-deficient adenoviral vectors are unable to replicate and infect other cells, thus transferring the exogenous nucleic acid to sufficient numbers of cancer cells (Puumalainen et al., 1998). Although targeting the p16/Rb/E2F pathway produces an anti-cancer effect in vitro, this imperfection of the vector system limits the therapeutic effect of the gene in vivo.

There is a continued need for additional treatments for cancer, particularly brain tumors, including the creation of additional oncolytic viruses that are capable of cell-specific replication. Additional treatments include an adenovirus with therapeutic capabilities or with an ability to be tracked in vivo.

SUMMARY OF THE INVENTION

The present invention provides an oncolytic adenovirus capable of killing target cells, such as a tumor cells, with a greater efficiency. The invention takes advantage of the discovery that an adenovirus encoding an E1A polypeptide unable to bind the tumor suppressor protein Rb may not replicate in or kill a cell that has a functional Rb pathway, but may replicate in and kill a cell that has a defective Rb pathway. In various aspects of the invention the oncolytic adenovirus is armed or encodes a therapeutic or diagnostic polypeptide. "Armed" is a term that indicates that the virus contains a heterologous nucleic acid sequence encoding a polypeptide of interest or a nucleic acid comprising a polynucleotide of interest. In certain embodiments, the nucleic acid encoding a therapeutic polypeptide may encode angiopoietin 2 (Ang-2), humanized yeast cytosine deaminase polypeptide (hyCD) or a sodium-iodide symporter (NIS) polypeptide. In further embodiments, the NIS polypeptide may be used in detecting the location of oncolytic adenovirus within a subject. The adenovirus of the present invention can be delivered by a number routes including, but not limited to intracranial (into the skull cavity) or intravenous administration. The tumor may be a primary tumor or it may be a tumor resulting from a metastasis to the skull or brain.

Embodiments of the invention include an oncolytic adenovirus and replication defective adenovirus, as well as wildtype adenoviruses. Certain aspects of the invention include an oncolytic adenovirus comprising an E1A deletion, in particular where the E1A deletion is a deletion of nucleotides encoding amino acids 122 to 129 of the E1A protein (Delta 24) and/or Delta-24-300 adenovirus and an expression cassette encoding a therapeutic or diagnostic gene, including but not limited to an Ang-2 gene, a yeast cytosine deaminase gene, a humanized yeast cytosine deaminase gene, and/or a NIS gene. The nucleic acid encoding the yeast cytosine deaminase polypeptide may be a humanized nucleic acid encoding a yeast cytosine deaminase polypeptide. In preferred embodiments, the humanized nucleic acid encoding the yeast cytosine deaminase comprises the nucleic acid sequence of SEQ ID NO:5.

An adenovirus of the invention may comprise additional modifications, such as a nucleic acid encoding a modified adenoviral fiber protein, which in certain aspects may comprise a heterologous peptide motif, which targets various proteins expressed on the surface of a cell, including but not limited to adhesion molecules and/or cell surface receptors, such as EGFR, EGFRvIII, Tie, and Tie2. The heterologous peptide motif can be an RGD motif, an EGFR targeting motif, or a Tie2 targeting motif. Typically, the targeting motif alters the tropism of the virus by providing a chimeric fiber protein that includes the particular targeting motif.

An adenovirus of the invention, typically, will selectively replicate in a cell having a defective Rb pathway. The defective Rb pathway may comprise a defective Rb protein or a defect in other proteins that make up the Rb pathway in a cell. However, some embodiments of the invention may be used in conjunction with replication defective adenoviruses or other replication selective, replication competent adenoviruses, or combinations thereof.

In further embodiments, methods of treating cancer in a patient are contemplated. The methods include administering to a patient an effective amount of a composition comprising an oncolytic adenovirus, preferably Delta 24, comprising an expression cassette encoding therapeutic gene, including but not limited to an Ang-2 gene, a yeast cytosine deaminase gene, a humanized yeast cytosine deaminase and/or a NIS, and administering an effective amount of a pro-drug, wherein the pro-drug is metabolized to a cytotoxic drug by a polypeptide encoded by the yeast cytosine deaminase gene. The nucleic acid encoding a yeast cytosine deaminase is preferably a humanized nucleic acid encoding a yeast cytosine deaminase. The cancer to be treated may include one or more cells comprising a mutated Rb pathway. The cancer may comprise one or more cells comprising a mutated Rb polypeptide. The cell to be treated may be a tumor cell or a brain tumor cell, more particularly a glial cell or glial derived cell. The methods of the invention may further comprise determining whether the cell or cells has a defect, e.g. a mutation, in a gene encoding a polypeptide in the Rb pathway, in a gene encoding Rb or both. A defect may be caused by a deletion or a mutation in the nucleic acid encoding a gene, include coding and non-coding regions of the gene. In certain aspects, a cell is not killed if it does not comprise a mutated polypeptide in the Rb pathway.

The oncolytic adenovirus may be suitably dispersed in a pharmacologically acceptable formulation. The composition may comprise a suitable buffer and may further comprise one or more lipids. The composition may be administered through various routes including: intradermal, transdermal, parenteral, intracranial, intravenous, intramuscular, intranasal, subcutaneous, percutaneous, intratracheal, intraperitoneal, intratumoral, perfusion, lavage, direct injection, and oral routes of administration. The compositions may be directly injected into a tumor. Furthermore, the administration of a composition may occur more than once and may be administered at least three times to the patient. The methods of the invention may further comprise administering to the patient a second therapy, wherein the second therapy is anti-angiogenic therapy, chemotherapy, immunotherapy, surgery, radiotherapy, immunosuppressive agents, or gene therapy with a therapeutic polynucleotide. The second therapy may be administered to the patient before, during, after or a combination thereof relative to the administration of the oncolytic adenovirus composition. Chemotherapy includes, but is not limited to an alkylating agent, mitotic inhibitor, antibiotic, or antimetabolite. The chemotherapy may comprise administration of CPT-11, temozolomide, or a platin compound. Radiotherapy may include X-ray irradiation, UV-irradiation, γ-irradiation, or microwaves. The oncolytic adenovirus may be administered to the patient preferably in doses of approximately $10^3$ to about $10^{15}$ viral particles; more preferably about $10^5$ to about $10^{12}$ viral particles even more preferably about $10^7$ to about $10^{10}$ viral particles.

In still further embodiments, methods include methods for treating a brain tumor in a patient comprising identifying a patient having a brain tumor; and contacting the tumor with an oncolytic adenovirus comprising an expression cassette, preferably an expression cassette comprising an Ang-2 gene, a yeast cytosine deaminase gene, and/or a NIS gene. The oncolytic adenovirus may also comprise a targeting moiety. The methods may include contacting the tumor with the adenovirus by injecting the adenovirus intracranially into the patient.

Embodiments of the invention include methods for treating a subject having a brain tumor by determining that a cell in the tumor has a mutation in the Rb pathway; administering intracranially to the patient an oncolytic adenovirus comprising an expression cassette, wherein the expression cassette comprises a therapeutic or diagnostic gene. The methods may further include administering to the patient a pro-drug that is converted by cytosine deaminase to a therapeutic drug.

Methods of the invention also include treatment of a subject having a tumor that has metastasized to the brain by determining that a cell in the tumor has a mutation in the Rb pathway; administering intracranially to the patient an oncolytic adenovirus and a therapeutic gene such as, but not limited to Ang-2 gene, yeast cytosine deaminase gene, humanized yeast cytosine deaminase, and/or NIS gene. The methods may further include administering to the patient a pro-drug that is converted by cytosine deaminase to a therapeutic drug, a therapeutic or an anti-angiogenic agent(s) (e.g., anti-sense VEGF or its equivalents).

Embodiments of the invention also include an adenovirus (e.g., Delta 24, Delta-24-300) comprising; and an expression cassette encoding a sodium-iodide symporter (NIS) gene. The nucleic acid encoding NIS may comprise the nucleic acid sequence of SEQ ID NO:1 or SEQ ID NO:3. Additionally, the adenovirus may further comprise additional modifications, such as a nucleic acid encoding a modified adenoviral fiber protein, which may comprise a heterologous peptide motif, preferably the heterologous peptide motif is an RGD, vIII, or PEPHC1 motif.

The expression cassette may comprise a chimeric polynucleotide encoding Ang-2, hyCD, or NIS and a nucleic encoding a second peptide or polypeptide, wherein a sequence encoding a protease-cleavable amino acid linker is between the NIS coding sequence and the nucleic acid encoding the second peptide or polypeptide. The protease-cleavable amino acid linker may be an auto-cleaving amino acid sequence. The sequence encoding a protease-cleavable linker can be fused in-frame to the 3' or 5' end of the Ang-2, NIS and/or hyCD encoding polynucleotide. In certain aspects, the protease cleavable linker is cleaved by furin. The protease-cleavable linker may be identical to a linker present in a cytoplasmic protein.

The expression cassette may comprises a chimeric polynucleotide comprising the Ang-2, NIS or hyCD encoding polynucleotide, or combination thereof, and a nucleic acid sequence encoding a second peptide or polypeptide, wherein the chimeric polynucleotide encode an internal ribosome entry site between NIS encoding polynucleotide and a second nucleic sequence encoding a second polypeptide.

Further embodiments of the invention include methods of monitoring the location of an oncolytic adenovirus or a nucleic acid encoding the oncolytic adenovirus in a mammal, comprising the steps of administering to a mammal an oncolytic adenovirus comprising a nucleic sequence encoding a sodium-iodide symporter (NIS), wherein the expression of the NIS sequence in cells permits cellular uptake of a diagnostic agent; administering to the mammal a diagnostic agent in an amount sufficient to permit transport of the diagnostic agent by the NIS and detection of transported diagnostic agent; and determining the location of the transported diagnostic agent in the mammal as an indication of the location of the oncolytic adenovirus or nucleic acid encoding the oncolytic adenovirus. The step of detecting can be performed quantitatively to determine the amount of transported diagnostic agent in the mammal. The diagnostic agent may be iodine. Iodine may be iodine radionuclides $^{131}$I, $^{123}$I, $^{124}$I, or $^{125}$I. The diagnostic agent may also be technesium pertechnetate, rhenium perrhenate, radioactive iodine, or other diagnostic elements used in the art. In certain aspects of the invention, a nucleic acid encoding an oncolytic adenovirus comprises a chimeric polynucleotide comprising a nucleic acid sequence encoding NIS and a second transgene. A second transgene may encode a second therapeutic polypeptide.

Embodiments of the invention include methods of treating cancer in a patient comprising administering to a patient an effective amount of a composition comprising an oncolytic adenovirus comprising an expression cassette encoding an Ang-2, NIS or hyCD polynucleotide; and administering an effective amount of a diagnostic agent, a therapeutic agent a therapy enhancing agent or an anti-angiogenic agent. In certain aspects, the diagnostic agent, the therapeutic agent or the therapy enhancing agent is transported into a cell by a NIS polypeptide encoded by the NIS polynucleotide. The cancer may comprise one or more cells comprising a mutated polypeptide in the Rb pathway, a mutated Rb polypeptide or both. The method may further comprise determining whether one or more cell has a mutation, resulting in a defective protein, in a gene encoding a polypeptide in the Rb pathway, in the gene encoding Rb, or both. The method may comprise assaying Rb activity. Rb activity may be assayed for using an anti-Rb antibody or by determining whether Rb in the cell inhibits E2F activation of transcription. A cell may be a glial cell and/or a tumor cell.

The methods may include an adenovirus composition suitably dispersed in a pharmacologically acceptable formulation. The composition may comprise a suitable buffer and/or a lipid. Composition may be administered by a variety of routes including intradermal, transdermal, parenteral, intracranial, intravenous, intramuscular, intranasal, subcutaneous, percutaneous, intratracheal, intraperitoneal, intratumoral, perfusion, lavage, direct injection, and oral routes of administration. In certain aspects of the invention the composition is directly injected into a tumor. Administration of a composition may occur more than once, twice, three times or more.

The method may further comprising administering to the patient a second therapy, wherein the second therapy is anti-angiogenic therapy, chemotherapy, immunotherapy, surgery, radiotherapy, immunosuppressive agents, or gene therapy with a therapeutic polynucleotide. The second therapy may be administered to the patient before, during, after or a combination thereof relative to the administration of the oncolytic adenovirus composition. Chemotherapy includes, but is not limited to an alkylating agent, mitotic inhibitor, antibiotic, or antimetabolite. The chemotherapy may comprise administration of CPT-11, temozolomide, or a platin compound. Radiotherapy may include X-ray irradiation, UV-irradiation, γ-irradiation, or microwaves. The oncolytic adenovirus may be administered to the patient preferably in doses of approximately $10^3$ to about $10^{15}$ viral particles; more preferably about $10^5$ to about $10^{12}$ viral particles even more preferably about $10^7$ to about $10^{10}$ viral particles.

Embodiments discussed in the context of a methods and/or composition of the invention may be employed with respect to any other method or composition described herein. Thus, an embodiment pertaining to one method may be applied to other methods of the invention as well.

The term "about" refers to the imprecision of determining virus, protein or other amounts and measures, and is intended to include at least one standard deviation of error for any particular assay, measure or quantification.

"A" or "an," as used herein in the specification, may mean one or more than one. As used herein in the claim(s), when used in conjunction with the word "comprising," the words "a" or "an" may mean one or more than one.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIGS. 12A-12F shows a specimen from a patient treated with a single injection of Ad-p53 as a dose of $3 \times 10^{10}$ vp in 1 ml (level 1). (FIG. 12A) photograph of surgical specimen that was removed en bloc. The injection catheter is protruding from the surface of the tumor. (FIG. 12B) formalin fixed tumor blocks. Specimen from A has been cur perpendicular to the catheter. The hole created by the catheter is evident. (FIG. 12C) low power view (300×) of same speciment immunostained with antibody to p53 protein. The hole from the catheter is at the top of the photomicrograph. Transfected tumor cells stain darkly and are distributed within 5 mm of the injection site. (FIG. 12D) High power view (500×) of same section a C demonstrating transfected cells. (FIG. 12E) View of adjacent section of that shown distribution as p53 staining (FIG. 12F) low power (10×) view of cress-section of whole speciment. The catheter was within the central hole. Blue staining around hole shows distribution of exogenous p53.

FIGS. 13A-13B shows Generation of Δ24-hyCD adenovirus. (FIG. 13A) The humanized yeast cytosine deaminase sequence is depicted as the complete nucleotide sequence of yeast CD as well as the nucleotide substitutions (highlighted in bold) for optimized humanized codon preference. A Kozak sequence is placed immediately before the starting codon (italicized). Proximal HindIII and distal XbaI restriction sites are placed between parentheses. (FIG. 13B) Schematic illustration of Δ24-hyCD showing the 24-bp deletion in the E1A region (nucleotides and corresponding amino acid residues are shown) and the insertion of the modified cytosine deaminase (hyCD) expression mini-cassette in the deleted E3 region.

FIGS. 14A-14B shows analyses of the expression and enzymatic activity of hyCD. (FIG. 14A) Western blot analyses of the expression of exogenous hyCD in U251MG cells. Expression was apparent by 24 h after infection in a dose-dependent manner. As expected, mock (M) or Δ24-treatment at an pfu/cell of 100 did not result in the expression of CD. The expression level of actin is showed as a loading control. (FIG. 14B) Thin layer chromatography analyses of cytosine deaminase. U251MG cells stably transfected with the hyCD encoding polynucleotide were treated with cytosine at the indicated times and assessed for hyCD activity. The migrated uracil spot was visualized with ultraviolet excitation at 260λ. Lanes 5 and 6 showed a dose-dependence positive result. Negative (cytosine) and positive (uracil) controls are shown in lanes 1 and 2, respectively.

(FIG. 16A) Crystal violet analyses of the cytopathic effect of Δ24-hyCD or Δ24 in U251MG cells treated with either 5-FU or 5-FC. Each well represents a different time period of 5-FU or 5-FC treatment indicated in days. (FIG. 16B) Quantification of the viability of U251MG cells by MTT assay, treated with Δ24 (left) or Δ24-hyCD (right) and 5-FC at the indicated doses. UVi, UV-inactivated adenoviral treatment, 5 MOI. (FIG. 16C) Demonstration of Δ24-hyCD-mediated bystander effect. U251MG cells were treated with Δ24-hyCD or Δ24 (at an pfu/cell of 10) 24 h after infection, and conditioned media was collected. In one set of studies, the conditioned media were inactivated by UV to ensure that no replication-competent virus was carried over. Conditioned media at the indicated volumes were transferred to fresh U251MG cultures and incubated for 48 h. Viability was assessed by MTT assay.

FIG. 18A shows Tie2 expression in glioma cell lines: a) RT-PCR, and b) Western blotting analysis (membrane subfraction) of the expression of Tie2 in a panel of glioma cell lines. HUVEC cells and NIH3T3 cells were used as positive and negative controls. FIG. 18B shows Ang-2 downregulates VEGF secretion. Shown here is the secreted VEGF expressed as a percentage relative to that of the mock-infected cells (equal to 100%) (ELISA). Values shown as mean±SD (+, P<0.005; *, P>0.5).

FIGS. 26A-26B show differential expression of Delta-24-300 viral proteins in glioma and normal human astrocyte (NHA) cultures. (FIG. 26A) Western blot analysis of the E1A and fiber proteins in U-251 MG and NHA cell extracts 16 hours after infection with Delta-24, Delta-300 or Delta-24-300 at an MOI of 50. (FIG. 26B) Actin expression is used as a loading control. Quantification of the fiber protein signal by densitometry following normalization to actin levels. Fiber levels from Delta-24-treated cultures are arbitrarily given the value of 100%.

FIGS. 27A-27B. FIG. 27A shows analyses or adenoviral-induced E2F-1 promoter activity. Proliferating NHA were transfected with the E2F-1 reporter construct, and 1 h later the cells were treated with the indicated adenovirus at 5 MOI. Luciferase activity was determined 20 h after infection. Data is shown as relative means±SEM of normalized luciferase measurements (Ad300, equal to 100%). FIG. 27B shows Viral replication analysis. Replicating NHA and U-87 MG glioma cell lines were infected with wt Ad, Delta-24, Delta-300 or Delta-24-300 at 1 MOI. Three days later viral titers were determined by TCID50 method. Viral titers from two independent experiments were normalized to wild-type adenovirus titers. Values in the chart represent the difference between the viral titers in U-87 MG cells and NHA.

FIGS. 34A-34B shows analysis of the Delta-24-vIII genome structure. FIG. 34A shows confirmation of the mutant-E1A region. DNA isolated from Delta-24-vIII adenovirus was subjected to PCR assay utilizing pair of primers flanking the deletion in the E1A region and FIG. 34B shows posteriorly subjected to restriction enzyme analysis using BstXI which cleaves tice in the E1A region amplified from Wild-type adenovirus, and one in the E1A from Delta-24. Two clones were asolited and tested (Clon#12 and #13). pVK500C and pVK.Delta24 were used as controls.

FIGS. 35A-35B Analysis of the Delta-24-vIII genome structure. FIG. 35A shows confirmation of the chimeric fiber. FIG. 35B shows DNA isolated from Delta-24-vIII adenovirus was subjected to PCR assay utilizing pair of primers as depicted below. Two clones were asolited and tested (Clons #12 and #13). pVK500C and pVK.Delta24 were used as controls.

DESCRIPTION OF ILLUSTRATIVE EMBODIMENTS

Figure 1:
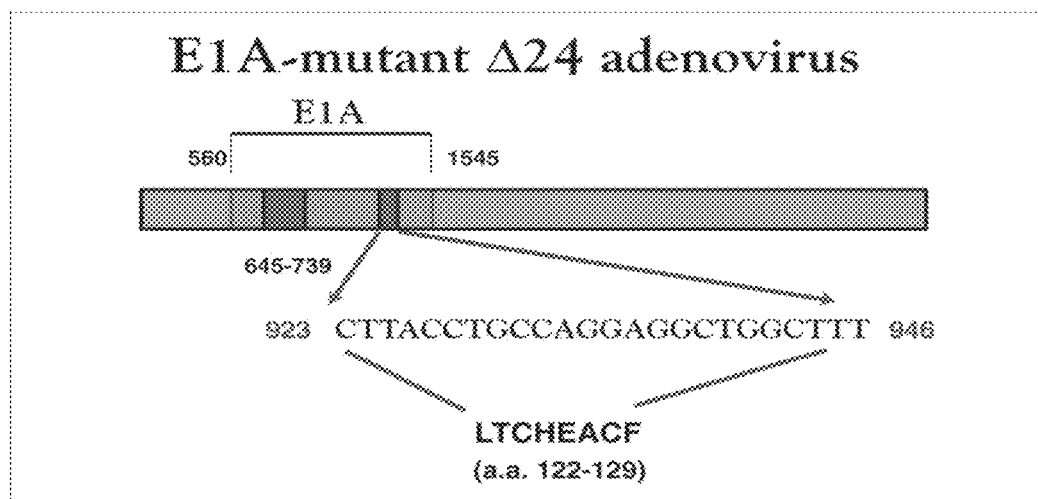
FIG. 1 is a schematic representation of the Δ24 adenovirus. Shown are the 2 Rb-binding regions of the E1A sequence (hatched boxes). The 24 nucleotides that have been deleted and the corresponding amino acid translation are indicated.

Malignant tumors that are intrinsically resistant to conventional therapies are significant therapeutic challenges. Such malignant tumors include, but are not limited to malignant gliomas and recurrent systemic solid tumors such as lung cancer. Malignant gliomas are the most abundant primary brain tumors having an annual incidence of 6.4 cases per 100,000 (CBTRUS, 2002-2003). These neurologically devastating tumors are the most common subtype of primary brain tumors and are one of the deadliest human cancers. In the most aggressive cancer, manifestation glioblastoma multiforme (GBM), median survival duration for patients ranges from 9 to 12 months, despite maximum treatment efforts (Hess et al., 1999). A prototypic disease, malignant glioma is inherently resistant to current treatment regimens (Shapiro and Shapiro, 1998). In fact, in approximately ⅓ of patients with GBM the tumor will continue to grow despite treatment with radiation and chemotherapy. Median survival even with aggressive treatment including surgery, radiation, and chemotherapy is less than 1 year (Schiffer, 1998). Because few good treatment options are available for many of these refractory tumors, the exploration of novel and innovative therapeutic approaches is essential.

One potential method to improve treatment is based on the concept that naturally occurring viruses can be engineered to produce an oncolytic effect in tumor cells (Wildner, 2001; Jacotat, 1967; Kirn, 2001; Geoerger et al., 2002; Yan et al., 2003; Vile et al., 2002, each of which is incorporated herein by reference). In the case of adenoviruses, specific deletions within their adenoviral genome can attenuate their ability to replicate within normal quiescent cells, while they retain the ability to replicate in tumor cells. One such conditionally replicating adenovirus, Δ24, has been described by Fueyo et al. (2000), see also U.S. Patent Application No. 20030138405, each of which are incorporated herein by reference. The Δ24 adenovirus is derived from adenovirus type 5 (Ad-5) and contains a 24-base-pair deletion within the CR2 portion of the E1A gene. Significant antitumor effects of Δ24 have been shown in cell culture systems and in malignant glioma xenograft models.

Oncolytic adenoviruses include conditionally replicating adenoviruses (CRADs), such as Delta 24, which have several properties that make them candidates for use as biotherapeutic agents. One such property is the ability to replicate in a permissive cell or tissue, which amplifies the original input dose of the oncolytic virus and helps the agent spread to adjacent tumor cells providing a direct antitumor effect.

Embodiments of the present invention couple the oncolytic component of Delta 24 with a transgene expression approach to produce an armed Delta 24. Armed Delta 24 adenoviruses may be used for producing or enhancing bystander effects within a tumor and/or producing or enhancing detection/imaging of an oncolytic adenovirus in a patient, or tumor associated tissue and/or cell. It is contemplated that the combination of oncolytic adenovirus with various transgene strategies will improve the therapeutic potential against a variety of refractory tumors, as well as provide for improved imaging capabilities. In certain embodiments, an oncolytic adenovirus may be administered with a replication defective adenovirus, another oncolytic virus, a replication competent adenovirus, and/or a wildtype adenovirus. Each of which may be adminstered concurrently, before or after the other adenoviruses.

Embodiments of the invention include the Delta 24 adenovirus comprising an expression cassette containing a heterologous gene. Examples of such heterologous genes include therapeutic genes, pro-drug converting enzymes, cytosine deaminase (to convert 5-FC to 5-FU), a yeast cytosine deaminase, a humanized yeast cytosine deaminase, an image enhancing polypeptides, a sodium-iodide symporter, anti-sense or inhibitory VEGF, Bcl-2, Ang-2, or interferons alpha, beta or gamma. In certain aspects of the present invention, a Delta 24 oncolytic adenoviral strategy is coupled with an Ang-2 transgene, sodium-iodide symporter (NIS) transgene, humanized yeast CD or a yeast CD transgene approach for augmenting bystander effects and/or obtaining imaging of the replicating virus within an in vivo tumor setting.

II. Armed Oncolytic Adenovirus Δ24

The in vitro and in vivo oncolytic effects of Δ24 adenovirus have been demonstrated. Generally, adenovirus is a 36 kb, linear, double-stranded DNA virus (Grunhaus and Horwitz, 1992). Adenoviral infection of host cells results in adenoviral DNA being maintained episomally, which reduces the potential genotoxicity associated with integrating vectors. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

A. Δ24-Sodium Iodide Symporter (NIS)

Embodiments of the invention include a Δ24 adenovirus encoding an NIS polypeptide. NIS is a transmembrane pump that was originally isolated from the thyroid gland and functions physiologically by concentrating iodide within thyroid tissue. NIS is also able to mediate the uptake and concentration of other diagnostic and therapeutically important radionuclides, such as Technicium-99m pertechnetate ($^{99m}TcO_4$) and Rhenium-188 perrenate ($^{188}ReO_4$). By combining a tumor-specific oncolytic adenovirus with expression of the NIS polypeptide radioisotopes may be concentrated in the presence of viral replication to allow superior imaging of an infected tumor while potentially augmenting therapeutic effectiveness.

The mechanism mediating iodide uptake across the basolateral membrane of thyroid follicular cells has been elucidated by cloning and characterization of the sodium iodide symporter (NIS) (Smanik et al., 1996; Dai et al., 1996). The human NIS encoding polynucleotide contains an open reading frame of 1,928 nucleotides and encodes a 643-amino acid trans-membrane protein, which has an expected molecular weight of 69 kDa. This pump has been shown to be capable of concentrating multiple isotopes within the intracellular compartment, including $^{123}I$, $^{125}I$ and $^{131}I$. NIS is an intrinsic membrane glycoprotein with 13 putative transmembrane domains which is responsible for the ability of cells of the thyroid gland to transport and sequester iodide. An NIS of the present invention is comprised of a polypeptide having the activity of a sodium iodide symporter, including, but not limited to polypeptides of SEQ ID NO:2 and 4 that are encoded by the nucleic acid sequences of SEQ ID NO:1 and 3, for human and rat respectively. NIS expression in thyroid tissues is dependent upon stimulation of the cells by pituitary-derived thyroid stimulating hormone (TSH) and can therefore be readily suppressed in this tissue by treatment with Thyroxine. TSH-regulated NIS expression is specific for thyroid cells, whereas many other organs do not concentrate iodine due to lack of NIS expression. Cloning and characterization of the human and rat NIS genes (SEQ ID NO:1 and SEQ ID NO:3 respectively; GenBank Accession numbers AC005796 and U60282 respectively) permits NIS encoding nucleic acid delivery into non-thyroid cells, thereby allowing these cells to trap and sequester radio-labeled iodine.

According to the present invention, NIS functions well as a localization tag for several reasons. The NIS is synthesized in the mammal, using the mammals own protein synthetic machinery, and thus is recognized as self, thereby avoiding a potential immune response. Furthermore, the NIS is a useful localization tag according to the present invention as it should have no significant effect on the biological properties of the genetically modified cells. Given that the only known function of the NIS is to transport iodine across the cell membrane, it should not adversely affect endogenous cellular function (U.S. Pat. No. 6,586,411, which is incorporated herein by reference).

The therapeutic index of successful treatment of thyroid carcinomas and their metastases by $^{131}I$ is based on the expression of the NIS within thyrocytes (Levy et al., 1998a; Kohrle, 1999; Levy, 1998b). Additionally, treatment failure parallels the loss of expression of NIS. Because radioisotopes are widely established in diagnostic nuclear radiographic studies as well as being useful in treatment strategies, a NIS encoding polynucleotide is an attractive target for radioisotope-mediated cancer gene therapy (La Perle et al., 2002). Recently, many tumor lines, including glioma cell lines, have been genetically modified to express NIS using both viral and nonviral transfer vectors (Cho et al., 2000 and 2002). All related studies had the concerns of complete vector delivery and specific tumor targeting. If NIS expression within cancer cells can approach or exceed its expression in typical thyroid tumor cells then accumulation of $^{131}I$ can result in tissue ablative doses of ionizing radiation. This interstitial dosing approximates brachytherapy. In addition, very short-lived isotopes, such as $^{99m}TCO_4$ ($T_{1/2}$ 6 hours), which is a common radioisotope tracer used in clinical practice, can easily be used to demonstrate the expression of NIS within a tumor focus. These features, coupled with the delivery features of Δ24, make this combination an attractive and powerful system that can be used both to image and treat tumors.

1. Expression of NIS in Tumors

A number of reports have demonstrated the uptake of various radionuclides in tumor models using the NIS pump. The human and the rat form of NIS have each been cloned and transfected into various tumor cell lines by multiple authors (e.g., Haberkorn, 2001; Cho et al., 2002; Cho et al., 2000; Haberkorn et al., 2001; Haberkorn and Altman, 2002). It is unknown whether this protein could effectively engage itself appropriately into the membrane of tumor cells. In fact, Eskandar et al. (1991) demonstrated that rat NIS (rNIS) could be expressed in *Xenopus laevis* oocytes. It was shown that this pump was sodium dependent and capable of transporting a wide variety of anions ($I^-$, $ClO^-$, $SCN^-$, $SeCN^-$, $NO_3^-$, $Br^-$, $BF_4^-$, $IO_4^-$; and $BrO_3^-$), although, perchlorate ($ClO_4$) inhibited the NIS pump. Cho et al. (2002) expressed hNIS in human glioma cells via transfection with a replication-deficient adenovirus, producing accumulation within mouse xenograft tumors and demonstrating accretion of $^{125}I$ and $^{99m}Tc$-pertechnetate. The uptake of $^{125}I$ was approximately 20-fold higher for tumors expressing hNIS compared with non-expressing tumors. Similar results were demonstrated by Haberkorn and Altmann (2001, 2002) who found that an hNIS-expressing hepatoma was able to concentrate $^{131}I$ as demonstrated by gamma camera imaging. Although different authors have shown the ability of NIS to concentrate various isotopes within a tumor expressing this pump, the lack of adequate and efficient delivery mechanisms is a problem that continues to plague investigators.

The compositions and methods described herein are designed to improve transgene expression by combining the power of an oncolytic virus with NIS expression for radionuclide accumulation.

B. Δ24-Cytosine Deaminase (CD)

Cytosine deaminase (CD, EC 3.5.4.1) catalyzes the hydrolysis of cytosine to uracil. The enzyme, which plays an important role in microbial pyrimidine metabolism (O'Donovan and Neuhard, 1970), has been isolated from several different microorganisms, but does not appear to be present in mammalian cells (Nishiyama et al., 1985).

The physical properties of CD from various organisms have been shown to differ significantly in terms of molecular weight, stability, and subunit composition. For example, CD from *Salmonella typhimurium* has been purified to homogeneity (by SDS-PAGE) and is composed of 4 subunits of 54 kilodaltons (kDa) each (West et al., 1982) while the enzyme from *Escherichia coli* has a molecular weight of 200 kDa and is composed of 35 and 46 kDa subunits (Katsuragi et al., 1986). Both of these enzymes are highly thermostable, and maintain high activity at 55° C.

Bakers' yeast (*Saccharomyces cerevisiae*) has also been used as a source for yeast CD. CD previously obtained from

*Saccharomyces cerevisiae* has a molecular weight of 34 kDa as determined by gel filtration (Ipata et al., 1971, 1978) and 32-33 kDa as determined by SDS-PAGE and amino acid analysis (Yergatian et al., 1977). The CD enzyme that has been previously isolated from bakers' yeast therefore appears to be a monomeric protein. In certain embodiments a humanized yeast cytosine deaminase (hyCD) (SEQ ID NO:5 and 6) may be used minimize any immune reactions to the protein.

Solutions of previously isolated bakers' yeast CD maintain activity for at least 48 hr when stored at 4° C. between pH 5-9 (Ipata et al., 1971, 1978). However, at 37° C., a crude preparation of bakers' yeast CD has been shown to lose half of its activity in 1 hr, and a purified form of the enzyme has a half-life of 30 min (Katsuragi, 1987). Thus, the thermal instability of CD from bakers' yeast, along with its low molecular weight, distinguish it from the bacterial enzymes described earlier.

CD has been used therapeutically for the conversion of the pro-drug 5-fluorocytosine (5-FC) to the anticancer drug 5-fluorouracil (5-FU) (Katsuragi et al., 1987; Nishiyama et al., 1985; Senter et al., 1991). However, bacterial sources of CD are impractical for such use, requiring large-scale cultivation in order to obtain adequate activity.

Yeast can be used as a source of CD to overcome these problems. However, the thermal instability of the previous yeast-derived product requires that the enzyme be immobilized prior to its use (Katsuragi et al., 1987). Thus, the isolation and purification of a thermally stable yeast CD provides an improved enzyme for use in anticancer therapy. Such novel constructs increase the efficiency or usefulness of the enzyme in anticancer therapy (U.S. Pat. No. 5,545,548, which is incorporated herein by reference).

1. Δ24 delivery of Cytosine Deaminase

To illustrate Δ24's ability to function as an effective delivery vector for the expression of exogenous genes and its potent augmentation of the oncolytic effect, high functional levels of cytosine deaminase were expressed in the setting of a Δ24 infection. The Δ24 backbone was modified using a yeast cytosine deaminase encoding polynucleotide cloned into the E3 region of Δ24. Derived from yeast, the cytosine deaminase gene has superior catalytic properties compared with the bacterial form of the enzyme (Kievit, 1999). Extremely high specific activity of this enzyme has been detected when the oncolytic virus is allowed to infect human glioma tumors. Assays have demonstrated a highly specific conversion of cytosine to uracil or 5-fluorocytosine (5-FC) to 5FU.

Additionally, preliminary studies using a MTT cell viability assay in U251MG and U87MG glioma cell lines reveal clear and separable cell killing based on a pro-drug bystander effect after infection with the Δ24 oncolytic virus containing the cytosine deaminase gene. One difficulty encountered in these early studies has been that the oncolytic properties of Δ24 are so powerful that it is difficult to distinguish the effects of viral replication and cell lysis from concomitant bystander effects (Wei et al., 1995). To date, the improvement seen in glioma cell killing appears to occur in a much shorter amount of time using the pro-drug-converting enzyme compared with using Δ24 alone. This finding is consistent with the notion that conversion to a cytotoxic compound (5-FC to 5-FU) can diffuse into a larger number of cells to more quickly kill the cells. These results appear to suggest that gene-dependent enzyme/pro-drug therapy (GDEPT) increases the oncolytic potency of the virus and serves as proof of concept that exogenous genes can be delivered using oncolytic adenoviral constructs.

C. Adenoviral Delivery of Anti-Angiogenics

Angiogenesis is critical for the development and maintenance of glioblastomas, the most malignant and common form of primary brain tumors. Current evidence indicates that recruitment of tumor vessels from the normal surrounding tissue requires a delicate balance between the timing and level of expression of two major angiogenesis factors: angiopoietin 2 (Ang-2) and the vascular endothelial growth factor (VEGF). Ang-2 is typically expressed at sites of vascular remodeling in the adult, notably in the female reproductive tract. Detailed localization of Ang-2 in the ovary by in situ hybridization revealed that in regions of active vascular remodeling it was either expressed together with VEGF at sites of vessel sprouting and ingrowth, or in the absence of VEGF at sites of frank vessel regression. These expression patterns led to the proposal that Ang-2 plays a facilitative role at sites of vascular remodeling in the adult by blocking constitutive stabilizing actions. Further, it is suggested that such destabilization by Ang-2 in the presence of high VEGF levels primes the vessels to mount a robust angiogenic response. However, such destabilization by Ang-2 in the absence of VEGF is instead proposed to lead to frank vessel regression. Thus, hypothetically, overexpression of Ang-2 in gliomas should result in the formation of poorly differentiated and inefficient tumor vessels that will undergo regressive changes overriding vessel proliferation. Therefore a maintained overexpression of Ang-2 in gliomas should have potent anti-glioma effect.

Combining oncolysis with anti-angiogenesis may produce a synergistic effect since the anticancer mechanisms are different but complementary. In addition, the success of the strategy is assisted by the relatively slow rhythm of oncolytic propagation. That allows time for an anti-angiogenic nucleic acid or polypeptide, sucy as, but not limited to an Ang-2 protein, to be produced, ultimately favoring delivery to the extracellular compartment. For that reason, the oncolytic adenovirus is used as an improved adenoviral vector to deliver high and continuous levels of Ang-2 to the tumor. Another use of replication-competent adenoviruses that are currently being pursued is applying replication-competent systems as facilitators for the delivery of replication-deficient E1-deleted adenovirus vectors. This is a useful approach because co-infection of a cancer cell with both a replication-deficient E1-deleted adenovirus and a replication-competent adenovirus results in the replication of both adenoviruses. This is because the replication-deficient vector uses the expression of the E1A protein by the replication-competent adenovirus to replicate. This system can thus generate and multiply the number of copies of exogenous protein. The inventors will use this strategy to simultaneously deliver an anti-angiogenic nucleic acid or polypeptide, such as Ang-2 (in a replication competent, oncolytic or replication defective adenovirus) and antisense VEGF (in a replication competent, oncolytic or replication defective adenovirus) (Im et al., 1999) adenoviruses to human glioma xenografts. In certain aspects of the invention a targeted or non-targeted gene therapy approach with Delta-24 adenovirus will be used (Fuego et al., 2002 and 2003).

The effects of Delta-24 based antiangiogenic agents may be compared to or used in conjunction with other antiangiogenesis agents that are or will be tested in clinical trials for patients with malignant gliomas. Second, in certain aspects, the inventors are using cell lines with a greater clinical relevance, as LN229 (SNB19 as alternative). These cell lines exhibit an invasive phenotype when implanted intracranially in animal models. Both cell lines express the Tie2 receptor and are tumorigenic in intracranial settings.

Finally, since it has been reported that E1A downregulates HIF-1α activity (Zoltan et al., 1996), methods and compositions are contemplated that will differentiate Ang-2-mediated regulation of HIF-1α and the regulation that adenoviral E1A exerts on the HIF-1α transcription factor.

Despite indications that VEGF regulates Ang-2 in tumors, there is not any evidence of a feedback signaling loop which will be required to coordinate and modulate the expression of the Ang-2 and VEGF molecules. The specific time when the expression of Ang-2 is required during the different stages of tumor formation is also not known. Finally, no treatments have been developed on the basis of dysregulation of the putative feedback loop and the consequent induction of an imbalance caused by the expression of Ang-2 together with the downregulation of VEGF.

The inventors put forth the idea that there is a regulatory signaling loop involving the coordinated and sequential expression of VEGF and Ang-2, and elucidating the underlying mechanisms can lead to developing a better model for the angiogenic process that occurs in human gliomas, as well development of improved compositions and methods or the treatment of such. Moreover, exploiting the interdependence between VEGF and Ang-2 could be used to develop more effective and rational anti-angiogenesis therapies for brain tumors than currently exist.

The inventors use oncolytic adenoviruses for the simultaneous targeting of Ang-2 or Ang-2 and VEGF (the inhibition or down regulation). The inventors also plan on characterizing the interaction between Ang-2 and VEGF; and the role of Ang-2 expression in a dynamic tumor model of glioma angiogenesis. The inventors will obtain efficacious preclinical evidence for supporting the translation of their studies to the clinic for single and/or combination anti-angiogenesis treatments for malignant gliomas.

Angiogenesis refers to vessel formation by remodeling the primary vascular network or by sprouting from existing vessels (reviewed in Yancopoulos et al., 2000). The "angiogenesis switch" is "off" when the effect of pro-angiogenic molecules is balanced by the activity of anti-angiogenic molecules, and is "on" when the net balance between the molecules is tipped in favor of angiogenesis (reviewed in Carmeliet and Jain, 2000). Angiogenesis has an essential role in the development and maintenance of solid tumors, including malignant gliomas.

Malignant gliomas, the most common subtype of primary brain tumors, are aggressive, highly invasive, and neurologically destructive tumors considered to be among the deadliest of human cancers. In its most aggressive manifestation, glioblastoma multiforme (GBM), median survival ranges from 9 to 12 months, despite maximum treatment efforts.

The striking and dramatic induction of angiogenesis in GBM has fueled the speculation that progression to GBM requires activation of angiogenesis and has stimulated significant efforts in the development of agents that will block this process. Two pathways in particular have received considerable attention. They are vascular endothelial growth factor (VEGF) and Angiopoietin 2. VEGF has been shown to be critical for the earliest stages of vasculogenesis, promoting endothelial cell proliferation, differentiation, migration, and tubular formation. Gene targeting studies have shown that a deficiency of VEGF or VEGF receptors, Flt-1, or Flk-1, results in early embryonic lethality caused by defects in angiogenesis and vasculogenesis (reviewed in Yancopoulos et al., 2000, Ferrara 2002). Specific VEGF inhibitors have recently been introduced into clinical glioma trials, and results are forthcoming. Encouragingly, the putative antiangiogenic agent, thalidomide, has been shown to have activity in patients with recurrent high-grade gliomas (Fine et al., 2000). VEGF inhibitors may include VEGF-neutralizing chimeric proteins such as soluble VEGF receptors. (See Aiello, PNAS, 92, 10457 (1995)). In particular, they may be VEGF-receptor-IgG chimeric proteins. Another VEGF inhibitor contemplated for use in the present invention is antisense phosphorothio oligodeoxynucleotides (PS-ODNs). Examples of anti-angiogenesis agents include, but are not limited to, retinoid acid and derivatives thereof, 2-methoxyestradiol, ANGIOSTATIN® protein, ENDOSTATIN® protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,1-3,4-dehydroproline, thiaproline], α,α-dipyridyl, β-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), β-1-anticollagenase-serum, α-2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. (Ferrara and Alitalo (1999) Nature Medicine 5:1359-1364. Calbiochem (San Diego, Ca) carries a variety of angiogensis inhibitors including (catalog number/product name) 658553/AG 1433; 129876/Amiloride, Hydrochloride; 164602/Aminopeptidase N Inhibitor; 175580/Angiogenesis Inhibitor; 175602/Angiogenin (108-123); 175610/Angiogenin Inhibitor; 176600/Angiopoietin-2, His•Tag®, Human, Recombinant, Mouse, Biotin Conjugate; 176705/Angiostatin K1-3, Human; 176706/Angiostatin K1-5, Human; 176700/Angiostatin® Protein, Human; 178278/Apigenin; 189400/Aurintricarboxylic Acid; 199500/Benzopurpurin B; 211875/Captopril; 218775/Castanospermine, Castanospermum australe; 251400/D609, Potassium Salt; 251600 Daidzein; 288500/DL-a-Difluoromethylornithine, Hydrochloride; 324743/Endostatin™ Protein, His•Tag®, Mouse, Recombinant, *Spodoptera frugiperda;* 324746/Endostatin™ Protein, Human, Recombinant, *Pichia pastoris;* 324733/Endostatin™ Protein, Mouse, Recombinant, *Pichia pastoris;* 329740 Eriochrome® Black T Reagent; 344845 Fumagillin, *Aspergillus fumigatus;* 345834 Genistein; 375670/Herbimycin A, *Streptomyces* sp.; 390900/4-Hydroxyphenylretinamide; 407293/a-Interferon, Mouse, Recombinant, *E. coli;* 407306/g-Interferon, Human, Recombinant, *E. coli;* 05-23-3700/Laminin Pentapeptide; 05-23-3701/Laminin Pentapeptide Amide; 428150/Lavendustin A; 454180/2-Methoxyestradiol; 475838/Mifepristone; 475843/Minocycline, Hydrochloride; 4801/Neomycin Sulfate; 521726/Platelet Factor 4, Human Platelets; 553400/Radicicol, Diheterospora chlamydosporia; 554994/RHC-80267; 565850/Shikonin; 573117/SMC Proliferation Inhibitor-2w; 572888/SU1498; 572632/SU5614; 574625/Suramin, Sodium Salt; 608050/TAS-301; 585970/(±)-Thalidomide; 605225/Thrombospondin, Human Platelets; 616400/Tranilast; 654100/TSRI265; 676496/VEGF Inhibitor, CBO-P11; 676493/VEGF Inhibitor, Flt2-11; 676494 VEGF Inhibitor, Je-11; 676495 VEGF Inhibitor, V1; 676480/VEGF Receptor 2 Kinase Inhibitor I; 676485/VEGF Receptor 2 Kinase Inhibitor II; 676475/VEGF Receptor Tyrosine Kinase Inhibitor, and other such agents known to those of ordinary skill in the medical arts.

In the case of the angiopoietins, genetic studies in mice have shown that angiopoietin-1 (Ang-1) promotes remodeling and stabilization of VEGF-induced vessels (Suri et al. 1996; Suri et al., 1998) through interactions between endothelial cells and surrounding pericytes and the extracellular matrix. Ang-2 appears to be a natural antagonist of Ang-1, responsible for destabilizing mature vessels in the context of vessel regression or angiogenesis in a VEGF-dependent manner (Maisonpierre et al., 1997). Consequently, Ang-2 expression results in reversal of the maturation process mediated by Ang-1, leading to a disruption of interactions between endothelial cells, pericytes, and the extracellular matrix. In the presence of VEGF activity, the Ang-2-mediated effect is followed by sprouting and ingrowth of new vessels (i.e., neovascularization). Conversely, in the absence of concomitant VEGF expression, Ang-2-mediated destabilization leads to the regression of blood vessels (Holash et al., 1999). On the basis of these results, the inventors envision a therapeutic strategy targeted to the tumor in which Ang-2 is induced in the setting of VEGF inhibition, a combination predicted to cause vascular collapse in the tumors. The strong genetic validation has justified ongoing angiopoietin-directed drug development initiatives.

Although the mechanism driving the angiogenic burst in GBM has yet to be elucidated, existing evidence points to a pivotal role for VEGF (Millauer et al. 1994; Cheng et al. 1996). It has long been held that the rapid proliferative rate of GBM creates local ischemia and hypoxia, leading to a VEGF-mediated induction of angiogenesis. This hypothesis is based on the observation that marked VEGF expression is localized to regions of perinecrotic (palisading) cells at expanding edges of the tumor (Plate et al. 1992). However, a recent study has shed doubt on this theory. Holash et al. (1999) and Zagzag et al. (2000) demonstrated that glioma cells implanted into murine brain actually home initially to existing vasculature. This co-potation of host vessels eventually leads to the induction of Ang-2 expression in the host endothelial cells and Ang-2-mediated destabilization (as manifested by the lifting of astrocytic foot processes away from endothelial cells and disruption of the normal pericyte cuffing) and subsequent regression of existing vessels and necrosis. Tumor cell necrosis resulting from vascular regression and hypoxia appear to trigger the expression of VEGF and the onset of angiogenesis. These intriguing findings support the view that a key mechanism in early tumor angiogenesis may be the direct effect of tumor cells on existing blood vessels rather than the orthodox view of new blood vessel growth into the hypoxemic, growing tumor bed.

The role of Tie2 in angiogenesis has been demonstrated in studies that have involved the deletion of this receptor. Specifically, Tie2 knockout mice die early in development because of immature blood vessels and lack of vessel development, (Sato et al., 1995). Ligands for the Tie2 receptor include Ang-1 and Ang-2 (Davis et al., 1996; Maisonpierre et al., 1997). Ang-1 phosphorylates Tie2 in cultured endothelial cells, whereas Ang-2 is a naturally occurring antagonist of Ang-1, competing with Ang-1 for binding to Tie2 (Maisonpierre et al., 1997). In solid tumors, newly formed tumor vessels are often tenuous, poorly differentiated and undergo regressive changes even as blood vessel proliferation continues. The failure of many solid tumors to form a well-differentiated and stable vasculature could indeed be attributable to the fact that newly formed tumor vessels continue to overexpress Ang-2. Thus, a persistent blockade of Tie2 signaling may prevent vessel differentiation and maturation, contributing to the generally tenuous and leaky quality of tumor vessels. Inhibition of Tie2 using a soluble receptor resulted in inhibition of tumor angiogenesis (Lin et al., 1998; Zadeh et al., 2004). Although, it was thought that Tie2 is a vascular-specific receptor, preliminary evidence suggests that the expression of Tie2 is not limited to endothelial cells (Valable et al., 2003; Poncet et al., (2003). Importantly, cells of neuroectodermic origin express Tie2 (Valable et al., 2003). Therefore, the negative regulation of the Tie2 receptor and the growth proliferation transduction signal that its activation triggers can be used as an anti-proliferation target in cells other than endothelial cells that express Tie2, including cancer cells.

Tumor angiogenesis begins when tumor cells release molecules that send signals to the surrounding normal host tissue. Such signaling activates specific genes in the host tissue that, in turn, generate proteins that encourage the growth of new blood vessels. Among these molecules, two proteins appear to be the most important for sustaining tumor growth: VEGF and Ang-2. Imbalances in the coordinated timing and expression of these molecules lead to vessel regression. The confirmation of the Ang-2-mediated downmodulation of HIF is underscored by the observation that the overexpression of HIF-1α has been associated with increased patient mortality in several cancer types. Moreover, in preclinical studies, inhibiting the activity of HIF-1 has marked effects on tumor growth. This approach may yield important mechanistic information about the abnormal regulation of angiogenesis in gliomas. Characterizing an active Tie2 pathway in glioma cells will have an enormous scientific and clinical relevancy. This description together with the explanation of the overall role of Tie2 role in cell proliferation will define a novel target for glioma therapy, one that will permit therapies to be simultaneously directed against the glioma cell mass as well as the angiogenic vascular network. Furthermore, the data obtained from these studies will provide a rational basis for the development of a phase I/II clinical trial to assess the toxicity and efficacy of a triple treatment for malignant gliomas, one that will combine the overexpression of Ang-2 a decrease in the effect VEGF, and the production of oncolysis.

D. Therapeutic Genes

Aspects of the invention include nucleic acids or genes that encode a detectable and/or therapeutic polypeptide. In certain embodiments of the present invention, the gene is a therapeutic, or therapeutic gene. A "therapeutic gene" is a gene which can be administered to a subject for the purpose of treating or preventing a disease. For example, a therapeutic gene can be a gene administered to a subject for treatment or prevention of diabetes or cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

In certain embodiments of the present invention, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell.

Examples of tumor suppressor nucleic acids within this definition include, but are not limited to APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS 1. Other exemplary tumor suppressor genes are described in a database of tumor suppressor genes at www-.cise.uffedu/~yy1/HTML-TSGDB/Homepage.html. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied in the present invention.

In certain embodiments of the present invention, the therapeutic gene is a gene that induces apoptosis (i.e., a pro-apoptotic gene). A "pro-apoptotic gene amino acid sequence" refers to a polypeptide that, when present in a cell, induces or promotes apoptosis. The present invention contemplates inclusion of any pro-apoptotic gene known to those of ordinary skill in the art. Exemplary pro-apoptotic genes include CD95, caspase-3, Bax, Bag-1, CRADD, TSSC3, bax, hid, Bak, MKP-7, PERP, bad, bcl-2, MST1, bbc3, Sax, BIK, BID, and mda7. One of ordinary skill in the art would be familiar with pro-apoptotic genes, and other such genes not specifically set forth herein that can be applied in the methods and compositions of the present invention.

The therapeutic gene can also be a gene encoding a cytokine. The term 'cytokine' is a generic term for proteins released by one cell population which act on another cell as intercellular mediators. A "cytokine" refers to a polypeptide that, when present in a cell, maintains some or all of the function of a cytokine. This definition includes full-length as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10 IL-11, IL-12; IL-13, IL-14, IL-15, IL-16, IL-17, IL-18, IL-19, IL-20, IL-24 LIF, G-CSF, GM-CSF, M-CSF, EPO, kit-ligand or FLT-3.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants. The nucleic acid molecule encoding a therapeutic gene may comprise a contiguous nucleic acid sequence of about 5 to about 12000 or more nucleotides, nucleosides, or base pairs.

E. Mechanism of Δ24 Oncolytic Virus

A dramatic increase in the cellular proliferation that is characteristic of the transformation from low-grade to intermediate-grade glioma is in large part related to dysregulation of the p16/Rb/E2F pathway (Fueyo et al., 2000; Fueyo et al., 1998; Chintala, 1997). Most compelling is the lack of mutational overlap seen among the various members of this pathway, which argues that an important therapeutic advance in the treatment of these tumors could be achieved by specifically targeting the Rb pathway (Kyritsis and Yung, 1996; Fueyo et al., 1999). Disrupted Rb status will likely provide opportunities to utilize agents that operate exclusively in Rb-deficient tumor cells (Fueyo et al., 1999). Most normal human brain cells are usually quiescent. Cells in the central nervous system (CNS) rarely divide, and these cells are specifically triggered to divide in a limited fashion. Tight regulatory controls have evolved which strictly limit cells from undergoing cell division. The p16/Rb/E2F pathway is an important pathway for maintaining the non-dividing status of fully differentiated cell or negatively regulates the cell-cycle progression of dividing normal cells.

Human adenovirus normally infects human cells, which are quiescent (nondividing) or dividing cells (normal or cancer cells). Upon introduction of this virus into a human cell (viral infection), the adenovirus DNA is immediately transcribed by the synthesis of E1A adenoviral protein. The CR2 region of E1A protein interacts specifically with Rb protein and leads to release of E2F, forcing cell entry into S-phase (the DNA Synthesis phase) of the cell cycle and maintaining the cell in the dividing cycle. This series of events effectively commandeers the host cell exclusively for the purpose of expressing virally encoded proteins. Active production of adenoviral particles depends on this ability to drive cells into an active mode of replication, a critical feature of oncolytic viruses. As a consequence of their biologic characteristics, tumor cells provide a replicating environment that favors such activity. Mutations in critical sequences of the viral genome render the adenovirus unable to bind to and inactivate tumor suppressor proteins. These modified adenoviruses are able to replicate exclusively in cells lacking a functional target tumor suppressor gene (tumor cells only).

Thus, the expression of an E1A protein with a 24 base pair deletion in the CR2 region prevents the protein from binding to and inactivating Rb. This attenuated E1A-mutant adenovirus is unable to replicate within normal quiescent cells that have a functionally active Rb pathway. In contrast, tumor cells are permissive to viral replication, which in turn efficiently invade and lyse human glioma cells both in vitro and in vivo.

Figure 2:
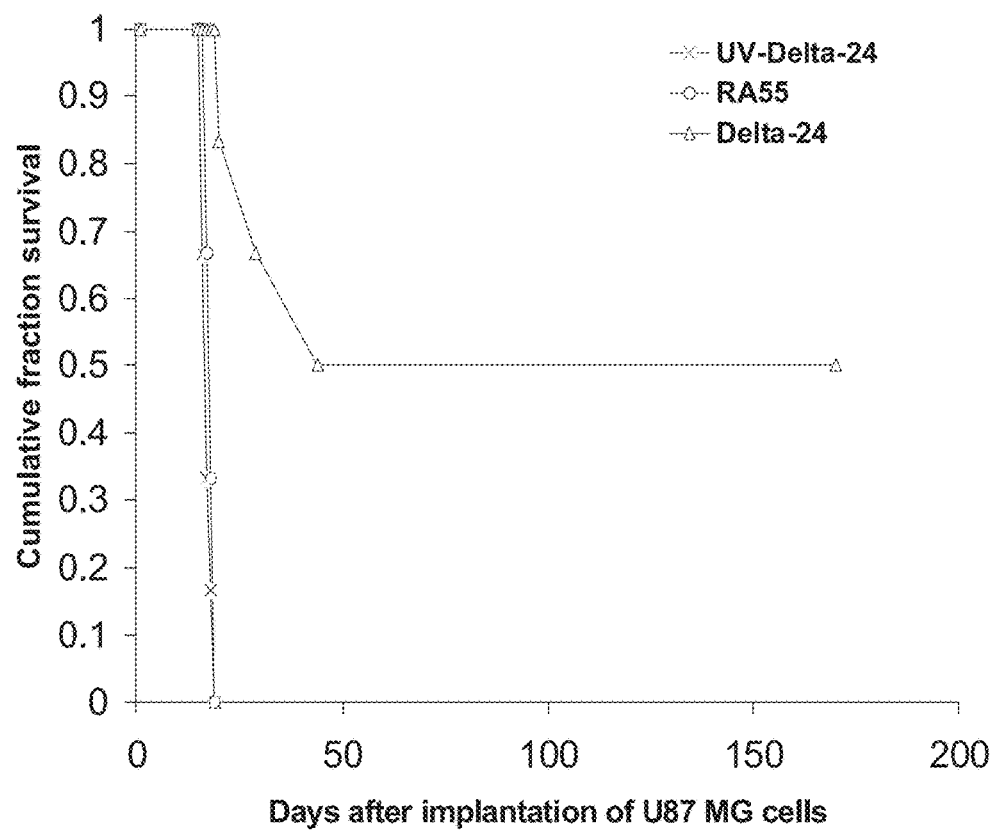
FIG. 2 shows the effects of Δ-24 in a mouse xenograft intracranial glioma tumor model.
Figure 3:
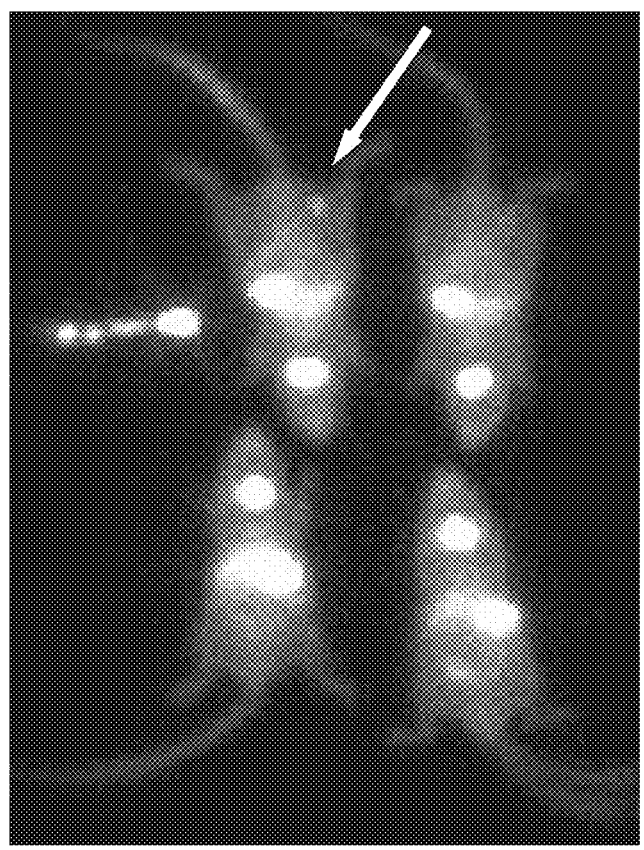
FIG. 3 shows visualization of NIS expression with a transfected U87MG tumor implanted subcutaneously in NuNu mice flanks. A 2-3 mm palpable tumor in the animal on the left is clearly visible after injection with 0.2 mCi of 99mTcO4 in 0.1 ml PBS. The animal to the right did not have a palpable tumor. The control animals below do not have hNIS expressing flank tumors.

The oncolytic potential of Δ24 is dramatic compared with other conditionally replication-deficient adenoviruses, such as Onyx-015. The effects of Δ24 in a mouse xenograft intracranial glioma tumor model are shown in FIG. 2. In this case, the curve representing RA55 carries the deletion in the E1B region as in Onyx-015. The oncolytic adenovirus does not have the same degree of potency as Δ24 at comparable doses used (in this case $1 \times 10^8$ pfu). Also shown is the negative control Δ24 that is inactivated by ultraviolet exposure. The antitumor effects of Δ24 have been demonstrated in various human tumor cell lines and in animal xenograft models with known defects of the p16/Rb/E2F pathway. Permissive replication of Δ24 in cell lines with p16/Rb/E2F defects is contrasted with the highly attenuated replication in normal astrocytes and normal quiescent fibroblasts. Additionally, the activity of this virus is attenuated when introduced into tumor cells in which Rb has been functionally restored through stable or transient transfection techniques.

Several factors favor the use of oncolytic adenoviruses for the treatment of brain tumors. First, gliomas do not metastasize, and therefore an efficient local approach should be enough to cure the disease. Second, every glioma harbors several populations of cells expressing different genetic abnormalities (Sidransky et al., 1992; Collins and James, 1993; Furnari et al., 1995; Kyritsis et al., 1996). Thus, the spectrum of tumors sensitive to the transfer of a single gene to cancer cells may be limited. Third, replication competent adenoviruses can infect and destroy cancer cells that are arrested in $G_0$. Since gliomas invariably include non-cycling cells, this property is important. Finally, the p16-Rb pathway is abnormal in the majority of gliomas (Hamel et al., 1993; Henson et al., 1994; Hirvonen et al., 1994; Jen et al., 1994; Schmidt et al., 1994; Costello et al., 1996; Fueyo et al., 1996b; Kyritsis et al., 1996; Ueki et al., 1996; Costello et al., 1997), thus making the Δ24 strategy appropriate for most of these tumors. Although the loss of the retinoblastoma tumor suppressor gene function has been associated with the causes of various types of tumors and is not limited to treatment of gliomas.

In other embodiments of the invention, an E1A mutation (e.g., a Δ24 mutation in E1A) may be used in combination with mutations in the E1B region of the same adenovirus, thus producing a double mutant adenovirus. In certain embodiments of the invention an adenovirus may comprise a Δ24 mutation and a deletion in the E1B region that prevents expression or function of the E1B55kD protein. The E1B55kD protein has been shown to bind to and inactivate p53. The E1B region mutation may include a deletion of adenovirus sequences from 2426 bp to 3328 bp of genebank accession number NC_001406, which is incorporated herein by reference.

In certain embodiments of the invention, an oncolytic adenovirus may be used as an adenovirus expression vector. "Adenovirus expression vector" is meant to include those vectors containing adenovirus sequences sufficient to (a) support packaging of the vector and (b) to express a polynucleotide that has been cloned therein. The insertion position of a polynucleotide encoding a heterologous polypeptide of interest within the adenovirus sequences is not critical to the invention. The polynucleotide encoding the polypeptide of interest may be inserted in lieu of the deleted E3 region in E3 replacement vectors as described by Karlsson et al., (1986) or other region that are not essential for viral replication in the target cell. Traditional methods for the generation of adenoviral particles is co-transfection followed by subsequent in vivo recombination of a shuttle plasmid and an adenoviral helper plasmid into either 293 or 911 cells (Introgene, The Netherlands).

If an adenovirus has been mutated so that it is unable to replicate or is conditionally replicative (replication-competent under certain conditions), a helper cell may be required for viral replication. When required, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, for example Vero cells or other monkey embryonic mesenchymal or epithelial cells. As preferred helper cell line is 293. Various methods of culturing host and helper cells may be found in the art, for example Racher et al., 1995. In the present invention, the adenovirus is typically replication-competent in cells with a mutant Rb pathway. After transfection, adenoviral plaques are isolated from the agarose overlaid cells and the viral particles are expanded for analysis. For detailed protocols the skilled artisan is referred to Graham and Prevac, 1991.

Alternative technologies for the generation of adenovirus or adenovirus expression vectors include utilization of the bacterial artificial chromosome (BAC) system, in vivo bacterial recombination in a recA+ bacterial strain utilizing two plasmids containing complementary adenoviral sequences, and the yeast artificial chromosome (YAC) system (PCT publications 95/27071 and 96/33280, which are incorporated herein by reference).

The nature of the adenovirus vector is not believed to be crucial to the successful practice of the invention. The adenovirus may be of any of the 42 different known serotypes or subgroups A-F. Adenovirus type 5 is the preferred starting material for use in the present invention. Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers (e.g., $10^9$-$10^{11}$ plaque-forming units (pfu) per ml), and they are highly infective. The life cycle of adenovirus does not require integration into the host cell genome.

F. Modifications of Oncolytic Adenovirus

Modifications of oncolytic adenovirus described herein may be made to improve the ability of the oncolytic adenovirus to treat cancer. The present invention also includes any modification of oncolytic adenovirus that improves the ability of the adenovirus to treat neoplastic cells. Included are modifications to oncolytic adenovirus genome in order to enhance the ability of the adenovirus to infect and replicate in cancer cells by altering the receptor binding molecules.

The absence or the presence of low levels of the coxsackievirus and adenovirus receptor (CAR) on several tumor types can limit the efficacy of the oncolytic adenovirus. Various peptide motifs may be added to the fiber knob, for instance an RGD motif (RGD sequences mimic the normal ligands of cell surface integrins), Tat motif, poly-lysine motif, NGR motif, CTT motif, CNGRL motif, CPRECES motif or a strept-tag motif (Rouslahti and Rajotte, 2000). A motif can be inserted into the HI loop of the adenovirus fiber protein. Modifying the capsid allows CAR-independent target cell infection. This allows higher replication, more efficient infection, and increased lysis of tumor cells (Suzuki et al., 2001, incorporated herein by reference). Peptide sequences that bind specific human glioma receptors such as EGFR or uPR may also be added. Specific receptors found exclusively or preferentially on the surface of cancer cells may used as a target for adenoviral binding and infection, such as EGFRvIII.

Cell surface receptors are attractive candidates for the targeted therapy of cancer. Growth factors and their receptors play important roles in the regulation of cell division, development, and differentiation. Among those receptors, EGFR was the first to be identified as amplified and/or rearranged in malignant gliomas. EGFR gene amplification in gliomas is often accompanied by gene rearrangement, resulting in deletions of the coding region. The most common variant, de2-7 EGFR or EGFRvIII, is characterized by an in-frame deletion of 801-bp spanning exons 2-7 of the coding sequence. This truncation removes 267 amino acids from the extracellular domain, producing a unique junctional peptide, and renders EGFR unable to bind any known ligand. EGFRvIII is expressed on the cell surface and contains a new tumor-specific protein sequence in its extracellular domain (Sugawa et al. 1990; Ekstrand et al. 1992). The frequency of the EGFRvIII expression in human gliomas is around 20 to 40% (Frederick et al. 2000). Several strategies have already been tested as means for binding the EGFRvIII receptor using peptides and antibodies. A peptide (PEPHC1) has been synthesized and tested for binding to EGFRvIII and EGFR (Campa et al., 2000, which is incorporated herein by reference in its entirety). In vitro assays, PEPHC1 bound the recombinant EGFRvIII extracellular domain or full-length EGFRvIII (solubilized from cell membranes) in preference to native EGFR. Monoclonal antibodies have been developed with specific activity against this mutant receptor (Lorimer et al. 1996). These antibodies are internalized into the cell after receptor binding. Therefore, this receptor is a desirable target for adenoviral tropism since the receptor-binding molecules are efficiently internalized and the mutant form offers the opportunity to develop tumor-selective targeting strategies.

Although none of the reported adenovirus strategies use the EGFRvIII receptor for adenoviral anchorage and internalization, several reports have characterized EGFR as a potential target in cancer cells. In these studies, the adenoviruses redirected to EGFR were more efficient (in some cases by more than 100 fold) and more selective than the adenoviruses using untargeted vectors to infect and transduce cancer cells. One of the systems relevant to this proposal uses our Delta-24 system in combination with EGFR targeting. In this study, Curiel's group (Hemminki et al. 2001) constructed an adenovirus expressing a secretory adaptor capable of retargeting the adenovirus to EGFR, resulting in a more than 150-fold increase in gene transfer. A replication-competent dual-virus system secreting the adaptor displayed increased oncolytic potency in vitro and therapeutic gain in vivo.

Lack of expression in normal cells and achievable targeting using peptides and antibodies make the EGFR and EGFRvIII systems very suitable for the development of targeted oncolytic adenoviruses with high therapeutic indices (Kuan et al., 2001).

III. Rb Pathway

Rb is a tumor suppressor gene whose loss of function is associated with tumor formation. Retinoblastoma protein or Rb, as used herein, refers to the polypeptide encoded by the retinoblastoma gene (Rb). The retinoblastoma gene is located at 13q14 in humans and encodes a protein of approximately 110 kiloDaltons (kD). Unphosphorylated Rb inhibits cell proliferation by sequestering transcription factors (e.g., E2F) and arresting cells in $G_1$ of the cell cycle. Transcription factors are released from Rb when Rb is phosphorylated. The binding of E1A to Rb causes transcriptional factor release in much the same manner as phosphorylation. Several viral oncoproteins target Rb for inactivation in order to facilitate viral replication. These proteins include adenovirus E1A, SV40 large T antigen, and papillomavirus E7.

The E1A protein is one of the first virus-specific polypeptides synthesized after adenoviral infection and is required for viral replication to occur (Dyson and Harlow, 1992; Flint and Shenk, 1997). Interaction of the Rb protein and the E1A protein results in release of E2F from preexisting cellular E2F-Rb complexes. E2F is then free to activate transcription from E2 promoters of adenovirus and E2F regulated genes of an infected cell. The transcriptional activation of these cellular genes in turn helps to create an environment suitable for viral DNA synthesis in otherwise quiescent cells (Nevins, 1992). Two segments of E1A are important for binding Rb; one includes amino acids 30-60 and the other amino acids 120-127 (Whyte et al., 1988; Whyte et al., 1989). Deletion of either region prevents the formation of detectable E1A/Rb complexes in vitro and in vivo (Whyte et al., 1989).

An adenovirus containing a Delta 24 mutation produces an E1A protein that cannot bind Rb, causing an infected cell to remain in $G_0$. Thus a mutant Rb pathway and a mutant E1A, along with E2F activation are necessary for Δ24 adenoviral transcription.

Retinoblastoma (Rb) pathway, as used herein, refers the interaction of a group of regulatory proteins that interact with Rb or other proteins that interact with Rb in regulating cell proliferation (for review see Kaelin, 1999). Proteins within the Rb pathway include, but are not limited to, Rb, the E2F family of transcription factors, DRTF, RIZ286, MyoD287, c-Ab1288, MDM2289, hBRG1/hBRM, p16, p107, p130, c-Abl tyrosine kinase and proteins with conserved LXCXE motifs, cyclin E-cdk 2, and cyclin D-cdk 4/6. Phosphorylation of Rb releases E2F, which is bound to unphosphorylated Rb. E2F stimulates cyclin E transcription and activity, which results in more Rb phosphorylation. Unphosphorylated Rb acts as a tumor suppressor by binding to regulatory proteins that increase DNA replication, such as E2F (The Genetic Basis of Human Cancer, Vogelstein and Kinzler eds., 1998).

Defective retinoblastoma pathway, as used herein, refers to inactivation, mutation, or deletion of the Rb or the inability of the upstream or downstream regulatory proteins that interact with Rb to regulate cell proliferation due to a mutation or modification of one or more proteins, protein activities, or protein-protein interactions. Mutations causing a defective Rb pathway include, but are not limited to inactivating mutations in Rb, INK4 proteins, and CIP/KIP and activating mutations in the cyclin genes, such as cyclin D/cdk 4, 6 and cyclin E, cdk 2. Mutations in one or another element of the Rb regulatory pathway, including p16, cyclin D, cdk4, E2F or Rb itself, may be mutated in almost 100 percent of human tumors (The Genetic Basis of Human Cancer, 1998). Rb associated tumors include gliomas, sarcomas, tumors of the lung, breast, ovary, cervix, pancreas, stomach, colon, skin, larynx, bladder and prostate.

IV. Methods for Treating Hyperproliferative Conditions

The present invention involves the treatment of hyperproliferative cells, preferably a cell with a disrupted Rb pathway. It is contemplated that a wide variety of tumors may be treated using the methods and compositions of the invention, including gliomas, sarcomas, lung, ovary, breast, cervix, pancreas, stomach, colon, skin, larynx, bladder, prostate, and/or brain metastases, as well as pre-cancerous cells, metaplasias, dysplasias, or hyperplasia.

The term "glioma" refers to a tumor originating in the neuroglia of the brain or spinal cord. Gliomas are derived form the glial cell types such as astrocytes and oligodendrocytes, thus gliomas include astrocytomas and oligodendrogliomas, as well as anaplastic gliomas, glioblastomas, and ependymomas. Astrocytomas and ependymomas can occur in all areas of the brain and spinal cord in both children and adults. Oligodendrogliomas typically occur in the cerebral hemispheres of adults. Gliomas account for 75% of brain tumors in pediatrics and 45% of brain tumors in adults. The remaining percentages of brain tumors are meningiomas, ependymomas, pineal region tumors, choroid plexus tumors, neuroepithelial tumors, embryonal tumors, peripheral neuroblastic tumors, tumors of cranial nerves, tumors of the hemopoietic system, germ cell tumors, and tumors of the sellar region.

Various embodiments of the present invention deal with the treatment of disease states comprised of cells that are deficient in the Rb and/or p53 pathway. In particular, the present invention is directed at the treatment of diseases, including but not limited to retinoblastomas, gliomas, sarcomas, tumors of lung, ovary, cervix, pancreas, stomach, colon, skin, larynx, breast, prostate and metastases thereof.

There are various categories of brain tumors. Glioblastoma multiforme is the most common malignant primary brain tumor of adults. More than half of these tumors have abnormalities in genes involved in cell cycle control. Often there is a deletion in the CDKN2A or a loss of expression of the retinoblastoma gene. Other types of brain tumors include astrocytomas, oligodendrogliomas, ependymomas, medulloblastomas, meningiomas and schwannomas.

In many contexts, it is not necessary that the cell be killed or induced to undergo cell death or "apoptosis." Rather, to accomplish a meaningful treatment, all that is required is that the tumor growth be slowed to some degree. It may be that the cell's growth is completely blocked or that some tumor regression is achieved. Clinical terms such as "remission" and "reduction of tumor" burden also are contemplated given their normal usage.

The term "therapeutic benefit" refers to anything that promotes or enhances the well-being of the subject with respect to the medical treatment of his/her condition, which includes treatment of pre-cancer, cancer, and hyperproliferative diseases. A list of nonexhaustive examples of this includes extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition.

A. Adenoviral Therapies

Those of skill in the art are well aware of how to apply adenoviral delivery to in vivo and ex vivo situations. For viral vectors, one generally will prepare a viral vector stock. Depending on the kind of virus and the titer attainable, one will deliver 1 to 100, 10 to 50, 100-1000, or up to $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ infectious particles to the patient in a pharmaceutically acceptable composition as discussed below.

Various routes are contemplated for various tumor types. Where discrete tumor mass, or solid tumor, may be identified, a variety of direct, local and regional approaches may be taken. For example, the tumor may be directly injected with the adenovirus. A tumor bed may be treated prior to, during or after resection and/or other treatment(s). Following resection or other treatment(s), one generally will deliver the adenovirus by a catheter having access to the tumor or the residual tumor site following surgery. One may utilize the tumor vasculature to introduce the vector into the tumor by injecting a supporting vein or artery. A more distal blood supply route also may be utilized.

The method of treating cancer includes treatment of a tumor as well as treatment of the region near or around the tumor. In this application, the term "residual tumor site" indicates an area that is adjacent to a tumor. This area may include body cavities in which the tumor lies, as well as cells and tissue that are next to the tumor.

B. Formulations and Routes of Administration to Patients

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. The routes of administration will vary, naturally, with the location and nature of the lesion, and include, e.g., intradermal, transdermal, parenteral, intracranial, intravenous, intramuscular, intranasal, subcutaneous, percutaneous, intratracheal, intraperitoneal, intratumoral, perfusion, lavage, direct injection, and oral administration and formulation. Preferred embodiments include intracranial or intravenous administration. Administration may be by injection or infusion, see Kruse et al. (1994), specifically incorporated by reference, for methods of performing intracranial administration. Such compositions would normally be administered as pharmaceutically acceptable compositions.

An effective amount of the therapeutic agent is determined based on the intended goal, for example, elimination of tumor cells. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. The engineered viruses of the present invention may be administered directly into animals, or alternatively, administered to cells that are subsequently administered to animals.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal. In certain aspects of the present invention, the compositions may be administered either in vitro, ex vivo, or in vivo. An example of in vivo administration includes direct injection of tumors with the instant compositions by intracranial administration to selectively kill tumor cells.

Intratumoral injection, or injection into the tumor vasculature is specifically contemplated for discrete, solid, accessible tumors including tumor exposed during surgery. Local, regional or systemic administration also may be appropriate. For tumors 1.5 to 5 cm in diameter, the injection volume will be 1 to 3 cc, preferably 3 cc. For tumors greater than 5 cm in diameter, the injection volume will be 4 to 10 cc, preferably 5 cc. Multiple injections delivered as single dose comprise about 0.1 to about 0.5 ml volumes, preferable 0.2 ml. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising the adenovirus. The perfusion may be continued post-resection, for example, by leaving a catheter implanted at the site of the surgery. Periodic post-surgical treatment also is envisioned.

Continuous administration, preferably via syringe or catheterization, also may be applied where appropriate, for example, where a tumor is excised and the tumor bed is treated to eliminate residual, microscopic disease. Such continuous perfusion may take place for a period from about 1-2 hr, to about 2-6 hr, to about 6-12 hr, to about 12-24 hr, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

The adenovirus also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride or Ringer's dextrose. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters. When the route is topical, the form may be a cream, ointment, or salve.

In a further embodiment of the invention, an adenovirus or a nucleic acid encoding an adenovirus may be delivered to cells using liposome or immunoliposome delivery. The adenovirus or nucleic acid encoding an adenovirus may be entrapped in a liposome or lipid formulation. Liposomes may be targeted to neoplasmic cell by attaching antibodies to the liposome that bind specifically to a cell surface marker on the neoplastic cell. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid construct complexed with Lipofectamine (Gibco BRL).

C. Combination Therapy

Tumor cell resistance to various therapies represents a major problem in clinical oncology. One goal of current cancer research is to find ways to improve the efficacy of chemo- and radiotherapy, as well as other conventional cancer therapies. One way is by combining such traditional therapies with oncolytic adenovirus therapy. Traditional therapy to treat cancers may include removal of all or part of the affected organ, external beam irradiation, xenon arc and argon laser photocoagulation, cryotherapy, immunotherapy and chemotherapy. The choice of treatment is dependent on multiple factors, such as, 1) multifocal or unifocal disease, 2) site and size of the tumor, 3) metastasis of the disease, 4) age of the patient or 5) histopathologic findings (The Genetic Basis of Human Cancer, 1998).

In the context of the present invention, it is contemplated that adenoviral therapy could be used in conjunction with anti-cancer agents, including chemo- or radiotherapeutic intervention, as well as radiodiagnostic techniques. It also may prove effective to combine oncolytic virus therapy with immunotherapy.

A "target" cell contacting a mutant oncolytic virus and optionally at least one other agent may kill cells, inhibit cell growth, inhibit metastasis, inhibit angiogenesis or otherwise reverse or reduce a hyperproliferative phenotype of target cells. These compositions would be provided in a combined amount effective to kill or inhibit proliferation of the target cell. This process may involve contacting the cells with the expression construct and the agent(s) or factor(s) at the same or different times. This may be achieved by contacting the cell with a single composition or pharmacological formulation that includes both agents, or by contacting the cell with two distinct compositions or formulations, wherein one composition includes the oncolytic adenovirus and the other includes the second agent.

Oncolytic adenoviral therapy may also be combined with immunosuppression. The immunosuppression may be performed as described in WO 96/12406, which is incorporated herein by reference. Examples of immunosuppressive agents include cyclosporine, FK506, cyclophosphamide, and methotrexate.

Alternatively, an oncolytic adenovirus treatment may precede or follow the second agent or treatment by intervals ranging from minutes to weeks. In embodiments where the second agent and oncolytic adenovirus are applied separately to the cell, one would generally ensure that a significant period of time did not expire between the time of each delivery, such that the second agent and oncolytic adenovirus would still be able to exert an advantageously combined effect on the cell. In such instances, it is contemplated that one would contact the cell with both modalities within about 12-24 hr of each other and, more preferably, within about 6-12 hr of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either oncolytic adenovirus and/or the second agent will be desired. Various combinations may be employed, where oncolytic adenovirus is "A" and the other agent is "B", as exemplified below:

| A/B/A   | B/A/B   | B/B/A   | A/A/B   | B/A/A   | A/B/B   |
|---------|---------|---------|---------|---------|---------|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B |         |         |

Other combinations are contemplated. Again, to achieve cell killing, both agents are delivered to a cell in a combined amount effective to kill the cell.

Agents or factors suitable for use in a combined therapy are any anti-angiogenic agent and/or any chemical compound or treatment method with anticancer activity; therefore, the term "anticancer agent" that is used throughout this application refers to an agent with anticancer activity. These compounds or methods include alkylating agents, topoisomerase I inhibitors, topoisomerase II inhibitors, RNA/DNA antimetabolites, DNA antimetabolites, antimitotic agents, as well as DNA damaging agents, which induce DNA damage when applied to a cell.

Examples of chemotherapy drugs and pro-drugs include, CPT11, temozolomide, platin compounds and pro-drugs such as 5-FC. Examples of alkylating agents include, inter alia, chlorambucil, cis-platinum, cyclodisone, flurodopan, methyl CCNU, piperazinedione, teroxirone. Topoisomerase I inhibitors encompass compounds such as camptothecin and camptothecin derivatives, as well as morpholinodoxorubicin. Doxorubicin, pyrazoloacridine, mitoxantrone, and rubidazone are illustrations of topoisomerase II inhibitors. RNA/DNA antimetabolites include L-alanosine, 5-fluorouracil, aminopterin derivatives, methotrexate, and pyrazofurin; while the DNA antimetabolite group encompasses, for example, ara-C, guanozole, hydroxyurea, thiopurine. Typical antimitotic agents are colchicine, rhizoxin, taxol, and vinblastine sulfate. Other agents and factors include radiation and waves that induce DNA damage such as, γ-irradiation, X-rays, UV-irradiation, microwaves, electronic emissions, and the like. A variety of anti-cancer agents, also described as "chemotherapeutic agents," function to induce DNA damage, all of which are intended to be of use in the combined treatment methods disclosed herein. Chemotherapeutic agents contemplated to be of use, include, e.g., adriamycin, bleomycin, 5-fluorouracil (5-FU), etoposide (VP-16), camptothecin, actinomycin-D, mitomycin C, cisplatin (CDDP), podophyllotoxin, verapamil, and even hydrogen peroxide. The invention also encompasses the use of a combination of one or more DNA damaging agents, whether radiation-based or actual compounds, such as the use of X-rays with cisplatin or the use of cisplatin with etoposide.

In treating pre-cancer or cancer according to the invention, one would contact the cells of a precancerous lesion or tumor cells with an agent in addition to the oncolytic adenovirus. This may be achieved by irradiating the localized tumor site with radiation such as X-rays, UV-light, γ-rays or even microwaves. Alternatively, the cells may be contacted with the agent by administering to the subject a therapeutically effective amount of a pharmaceutical composition comprising a compound such as, adriamycin, bleomycin, 5-fluorouracil, etoposide, camptothecin, actinomycin-D, mitomycin C, podophyllotoxin, verapamil, or more preferably, cisplatin. The agent may be prepared and used as a combined therapeutic composition, or kit, by combining it with an oncolytic adenovirus.

Agents that directly cross-link nucleic acids, specifically DNA, are envisaged to facilitate DNA damage leading to a synergistic, anti-neoplastic combination with an oncolytic adenovirus. Cisplatinum agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally. Bleomycin and mitomycin C are other anticancer agents that are administered by injection intravenously, subcutaneously, intratumorally or intraperitoneally. A typical dose of bleomycin is 10 m g/m$^2$, while such a dose for mitomycin C is 20 mg/m$^2$.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used or as alternative 5-FC may be administered and converted in a target tissue or target cell.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Immunotherapy may be used as part of a combined therapy, in conjunction with mutant oncolytic virus-mediated therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. Antibodies specific for CAR, integrin or other cell surface molecules, may be used to identify cells that the adenovirus could infect well. CAR is an adenovirus receptor protein. The penton base of adenovirus mediates viral attachment to integrin receptors and particle internalization.

The skilled artisan is directed to "Remington's Pharmaceutical Sciences" 15th Edition, 1980. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that local, regional delivery of oncolytic adenovirus to patients with retinoblastoma-linked cancers, pre-cancers, or hyperproliferative conditions will be a very efficient method for delivering a therapeutically effective gene. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining oncolytic adenovirus therapies with chemo- and radiotherapies, it also is contemplated that combination with other gene therapies will be advantageous. For example, targeting of a oncolytic adenovirus in combination with the targeting of p53 at the same time may produce an improved anti-cancer treatment. Any tumor-related gene or nucleic acid encoding a polypeptide conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

It is further contemplated that the therapies described above may be implemented in combination with all types of surgery. Approximately 60% of persons with cancer will undergo surgery of some type, which includes preventative, diagnostic or staging, curative and palliative surgery. These types of surgery may be used in conjunction with other therapies, such as oncolytic adenovirus therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection, systemic administration, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. Furthermore, in treatments involving more than a single treatment type (i.e., construct, anticancer agent and surgery), the time between such treatment types may be about 1, 2, 3, 4, 5, 6, 7, 8, 9, 10, 11, 12, 13, 14, 15, 16, 17, 18, 19, 20, 21, 22, 23, or about 24 hours apart; about 1, 2, 3, 4, 5, 6, or 7 days apart; about 1, 2, 3, 4, or 5 weeks apart; and about 1, 2, 3, 4, 5, 6, 7, 8, 9, 10, 11, or 12 months apart, or more.

It also should be pointed out that any of the foregoing therapies may prove useful by themselves. In this regard, reference to chemotherapeutics and non-mutant oncolytic virus therapy in combination also should be read as a contemplation that these approaches may be employed separately.

V. Screening Methods

Animal models may be used as a screen for tumor suppressive effects of oncolytic adenoviruses. Preferably, orthotopic animal models will be used so as to closely mimic the particular disease type being studied and to provide the most relevant results. One type of orthotopic model involves the development of an animal model for the analysis of microscopic residual cancer cell(s) and microscopic seeding of body cavities.

The first step in the development of an exemplary animal model is to create a tissue flap in the experimental animal. The term "tissue flap" means any incision in the flesh of the animal that exposes the target tissue. It is generally preferred that an incision be made in the dorsal flank of an animal, as this represents a readily accessible site. However, it will be understood that an incision could well be made at other points on the animal, and the choice of tissue sites may be dependent upon various factors such as the particular type of therapeutics that are being investigated.

Once a target tissue site is exposed, cancer cells, either individually or in tumors, are contacted with the tissue site. Cancer cell application may be achieved simply using any convenient applicator. Naturally, this procedure will be conducted under sterile conditions.

In a particular example, $1 \times 10^7$ cells are inoculated into the exposed tissue flap of a nude mouse. Those of skill in the art will be able to readily determine, for a given purpose, what the appropriate number of cells will be. The number of cells will be dependent upon various factors, such as the size of the animal, the site of incision, the replicative capacity of the tumor cells themselves, the time intended for tumor growth, the potential anti-tumor therapeutic to be tested, and the like. Although establishing an optimal model system for any particular type of tumor may require a certain adjustment in the number of cells administered, this in no way represents an undue amount of experimentation. For example, this can be accomplished by conducting preliminary studies in which differing numbers of cells are delivered to the animal and the cell growth is monitored following resealing of the tissue flap. Naturally, administering larger numbers of cells will result in a larger population of residual tumor cells. Those skilled in the area of animal testing will appreciate that such optimization is required.

Other orthotopic animal models are well known in the art. The skilled artisan will readily be able to adapt or modify each particular model for his intended purpose without undue experimentation.

A. Screening for a Defective Rb Pathway

With adenovirus Δ24 and other mutant adenovirus that are unable to bind Rb, it is necessary for the Rb pathway to be defective in order for the cell to transcribe and translate viral proteins. The Rb pathway is required to be defective in the sense that it is not able to repress the transcription-activating activity of E2F. E2F activates the transcription of cellular genes and adenoviral DNA if its activity is not repressed. Examples of ways in which E2F could escape repression include, but are not limited to, Rb not being able to bind E2F (i.e., E1A binding to Rb), overexpression of E2F, less Rb than E2F and situations in which Rb remains phosphorylated.

B. Antibodies

Antibodies can be used to detect adenoviral proteins (e.g., E1A), Rb, and other proteins of the Rb pathway. In certain aspects of the invention, one or more antibodies may be produced that are immunoreactive with multiple antigens. These antibodies may be used in various diagnostic or therapeutic applications, described herein below.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. Means for preparing and characterizing antibodies are also well known in the art (See, e.g., Harlow and Lane (1988), incorporated herein by reference).

Monoclonal antibodies (MAbs) are recognized to have certain advantages (e.g., reproducibility and large-scale production). The invention thus provides for monoclonal antibodies of the human, murine, monkey, rat, hamster, rabbit and even chicken origin. Due to the ease of preparation and ready availability of reagents, murine monoclonal antibodies may be preferred.

However, "humanized" antibodies are also contemplated, as are chimeric antibodies from mouse, rat, or other species, bearing human constant and/or variable region domains, bispecific antibodies, recombinant and engineered antibodies and fragments thereof.

The methods for generating monoclonal antibodies (MAbs) and polyclonal antibodies are well known in the art. MAbs may be readily prepared through use of well-known techniques, such as those exemplified in U.S. Pat. No. 4,196,265, incorporated herein by reference. It is also contemplated that a molecular cloning approach may be used to generate monoclonals. Alternatively, monoclonal antibody fragments encompassed by the present invention can be synthesized using an automated peptide synthesizer, or by expression of full-length gene or of gene fragments in *E. coli*.

C. Antibody Conjugates

Certain embodiments of the invention provide antibodies to antigens and translated proteins, polypeptides and peptides that are linked to at least one agent to form an antibody conjugate. In order to increase the efficacy of antibody molecules as diagnostic or therapeutic agents, it is conventional to link or covalently bind or complex at least one desired molecule or moiety. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

1. Imaging

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging." Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens and Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnos- D. Immunodetection Methods Adenoviral gene expression in a population of cells will be determined by western blot analysis using antibodies as probes to adenoviral proteins. The level of viral proteins detected would indicate whether viral protein expression is occurring in the cell. Immunodetection using monoclonal antibodies that recognize various epitopes within the Rb protein or another protein of the Rb pathway can be used to see if Rb or a protein in the Rb pathway has been mutated.

The present invention concerns immunodetection methods for binding, purifying, removing, quantifying and/or otherwise generally detecting biological components such as protein(s), polypeptide(s) or peptide(s) involved in adenoviral replication or the cellular Rb or p53 pathways. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

1. ELISAs

Immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, an antibody that recognizes an antigen is immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that recognizes the antigen and is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

Irrespective of the format employed, ELISAs have certain features in common, such as coating, incubating and binding, washing to remove non-specifically bound species, and detecting the bound immune complexes.

2. Immunohistochemistry

Antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990, all of which are incorporated herein by reference).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

E. Nucleic Acid Detection

The nucleic acid sequences disclosed herein have a variety of uses. For example, they have utility as probes or primers for embodiments involving nucleic acid hybridization. They can be used to determine whether viral genes are being transcribed. In certain embodiments of the invention adenoviral genes may be transcribed in cells with a mutant Rb or p53 pathways. Nucleic acid detection may be used to determine if there is a mutation within the Rb gene, p53 gene or other genes encoding proteins of the Rb pathway. The DNA sequences of genes of the present invention may be determined by methods known in the art to identify mutations within the sequence.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected.

2. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ amplification procedure may be performed to quantify the amount of mRNA amplified. Methods of reverse transcribing RNA into cDNA are well known and described in Sambrook et al., 2001. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application 2 202 328, and in PCT Application PCT/US89/01025, each of which is incorporated herein by reference in its entirety.

Qbeta Replicase, described in PCT Application PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

Other nucleic acid amplification procedures include Strand Displacement Amplification (SDA), disclosed in U.S. Pat. No. 5,916,779; transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In particular embodiments, detection is by Southern blotting and hybridization with a labeled probe. The techniques involved in Southern blotting are well known to those of skill in the art. See Sambrook et al., 2001. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

5. Biopsy

A tumor may be biopsied and the above tests performed upon it to determine whether the cells have a functional Rb pathway. An example of a biopsy protocol is as follows. The stereotactic biopsy is the precise introduction of a metal probe into the brain tumor, cutting a small piece of the brain tumor, and removing it so that it can be examined under the microscope. The patient is transported to the MRI or CAT scan suite, and the frame is attached to the scalp under local anesthesia. The "pins" of the frame attach to the outer table of the skull for rigid fixation (frame will not and can not move from that point forward until completion of the biopsy). The scan (MRI or CT) is obtained. The neurosurgeon examines the scan and determines the safest trajectory or path to the target. This means avoiding critical structures. The spatial coordinates of the target are determined, and the optimal path is elected. The biopsy is carried out under general anesthesia. A small incision is created over the entry point, and a small hole is drilled through the skull. The "dura" is perforated, and the biopsy probe is introduced slowly to the target. The biopsy specimen is withdrawn and placed in preservative fluid for examination under the microscope. Often the pathologist is present in the biopsy suite so that a rapid determination of the success of the biopsy can be made.

F. Diagnostic and In Vitro Uses

Any of the methods above can be used in the present invention for diagnostic and in vitro uses. The oncolytic adenoviruses of the present invention may be used in diagnostic assays to detect the presence of cells with a defective Rb and/or p53 pathway. A sample of cells could be infected with the oncolytic adenovirus of the present invention and after an incubation period, the number of cells exhibiting adenovirus replication can be quantified to determine the number of neoplastic cells in the sample. This may be useful to determine if the adenovirus would be effective in treating the tumor from a patient from which a cell sample was taken. Other uses are to diagnose a neoplasm as having a defective Rb and/or p53 pathway and to evaluate tumor cell load following treatment.

Alternate diagnostic uses and variations include an adenovirus with a Rb binding mutation in the E1A or an E1B55kD-mutation and a reporter gene to score whether cells have been transformed by detecting reporter gene expression. Expression of the reporter gene can be correlated with a phenotype of adenoviral replication indicating a lack of a functional Rb and/or p53 pathway.

VI. Polynucleotide and Polypeptide Variants

Amino acid sequence variants of the polypeptides discussed above and throughout this application, specifically including Ang-2, NIS and hyCD, may be substitutional, insertional or deletion variants. Deletion variants lack one or more residues of the native protein. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a particular polypeptide, such as E1A, provided the biological activity of the protein is maintained.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues or nucleotides, such as additional N- or C-terminal amino acids or 5' or 3' nucleic acid sequences. The addition of terminal sequences particularly applies to nucleic acid sequences that may, for example, include various non-coding sequences flanking either of the 5' or 3' portions of the coding region or may include various internal sequences, i.e., introns, which are known to occur within genes.

In making amino acid changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

A. Polynucleotides

The present invention concerns polynucleotides that are capable of expressing a protein, polypeptide, or peptide discussed above, such as one derived from the Ang1 gene, Ang-2 gene, NIS gene or a yCD gene. A nucleic acid segment or polynucleotide encoding a Ang1 gene, Ang-2 gene, NIS or yCD polypeptide refers to a nucleic acid segment or polynucleotide comprising a polynucleotide encoding wild-type, polymorphic, or mutant Ang1 gene, Ang-2 gene, NIS or yCD polypeptide. Included within the term nucleic acid are a polynucleotide or polynucleotides, DNA segments, and recombinant vectors. Recombinant vectors may include plasmids, cosmids, phage, viruses, and the like. In certain embodiments recombinant adenoviruses are contemplated. In particular, an adenovirus comprising an expression cassette encoding a Ang1 gene, Ang-2 gene, NIS or a yCD.

Mutation may be a substitution, insertion, or deletion. In some embodiments, a mutation introduces a stop codon or introduces a frame shift that results in a premature stop codon. It is further contemplated that nonfunctional polypeptides may be encoded by polynucleotides, such as truncated polypeptides. Moreover, it is contemplated the polynucleotides of the invention may be mutated to produce a polypeptide that lacks 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or more contiguous amino acids, including the full-length polypeptide, including the polypeptides of SEQ ID NO:2 and SEQ ID NO:4.

As used in this application, the term "polynucleotide" refers to a nucleic acid molecule of greater than 3 nucleotides. Therefore, a "polynucleotide encoding a Ang1 gene, Ang-2 gene, NIS or yCD" refers to a DNA segment that contains a wild-type, a polymorphic, or a mutant Ang1 gene, Ang-2 gene, NIS or yCD polypeptide; similarly, a "polynucleotide encoding wild-type Ang1 gene, Ang-2 gene, NIS or yCD" refers to a DNA segment that contains wild-type Ang1 gene, Ang-2 gene, NIS or yCD polypeptide coding nucleic acid or DNA sequences.

Similarly, a polynucleotide comprising an isolated or purified wild-type, polymorphic, or mutant nucleic acid encoding a Ang1 gene, Ang-2 gene, NIS or a yCD polypeptide refers to a nucleic acid segment comprising wild-type, polymorphic, or mutant Ang1 gene, Ang-2 gene, NIS or yCD polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art, this functional term includes genomic sequences, cDNA sequences, and smaller engineered nucleic acid segments that express, or may be adapted to express, proteins, polypeptides, domains, peptides, fusion proteins, and mutants. The nucleic acid encoding Ang1 gene, Ang-2 gene, NIS or yCD may contain a contiguous nucleic acid Ang1 gene, Ang-2 gene, NIS or yCD sequence encoding all or a portion of Ang1 gene, Ang-2 gene, NIS or yCD of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, or more nucleotides, nucleosides, or base pairs.

"Isolated substantially away from other coding sequences" means that the nucleic acid of interest, for example the polynucleotide encoding a wild-type, a polymorphic, or a mutant Ang1 gene, Ang-2 gene, NIS or yCD polypeptide, forms part of the coding region of the nucleic acid segment, and that the nucleic acid segment does not contain large portions of naturally-occurring coding DNA. Of course, this refers to the nucleic acid segment as originally isolated, and does not exclude nucleic acid sequence, polynucleotide or coding regions later added to the segment by human manipulation.

The nucleic acid segments used in the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The DNA segments used in the present invention may encompass biologically functional equivalent Ang1 gene, Ang-2 gene, NIS or hyCD and derivative peptides. Such sequences may arise as a consequence of codon redundancy and functional equivalency that are known to occur naturally within nucleic acid sequences and the proteins thus encoded.

Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to decrease the antigenicity of the protein or to inhibit binding to a given protein.

B. Cloning, Nucleic Acid Transfer, and Expression

Adenoviruses of the present invention can be constructed using methods known in the art and described herein. Expression requires that appropriate signals be provided which include various regulatory elements, such as enhancers/promoters that may be derived from both viral and mammalian sources that drive host cell expression of the genes of interest. Elements designed to optimize messenger RNA stability and translatability in host cells also are defined.

1. Regulatory Elements

In preferred embodiments, the nucleic acid encoding a transgene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. In certain aspects of the invention a promoter is a heterologous promoter, that is the promoter is associated with a nucleic acid that is not associated with its natural location.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of a polynucleotide of interest, which may or may not encode a polypeptide of interest. Promoters that permit expression of a protein of interest generally under most conditions and in most cell types is termed constitutive, and an example of this is the CMV promoter. A tissue-specific promoter is a regulatable promoter that is allows expression only in particular tissues or cells. Tables 2 list several elements/promoters that may be employed, in the context of the present invention, to regulate the expression of the nucleic acid of interest. This list is not intended to be exhaustive of all the possible elements involved in the promotion of polynucleotide expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins. Enhancer/Promoters include but are not limited to enhancers/promoters of Immunoglobulin Heavy Chain, Immunoglobulin Light Chain, T-Cell Receptor, HLA DQ α and DQ β, β-Interferon, Interleukin-2, Interleukin-2 Receptor, MHC Class II 5, MHC Class II HLA-DRα, β-Actin, Muscle Creatine Kinase, Prealbumin (Transthyretin), Elastase I, Metallothionein, Collagenase, Albumin Gene, α-Fetoprotein, γ-Globin, β-Globin, c-fos, c-HA-ras, Insulin, Neural Cell Adhesion Molecule (NCAM), α1-Antitrypsin, H2B (TH2B) Histone, Mouse or Type I Collagen, Glucose-Regulated Proteins (GRP94 and GRP78), Rat Growth Hormone, Human Serum Amyloid A (SAA), Troponin I (TN I), Platelet-Derived Growth Factor, Duchenne Muscular Dystrophy, SV40, Polyoma, Retroviruses, Papilloma Virus, Hepatitis B Virus, Human Immunodeficiency Virus, Cytomegalovirus, or Gibbon Ape Leukemia Virus. Element with related inducer include MT II/Phorbol Ester (TPA) and Heavy metals; MMTV (mouse mammary tumor virus)/Glucocorticoids; ß-Interferon/poly(rI)X and poly(rc); Adenovirus 5 E2/E1A; c-jun/Phorbol Ester (TPA), $H_2O_2$; Collagenase/Phorbol Ester (TPA); Stromelysin/Phorbol Ester (TPA), IL-1; SV40/Phorbol Ester (TPA); Murine MX Gene/Interferon, Newcastle Disease Virus; GRP78 Gene/A23187; α-2-Macroglobulin/IL-6; Vimentin/Serum; MHC Class I Gene H-2kB/Interferon; HSP70/E1a, SV40 Large T Antigen; Proliferin/Phorbol Ester-TPA; Tumor Necrosis Factor/PMA; Thyroid Stimulating Hormone a Gene/Thyroid Hormone; Insulin E Box/Glucose The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the nucleic acid transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

C. Selectable Markers

The markers listed below can be inserted as a heterologous sequence in the adenovirus genome. In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also may be employed. The selectable marker employed is not believed to be important, so long as it is capable of being expressed simultaneously with the nucleic acid encoding a polypeptide of interest. Further examples of selectable markers are well known to one of skill in the art.

D. Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message. An example of such a construct is described in U.S. Pat. No. 5,665,567, which is herein incorporated by reference.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single vector and a single selectable marker.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Delta 24 Studies

A. Material and Methods

Regional Glioma Models.

Figure 4:
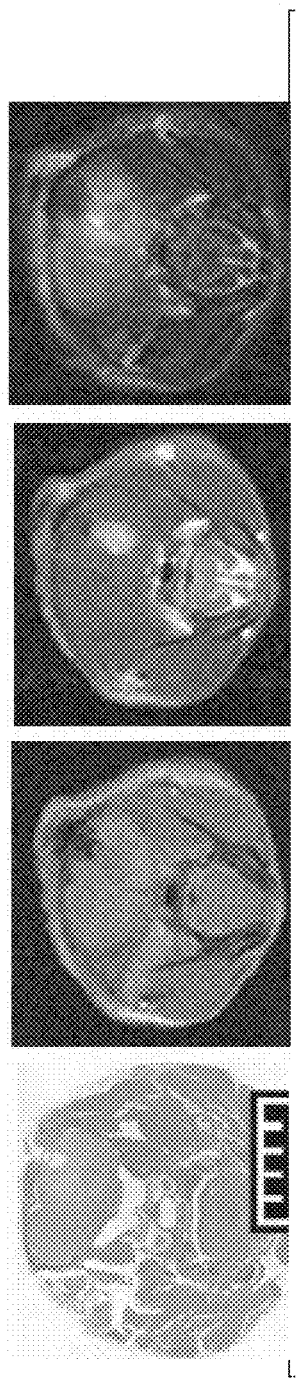
FIG. 4 shows an MRI of nude mouse glioma xenograft model using U87MG cells and a correlated pathologic section (H&E). The MRI panels from left to right show the noncontrast $T_1$, and Gd-contrast $T_1$, and $T_2$ sequences. The increase in hematoxylin staining of the tumor can be appreciated in the pathologic sections immediately inferior to the Teflon screw.

U87MG and U251MG glioma cell human xenograft models utilize human tumor cell lines obtained from patients, which are placed into short or long-term tissue culture. The advantages of this system are that the tumor cells are of human origin and have readily identifiable characteristics such as expression levels of various growth factors and receptors. These studies, however, require immunocompromised animals to prevent tumor rejection, eliminating analysis of the role of the immune system in tumor biology and response to treatments. Most xenograft models are well established and form predictable and reliable intracranial tumors with fairly uniform animal deaths occurring at 20-22 days. However, these tumors lack the heterogeneity seen in the clinical setting. Furthermore, most xenograft models do not demonstrate extensive invasion of the surrounding brain parenchyma. The implanted tumors tend to grow spherically and animal death is related to intracranial pressure associated with ventricular system compression and herniation, as seen after necropsy. For assessing antiangiogenic treatments, particularly with a non-invasive imaging component, the localized and spherical growth of the xenograft implant may be an advantage and has been used extensively for this purpose. The defined localization of the tumor simplifies the correlation of histopathologic findings with imaging results (FIG. 4).

U87MG human xenograft model implanted intracranially into the mouse putamen has a demonstrated reliability (nearly 100% tumor production) and highly predictable growth and survival parameters (median survival 21 days rt 1 day). Furthermore, use of the intracranial screw technique (Lal et al., 2000) ensures reproducible placement of tumor and the ability to access tumor either for sampling or for injecting treatments (local delivery of viruses) or markers into the tumor mass. An additional feature that improves the reproducibility of this technique is the use of a pump that simultaneously injects prepared tumor cells into 10 animals.

This technique produces uniform injection times and consistent quality of the cell preparations.

Systemic Lung Cancer Models.

Reproducible lung cancer models are routinely used to take advantage of distinctly different patterns of organ involvement. Lung cell lines H1299 and A549 when injected through tail veins, develop very reproducible systemic animal tumor burdens. In the case of H1299, strictly bilateral lung tumors are produced. In contrast, when an A549 cell line is used, all systemic organs (except the CNS) are at risk for tumor development.

Retinoblastoma Pathway Status.

The Rb pathway status has been evaluated in various cell lines, including the cell lines described herein: (U87MG, U251MG, H1299, and A549). The Saos-2 cell line is used for the Rb-null and Rb restoration studies.

Coxsackie Adenoviral Receptor (CAR) in the Cell Lines Used.

To ensure that the cell line can be infected by adenovirus, including Δ24 and Δ24-NIS the status of CAR expression was assessed in the various cell lines.

Imaging Models.

Nuclear imaging may detect radiation signals from radiopharmaceuticals that have been systemically administered to experimental animals. Conventional nuclear imaging is performed using a gamma camera that can detect photons with energies between 60 and 600 eV (usually between 80 and 400 keV). One of the advantages to whole body scanning is rapid sequential imaging (typically 1 image per 30-60 seconds) and the ease by which animals can be anesthetized and placed in a lane-prone position. The utility of this system is also evident by its widespread use in clinical medicine, thus creating a convenient bridge between animal and human studies.

B. Initial Results

Δ24 Oncolytic Adenovirus.

The conditionally replication selective adenovirus Δ24, has been shown to selectively replicate in tumor cells that have a functional defect in the p16/Rb/E2F pathway, a defect that occurs in more than 90% of malignant glioma tumors. To determine if Δ24 replicates in vivo, studies were conducted in which human U87MG glioma cells are injected ($5 \times 10^5$) intracranially in nude mice. Three days later, $1 \times 10^8$ plaque forming units of Δ24 are injected into the tumor using a screw-guided system. The animals are sacrificed arbitrarily on day 25 post-treatment to examine the extent of Δ24 adenoviral dissemination within the tumor.

Figure 5:
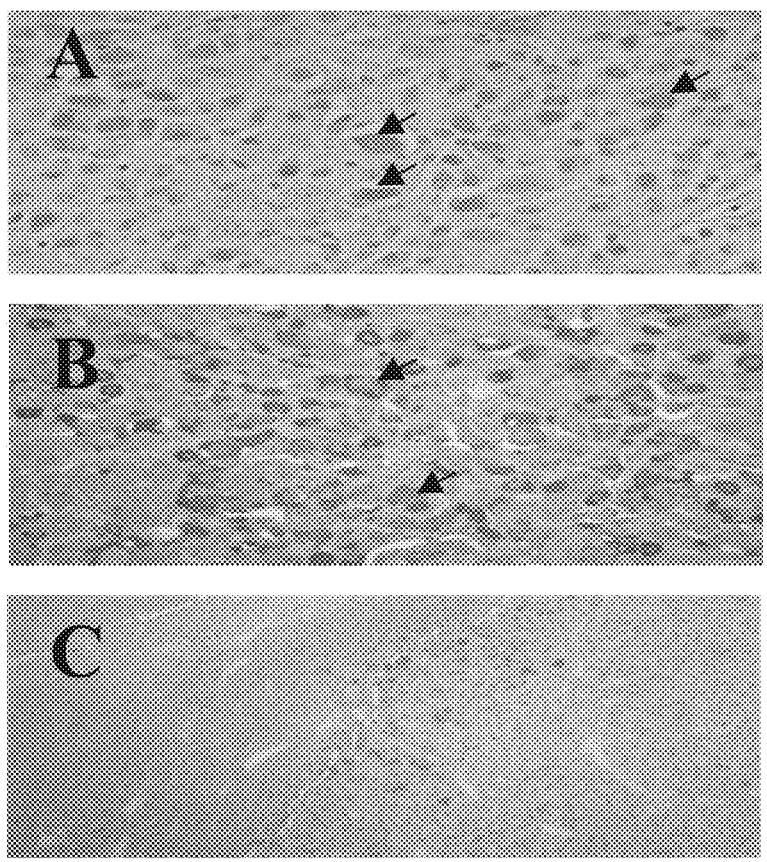
FIGS. 5A-5C shows viral inclusion bodies (indicative of actively replicating adenovirus), FIG. 5A, staining for late transcribed viral genes (hexon protein), FIG. 5B and the typical "zonal" spread through a tumor, FIG. 5C U87MG xenograft infected with Δ24-RGD incubated with E1A antibody.

Microscopic examination shows a highly vascularized glioma localized in the right frontal basal ganglia. Three different areas are observed: (1) central area of necrosis, (2) highly infected glioma cells (characterized by nuclear viral inclusions) and, (3) minimally infected/uninfected tumor tissue. Previous studies showed that a 25-day U87MG xenograft treated with Δ24 does not demonstrate areas of necrosis greater than 10% of the total volume of the tumor. In tumor-bearing animals treated with Δ24, the areas of necrosis (debris from viral infected lysed tumor cells) are approximately equivalent to 30%-60% of the total volume of the tumor. The infected cells, are easily identifiable because they display viral nuclear inclusions, surround the area of necrosis, and are separated from normal brain tissue by a zone of minimally infected versus uninfected cells (FIG. 5). This pattern of clearly different areas suggests that the virus spreads from the center of the tumor to its periphery.

The tumors are examined after immunostaining with an antibody specific for the adenovirus hexon protein (an encoded adenoviral late gene). The presence of hexon protein indicates and correlates well with viral replication. The characteristics of the staining in both nuclear and cytoplasmic regions, are due to the presence of capsid proteins produced in the cytoplasm and transported to the nucleus for viral assembly.

Transgene Expression by Δ24 Virus.

The expression of an exogenous transgene mediated via Δ24 transport (as an effective delivery vector), is described herein. Others have shown exogenous transgene expression with the use of other oncolytic viral vectors. Based on western blot analysis and quantitative RT-PCR analyses (FIG. 6), which demonstrated that a tumor-selective oncolytic adenovirus (Δ24-hyCD) can be used to efficiently transduce high levels of an exogenous hyCD gene, resulting in a potent anti-glioma effect in vitro and in vivo. This finding is important because gene therapy has been hampered by various obstacles (Roth and Cristiano, 1997). In particular, gene therapy is hampered by inadequate nucleic acid delivery to a large number of tumor cells. Targeting of tumor cells and extension of lethality to tumor cells that are a modest distance away from the major tumor mass by a "bystander effect" (Springer et al., 2000) is one aspect of this invention. Viral constructs were designed to gain tumor selectivity by targeting the defective p16/Rb/E2F pathway in malignant gliomas by using Δ24 adenovirus that contains a deletion in the E1A gene. This technique is designed to improve exogenous nucleic acid delivery to tumor cells by using a replication-competent adenovirus and to obtain a bystander effect via transgene expression.

Figure 6:
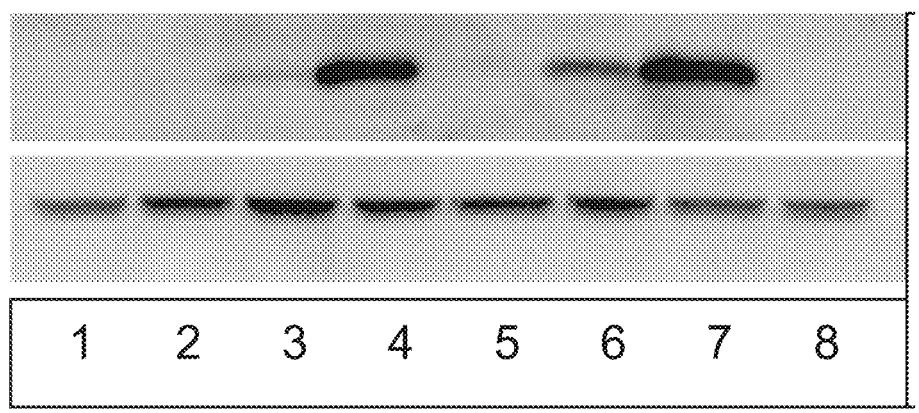
FIG. 6 shows a western blot of the transgene expression of yeast CD in U87MG glioma cells using Δ24 adenovirus: lane 1 U87MG cells uninfected; lane 2 Δ24-CD at 1 MOI and 24 h post-infection; lane 3 Δ24-CD at 10 MOI and 24 h post-infection; lane 4 Δ24-CD at 100 MOI and 24 h post-infection; lanes 5-7 are similar to lanes 2-4 except that they are 48 h post-infection instead of 24 h; lane 8 Δ24 adenovirus.
Figure 7:
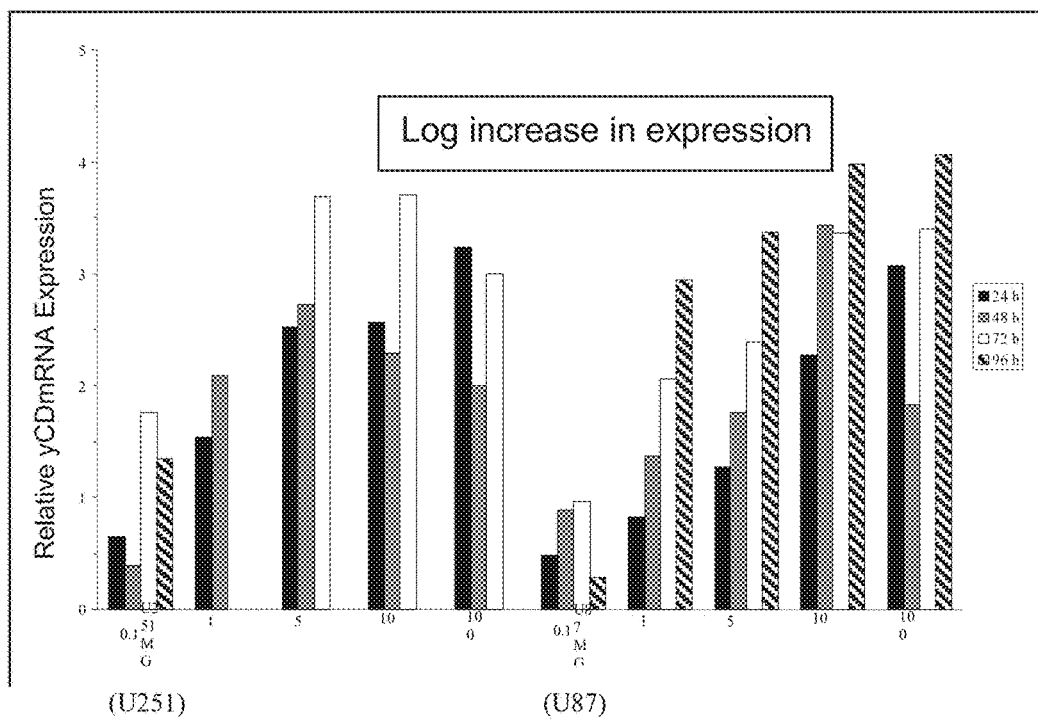
FIG. 7 shows expression of cytosine deaminase by Δ24-hyCD relative to a stable expressing clone. The X-axis demonstrates two cell lines at increasing MOI from 0.1 to 100 MOI and from 24 to 96 h. The Y axis shows the increase of expression in logarithmic increase.

Tumors such as malignant gliomas, which are intrinsically resistant to radiation therapy and chemotherapy and recur exclusively in a local manner, are excellent candidates for gene therapy strategies (Puumalainen et al., 1998). FIG. 6 shows that an exogenous nucleic acid product (hyCD encoding polynucleotide) can be effectively expressed in target tumor cells by using the Δ24-hyCD oncolytic virus. The hyCD encoding polynucleotide is expressed at very high levels and is able to actively convert 5-FC into 5-FU, which exhibits superior activity against glioma cell lines. Notably, adding 5-FC to cell cultures or administering it to animals treated with Δ24-hyCD did not interfere with the oncolytic potential of the virus. One concern is that the hyCD encoding polynucleotide will not have enough time to be efficiently expressed in an oncolytic setting. The inventors are also concerned that adding 5-FC could "poison" the infected producer cells, thereby blunting the oncolytic effect. The inventors selected a gene dependent enzyme/pro-drug therapy (GDEPT) strategy using the Δ24-hyCD oncolytic virus for additional study. The results show that the system provides a window of opportunity that is sufficient to produce a dramatic expression of exogenous nucleic acid without abrogating effective oncolysis. It was also found that the optimal production of hyCD mRNA is time- and dose-dependent with respect to the particular cell line infected. Specifically, U251 MG cells can produce approximately a 3-log higher amounts of mRNA than U87MG cells (FIG. 7). This finding may relate to differences in the rate of infectivity of U87MG versus U251MG cells (Suzuki et al., 2001). It was also found that input titer and incubation time strongly affected hyCD mRNA production in a cell line-specific fashion. These results were confirmed by pathologic examinations confirming the desired effect. Histopathologic sections of brains from animals treated with Δ24-hyCD recapitulate the characteristic process of "zonal" replicative advancement of an infectious "wave" propagating through a tumor mass. Moreover, the exogenous genetic burden of hyCD, with or without 5-FC, did not seem to impede this infectious wave within the tumor. The realization that nucleic acid delivery strategies can be effectively accomplished when an oncolytic or replication-competent virus is used makes devising improved therapeutic strategies plausible (Hermiston et al., 2000). Several reports have documented improved infectivity by inserting an RGR motif into the Δ24 fiber-knob (Suzuki et al., 2001); improved selectivity in an environment in which cells are actively dividing; and, recently, an improved anticancer effect accomplished by combining radiotherapy with oncolysis.

Autoradiography.

Figure 8:
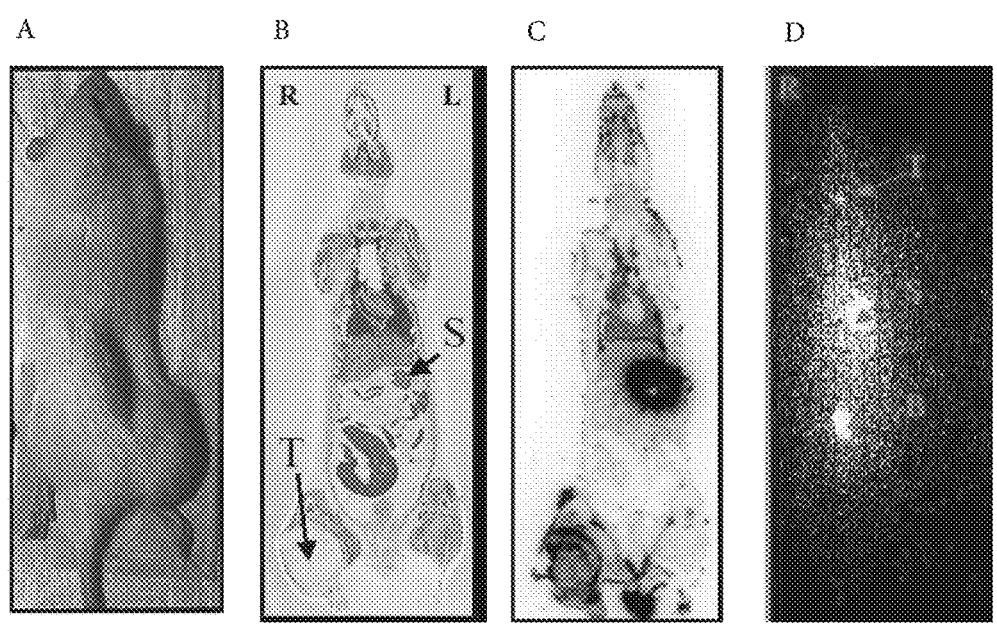
FIGS. 8A-8D shows a demonstration of animal whole-mount preparation and autoradiography imaging of NIS expression by $^{188}$Re accumulation. Breast tumor (13762F) bearing rat was injected with the eluent from W-188/Re-188 generator. Panels shown are of (FIG. 8A) an anesthetized animal, (FIG. 8B) whole animal mount gross anatomy, (FIG. 8C) autoradiography and (FIG. 8D) gamma imaging (T=tumor, B=bladder, S=stomach).
Figure 9:
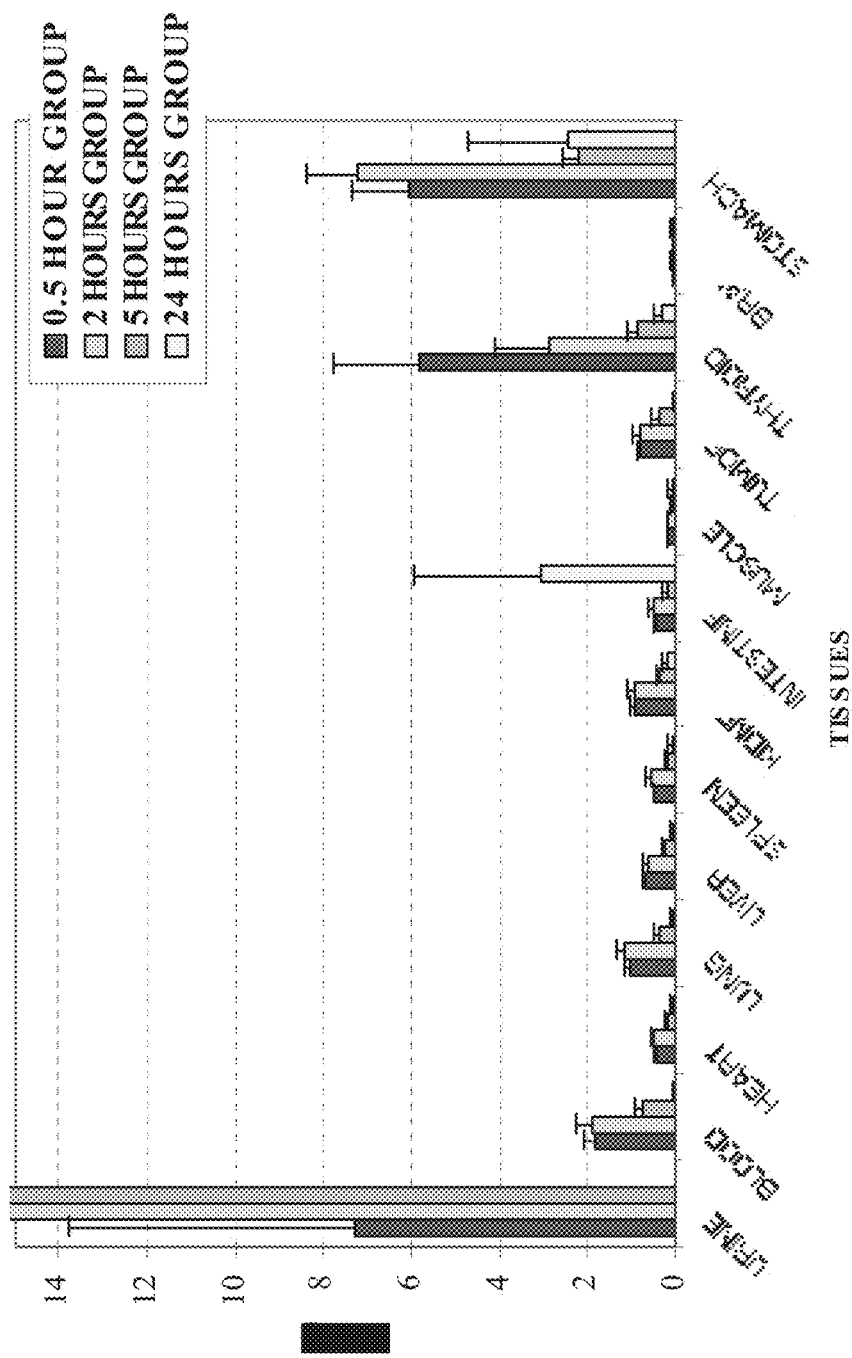
FIG. 9 shows the pharmacodynamic studies of animals injected with eluant from an W/Re-188 Rhenium generator at 100 μCi. The uptake of $^{188}$ReO4 corresponds to tissues that express NIS (thyroid and stomach). Urine and later fecal accumulation (at 24 hours) is also observed. Importantly, the organ tumor sites to be examined (brain and lung) do not demonstrate NIS-dependent active accumulation of radionuclides.

Whole-mount sections of animals were prepared after tail vein injection of $^{188}$Re elutant produced by a Rhenium generator at 100 μCi, which provides additional conformation of the anatomic localization of the images provided by gamma camera assessment. Besides thyroid tissue, NIS expression is present in the gut (predominantly the stomach) as can be demonstrated in the images shown in FIG. 8. The bladder where the isotope is being eliminated is also visualized. Individual organs can be harvested and isotope counts can be determined per gram of tissue as a quantitative measure of radionuclide uptake. As shown in FIG. 9 uptake of $^{188}$ReO$_4$.

Sodium/Iodide Symporter In Vitro Activity.

U251MG and U87MG glioma cell lines are transiently transfected, then incubated with $^{99m}$TcO$_4$. These in vitro techniques are modifications of an assay developed by Petrich et al. (2002). Briefly, cells are plated into 24-well plates and allowed to achieve 90% confluence. Various titers of Δ24-NIS are added, incubating and infecting the cells for 2 h. The cells are then washed, and the assay performed at 24, 48, and 72 h. The cells are pre-incubated at 37° C. for 30 min in 1 ml of HEPES-buffered Hanks balanced salt solution (bHBSS). 18.5 to 37.0 kBq per ml (0.5-1 mCi per ml) of $^{99m}$TcO$_4$ will be added after a 1 h incubation time. The medium is removed and the cells washed twice with ice-cold bHBSS. Cellular radioactivity is released with 1 ml ice-cold 100% ethanol for 20 min, and counted in a cross-calibrated gamma counter. Protein content of the 6 wells per cell line are determined using a BCA assay kit.

Cell Mixing Experiments.

Figure 10:
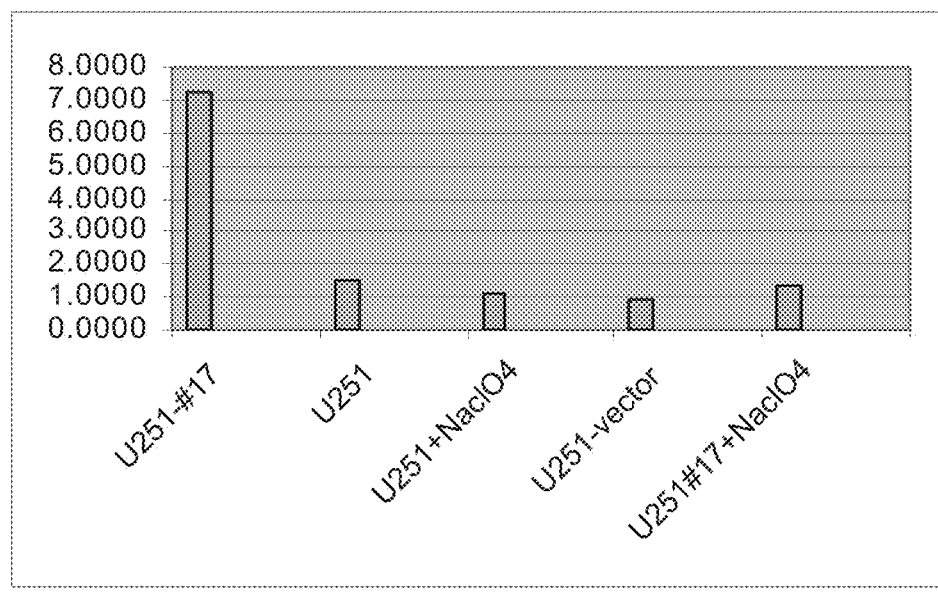
FIG. 10 shows accumulation of $Tc^{99}O_4$ in a U251MG glioma cell line after transient transfections with the hNIS-containing plasmid (pcDNA3.1-Zeo). Comparing the accumulations of $Tc^{99}O_4$ perechnetate is determined by cpm after incubation for 30 min with 2 μCi. Cells were then washed with ice-cold Hanks balanced salt solution and $Tc^{99m}O_4$ released by adding absolute ethanol. Parental cell line was compared to the active clone in the first two lanes. Controls using the inhibitor to the hNIS pump (NaClO$_4$) against the parental cell line, vector control and finally positive clone simultaneously inhibited by NaClO$_4$.
Figure 11:
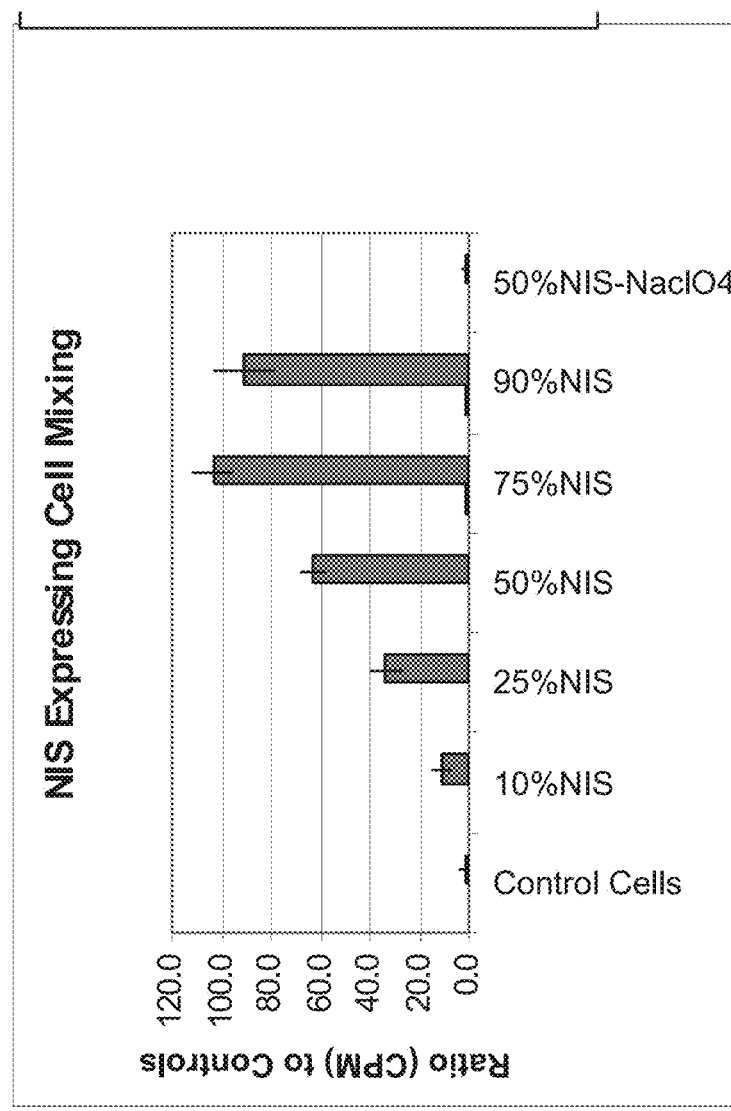
FIG. 11 shows accumulations of $Tc^{99}O_4$ in U251 glioma cell line infected with Δ24-NIS. Cells incubated with virus for 1.5 h then washed extensively and mixed at different percentages with uninfected U251 cells. Uptake assays were then performed at 48 h and values are given as fold increase (ratios) of $Tc^{99}O_4$ within the cells compared to control cells. A clear progressive fold increase in the uprake of radionuclide is demonstrated. Additionally, complete inhibition of NIS activity is seen with the addition of sodium perchlorate.

Because of the concern that an oncolytic virus could destroy the cells expressing the NIS transgene and blunt the ability to concentrate-adequate amounts of radionuclide, a study were performed to determine the percentage of cells required to obtain significant concentrations of isotope. These cell-mixing experiments were performed in a similar fashion to the $^{99m}$TcO$_4$ accumulation studies for stable clone expression studies shown in FIG. 10. The mixing studies were performed by first infecting U251 cells with Δ24-NIS and then after washing, mixing various concentrations of infected cells with uninfected U251 cells. The result is shown in FIG. 11 and is expressed as fold increase (ratios) over control cells. These studies demonstrate that even at 10%, cells expressing NIS from Δ24-NIS accumulate approximately 10-fold Tc$^{99}$O$_4$ over control cells. This also demonstrates the ability of adenovirus to express transgenes to much higher levels than even stable transfected cell lines.

En-Bloc Tumor Resection.

Adenoviral gene therapy trials have been recently completed, adenoviral P53 (Ad-P53) phase I clinical trial. Patients with recurrent malignant glioma were enrolled after meeting entry criteria and underwent stereotactic biopsy with subsequent injection of Ad-p53. The injection catheter was cut at the level of the dura and ligated to maintain a geographic marker of the actual injection site. Two weeks after injection the patient returned for en bloc tumor resection under the direction of Dr. Frederick Lang, M.D. Anderson Cancer Center. The tumor mass was carefully dissected circumferentially, preserving the architecture along with the injection catheter and internal injection site. The en bloc tumor specimen was sectioned perpendicular to the catheter placement to allow inspection and measurement of the distance of viral spread. As demonstrated in FIG. 12, this technique allows one to correlate the distance of oncolytic viral spread with data obtained from the Ad-P53 clinical trial, as well as correlating the results with imaging findings obtained prior to tumor resection.

FIG. 12 shows a specimen from a patient treated with a single injection of Ad-P53 at a dose of $3 \times 10^{10}$ vp in 1 ml. FIG. 12A is a photograph of a surgical specimen that was removed en bloc. The injection catheter is protruding from the tumor. FIG. 12B are formalin-fixed tumor blocks. Specimen shown in panel a has been cut to the catheter. The hole created by the catheter is evident. FIG. 12C is a low-power view (300×) of the same immunostained with antibody to p53 protein. The hole from the catheter is at the top of the photograph. Transfected tumor cells stain darkly and are distributed within 5 mm of the injection site. FIG. 12D is a view (500×) of the same section as FIG. 12C demonstrating positive immunostaining for P53 within the transfected cells. FIG. 12E is a view of adjacent section of that shown in FIG. 12 C demonstrating staining for p21/waf in same distribution as P53 staining FIG. 12F shows a low power (10×) view of cross-section. The catheter was within the central hole. Blue staining around hole shows distribution of Ad-P53.

Example 2

Construction and Characterization of Delta 24-NIS

To determine whether the expression pattern of NIS is controlled by the status of the Rb pathway in Δ24-NIS-infected glioma cells the inventors studied the correlation between an E2F-promoter driven NIS expression with the replication ability of Δ24 in glioma cells and normal human astrocytes with different cell cycle profiles (from quiescence to active proliferation). The expression of NIS under the control of the tumor-specific promoter hTERT was also studied. Furthermore, the capability of Δ24-NIS infected cells to effectively take up various radionuclides was characterized.

A. Material and Methods

Materials and Methods used in these studies include the construction and characterization of a replication-competent Δ24 adenovirus encoding a therapeutic or diagnostic transgene, e.g., Δ24-hyCD or Δ24-NIS, see schematic representation shown in FIG. 13. Also described are the material and methods used for assessing transgene expression in various tumor types and under the controls of diverse promoters to demonstrate its applicability to multiple, varied tumors. Exemplary materials and methods include"

NIS In Vitro Activity.

Cloning of the human NIS into pcDNA3.1-Zeo (invitrogen) will be preformed by RT-PCR of human thyroid mRNA. U251 MG and U87 MG glioma cell lines will be transiently transfected, then incubated with $^{99m}$TcO$_4$. These in vitro techniques have already been carried out in our laboratory and modified based on an assay developed by Petrich et al. Briefly, cells will be plated into 24 well plates and allowed to achieve 90% confluence. Various titers of Δ24-NIS will be added, incubating and infecting the cells for 2 hrs. The cells will then be washed, and the assay performed at 24, 48, and 72 hrs. the cells will be pre-incubated at 37° C. for 30 min in 1 ml of HEPES-buffered Hanks balanced salt solution. 18.5 to 37 kBq per ml (0.5-mCi per ml) of $^{99m}TcO_4$ will be added after a 1 hr incubation time. The medium will be removed and the cells washed twice with ice-cold bHSS. Cellular radioactivity will be released with 1 ml ice-cold 100% ethanol for 20 min, and counted in a cross-calibrated γ counter. Protein content of the 6 wells per cell line will be determined using a BCA assay kit.

Because of the concern that an oncolytic virus could destroy the cells expressing the NIS transgene and blunt the activity to concentrate adequate amounts of radionuclide, studies were performed to determine the percentage of cells required to obtain significant concentrations of isotope. These cell mixing studies were performed in a similar fashion to the $^{99m}TcO_4$ accumulation experiments for the stable clone expression experiments shown in FIG. 10 the mixing experiments were performed by first infection U251 cells with Δ24-NIS and then after washing, mixing various concentrations of infected cells with uninfected U251 cells with Δ24-NIS and then after washing, mixing various concentration of infected cells with uninfected U251 cells. The result is shown in FIG. 11 and is expressed as fold increase (ratios) over control cells. These experiments demonstrate that even at 10% cells expressing NIS form Δ24-NIS accumulate approximately 10 fold $Tc^{99}O_4$ over control cells. This also demonstrates the ability of adenovirus to express transgenes to a much higher levels than even stable transfected cell lines.

E2F or hTERT Driven Transgene.

Exemplary E2F-driven NIS expression vectors are constructed in a fashion similar to the construction of cytomegalovirus (CMV) driven NIS. Specifically, the CMV promoter on pcDNA3.1-Zeo (Invitrogen) is excised using restriction enzymes Apa I and Nhe I, and the promoters for E2F and hTERT are amplified by PCR with primers that contain these restriction sites at the 5'-ends of their sequence. These promoters are cloned into the immediate proximal region of the NIS gene. Replication competent viruses are produced by cloning into the appropriate shuttle vectors. These shuttle vectors are then co-transfected into 293 cells for recombination to active virus. These viral constructs are used in subsequent studies to determine their efficiency of expression against various cellular backgrounds.

Different promoter constructs are produced by using standard cloning techniques. For example hTERT-NIS (plasmid p-hTERT was kindly provided by Dr. Fang, M.D. Anderson Cancer Center) and have the NIS encoding polynucleotide inserted between the XhoI and HindIII sites just proximal to the NIS encoding polynucleotide. This cassette is amplified by PCR and cloned into a shuttle vector. The methods culminating with co-transfections into 293 cells.

Similarly, the E2F promoter will be obtained from plasmid pE2F1-neo (kindly provided by Dr. Ta Jen Liu, M.D. Anderson Cancer Center): however, both the promoter and final cassettes will typically be cloned by PCR amplification. The steps described above are repeated to obtain Δ24 containing NIS or hyCD under the control of E2F or hTERT.

Cell Lines and Culture Conditions.

U87MG cells, A549 cells, and H1299 cells (obtained from the American Type Culture Collection, Manassas, Va.), U251 MG human glioma cell lines (kindly provided by Dr. Yung laboratory), and Saos-2 cell line (kindly provided by Dr. Fueyo's laboratory) are cultured in Dulbecco's modified Eagle/F12 medium (1:1, vol:vol) (Media Tech, Herndon, Va.) containing 5% fetal bovine serum (DIFCO) and 2 nM glutamine. Cells are grown in culture at 37° C. at 5% $CO_2$ without antibiotics and passaged fewer than 12 times during the studies.

Adenoviruses.

Construction of the Δ24 adenovirus has been described elsewhere (Fueyo et al., 2000, incorporated herein by reference). This construct has a 24 bp deletion in the CR2-region of the E1A gene (nucleotides 923 to 946, both included) corresponding to the amino acids $L_{122}TCHEAGF_{129}$.

To construct Δ24-NIS oligonucleotides spanning the full length of NIS are used to obtain the first clone of the human homologue of the transport pump. Oligonucleotide primers (Midland Certified Reagent Co., Midland, Tex.) with the following sequences are used: Forward primer: 5'-AGCCT-GTGCAATCAGGGTC-3' (SEQ ID NO:7) and Reverse primer: 5'GGGTACCATATGCGCT-3' (SEQ ID NO:8).

After a full-length (1.9 kb) fragment is obtained, it is subsequently cloned into the mammalian expression vector pcDNA3.1-Zeocin (Invitrogen). In addition, the 5'-distal region contains the natural Kozac sequence. Colonies are isolated after transformation into DH5-α competent cells. Bacterial clones are picked and their plasmids sequenced. Several clones with the DNA sequence of interest are then transiently and stably transfected into U87MG and U251MG glioma cell lines and assayed for enzyme activity. Suitable clones expressing enzyme activity are cloned into the E3 region of pBHG10 (Microbix). pBHG10-hNIS and pXC1-Δ24 are cotransfected into 293 cells to allow homologous recombination, as previously described (Fueyo et al., 2000).

The viruses are propagated in 293 cells and purified by ultracentrifugation in a cesium chloride gradient. All viruses are titered using a plaque method as well as optical density measurements. Viruses are maintained at –80° C. until used. Single lots of adenovirus Δ24, adenovirus Δ24-hyCD and adenovirus Δ24-NIS are used in the following studies. As controls, non-replication-competent Ad-5 is used as a control (E1A-deleted with the NIS encoding polynucleotide cloned into the E1A region). Additional controls of wild-type adenovirus as well as Δ24-NIS that had been inactivated by UV light and cells that had been mock-infected with culture medium are also used.

In Vitro Expression of NIS.

In vitro expression studies are to demonstrate that the use of NIS in a Δ24 vector can concentrate various radioisotopes, including $^{99m}TcO_4$ and $^{123}I$ or $^{131}I$, within an oncolytically infected xenograft glioma tumor. These studies are carried out in tissue culture using the U251MG, U87MG and D54 glioma cell lines. These in vitro techniques have been modified by the inventors based on an assay developed by Petrich et al. Briefly, cells are plated onto 24-well plates and allowed to achieve 90% confluence. Various titers of Δ24-NIS are added and allowed to incubate and infect the cells for 2 h. Cells are prepared and assayed at 24, 48, and 72 h. The cells are pre-incubated at 37° C. for 30 min in 1 ml of HEPES-buffered Hanks-balanced salt solution (bHBSS). 18.5 to 37.0 kBq per ml (0.5 to 1 mCi per ml) of $^{99m}TcO_4$ is added after 1 h of incubation time. The medium is removed and the cells are washed twice with ice-cold bHBSS. Cellular radioactivity is released with 1 ml ice-cold 100% ethanol for 20 min, and counted in a cross-calibrated gamma counter. Protein content of the 6 wells per cell line will be determined using a BCA assay kit. Sodium perchlorate ($NaClO_4$) is used to inhibit the NIS pump and as a negative control.

Real-Time Quantitative Polymerase Chemical Reaction (PCR).

To assess transgene expression in tumor cell lines infected with Δ24-NIS, quantitative RT-PCR is used. U251MG and U87MG cell lines are grown to 95% confluency, harvested with 0.25% trypsin/EDTA, replanted into T25 flasks to a total of $2 \times 10^6$ cells; and incubated overnight. The media is aspirated and 2 ml of adenovirus Δ24-hyCD or Δ24-NIS will be added at 0.1, 1, 5, 10, or 100 MOI to duplicate samples from a viral stock of $1 \times 10^{11}$ pfu/ml, and incubated for 1 h with continuous shaking. The virus is aspirated and cells are washed twice with phosphate-buffered saline (PBS). Fresh complete medium containing 10% fetal bovine serum (FBS) is replaced and the cells incubated at 37° C. for 24, 48, 72, or 96 h. The cells are washed twice with PBS. Floating cells are centrifuged, immediately frozen, and stored at −80° C. before harvesting mRNA. The cell pellets are lysed with Trizol reagent (Life Technologies) and the RNA is purified according to the manufacturer's recommendations for subsequent amplification by TAQ-Man. A forward primer sequence of 5'-CAACATGAGGTTCCAGAAGGG-3' (SEQ ID NO:9), a reverse primier sequence of 5'-CAGTTCTC-CAGGGTGGAGATCT-3' (SEQ ID NO:10) and a TaqMan probe with a sequence of 5'-TCCGCCACCCTG CACGGC-3' (SEQ ID NO:11) are used for the amplification of NIS.

The primers or probe are typically labeled with a FAM label at the 5' end and TAMRA label at the 3' end for human NIS. Control primers and probes are used for the S9 housekeeping gene. The expression of mRNA for NIS is quantified and reported relative to a stable NIS expression clone of the U251 MG glioma cell line. Expression levels are determined by using the ABI 7000 sequence detection system (Applied Biosystems, Foster City, Calif.).

Western Blot Analysis.

U251MG and U87MG cell lines are prepared in 6-well plates and treated with Δ24, Δ24-NIS, nonreplication competent Ad-NIS, or PBS (mock-treatment), as described above. The cells are harvested at 24, 48, 72, or 96 h after treatment. Total cell lysates are prepared by incubating cells with 1× sodium dodecyl sulfate (SDS) sample buffer (62.5 mM Tris-HCl pH 6.8, 2% w/v SDS, 10% glycerol, 50 mM dithiothreitol). Protein concentration are typically quantified using a bicinchoninic acid (BCA) method (Pierce, Rockford, Ill.). Protein samples (20 μg) are boiled at 98° C. for 5 min, and lysates separated on a 15% SDS-Tris glycine polyacrylamide gel, while being subjected to electrophoresis at 95 V for 2 h. The separated proteins are then transferred to a nitrocellulose membrane. The membrane is blocked with 3% nonfat milk, 0.05% Tween 20, 150 mM NaCl, and 50 mM Tris (pH 7.5) and incubated with primary antibody for hNIS (provided by Brahms Institute, Germany). Typically the secondary antibody is horseradish peroxidase-conjugated goat antimouse IgG (Pierce, Rockford, Ill.). The membranes are developed according to Amersham's enhanced chemiluminescence protocol (Amersham Corp., Arlington Heights, Ill.).

Cell Viability Assays.

U251MG and U87MG cell lines are grown to 95% monolayer confluence, trypsinized and harvested with 0.25% trypsin/EDTA, plated in 6-well tissue culture plates, and allowed to adhere overnight at 37° C. in 5% $CO_2$ in humidified incubators. The cell lines are then treated with various concentrations of virus, either with Δ24, Δ24-NIS, nonreplication competent Ad-NIS, UV-inactivated Δ24-NIS or PBS (MOI ranging from 0.1 to 100). The addition of radionuclides at various concentrations will not exceed a 2 mCi total dose. The cells will be incubated at 37° C. for 5 days. Cell viability is determined by cellular respiration using 3-(4,5-methylthiazol-2-yl)-5-(3-carboxymethoxyphenyl)-2-(4-sulfonyl)-2H-tetrazolium) (Promega, Madison, Wis.) as suggested by manufacturer. The cell survival fraction is measured at each drug concentration as the ratio of absorbance at 490 nm. This calculation is normalized for background absorbance of the culture medium alone. The cell survival fraction is plotted against the logarithm of the drug concentration, and ICW values extrapolated via linear regression into the drug concentrations producing a 50% reduction of normalized absorbance. Crystal violet assays are performed, as described Fueyo et al. (2000), to determine the oncolytic potential of the various constructs with virus and isotopes as described for MTT assays.

Tumor kill derived from oncolytic virus versus radiotherapy is distinguished by FACS analysis, as well as detection of apoptotic markers, since cell death from adenovirus is mediated through cell lysis rather than apoptosis.

RB-Null and RB-Restored Cell Lines.

To confirm that Δ24-NIS adenovirus replicates in a cell-cycle restricted manner when the Rb pathway is functionally normal, the ability of the mutant adenovirus to replicate in arrested cells expressing wild-type Rb is evaluated. For these experiments, Saos-2 osteosarcoma cell line is used. Saos-2 cells have a well-characterized disruption of the Rb pathway, have a well-characterized response to the transfer of exogenous Rb, and can be easily infected with adenovirus. Saos-2 cells are infected with 100 MOI of an adenoviral vector carrying the exogenous wild-type Rb cDNA or the Ad5CMV-pA adenovirus. 72 hrs later the cells are infected with 10 MOI of either the E1A-mutant adenovirus or the UV-Δ24-NIS adenovirus. It is contemplated that cells pretreated with a vector control, Ad5CMV-pA will be permissive for adenoviral replication and expression of the reporter gene. By contrast, cells infected with the Ad5CMV-Rb vector should acquire an oncolytic-resistant phenotype with an inability to display disseminated NIS expression. Because the effect of the E1A-mutant adenovirus is theoretically restricted by cell-cycle factors, flow cytometric analyses of DNA content is used to monitor the changes in the cell-cycle profile of Saos-2 cells in parallel to the studies described herein. These studies should explain if restoring Rb renders the Δ24-NIS virus unable to efficiently induce the entry of cells into the S phase, therefore precluding viral replication and a high expression of NIS. To further confirm the virus-suppressive effect of the Rb protein, the effect of cyclin-dependent-kinase inhibitor p21, a regulator of Rb function, will be evaluated for reducing the effect of the E1A-mutant adenovirus on the viability of wild-type Rb cells and the expression of NIS. D54MG cells are infected with 100 MOI of an adenoviral vector carrying the exogenous wild-type p21 cDNA or Ad5CMV-PA, and 3 days later is infected with the Δ24-NIS virus at 10 MOI.

Statistical Analysis.

Graphical displays and descriptive summary statistics, including means (standard deviations) and medians (range) for continuous variables, are used. Ninety-five percent confidence intervals are estimated. Categorical outcomes will be summarized using contingency tables.

Construction Δ24-NIS.

The human form of NIS (hNIS) has been cloned and its activity demonstrated by transient transfection in glioma cell lines. The Δ24-NIS adenoviral construct has recently been obtained and superior radionuclide accumulation with this virus has been seen as compared to stably transfected cell lines. In other embodiments of the invention a transgene may be put under the control of an inducible promoter system, such as the Tet/on or Teff/off systems.

Example 3

Characterization of In Vivo Effects of Radionuclide Accumulation for Imaging Tumors These studies are conducted to determine the level of Δ24-NIS propagation in intracranial glioma tumor-bearing animals through the imaging of various radionuclides, to correlate imaging at multiple time points with pathologic material to determine regional aspects of viral spread throughout tumors both in intracranial gliomas and systemic lung cancer models with liposome: Δ24-NIS complexes, and to determine, by in vivo imaging, the efficiency and specificity of delivery of Δ24-NIS mediated mesenchymal stem cell delivery to a systemic lung cancer model.

A. Characterizing the In Vivo Effects of Radionuclide Accumulation for Imaging Tumors It is critical to the future of oncolytic gene therapy trials to have the ability to monitor the infective spread of virus throughout a tumor. A sensitive and convenient method is needed to image this viral progress. This may have implications in the future for administering antiviral therapies to a patient after a tumor has been effectively eradicated, or perhaps in providing a patient with immunosuppressive medications to allow the oncolytic virus to adequately destroy the target tumor without interference by host immune responses. These processes would be very difficult to assess without the ability to track the progress of the oncolytic virus through an imaging-based system. For this reason the development of imaging techniques using NIS will be studied in animal models using various isotope detection techniques. Additionally, the possibility of tracking the oncolytic virus Δ24-NIS both after direct intratumoral injection (the intracranial glioma model) and following a method of systemic delivery using DOTAP: cholesterol encapsulated in Δ24-NIS (in the systemic lung cancer models) is studied. These studies will establish a basis for clinical trials for effectively imaging the progression of oncolytic therapies. The objective of this study is to determine the level of Δ24-NIS propagation in intracranial glioma tumor-bearing animals and systemic lung cancer models through imaging radionuclide expression using different delivery methods.

U251MG and U87MG glioma cell lines will be injected intracranially into 4 to 6 week old nude mice. After 5 days of tumor growth Δ24-NIS virus will be injected intracranially. After 5 days, the animals will be anesthetized and injected through the tail vein with a radioisotope (e.g., $^{99m}TcO_4$ or $^{131}I$). The mice will then be positioned on a gamma camera with a 140 keV-high resolution collimator. The images will be obtained at 5, 15, 30, 60, 90 and 120 min after injection of the radioisotope. These time points have been selected because the optimal signal to noise ratios (SNR) will not initially be known. Because the clearance of isotope and uptake by the NIS pump may vary in different animals, the maximum SNR observed for each animal ($M_{obs}SNR$) for calculations at any given time point is used.

Radioiodide-Uptake Assay.

U87MG and U251MG glioma cells are seeded in E-well microtiter plates ($5\times10^5$ cells per well) and incubated for 24 h at 37° C. with 5% C02 and 10% FBS. On the following day, cells are washed twice with PBS and replaced with fresh media without FBS. The replacement media will contain either 2.0 μCi of $Na^{123}I$ along with 5 μM of NaI as a carrier. The cells will then incubate for 1 h and then washed with ice-cold Hanks-balanced salt solution (HBSS). The cells will be lysed with 95% ethanol, counted, and measured using a gamma counter (Packard Instruments, IL). All studies will be performed in triplicate (Haberkorn, 2001; Cho et al., 2002).

Radioiodide (Autoradiography) Assay In Vivo.

U87MG and U251 MG glioma cells are harvested by trypsinization after being washed with PBS cells and $5\times10^5$ cells concentrated in 10 μl of serum-free sterile medium. The cell suspension is injected intracranially into 4 to 6 week old nude (nu/nu) mice using a screw-guide technique. Five days post glioma-injection, the mice will be injected once with $1\times10^8$ PFU Δ24-NIS virus using the screw-guide method. Five days post-viral injection, the mice will have radioisotopes (e.g., $I^{123}$ or $I^{131}$) injected through a tail vein at a dose of about 0.5 μCi per gram of animal body weight. Two hours after tail-vein injection the animals are euthanized and tissues perfused with formalin/saline for autoradiography. The brain and other tissues are harvested and sectioned for gamma-autoradiography using a counter Cobra E5003 device (Packard instruments). The radioactivity is expressed in (counts of tissue of interest per milligram of tissue of interest)/(the counts obtained in the liver per milligram of liver tissue).

Imaging.

Whole body gamma camera imaging will be performed in the small animal imaging facility at M.D. Anderson, Houston, Tex., which includes a dedicated 4.7 Tesla animal MRI, animal CT, animal Single Photon Emitted Computed Tomography (SPECT), as well as a purchased animal Positron Emission Tomography (PET) scanner. For the animal models described, multiple imaging techniques will be used both to gain information regarding the spread of Δ24-NIS and to correlate and validate the findings from the various imaging techniques used. Specifically, small animal MR imaging with a 4.7 Tesla Brucker magnet will be performed in the small animal facility to ensure uniform tumor take. Additionally, whole animal gamma camera imaging will be performed with a dedicated mouse gamma camera unit, also in the small animal imaging facility.

The Emission Tomography nuclear imaging technique measures emitted radiation signals from different locations and reconstructs the images based on the geometry of detection to provide the exact locations of the initial source's signals. As in PET imaging, this method takes advantage of compounds that emit positrons that undergo very rapid annihilation with neighboring electrons and yields 2 gamma photons, which exit at 180° from each other. More complete geometric information is obtained by the simultaneous capture of gamma photons emitted in opposite directions. In the proposed studies, $^{124}I$, which has a half-life of approximately 4 days, is ideally suited for the evaluation of the Δ24-NIS construct. In SPECT, the measured radiation is detected from different projections, using a conventional gamma camera. This approach typically involves a dual-head gamma camera system, which allows for the detection and geometrical calculation of its emission source. The advantage of SPECT imaging is the reduced cost of using more readily available gamma-emitting radioisotopes, such as $^{99m}TcO_4$, $^{123}I$, or $^{131}I$. Another advantage of using nuclear imaging to detect oncolytic viral spread is that such small quantities of radioisotope are required for adequate imaging (typically much less than microgram quantities) and only minimal pharmacodynamic perturbation or toxic effects occur in the organ systems of the animals or the patients. When the level of chemical toxicity is minimal, it allows a large variety of useful radiopharmaceuticals to be produced for assessing physiologic and pathophysiologic processes in tumor biology.

In Vivo $^{99m}TcO_4$ Scintigraphy.

U251MG and U87MG glioma cell lines are injected intracranially as described above into 6-10 week old nude mice. After 5 days of tumor growth $1\times10^8$ PFU of Δ24-NIS virus is injected intracranially through the screw guide. The animals are then injected through tail vein with 0.5 mCi of $^{99m}$Tc-pertechnetate in 200 μl of sterile saline. The mice are then positioned on a gamma camera with a 140 keV-high resolution collimator. Images are obtained at 5, 15, 30, 60, 90 and 120 min after injection with $^{99m}TcO_4$ using 1 and 2 min acquisition times.

Human Xenograft Models.

A reproducible malignant glioma animal model is a component of the studies described herein. The U87MG model was selected for comparing tissues and evaluating the presence of adenoviral replication, as well as for correlating these changes with alterations observed using radioisotope imaging techniques. This cell line has been well characterized. It emulates many of the characteristics of de novo human gliomas including response to growth factors (Pollack et al., 1990), and is readily and reproducibly used to create an intracranial model of human glioblastoma. The studies described herein also utilize the U87MG model to assess if there is an improved therapeutic potential when therapeutic doses of radionuclides are used in conjunction with Δ24-NIS administration. The U87MG cell line is a stable, immortalized human glioblastoma cell line. U87G tumor cells readily grow in the brain of nude mice. For example, in initial studies there was a 100% tumor take in mice, which without treatment results in the need for sacrifice at 21 days (±2 days). Molecular characteristics of the U87MG model include marked expression of coxsackie and adenoviral receptor (CAR), as well as Rb, p16, and p53. The reproducibility of the intracranial animal model is based on the implantable screw-guide system developed by Frederick Lang, M.D., M.D. Anderson Cancer Center. In brief, a guide screw is implanted into a small drill hole in the skull 2.5 mm laterally and 1.0 mm anteriorly to the bregma. Tumor cells ($5\times10^5$) are then slowly injected using an automated injection system, the depth of injection controlled by a collar on the syringe. Early studies showed a 97% success rate with successful delivery of agents into an established tumor.

Harvesting Technique.

To permit optimal comparison between tissue-based immunohistochemistry (IHC) measures and in vivo imaging measures, the orientation of the animal's head and tumor in the axial and saggital planes are registered at the time of tissue harvest. At the time of IHC analysis sections will be created from tumor blocks cut out of these planes so that the spatial relation to the acquired images can be maintained. A group of animals will also be harvested for whole-animal cryo-sectioning to produce correlative autoradiography registration with the images obtained. In the animals undergoing MRI examinations (with subsequent sacrifice for tissue samples), the extent and orientation of the tumor will be carefully marked with permanent dye ink; the center of each scan plane will also be marked. Each animal will be sacrificed by $CO_2$ inhalation after adequate sedation is confirmed by the toe pinch technique. The tumor will be resected en bloc while maintaining careful attention to preserving the orientation of the tumor with respect to the imaging scan plane and range. The MRI scan plane that traverses the maximum diameter of the tumor will be marked, and the tumor will be sectioned into two pieces along this plane. One section of the tumor will be embedded in OCT (Miles Inc., Elkart, Ind.), frozen in liquid nitrogen, and stored at −70° C. The other sections will be fixed in formalin and embedded in paraffin. The tumor specimens resected from the animals injected with Evans Blue will be similarly embedded in paraffin. Cell implantation and adenoviral treatment are performed as described previously. Animal studies are conducted in the veterinary facilities of M.D. Anderson Cancer Center in accordance with institutional guidelines.

Immunohistochemical Pathologic Analysis of Xenograft Tumor Sections.

Animal brains are harvested, fixed in formalin, embedded in paraffin, and sections prepared after initial baking at 60° C. for 30 min. The sections will be blocked with 0.3% $H_2O_2$ and 100% methanol for 30 min and rinsed in 10 mM PBS with 0.2% Triton X-100. The rinsed sections are treated for 20 min in 1:50 Triton:PBS. The following antibodies are used: anti-hexon antibody (diluted 1:150; Chemicon, Temecula, Calif.), anti-human NIS antibody (Brahms Institute, Germany) and anti-EIA (diluted 1:200; Santa Cruz Biotech, Santa Cruz, Calif.). Sections will be incubated with secondary antibodies at appropriate and standard conditions.

Non-Viral Delivery of NIS.

Non-viral delivery of NIS is accomplished by liposomal delivery by synthesis of liposome:adenovirus complexes (LAdC). Liposome (20 mM DOTAP:Chol) are synthesized and extruded through Whatman filters (Kent, UK) of decreasing sizes (1.0, 0.45, 0.2, and 0.1 nm). For preparation of LAdC, liposomes will be mixed with varying concentrations of adenovirus particles ($10^2$, $10^3$, and $10^4$) in 5% dextrose to yield a final concentration of 4 mM liposome containing the appropriate viral particles. Freshly prepared LAdC will be analyzed for mean particle size using a N4 particle size analyzer (Coulter, Miami, Fla.).

In vitro Transduction Efficiency. Initial studies are carried out using an adenovirus carrying a polynucleotide encoding a marker polypeptide (β-gal) to determine the transduction efficiency. Human glioma cell lines U251 MG, U87MG, and human lung tumor cell lines A549, and H1299m, as well as normal fibroblasts, are seeded in 6-well plates at $5\times10^5$ cells/well. The following day, cells are transfected with LAdC, and Ad-β-gal in serum-free medium for 3 h. Following transfection, cells are replenished with appropriate medium and incubation continued. Cells will be harvested at 24 and 48 h after transfection and stained for (3-galactosidase expression using the β-galactosidase staining kit (Promega, Madison, Wis.). Untransfected cells will serve as controls in these experiments. Based on the transduction efficiency, an appropriate viral titer is determined for encapsulation in the liposome.

In Vivo Studies.

In vivo studies involves the systemic delivery of LAdC in an experimental lung metastasis model. Human lung cancer cell lines H1299m and A549 are used to establish an experimental lung metastasis model in nude mice or in SCID/Beige mice. These tumor models are well established in the inventor's laboratory and routinely used. A549 and H1299m tumor cells ($1\times10^6$) are inoculated intravenously via the tail vein of nude mice and SCID/Beige mice, respectively, to establish experimental lung metastasis. Treatment will be initiated at 6 to 10 days after tumor cell injection at which time microscopic tumors in the lungs are established (data not shown). Treatment for macroscopic tumors will be initiated on day 21 to 25, at which time large macroscopic tumors in the lungs (A549) and other organs (H1299m) are established. Animals are divided into groups and injected intravenously with the virus alone, liposome alone, and LAdC via tail vein (100 μl/animal). The amount of virus to be complexed with the liposome and injected is determined as above. Animals are subsequently monitored for transgene expression in the lung tumors by imaging. This study will allow the assessment of (a) the possible use of Δ-NIS complexed to liposomes for systemic delivery to treat disseminated metastases and (b) possible treatment-related toxicity.

Statistical Analysis.

The main analytical goal of these studies is to determine at which timepoint the signal-to-noise ratio ($M_{obs}$SNR) is maximized for the two radioisotopes being examined. The signal is defined as the number of gamma counts in the tumor/labeled tumor cells and the noise is defined as a ratio between the number of gamma counts in the liver/the number of liver cells. Graphic displays of the mean SNR by time are to be provided for each isotope. Furthermore, likelihood-based methods are used to model the relationship between the SNR and time, and to determine the timepoint at which the SNR is the greatest. Radioisotope uptake in tumors infected with Δ24 versus Δ24-NIS are quantified through gamma camera imaging and autoradiography. In addition, the infected tumors are harvested at multiple time points and the amount of radiation is normalized for the amount of radiation expressed as counts per minute (CPM) against CPM of spleen. The inventors propose to use 30 mice per group and provided power estimates for various effect sizes so that $\mu_1$ is mean maximum SNR for iodine-133, $\mu_2$ is the mean maximum SNR for $^{99m}TcO_4$ and s is the common standard deviation for both groups. The power estimates for the proposed sample size use a Wilcoxon rank-sum test for various effect sizes (where effect size=$\mu_1$-$\mu_2$/σ) and assume an alpha error rate of 0.05.

B. Results

The imaging component of these studies relies on the ability of NIS to concentrate radioisotopes at a level sufficient for them to be visualized above background. Current hNIS clones are able to concentrate $^{99m}TcO_4$ pertechnetate approximately 7-fold with only transient transfection experiments in U251 MG cells. This cell line usually does not support very high levels of transfection (somewhere in the range of 15% to 20%), and it is anticipated that the increased transfection efficiency that is afforded by adenoviral constructs will significantly improve this SNR. Cell-mixing experiments with Δ24-NIS demonstrate a much higher level of radionuclide accumulation at 1000% (10-fold) over control cells at only a 10% infection rate. One potential issue is maintenance of isotopes within the cell, typically organification of the anion is required. Such organification improves the accumulation of these isotopes. Cho et al., (2000) have shown that the U1240 glioma cell line was able to organify iodide to approximately 5%-6% within the cells compared with approximately 10%-12% radioiodide organification in cultured thyroid cells (a 50% retention would still allow 500% accumulation at a 10% rate of infection). If signal is not adequate in the cell lines, similar washout experiments will be performed to gauge the retention characteristics of U87MG and U251 MG cells. Retention/efflux of isotopes may also be addressed by treating animals with sodium perchlorate 15-30 min after the isotope is given to the animals.

Example 4

Characterize Δ24-NIS as a Therapeutic

Characterization of Δ24-NIS as a therapeutic will include assessing the effectiveness of Δ24-NIS plus therapeutic radionuclide delivery in improving animal survival, and assessing the dosimetry models of radionuclide therapy of a β-emitter through imaging using NIS-accumulated gamma emitter radionuclides.

Typically, current gene therapy methods are sub-optimal for the treatment of cancer. In one aspect of the invention, is the improvement of oncolytic adenovirus treatment strategies, particularly for refractory tumors. The Δ24-NIS system may be used for concentrating useful isotopes such as $^{131}I$ as well as $^{188}ReO_4$. Use of the Δ24 system will be studied in an animal model system. Specifically, improvement in animal survival will be assessed after infection with either Δ24 or Δ24-NIS with subsequent administration of therapeutic concentrations of these radioisotopes. Any potential improvement in the "bystander effect" needs to be assessed in animal models prior to future contemplation of using these strategies in human clinical trials. Additionally, these studies will also help to apply and modify current dosimetry models by using gamma emitter isotopes for predicting accumulated dosing within tumors by NIS for eventual use of beta-emitter radioisotope therapy.

Any additive effects of oncolysis and radionuclide accumulation via concentration by the NIS transgene translates into improved therapy will be assessed, particularly for the intracranial glioma mouse xenograft model. The endpoint will be survival and since the glioma model used has such a short and steep death curve, assessing modest increments in animal survival is feasible. However, due to the uncertainty of type, dose, and timing of the radionuclides being used, the number of combinations, and therefore animals, could be quite large. To adequately deal with this large number of potential combinations and to have statistical confidence in finding the best therapeutic combination, an adoptive randomization design will be employed. This method will limit the number of animals needed and increase the chances of successfully identifying therapeutically active combinations. Additionally, matched sets of animals will receive pure gamma-emitters at doses appropriate for imaging but not therapy. These will simultaneously act as controls for tumor kill associated with radioactivity and also allow for dosimetry model confirmation.

The ability of Δ24-NIS transfected tumor cells to concentrate $^{131}I$ analogs, $^{99m}TcO_4$, $Na^{123}I$ and $^{188}ReO_4$. $^{99m}TcO_4$ is a routinely used radiopharmaceutical. Its low radiotoxicity makes it suitable for imaging and pharmacokinetic measurements. The radionuclide $Na^{131}I$ is used routinely by the inventors and is preferred for many of the studies because of its short half-life and ease of use. The radionuclide $^{188}ReO_4$ has about 4 times the radiotoxicity of $^{131}I$ and is also suitable for external imaging. After initial experiments to establish the efficiency of the transfected tumor cells in animal models, treatment with $^{99m}TcO_4$ and $Na^{123}I$ will be performed. To assess therapeutic dosing of radioisotope administration to animal xenografts, studies will be carried out with $Na^{131}I$ and $^{188}ReO_4$. Treatment efficacy will be correlated with the theoretical dosimetry models and dosimetry measured from imaging. The purpose is to determine preclinical survival advantage and pathologic changes seen in tumor samples harvested after injection of Δ24-NIS with co-administration of $^{188}ReO_4$ or $Na^{131}I$.

The current tumor model of oncolytic virus transgene expression of NIS in tumor cells does not provide a mechanism for organification and the producer cells are lysed by the virus after a few days post-infection. Thus the retention time of exposure to radionuclides is transient. Because of the relatively short exposure times (about 0.5 h) compared with the long physical half-lives (6 to 1440 h), the relative potency of radionuclides for therapy depends predominantly on the absorbed dose rates of radiation. The dose rates, or S-values for a 1- or 2-gram tumor are provided by MIRDose in Table 1.

TABLE 1

| CGy/mCi-Hr (S-value) | 1 gm MIRDose | 2 gm MIRDose | 2 gm + depth dose |
|---|---|---|---|
| $Tc^{99mm}O_4$ | 37 | 18 | 19 |
| $^{125}I$ | 46 | 24 | 25 |
| $^{123}I$ | 66 | 33 | — |
| $^{124}I$ | 331 | 179 | 173 |
| $^{131}I$ | 393 | 200 | 195 |
| $^{188}ReO_4$ | 1270 | 673 | 633 |

A comparison will be made with 2-gram spherical models to assess the level of dosage delivered to surrounding tissues. Because of this, radionuclides with long half-lives (such as I) are not as convenient for this system compared to radionuclides such as $^{131}I$. Additionally, $^{131}I$ is a convenient agent of choice for treatment because of its ready availability whereas $^{188}Re$-perrhenate is the radionuclide with the highest dose rate for treatment. $^{99m}TcO_4$ pertechnetate is the radionuclide of choice for detection purpose because of its low dose rate. As for potential toxicity from the radionuclides, the thyroid is the critical organ for assessing the effect of radio-iodide usage. Because of the transient nature of the uptake of pertechnetate and perrhenate, the GI tract, especially the stomach will be the critical organ (0.2 cGy/mCi for $^{99m}TcO_4$ or 6 cGy/mCi for $^{188}ReO_4$). Additionally, the safety of thyroid ablation with radio-iodide treatment is well established for patients with Grave's disease as well as for patients with thyroid carcinoma. Doses between 100-200 mCi are routinely used for this purpose with limited to no systemic toxicity. In fact doses as high as 400 mCi have been administered to patients with only minimal grade I-II hematologic toxicity being seen as the major problem.

These studies are designed to assess therapeutic advantage and survival of tumor-implanted animals. Additionally, pathologic examination of tumors from treated animals will be analyzed at various time points. Any treatment-induced anti-tumor effect and treatment-induced pathologic changes to normal and surrounding brain tissue will be noted. Immunohistochemical staining of pathologic material will use antibodies to NIS and to late viral proteins such as hexon protein to help determine viral spread and the extent of expression of NIS protein. This information will also be of value in assessing dosimetry, since depth dosimetry spheres can be calculated based on this information. A typical centripetal pattern of oncolytic viral spread throughout the tumor is expected. Centripetal spread has already been documented in tumors treated with Δ24 adenovirus.

Dosimetry and Diagnostic Imaging with NIS.

NuNu mice with transfected tumors at different stages (different size tumors) will be injected with 0.1-0.3 mCi of $^{99m}TcO_4$, $Na^{131}I$, or $^{188}ReO_4$ and whole body images will be obtained at 0.2, 0.5, 1, 2, 4, 6, 16, 24 and 48 h to determine the distribution and quantity of tracer in tumors and organs. No imaging will be performed at 24 and 48 h for $^{99m}TcO_4$ due to its short half-life. The effectiveness of the treatment (tumor growth curve) will be correlated with the dose injected (higher doses for $Na^{131}I$ or $^{188}ReO_4$) and size of tumors. These results will be compared with the inventors' dosimetry models.

Animal Design and Statistical Analysis.

In this randomized preclinical study, mice will receive 1 of 5 doses of virus ($3\times10^8$, $10^9$, $10^{10}$, $3\times10^{10}$, $10^{11}$) combined with 1 of 2 therapeutic radionuclides. Three dose levels of the radionuclides will be used, $Na^{131}I$ (1.0 mCi, 1.5 mCi and 2.0 mCi) and $^{188}ReO_4$ (1.0 mCi, 2.0 mCi and 3.0 mCi). Based on this design 30 different dose/virus/radionuclide combinations and a control arm will be used (a total of 31 groups). This high number of combinations will require between 240 and 300 mice to be sacrificed (assuming there are 8 to 10 mice per treatment). An alternative strategy is to use Bayesian outcome-adaptive randomization.

For purposes of this adaptive outcome design the assumption is that time to death follows an exponential distribution (with the mean time to death for the jth combination being $\lambda j$). A vague gamma (2.70, 0.30) prior value is assumed for each $\lambda j$. A maximum of 200 mice will be used with a maximum of 12 mice/combination. Mice will be randomized to a given combination using the Bayesian adaptive randomization scheme. At the start of the trial, 4 mice will be assigned to each treatment combination. After the dose/radionuclide-survival data are accumulated (after 35 days) for the first 4 mice per group, the posterior probability $pj=prob(\lambda, >\lambda_0|$ data) will be calculated, where $\lambda_0$ is the mean time to death for the control arm. The 9 treatment combinations with the greatest probability of being better than the control will be used. This will be followed by randomizing another 8 mice to the same treatment combinations while randomizing 8 other mice to the control arm. After the second stage the posterior probability for the data accumulated thus far in the experiment will be calculated. Once data from the second stage are accumulated the best two treatment/combinations will be selected based on the value of the calculated posterior probability. A confirmatory experiment comparing the best two combinations with the control will be conducted.

Operating Characteristics.

Based on data from studies with these mice, the survival times of control mice follow an approximate exponential distribution, whereas efficacious treatments follow a location-shifted distribution. Thus to evaluate the effectiveness of the strategy while collecting data from the study, the inventors assumed that treatment arms will be categorized into three groups. The first group is the best treatment and has only one arm. The second group is moderately effective treatments after 0, 3, or 6 treatments, and the last and largest group use placebo like substances with 23, 27, or 30 treatments for the group. Under the alternative hypothesis, the best treatment follows a shifted exponential with distribution with expected survival time of 60 days. The moderately effective treatments follow a shifted exponential distribution with an expected survival of 45 days; and with control like treatments follow an exponential distribution with an expected survival of 30 days. These are conservative estimates as the mean survival duration in our tumor model is 21 days with a small variance of 2.3 days. The following results are obtained from 1000 simulations from each of the scenarios mentioned above plus a null scenario where no arms are more effective than the control. In each of the simulations although the data were generated from distributions having mean survival times greater than 35 days the simulations censored observations to ensure that the simulation and the actual studies are in accord.

Following these adaptive randomization experiments the inventors will validate the favored combination with an additional test sets of animals. The best combination will be compared with the "next best" and "least best" conditions.

Expectation based on projected models is that the inventors would have selected the best combination with a probability of 94%.

Since efflux of the radionuclide may present the problem of sustained exposure to therapeutic doses of a particular isotope, using a replication-competent adenovirus permits multiple treatments as the virus propagates through the tumor. Like a "ripple" through a pond, the next wave of viral spread provides an opportunity to re-dose with radionuclides. The inventors have extensive experience using intracranial glioma xenograft and systemic lung cancer modes. Additionally, since the intracranial glioma xenograft model has death curves in a narrow range, any improvements in oncolytic effect from therapeutic radioisotopes will be easily identifiable. Also by using a continuous adoptative allocation statistical model (Bayesian) a more rapid throughput and reduced number of experimental animal models will be needed to assess multiple dosing schemes of the Δ24-NIS as well as dosing schemes for the therapeutic radioisotopes. An alternative method will be to assess if NIS under the control of a different promoters will increase the therapeutic advantage. Additionally, consideration of dose adequacy will be determined assessing systemic toxicity in histopathologic specimens. If no toxicity is observed, additional groups of animals will be enrolled, using an adoptive randomization scheme to assess effects from higher doses of radionuclides.

Example 5

Assessing the Imaging Capabilities of Δ24-NIS

A. Methods

These studies will track Active oncolytic spread of Δ24-NIS in a cohort of patients in a phase I clinical trial, confirm dosimetry models for therapeutic beta-emitter administration in the phase I clinical trial by imaging NIS-accumulated gamma emitter radionuclides, and correlate imaging data in patients receiving Δ24-NIS with pathologic material harvested after viral administration.

In an attempt to translate the imaging component of this project to a human clinical trial, a third cohort of patients to receive Δ24-NIS will be added to those patients in an already approved phase I clinical trial using Δ24-RGD. This will be coupled with administration of $^{99m}TcO_4$ pertechnetate for gamma camera assessment, a necessary step in the implementation of a phase I toxicity trial to assess the propagation potential of oncolytic viral therapy.

Based on these in vitro and in vivo data, a phase I clinical trial is designed that is intended (1) to provide for evaluation of the safety, tolerability, and feasibility of administering Δ24-RGD to patients with malignant glioma, and a wide basic information about the biologic effect of injecting Δ24-RGD into human brain tumors in situ. This study has been approved by M. D. Anderson's IRB. To achieve these goals, the study will involve two groups of patients. A first group (Group A) will undergo a standard dose escalation study in which Δ24-RGD is administered by direct intratumoral injection and patients are followed for clinical and radiographic toxicity. This stage will determine the maximal tolerated dose (MTD) for intratumoral injection alone, defined as one-half of a logarithm below the toxic dose. The second group (Group B) includes only patients with resectable tumors. These patients will first undergo stereotactic injection of Δ24-RGD via a catheter that has been permanently implanted into the center of the tumor. After 14 days, the tumor will be resected with the catheter in place, providing a biologic specimen for pathologic and molecular analysis. After tumor removal, Δ24-RGD will be injected into the microscopic residual tumor surrounding the resection cavity. This will allow patients to be followed for toxic effects of injection into a brain infiltrated with microscopic tumor cells. These patients will undergo dose escalation similar to Group A except that one less level of dosage will be used for Group B than for group Group A. In addition to these two groups an additional cohort (Group C) will be included to evaluate the suitability of Δ24-NIS for imaging. Although the small numbers of patients will preclude statistical analysis, results from both Group A and B will provide valuable information about response and efficacy.

Under local anesthesia, a stereotactic headframe (such as the CRW or Leksell systems) will be attached to the patient. After injection with intravenous gadolinium a stereotactic MRI will be performed to localize the tumor mass and a stereotactic biopsy will be carried out. An initial specimen will be sent for frozen section (OCT block) to be analyzed by a certified neuropathologist to provide histologic confirmation of the presence of tumor. A second specimen will be sent for routine fixing and H&E staining (paraffin-embedded fixed block). The third specimen will be snap frozen in liquid nitrogen.

If biopsy confirms the presence of recurrent glioma, the patient will then undergo stereotactic-guided placement of an injection needle. Investigators will be supplied with a vial containing Δ24-RGD or Δ24-NIS. One ml containing the appropriate dose of Δ24-RGD or Δ24-NIS will be injected over 10 min at 1 to 4 sites at the surgeon's discretion. The needle will be flushed with normal saline to assure delivery of the virus (prior to needle placement the volume of the needle must be determined so that only the 1 ml of virus and not the flushing solution is delivered). For this injection the volume will be fixed regardless of tumor size.

After stereotactic injection patients will be observed in the hospital for a period of observation determined by the treating investigator. A non-contrast CT will be performed to verify the injection site and to identify any acute asymptomatic hematomas. Patients will be evaluated daily for adverse signs and symptoms while in the hospital. Patients will be discharged at the physician's discretion and in accordance with biosafety standards.

Group A: Intratumoral Maximum Tolerant Dose (MTD).

Cohorts of 3 patients will receive an intratumoral injection of Δ24-RGD to determine the MTD. Cohorts of patients will be entered at each dose level as follows: Dose Level (Δ24-RGD in pfu) $3 \times 10^8$, $1 \times 10^9$, $1 \times 10^{10}$, $3 \times 10^{10}$, or $1 \times 10^{11}$. The total volume of injection will depend upon the size of the tumor, but the dose within the volume will be fixed. The maximal injection volume for each injection site will be 200 µl per site, evenly distributed. If the calculated volume is greater than 200 µl per injection, additional injection sites should be established. A stereotactic biopsy will be carried out, and an initial specimen will be sent for frozen section to be analyzed by a neuropathologist to provide histologic confirmation of the presence of tumor. A second specimen will be sent for a routine paraffin-embedded fixed block. The third specimen will be snap frozen in liquid nitrogen.

Group B: Biologic Effects of Δ24-RGD and Maximum Tolerant Dose (MTD) after Intramural Injection.

The goal of this second group is to assess the biologic effect of Δ24-RGD within a tumor and to determine the toxicity resulting from administering Δ24-RGD into the post-resection cavity containing infiltrating tumor cells. To obtain a biologic specimen and determine toxicity, a two-stage approach will be undertaken. The first stage will be a stereotactic injection of Δ24-RGD into the tumor via an implantable permanent catheter. The second stage will be an open craniotomy 2 weeks later with en bloc resection of the previously injected tumor mass (to provide a specimen that can be evaluated for Δ24-RGD effects) followed by injection of Δ24-RGD into the walls of the resection cavity (for assessment of toxicity).

Stage 1—Δ24-RGD will be stereotactically injected using a silastic catheter. After injection, the catheter will be cut at the level of the skull, closed with a hemoclip and be left in place until the craniotomy is performed.

Stage 2—Fourteen days after the initial stereotactic injection, a long enough time to for adequate uptake and replication of Δ-24-RGD, patients will undergo open craniotomy (Day 15). The tumor will be removed as a single mass with particular effort to avoid internal debulking and suctioning of the site of prior Δ24-RGD injection. The previously placed catheter will be used for localization of the injection sites. After tumor resection, Δ24-RGD will be administered by injections into the wall of the resected tumor cavity. The goal of injection is to distribute Δ24-RGD throughout the tumor wall. A grid of approximately 1 cm² squares will be established. Each 1 cm² square will be injected with Δ24-RGD. Injection will be performed using a 20 g blunt tip Dandy needle attached to a 1 cc syringe. The needle will be inserted 1-2 cm within the parenchyma and Δ24-RGD infused for 1 min per injection. Minimal irrigation will be used after injection. The volume to be injected at each site will be calculated as follows: Volume per injection sites=Total volume at dose level/number of injection sites.

The total volume of injection will depend upon the size of the tumor, but the dose within the volume will be fixed. The maximal injection volume for each injection site will be 200 µl per site evenly distributed. If the calculated volume is greater than 200 µl per injection, then additional injection sites should be established by adjusting the grid. During the second stage of the study, the biological data obtained from stage 2 will be reviewed, and the protocol may be modified, including but not limited to the interval between stereotactic injection and open craniotomy, as well as the number, volume, and depth of stereotactic and open craniotomy injections.

After the craniotomy and Δ24-RGD injection, patients will be monitored according to customary standards with additional biosafety level precautions. Patients will be evaluated daily for adverse events while in the hospital and will be discharged at the discretion of the treating physician. Patients in Group 2 will not be entered into the study until the toxicity profile from intratumoral injection in Group A patients is established. To further ensure safety, Group 2 patients will not be evaluated until the cohort of patients from Group A has been analyzed. Thus, patients in Group 2 will lag behind Group 1 by at least one level. The entry criteria will be similar to a recently completed NABTC phase I clinical trial of adenovirus p53

Group C: Intratumoral MTD with Intratumoral Imaging.

The third group (Group C) includes only patients with resectable tumor as in the Group B patients. These patients will first undergo a stereotactic biopsy followed by stereotactic injection of Δ24-NIS through a catheter that has been permanently implanted in the center of the tumor. After 14 days the tumor will be resected in an en-bloc with the catheter left in place. This will provide pathologic specimens for molecular analysis and immunohistochemical staining for assessing viral spread. After the tumor is removed, Δ24-NIS will be injected again into the microscopic residual tumors surrounding the resection cavity. The patients will then be followed for toxic effects from the injection site intruding into the infiltrated surrounding brain. These patients will also be followed clinically and radiographically for signs or symptoms of toxicity. Because there is concern about inter-patient variability, the inventors will look at only one dose level corresponding to the MTD obtained from analysis of Group B patients. This cohort of patients (15) will be used to evaluate the timing of $M_{obs}SNR$ over the observational imaging days post-injection. The amount of virus that will be injectable will be identical to that used for the previously described for Group B patients and the injection of the resected cavity wall will be identical to that previously described for Group B patients.

Pathologic and Imaging Correlates.

By using the established en bloc resection technique previously used in a p53 adenoviral glioma trial, the inventors will be able to accurately determine the extent and geometry of active viral spread throughout the tumor bed. These measurements will be compared to nuclear imaging of patients with isotopes injected at days 3, 7, 10 and 14 prior to the 14-day surgical resection interval. Again, analysis of tumor volume measurements at this dose level will be compared to the imaging results from day 14 and characterization of this material will be related to those patients having $M_{obs}SNR$ at that time point.

Statistical Analysis.

The primary statistical analysis for this cohort of patients is to determine at which time point (day) the signal-to-noise (STN) ratio is maximized ($M_{obs}STN$). A $M_{obs}SNR$ will be obtained for each patient on each day of imaging, obtained by choosing the time point which yields the best SNR (in minutes after giving the radionuclide tracer). This measurement will be used to calculate the relative functional uptake of the radionuclide over the observed time points (in intervals of days post viral infection). The variable of interest is $M_{obs}STN$. The inventors plan to report the mean and standard deviation of maximum STN by day and dose level. The general linear model for modeling $M_{obs}STN$ as a quadratic function of day will be used. Because the sample size is small, an exploratory will follow the following procedure: The inventors will generate a large number of bootstrap samples from patients' vectors of $M_{obs}STNs$. The $M_{obs}STN$ will be calculated for each day. Lastly, the proportion of times a given day is chosen for having the maximum STN ratio will be calculated. This proportion approximates the probability that a given day has the highest signal-to-noise ratio.

Operating Characteristics.

The $M_{obs}STN$ ratios of 10 or greater are expected on the optimum day after inoculation (which presumptively will be on day 14 for each dose level assuming 10% of the tumor cells are infected and the potential susceptible tumor cells are not limiting). Concomitantly a minimal STN ratio of 1 is expected for days 1 through 3 (first-pass viral incubation time). Given this input, 3 simulated scenarios will be drawn from a multivariate normal distribution with a Variance-Covariance Matrix following an AR (1) process (correlation of 0.5; variance=9). In the first scenario it is assumed that the mean $M_{obs}STN$ ratios for days 3, 7, 10, and 14 were 1, 3, 8, and 10 respectively. In the second scenario it is assumed that the mean $M_{obs}STN$ ratios were 1, 3, 10, and 8 and for the third scenario it is assumed that the mean $M_{obs}STN$ ratios were 1, 10, 8, and 3.

B. Results

The inventors have experience in using Adp53 in a phase I clinical trial and do not anticipate problems in the proposed phase I clinical trial. M.D. Anderson Cancer Center has experience harvesting en bloc resected tumors specimens with anatomical markers maintained along with an intact injection catheter in place. Patients who are selected for this study with recurrent GBM that requires surgical debulking have tumors that are sizable enough to be adequate for imaging, but it is recognize that this group of patients may not be representative of all patients with tumor recurrence who are not surgical candidates. However, given the objectives of trying to initially visualize the tumor through the use of Δ24-NIS, it is believe that the hypothesis can be adequately tested.

Example 6

Delta 24-Hycytosine Deaminase (Δ24-Hycd)

A. Materials and Methods

Cell Lines and Culture Conditions.

U87MG cells (obtained from the American Type Culture Collection, Manassas, Va., cat. #HTB-14) and U251MG human glioma cell lines (kindly provided by Dr. Yung's laboratory) were cultured in Dulbecco's modified Eagle/F12 medium (1:1, vol:vol) (Media Tech, Herndon, Va.) containing 5% fetal bovine serum (DIFCO) and 2 nM glutamine. Cells were grown in culture at 37° C. and at 5% $CO_2$ without antibiotics and were passaged fewer than 12 times during the studies.

Adenoviruses.

Construction of Δ24 has been described elsewhere (Fueyo, 2000). This construct has a 24-bp deletion in the E1A gene (nt 923 to 946, both included), a region known to be necessary for Rb protein binding (Whyte, 1989), corresponding to the amino acids $L_{122}TCHEAGF_{129}$.

To construct Δ24-hyCD, a humanized form of the nucleic acid encoding yeast cytosine deaminase (hyCD) was inserted into the E3 region of the Δ24 adenovirus. Yeast CD was chosen because of its superior enzymatic kinetics over the traditional bacterial form (Hamstra, 1999). The yeast CD gene (fcy1) is derived from *Saccharomyces cerevisiae* and its product has an approximate catalytic efficiency that is 280 times higher than from the bacterial form of the enzyme. A series of 24 synthesized, overlapping oligonucleotide primers (Midland Certified Reagent Co., Midland, Tex.) with pairs that were sequentially elongated by PCR was used to construct Δ24-hyCD. The process was repeated with progressively longer pieces until the full-length gene was obtained. In addition, the 5' most distal oligonucleotide contained an idealized Kozac consensus sequence, a proximal HindIII, and a distal XbaI restriction site for cloning. The nucleotide sequence of the synthesized polynucleotide was also changed significantly (102 of 460 coding base pairs) to optimize a human codon rather than a yeast codon preference. The full-length synthesized polynucleotide was cloned into pcDNA3.1 (Invitrogen) and clones were isolated and subsequently sequenced. Several clones with the DNA sequence of interest were then transiently and stably transfected into U87MG and U251MG glioma cell lines and assayed for enzyme activity, as described below. Suitable clones expressing enzyme activity were then cloned into the E3 region of pBHG10 (Microbix). pBHG10-hyCD and pXC1-Δ24 were cotransfected into 293 cells to allow homologous recombination, as previously described (Fueyo, 2000).

The viruses were propagated in 293 cells and purified by ultracentrifugation in a cesium chloride gradient. All viruses were titered using a plaque method as well as optical density measurements and were maintained at −80° C. until use. Single lots of adenovirus Δ24 and adenovirus Δ24-hyCD were used in the experiments. As controls, Δ24-hyCD that had been inactivated by UV light and cells that had been mock-infected with culture medium were used.

Chemicals.

5-FU was purchased from Sigma Chemical Company (St. Louis, Mo.) and 5-FC from SP Pharmaceuticals (Albuquerque, N. Mex.).

Real-Time Quantitative.

PCR U251MG and U87MG cell lines were grown to 95% confluence, harvested with 0.25% trypsin/EDTA, replanted into T25 flasks to a total of $2\times10^6$ cells, and then incubated overnight. Media were aspirated and 2 ml of adenovirus Δ24-hyCD was added at 0.1, 1, 5, 10, or 100 pfu/cell to duplicate samples from a viral stock of $1\times10^{11}$ pfu/ml, and the flasks were incubated for 1 h with continuous shaking. The virus was aspirated and cells were washed twice with PBS. Fresh complete medium containing 10% FBS was replaced and the cells were incubated at 37° C. for 24, 48, 72, or 96 h. At that time, the harvested tissue cultures were washed twice with PBS. Floating cells were saved by centrifugation, immediately frozen, and stored at −80° C. before the mRNA was harvested. Then, cell pellets were lysed with Trizol reagent (Life Technologies) and the RNA was purified according to the manufacturer's recommendations for subsequent amplification by TaqMan quantitative RT-PCR as previously described (Miller, 2002). The following primers and probe were used for the amplification and detection of the hyCD transgene: Forward Sequence: 5'-CAACATGAGGTTCCAGAAGGG-3' (SEQ ID NO:12); Reverse Sequence: 5'-CAGTTCTCCAGGGTGGAGATCT-3' (SEQ ID NO:13); TaqMan probe: 5'-TCCGCCACCCTG CACGGC-3' (SEQ ID NO:14).

The primers were labeled with FAM label at the 5' end and TAMRA label at the 3' end for yeast CD mRNA. Control primers and probes were used for the ribosomal RNA housekeeping gene S9, a gene with little expression variability in human gliomas (Blanquicett, 2002). The expression of mRNA for hyCD was quantified and reported relative to a stably expressing hyCD clone of the glioma cell line U251MG. Expression levels were determined with the ABI 7000 sequence detection system (Applied Biosystems, Foster City, Calif.).

Cytosine Deaminase Enzymatic Assays.

Separation of uracil from cytosine or 5-FU from 5-FC was achieved by thin layer chromatography as modified from Rubery and Newton (1971). Briefly, aluminum-backed silica gel sheets were used (silica gel 60-F-254, EM Science, Germany). Each sheet was spotted with a total of 5 μl of a reaction mix or standards at 1 μl successive spots, with drying before additional spotting. The gel sheets were then resolved in a chromatography tank containing a mixture of 80% chloroform and 20% methanol. The solvent front was quite rapid, with the sheets being resolved within 2-3 min. The separated cytosine and uracil or 5-FC and 5-FU were then visualized with UV excitation at 254 nm. For quantitative enzyme assays, these resolved spots were cut out, placed in scintillation vials, and counted.

To measure enzyme activity, a procedure adapted by Hamstra et al. (1999) was used. Briefly, U251MG or U87MG glioma cells transfected with 10 pfu/cell of virus were harvested after 24 h in an assay buffer (100 mM Tris pH 7.8, 1 mM EDTA) and freeze-thawed 3 times. Protein concentrations were assessed by the Bradford method. For the conversion assay, 5-FC at 100 mM was spiked with 0.5 mM tritiated 5-FC (2 μCi/mM) and diluted at various concentrations to 30 μl reaction volumes, and either 0.3 or 0.75 μg of protein extract was added. The reaction mixtures were allowed to incubate for 1, 5, 10, or 15 min at 37° C., after which they were quenched by the addition of 1 M acetic acid and placed on ice. The extent of reaction conversion was based on the fraction of produced 5-FU divided by the total counts of both the 5-FC and 5-FU bands. The percentage converted was used to calculate the production of 5-FU per µg of protein extract per min of reaction time. The apparent $K_m$ and apparent $V_{max}$ values were based on non-linear regression analysis using Graph Pad's Prism program (Graph Pad Software, San Jose, Calif.). All assays were done in triplicate.

Western Blot Analysis.

U251MG and U87MG cell lines were prepared in 6-well plates and treated with Δ24, Δ24-hyCD, or PBS (mock-treatment condition) as described above. The cells were harvested at 24, 48, 72, or 96 h after treatment. Total cell lysates were prepared by incubating cells with 1×SDS sample buffer (62.5 mM Tris-HCl pH 6.8, 2% w/v SDS, 10% glycerol, 50 mM dithiothreitol), and protein concentration was quantified by using the bicinchoninic acid (BCA) method (Pierce, Rockford, Ill.) and read on a Beckman spectrophotometer. Protein samples (20 µg) were boiled at 98° C. for 5 min, and lysates were separated on a 15% SDS-Tris glycine polyacrylamide gel, subjected to electrophoresis at 95 V for 2 h, and transferred to a nitrocellulose membrane. The membrane was blocked with 3% nonfat milk, 0.05% Tween 20, 150 mM NaCl, and 50 mM Tris (pH 7.5) and incubated with primary antibody for yeast CD (1:500; Biogenesis Inc., Kingston, N.H.). The secondary antibody was horseradish peroxidase-conjugated anti-sheep IgG (Pierce, Rockford, Ill.). The membranes were developed according to Amersham's enhanced chemiluminescence protocol (Amersham Corp., Arlington Heights, Ill.).

Cell Viability Assays.

U251MG and U87MG cell lines were grown to 95% monolayer confluence. The cells were trypsinized and harvested with 0.25% trypsin/EDTA, plated in 6-well tissue culture plates, and allowed to adhere overnight at 37° C. in 5% $CO_2$ humidified incubators. 5-FU or 5-FC in serial 0.5-log concentrations in 100 µl aliquots was added directly to the cells to achieve final concentrations, as previously described (Miller, 2002). Cells were incubated at 37° C. for 5 days and cell viability by cellular respiration was determined using 3-(4,5-methylthiazole-2-yl)-5-(3-carboxymethoxy-phenyl)-2-(4-sulfonyl)-2H-tetrazolium) (Promega, Madison, Wis.) according to the manufacturer's protocol. The cell survival fraction was measured at each drug concentration as the ratio of absorbance at 490 nm relative to untreated cells. This calculation was normalized for background absorbance of the culture medium alone. The cell survival fraction was plotted against the logarithm of the drug concentration, and $IC_{50}$ values were calculated using a sigmoidal dose-response curve with variable slope in GraphPad Prism 3.01.

The crystal violet assay was performed as described previously (Fuego, 2000). Briefly, cells were seeded at $10^5$ cells per well in 6-well plates, allowed to grow for 20 h, and then infected with Δ24-hyCD, Δ24, or UV-inactivated Δ24-hyCD at 10 MOI. Either 5-FU (at 0.25 mM) or 5-FC (at 0.5 mM) was added to the cultures at different times after infection (0 to 6 days). Cell monolayers were washed with PBS and fixed and stained with 0.1% crystal violet in 20% ethanol. Excess dye was removed with several water rinses.

In vitro cytotoxicity was quantified by using the tetrazolium salt 3-(4-5-dimethylthiazol-2-yl)-2,5-diphenyltetrazolium bromide (MTT) (Sigma) to measure cell viability. For this assay, $10^4$ cells were seeded in 96-well microtiter plates and infected 24 h later with 0, 2, or 5 pfu/cell of Δ24-hyCD or Δ24. Sixteen wells were seeded with untreated glioma cells as a viability control, and 16 wells containing only complete medium were used as a control for nonspecific dye reduction. 5-FC (at 0.5 mM) or 5-FU (at 0.25 mM) was added to the cultures 1 day after infection. Medium was removed 7 days after Δ24-hyCD or Δ24 treatment, and 100 µl/well (1 mg/ml) of MTT was added to each well. The plates were incubated for an additional 4 h and then read on a microplate reader at a test wavelength of 570 nm. Quadruplicate wells were used for each condition.

Animal Studies.

Cell implantation and adenoviral treatment were performed as described previously (Lal, 2000). Briefly, implants were placed in 6- to 8-week old female NuNu mice by using screw-guide hardware with coordinates of 1 mm anterior and 1.2 mm lateral to the bregma. The mice were allowed to heal for 7 days, after which U87MG glioma cells were injected at a depth of 4 mm in the region of the putamen at a concentration of $5\times10^5$ cells in 10 µl of PBS. Three days after tumor-cell implantation, a single intratumoral injection of $1.5\times10^8$ pfu of Δ24-hyCD, Δ24, or 10 µl of PBS was injected 3 times total on days 3, 5, 7 for each experimental group. At 5 or 15 days after the single intratumoral injection, the animals were given i.p. PBS or 5-FC at 500 mg/kg once daily, Monday thru Friday, until the mice displayed signs of neurologic dysfunction (primarily a lack of avoidance behavior or being hunched over in a posterior position) or until they were killed. Mice were killed by $CO_2$ inhalation and the brains were collected for histopathologic examination and immunohistochemical staining Animal studies were conducted in the veterinary facilities of the M. D. Anderson Cancer Center in accordance with institutional guidelines.

Immunohistochemical Analysis of Xenograft Tumor Sections.

Animal brains were harvested, fixed in formalin, embedded in paraffin, and sections were prepared after initial baking at 60° C. for 30 min. The sections were blocked with 0.3% $H_2O_2$ and 100% methanol for 30 min and rinsed in 10 mM PBS with 0.2% Triton X-100. The rinsed sections were then treated for 20 min in 1:50 Triton/PBS. The following antibodies were used: anti-hexon antibody (diluted 1:150; Chemicon, Temecula, Calif.), anti-yeast cytosine deaminase (diluted 1:150; Biogenesis Inc., Kingston, N.H.), and anti-E1A (diluted 1:200; Santa Cruz Biotech, Santa Cruz, Calif.). Sections were then incubated with secondary antibodies at a 1:50 dilution at room temperature for 1 h. Staining was performed with acid-fast 3, 3' amino diaminobenzidine tablets (Sigma). The sections were counterstained with 0.01% methanol green.

Statistical Analysis.

The anticancer effect in vivo was assessed by plotting survival curves according to the Kaplan-Meier method, and survivals among treatment groups were compared by using the logrank test in GraphPad Prism.

B. Results

The Δ24-hyCD Adenovirus.

To generate Δ24-hyCD the Δ24 adenovirus genome, which includes a 24-base-pair deletion in the Rb-binding region of the E1A gene (Fueyo, 2000), was modified and inserted an expression mini-cassette in lieu of the deleted E3 region. The expression cassette is driven by the human cytomegalovirus promoter placed immediately proximal to the hyCD sequence. A bovine growth hormone polyadenylation region is immediately distal to the stop codon of the synthesized CD gene. This construct was confirmed by sequencing the mini-cassette using a series of primers that covered the entire sequence with some overlap (data not shown). The altered nucleotide sequence that confers human codon preference was confirmed by sequence analysis.

Production of Cytosine Deaminase.

To determine if Δ24-hyCD expressed a functional exogenous gene, the inventors initially assessed yeast CD messenger (mRNA) expression by using real-time quantitative PCR. U251MG and U87MG glioma cell lines were exposed to various concentrations of Δ24-hyCD and allowed to incubate for various periods of time Table 4. The production of mRNA was compared to the amounts of mRNA produced by a U251MG stable clone expressing hyCD (the table displays some negative values which reflects less mRNA production than the stable clone at the early time points and at initial low titer experiments). A dose- and time-dependent trend in increasing mRNA production was evident, indicating that mRNA was increasingly produced with increasing virus as well as with longer incubation times. The production of mRNA was abated at the longest incubation times and at the highest viral titers, probably secondary to improved viral oncolysis. In the 100 pfu/cell treatment condition, the vast majority of cells were floating at 96 h (data not shown). The U251MG cell line generated higher peak concentrations of mRNA than U87MG cells, likely a result of their more efficient transducibility (Miller, 2002). Production of a 2.07-log increase in CD mRNA over that of controls was seen at only 1 pfu/cell and at 72 h in the U251MG cells. This amount was approximately 10 times the production at 48 h (1.08-log) and is a dramatic increase over that produced at 24 h (0.69-log). In contrast, mRNA production in the U87MG cell line required 96 h or a titer of 100 pfu/cell to reach a 2-log increase of mRNA production over controls. In the U251MG cell line, production of mRNA was maximal at a lower pfu/cell input dose (i.e., 1 MOI) but at a long (96-h) incubation time (5.04-log) Table 4. This finding further indicates that the replication competency of Δ24-hyCD directly influences the production of an exogenously expressed gene. As expected, the efficiency of hyCD mRNA production was influenced by the differential infectivity of cell lines and by the differential kinetics of viral production in the different cells.

TABLE 2

Expression of humanized yeast cytosine deaminase mRNA after infection with Δ24-hyCD.

| Cell Line | Infection Times | Multiplicity of Infection (MOI) | | | |
|---|---|---|---|---|---|
| | | 0.1 | 1 | 5 | 10 |
| U251MG | 24 h | −0.49 | 0.69 | 1.47 | 1.42 |
| | 48 h | −2.00 | 1.08 | 1.55 | 1.25 |
| | 96 h | 2.88 | 5.04 | 3.96 | 3.93 |
| U87MG | 24 h | −0.92 | 0.21 | 0.38 | 1.18 |
| | 48 h | −0.02 | 0.45 | 0.76 | 2.15 |
| | 96 h | −1.70 | 1.56 | 1.65 | 1.94 |

Consistent with the increase in the mRNA production, levels of CD protein were also augmented in a time- and dose-related fashion. Western blot analyses of U87MG glioma cells infected with Δ24-hyCD showed a marked increase in the amount of protein expressed relative to mock-infected U87MG controls or to U87MG cells treated with Δ24 alone (FIG. 14A). These analyses also revealed that saturation of the expressed or translated polypeptide is limited by the lysing of cells as the incubation times increase, in combination with large viral input doses. Together, these findings show that Δ24-hyCD efficiently transduced high levels of the hyCD exogenous gene.

Next the inventors determine if exogenous hyCD protein demonstrated enzymatic activity. In initial experiments, hyCD enzyme activity was qualitatively assessed by thin layer chromatography. No identifiable conversion of cytosine to uracil was evident in uninfected cells, a finding consistent with the lack of this pyrimidine salvage pathway in human cells. However, enzymatic activity in the Δ24-hyCD-treated U251MG cells rapidly converted cytosine into uracil (FIG. 15B). Enzymatic activity was verified by using a tritiated cytosine radioisotope. Quantitative enzymatic determination of the 5-FC-to-5-FU conversion resulted in an apparent V. of 8.4 (±1.0) μM/min/mg protein and an apparent $K_m$ of 0.63 (±0.04) 1/mM for hyCD-expressing U251MG cells. The enzyme activity in crude extracts of cells infected with 10 pfu/cell Δ24-hyCD and harvested 24 h later is summarized in Table 5. The percent conversion of 5-FC to 5-FU by U87MG cells (49.7±4.8 at 5 min and 90.3±6.1 at 15 min) is similar to that previously reported for the non-humanized yCD (Kievit et al., 1999). Taken together, these observations indicate that Δ24-hyCD is an efficient vector that can be used to deliver an enzymatically active form of hyCD to glioma cells in vitro.

TABLE 3

Percentage conversion of 5-FC to 5-FU by 0.75 mg cell extract previously incubated for 24 h with 10 pfu of Δ24-hyCD per cell

| Cell Type | Conversion of 5-FC to 5-FU, % | | | $K_m$ | $V_{max}$ |
|---|---|---|---|---|---|
| | at 0 min | at 5 min | at 10 min | | |
| U251MG | 1.4 ± 0.9 | 48.6 ± 4.2 | 82.7 ± 5.6 | 0.63 ± 0.04 | 8.4 ± 1.0 |
| U87MG | 1.3 ± 0.7 | 49.7 ± 4.8 | 90.3 ± 6.1 | 0.67 ± 0.05 | 8.3 ± 1.2 |

$V_{max}$ is expressed as μmol/min/mg lysate; $K_m$ is expressed as the reciprocal of mM.

Increased Glioma Cell Sensitivity to 5-FC when Expressing hyCD.

Figure 15:
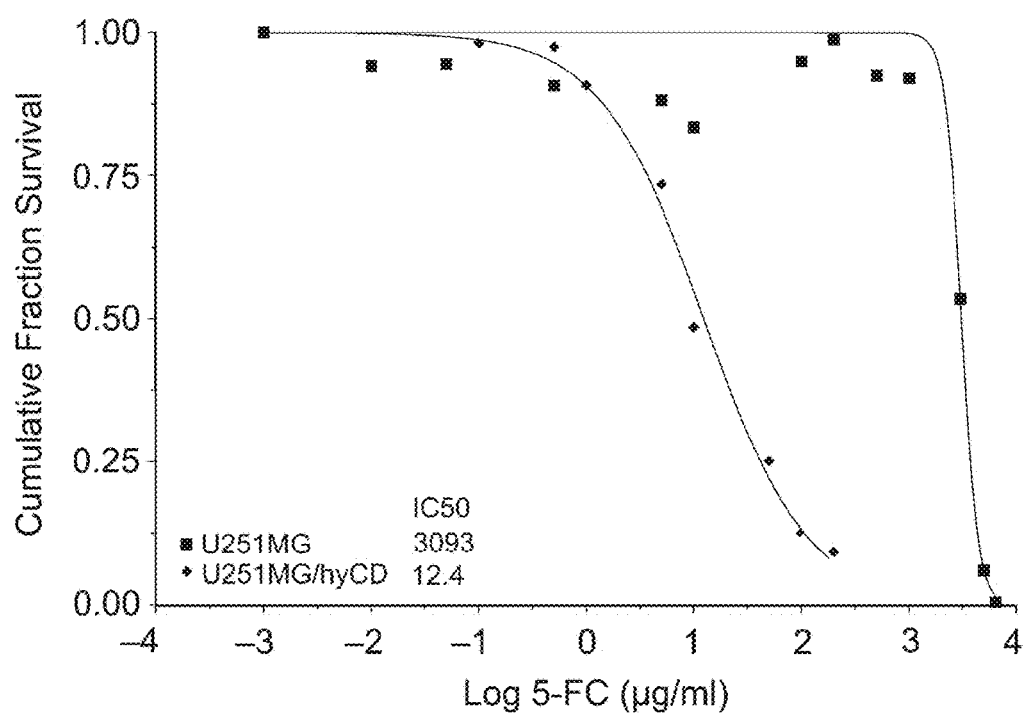
FIG. 15 shows dose response curves of parental and hyCD stable-transfected U251MG cells treated with 5-FC, as assessed by cell viability assay. Note the shift to the left of the $IC_{50}$ curve for the hyCD stable-transfected U251MG cells in the presence of 5-FC. $IC_{50}$ values for both cultures are indicated.

To demonstrate the increased sensitivity of glioma cells expressing hyCD, U251MG cells were exposed to 5-FC at increasing concentrations and assayed for viability. Cells expressing hyCD were approximately 3 orders of magnitude more sensitive than parental cells to 5-FC ($IC_{50}$, 12.4 μg/ml vs. 3094 μg/ml) (FIG. 15). This increased sensitivity of glioma cells expressing hyCD suggests that Δ24-hyCD should be superior to Δ24 as an antiglioma agent.

Comparison of the Antiglioma Effect of Δ24-hyCD and Δ24.

The inventors infected human glioma cells with Δ24-hyCD or Δ24, with or without 5-FC or 5-FU, to analyze adenovirus- and/or drug-induced cell death. Cell death was determined by crystal violet staining of viable cells. The effect of 5-FU on cell killing was no different for Δ24 versus Δ24-hyCD in U251MG (FIG. 16A) or U87MG glioma cell lines (not shown). However, the addition of 5-FC to Δ24-hyCD-transduced cells improved cell killing, presumably because of the hyCD enzymatic activity provided by Δ24-hyCD. The addition of 5-FC to Δ24-transduced cells did not affect cell killing at these incubation times and viral titers.

Figure 16:
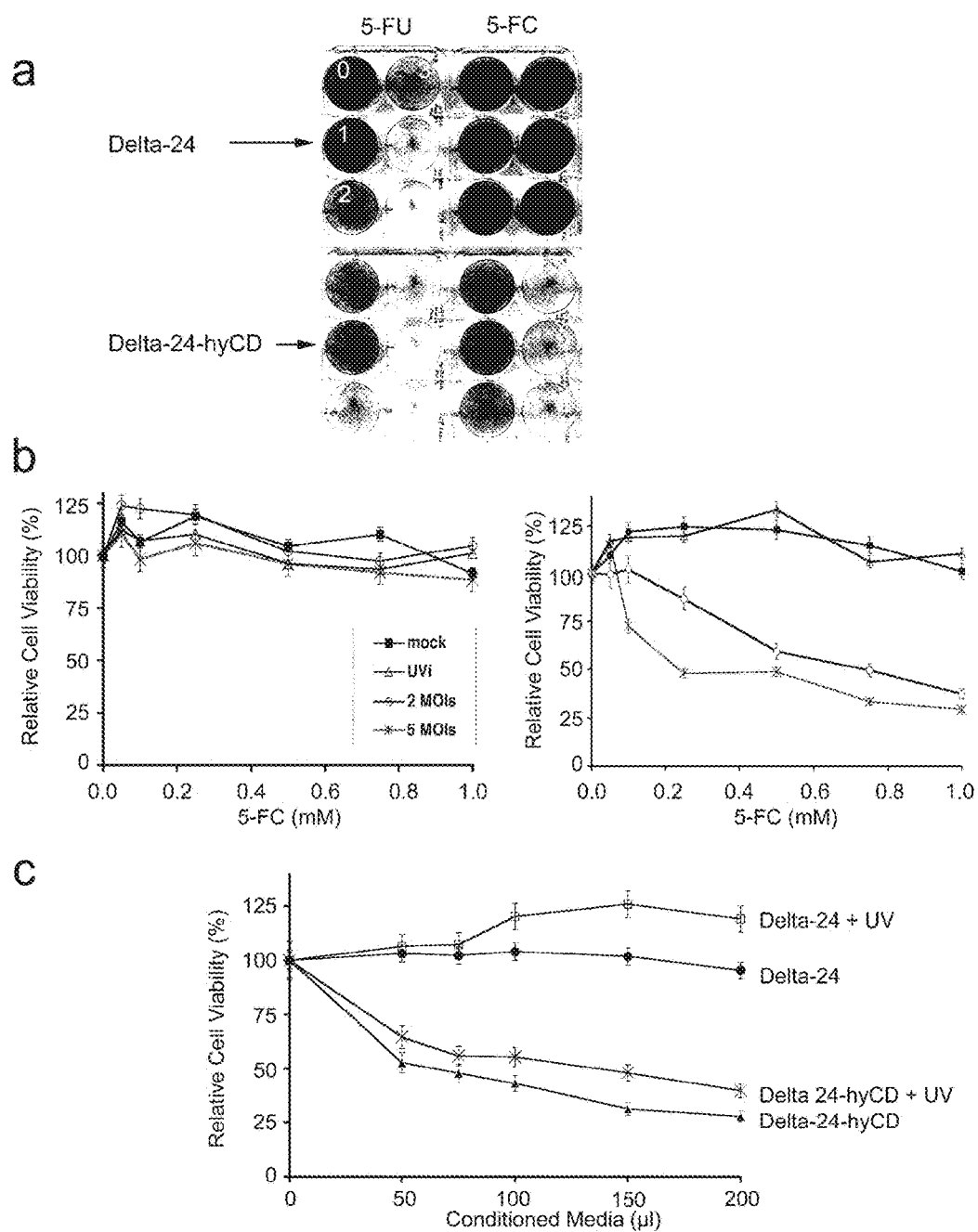
FIGS. 16A-16C shows in vitro antiglioma effect of Δ24-hyCD.

Next, to compare the induction of cell death after addition of 5-FC to Δ24 and Δ24-hyCD, an MTT assay was used to assess cell death and found that Δ24-hyCD essentially reduced the amount of virus required for cell killing by approximately 5-fold (FIG. 16B). These findings suggest an additive or perhaps a "bystander" effect. To accurately assess the existence of a bystander effect, U87MG cells were infected with Δ24 or Δ24-hyCD for 1 h, the plates were washed, fresh media with 5-FC was added, and the conditioned medium was collected 24 h later (FIG. 16C). This medium was treated with UV to inactivate any viral activity, and then added it to uninfected U87MG cell cultures. No effect was seen in 5-FC treated cells with either conditioned medium from Δ24 or from UV-inactivated Δ24. In contrast, cell death was evident in cells treated with conditioned medium from cultures treated with Δ24-hyCD+5-FC with UV inactivation. Therefore, a diffusible substance in the conditioned medium, presumably 5-FU, was responsible for the bystander effect.

Antiglioma Effect In Vivo.

To compare the therapeutic efficacy of Δ24 and Δ24-hyCD and 5-FC in vivo, U87MG xenografts were implanted intracranially in athymic nude mice. The U87MG cell line was selected because it produces glioma tumors in nude mice with highly predictable pathologic features and growth dynamics. In addition, the inventors have previously shown (Miller, 2002) that among three intracranial xenograft models of human glioma, including D54MG, U251MG, and U87MG, U87MG is the most refractory to CD/5-FC GDEPT. An implantable guide-screw system developed in the M. D. Anderson Department of Neurosurgery (Lal, 2000) was used to perform precise tumor implantation and intratumoral injection of a therapeutic agent. A study was performed similar to that previously reported (Fuego, 2000) with 3 injections of 1×10$^8$ plaque-forming units (pfu). The results are shown in. Three independent studies were performed, with 6 to 10 animals per group in each experiment. A significant improvement in the median survival (P<0.001) over control groups (34 and 38 days, respectively) was seen for both Δ24 (55 days) and Δ24-hyCD plus 5-FC (74 days). Additionally, there was a significant difference (P<0.002) in the median survival time between Δ24 and Δ24-hyCD plus 5-FC in these experimental groups.

Figure 17:
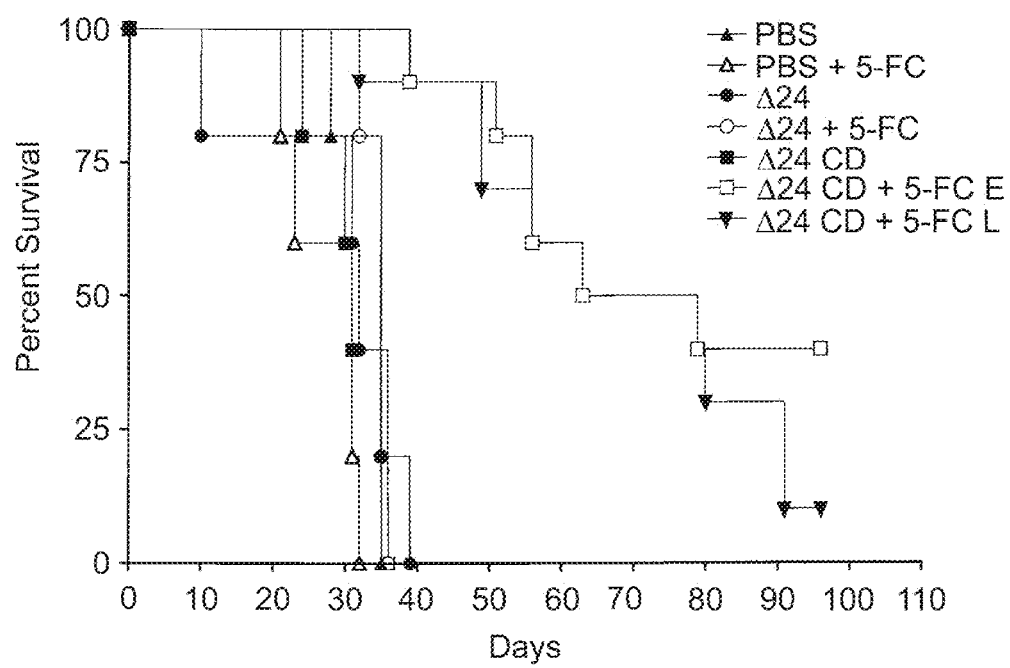
FIG. 17 shows the treatment with Δ24-hyCD+5-FC significantly improves survival of nude mice implanted with U87MG intracranial xenografts. Data are represented as Kaplan-Meier survival curves from the day of U87MG intracranial implantation (day 0) after intratumoral injection (day 3) with a single dose of experimental viral groups or PBS alone controls. 5-FC was administered on day 5 after treatment (E) or on day 15 after treatment (L). At both time points, the combination of Δ24-hyCD-mediated oncolysis and 5-FC effects resulted in a significant increase in survival compared with vehicle, Δ24 alone, or in combination with 5-FC, or Δ24-hyCD alone. The P value (determined by logrank test) compared Δ24-hyCD with the combination of Δ24-hyCD and 5-FC. Shown are results from a representative experiment. The median survival of the animals receiving Δ24-hyCD treated early (E=5 days) or late (L=15 days) were not different.

The anticancer effect of a single injection of 1×10$^8$ pfu of Δ24 was compared with a single injection of 1×10$^8$ pfu Δ24-hyCD, which is designed to minimize the oncolytic effect on survival by this rapidly expanding tumor system. Control animals were concomitantly treated with phosphate-buffered saline (PBS). Some of the treated animals were given 5-FC to determine if an added benefit would result. In all experiments, the median survival time for control groups (PBS or PBS+5-FC) was consistently between 30 and 36 days. For animals treated with Δ24 or with Δ24+5-FC, the median survival times were 35 and 32 days, respectively. Δ24-hyCD treatment without 5-FC led to a median survival time of 33 days, results which did not differ from the Δ24 or the Δ24+5-FC groups at a 0.05 level of significance. For the Δ24-hyCD-plus-5-FC condition, two 5-FC dose schedules were tested, "early" (5 days after viral injection) or "late" (15 days after viral injection). The combined median survival time of animals treated with Δ24-hyCD+5-FC was significantly longer than the median survival of animals treated with Δ24 alone or with 5-FC as well as the control animals (P<0.0001) FIG. 17. The experiment was arbitrarily terminated at day 98 by killing the long-term survivors: 4 animals (40%) in the early-5-FC treatment group and 1 animal (10%) from the late-5-FC treatment group. Median survival time was no different in the early-versus late-treated groups.

Histopathologic Examination of the Tumors and Brains.

After the mice were killed, the brains were removed, fixed in formalin, embedded in paraffin, and sectioned. Microscopic examination of control animal brains revealed non-infiltrative tumors growing in a sphere-like pattern, with a high level of cell proliferation, hypervascularity, and absence of necrotic areas. Lateral displacement of hemispheric structures and collapse of the ipsilateral ventricle indicated that a mass effect was responsible for the animals' deaths. The brains of animals that had survived for long periods, in contrast, showed complete tumor regression. Tumor sequalae, including dystrophic calcification and microcyst formation, were identified at the tumor implantation site in the right caudate nucleus (data not shown).

Examination of the brains of animals treated with Δ24-hyCD that died before the arbitrary 98-day termination point demonstrated that death resulted from mass effect of voluminous ellipsoid tumors. High magnification examination revealed a pattern of three distinct, concentric tumor zones: (1) an innermost central core consisting of necrosis and cellular debris (a pathologic finding that was not present in control tumors); (2) a middle zone consisting of large numbers of tumor cells that displayed prominent viral inclusions admixed with apparently intact tumor cells; and (3) an outer zone composed of intact tumor cells with a few scattered cells showing signs of infection. Immunohistochemical analyses revealed that Δ24-hyCD adenovirus was able to transduce late (hexon) genes, consistent with an active replication process. Notably, immunohistochemical staining for hyCD showed that Δ24-hyCD efficiently transduced exogenous hyCD protein into human glioma cells in vivo. Expression of the enzyme was detected in the cytoplasm of the glioma cells and correlated with cells infected with the adenoviral vector, as demonstrated by anti-yeast-CD antibody staining of glioma cells within the field of cells characterized by the presence of viral inclusion bodies. To examine the consistency of CD expression, two Δ24-hyCD-treated animals were killed at 7 and 14 days after tumor implantation. Immunostaining for CD was positive in the infected cells at both time points, indicating that Δ24-hyCD was able to transduce high levels of hyCD for at least 2 weeks after treatment in the U87MG animal model. Collectively, these observations demonstrate that Δ24-hyCD could infect and replicate in vivo and, more importantly, that Δ24-hyCD could efficiently and consistently transduce the hyCD gene. The combination of these effects resulted in significantly extending survival time.

Example 7

Ang-2-Mediated Regulation of VEGF

This study investigates the mechanisms underlying the Ang-2-mediated regulation of VEGF; to ascertain the role of Ang-2 expression in a dynamic tumor model of glioma angiogenesis; and to develop an effective treatment based on the simultaneous targeting of Ang-2 using oncolytic adenoviruses and/or antisense-VEGF. Mechanistically, the inventors found that Ang-2 downmodulates HIF-1 at the posttranscriptional level and inhibits HIF-1-induced transcriptional activation of VEGF expression. Preliminary data shows Tie2 expression in glioma cells and suggests that Ang-2 function is receptor-mediated.

A. Methods

Construction and Generation of the AdAng-2 and Delta 24-Ang-2.

Ang-2 cDNA (1,504-bp; Gene Bank, accession #AF 004327) which are incorporated herein by reference was amplified by RT-PCR using the following primers: 5'-TACT-GAAGAAAGAATGTGG-3' (forward) (SEQ ID NO:15) and 5'-TTAGAAATCTGCTGGTCGG-3' (backward) (SEQ ID NO:16) from HUVEC cells. Subsequently, Ang-2 cDNA was cloned into an expression cassette (CMV promoter, SV40 pA) in the shuttle adenoviral vector pΔE1sp1A (Microbix Biosystems). pΔE1sp1A-Ang-2 was cotransfected with the plasmid pJM17 (Microbix Biosystems) into human embryonic kidney cell line 293 (ATCC, Rockville, Md.). After cotransfection, individual viral plaques were isolated, and AdAng-2 identified by PCR and restriction enzyme digestion, and propagated in 293 cells. In addition, adenoviral plasmid, pBGH10-Ang-2, which has an expression cassette consisting of the CMV promoter, Ang-2 cDNA, and the SV40-pA in the deleted-E3 region of the adenovirus, was cotransfected with pXC1-Delta-24 encompassing the 24-bp deletion of the E1A region (923-946), corresponding to the region required for Rb binding-in 293 cells (Fuego et al., 2000). PCR and restriction analyses confirmed the E1A deletion and the insertion of the Ang-2 cDNA.

Exogenous Ang-2 Expression.

Western blot analysis was used to confirm the expression of the Ang-2 protein in U-87 MG, D54 MG and U-251 MG (data not shown) glioma cell lines. Secreted Ang-2 was detected by immunoblot analyses of conditioned media (CM) from AdAng-2 or AdCMV-treated U-87 MG cells. Exogenous Ang-2 was secreted in the media, mimicking the dynamics of the endogenous Ang-2 protein.

mRNA and Protein Expression.

RT-PCR analysis was performed on mRNA extracted from human glioma cell lines and cultures. Primers and conditions for the PCR reaction were published previously (Poncet et al., 2003).

Cell Lines:

To assess the effect of overexpression of Ang-2 in vitro, the inventors selected glioma cell lines having an 80% to 100% transduction efficiency of replication-competent adenoviral vectors and express VEGF-A (U-87 MG, U-251 MG, LN229, SNB19, and D54 MG) (Gomez-Manzano et al., 1995). U-87 MG cells have been stably transfected with antisense VEGF. The D54 MG cells expressing VEGF 165 and regulatable-Ang-2 expressing cell lines were developed as described in Ke et al. (2002).

Infection Conditions:

Infection of the cell lines will be carried out by dilution of viral stock to particular concentrations, addition of viral solutions to cell monolayers (0.5 ml per 60 mm dish), and incubation at 37° C. for 30 min with brief agitation every 5 min. This procedure will be followed with the addition of culture medium and return the infected cells to the 37° C. incubator.

Enzyme-Linked Immunosorbent Assay (ELISA):

Human VEGF ELISA analysis will be performed to quantify secretory VEGF165 in the conditioned media according to the manufacturer's instructions (R & D Systems, Minneapolis, Minn.).

Immunoblotting, Immunoprecipitation, and Northern Blot Assays:

Studies will be performed using commercial antibodies and as described in Gomez-Manzano et al., 2003 and Fueyo et al., 2000.

Immunohistochemistry.

VEGF-A, PCNA, αSMA will be detected by immunostaining Similar procedures will be used for the detection of CD34 (Novocastra, Newcastle, UK) and Ang-2 (Santa Cruz, Calif.). Alternative in situ hybridization methods are described in Brown et al., 2000. The presence of E1A and hexon adenoviral proteins in the treated xenografts will be assessed through immunohistochemistry. Paraffin-embedded sections from the mice tumors will be de-paraffinized and rehydrated through xylene and ethanol into PBS. Endogenous peroxidase activity will be quenched by incubation for 30 min in 0.3% $H_2O_2$ in methanol. Sections will be treated with goat anti-hexon (Chemicon Inc., Temecula, Calif.) or goat anti-E1A (Santa Cruz Inc., Santa Cruz, Calif.). Immunohistochemical staining will be performed using diaminobenzidine according to the manufacturer's instructions with the Vector laboratories ABC kits (Amersham).

Transcription Experiments:

Details on the constructs and methodology are described in Gomez-Manzano et al., 2003. For mutational analyses of the HIF responsive element the methodology described in Forsythe et al., (1996) will be followed. Briefly, the (−985) to (−939) sequence containing the 47-bp hypoxia response element will be amplify by PCR as a positive construct (5'-CCACAGTGCATACGTGGGCTCCAACAGGTC-CTCTTC CCTCCCATGCA-3') (SEQ ID NO:17) and using a mutated forward primer, the same region with a 3-bp substitution (bold and underlined above will be substituted for by AAA) will be amplified. These fragments will be inserted in the pGL2-Basic (Promega) for lucifase assays.

HIF-1 DNA-Binding Activity:

DNA-binding activity of HIF-1α was determined using an ELISA-solid phase system. Briefly, the procedure was performed as following: U-87 MG cultures were plated at a density of $10^6$ cell/100-mm dish; 20 h later cultures were treated with AdAng-2 or the adenovirus control AdCMV-pA at a dose of 80 MOIs, or were mock-infected. Two days after treatment parallel cultures were placed in a sealed modular incubator under hypoxic conditions (0.5% $O_2$) for 6 h. Nuclear extract was prepared as described in Gomez-Manzano et al. (2001). To quantify HIF-1 activation, TransAM HIF-1 transcription factor assay kit from Active Motif (Carlsbard, Calif.) was used. This consists of an ELISA-format assay where oligonucleotides containing a HRE motif are immobilized in a 96-well plate. The addition of anti-HIF-1α antibody, followed by a secondary HRP-conjugated antibody was assessed by spectrophotometry.

HIF-1 Protein Translation Assay:

Cells will be plated in 6-well plates and pretreated overnight with 25 µM 2ME2 or DMSO (0.025% vol/vol). Then, medium will be changed to methionine- or cysteine-free as well as serum free medium for 2 hrs. After this time, cells will be labeled by incubation with methionine- or cysteine-free medium containing $^{35}$S-methionine at a final concentration of 100 µCi/well at 37° C. for the proposed times. Subsequently, cells will be washed twice with ice-cold PBS, lysed, and subjected for immunoprecipitation using anti-HIF antibody and protein G-agarose beads.

Endothelial Cell Growth Assay and Endothelial Cell Migration Assay:

These studies will be performed as described in Gomez-Manzano et al., 2003.

Tube Formation Assay:

This assay will be performed using an in vitro angiogenesis kit (Chemicon, Temecula, Calif.) according to the manufacturer's instructions. Wells in a 96-well plate will be coated with ECMatrix solution, and $5\times10^3$ cells will be plated in triplicate wells in a volume of 50 µl of EGM (Clonetics Corp.) containing 2% FBS. The cells will be incubated for 18 h at 37° C., and tube formation will be evaluated by phase-contract microscopy. To determine the viability of cells in these assays, cells will be stained with Hoechst 33342 (5 µg/ml, Sigma) and propidium iodide (2.5 µg/ml, Sigma) for 5 min at 37° C. and analyzed by fluorescence microscopy.

Angiogenesis Assay in Chicken Embryos.

Fertilized chicken eggs (SPAFAS; Charles River Lab., Wilmington, Mass.) will be incubated at 37° C. at 55% humidity for 9 days. An artificial air sac will be created over a region containing small blood vessels in the CAM as described (Brooks et al., 1999). A small window will be cut in the shell after removing 3 ml of albumen. Filter disks (6 mm in diameter) will be coated with cortisone acetate in absolute ethanol (3 mg/mL). The CAM will be locally treated with filter disks saturated with a solution containing bFGF (50 ng/disk; R&D Systems, Minneapolis, Minn.) and VEGF121/rGel (at 1 or 10 nM), rGel (at 1 or 10 nM), or buffer (PBS). The filter will be placed on the CAM in a region with the lowest density of blood vessels, and in the vicinity, as reference, of a large vessel. Angiogenesis will be monitored by photography 3 days after treatment. Images will be captured using an Olympus stereomicroscope (SZx 12) and Spot™ Basic software (Diagnostic Instruments, Inc.). The relative vascular area will be determined by measuring the area taken up by blood vessels. This analysis will be performed on a Macintosh computer using the public domain NIH Image program (available on the Internet at rsb.info.nih.gov/nih-image). The number of blood vessel branch points will be quantify by two researchers, and compared to the treatment controls (Brooks et al., 1999).

Study of Ang-2 Modification In Vivo, Using the Chorioallantoid Membrane.

Data has shown that Ang-2 is responsible for disrupting the angiogenic process, primarily reducing branching. The inventors will study this effect further by stimulating angiogenesis using rhVEGf165 and bFGF, prior to Ang-2 treatment. It will be determined if Ang-2-mediated modulation of the angiogenic process in the CAM model overrides the VEGF or bFGF stimulus. For branching quantification, CAMs will be pictured using a stereomicroscope and a Sony Digital camera. Images will be analyzed using Adobe Photoshop 6.0. and number of branching points will be quantified. Vessel density will be quantified by using Scion Image 1.63.

DNA Constructs:

Regulatable vector constructs are based on the BD Tet-On gene expression system (Clontech). In certain aspects, a switchable Ang-2 expression system will be developed, based on the BD Tet-On Expression System from Clontech (Palo Alto, Calif.). A Tet-responsive Ang-2-expression cassette will be made by cloning Ang-2 cDNA into pTRE2 between BamHI and EcoRV (Clontech). Cell lines will be first transfected with the pTet-On vector and selected clones will be then transfected with pTRE2-Ang-2. Clones will be selected by determining Ang-2 expression under doxycycline (Dox) control, selecting optimal induction and low background. Establishing effective concentrations of Dox will be performed in a pilot study using 100 ng-1 µl/ml, and checking the expression of Ang-2 after infection/drug exposure. After determining the effective concentrations of Dox, the expression of Ang-2 will be analyzed at different time points following drug exposure, as well as at different time points following drug withdrawal.

Doxycycline Administration:

determination of the effective concentration of Dox (Clontech) in isogenic U-87 MG cells will be performed in a titration experiment using different dilutions (e.g., 1, 0.1, 0.001, 0.0001, and 0 µg/ml).

Engrafting Human Glioma Cells and Intratumoral Therapeutic Injection:

The methodology developed by Lal et al., 2000 will be used.

Quantification of Microvessel Density (MVD).

Experiments will be performed as described in Im et al., 2001,

Quantification of PCI and MPI.

At least 5 independent microscopic fields per tissue section will be analyzed to count PCNA-positive tumor cells and endothelial cells. Tumor cell proliferation and endothelial cell proliferation will be quantified in vascular hot spots that are identified by screening for areas with highest vessel density at low magnification. PCI will be determined by calculating the ratio between the number of microvessels that colocalized endothelial cell staining (CD34) and pericyte staining ($\alpha$-SMA).

TUNEL Histochemistry:

TUNEL histochemistry will be performed using an In Situ Cell Detection Kit, POD (Roche Diagnostics Co.).

Laser Scanning Cytometry (LSC).

LSC Analysis of Tumor Microvessels is being described in Davis et al., 2004.

CPE Assays:

The MOI resulting in the destruction of 50% of the cell monolayer (MOI50) will be determined for each virus (wild-type Ad300, UV-inactive-Ad, Delta-24, Delta-24-Ang-2, AdAng-2) in vitro. At indicated time points post-infection, the cells are either stained with crystal violet or photomicrographed. For staining with crystal violet, the medium is removed and cells are fixed for 3 min in 3.7% formaldehyde at room temperature. The formaldehyde is discarded, and the cells are incubated for 3 min in 1% crystal violet. After staining, the crystal violet solution is removed, and the cells are rinsed twice in 3 ml of water and then air-dried. A Trypan blue exclusion test will be performed as described in Fueyo et al., 2000.

Viral Replication Experiments:

Viral production will be quantified by TCID50. At the required time after infection, the cells will be scraped into culture medium and lysed with 3 cycles of freezing and thawing. The Tissue Culture Infection Dose50 method to determine the final viral titration. Briefly, the cell lysates are clarified by centrifugation and the supernatants are serially diluted in medium for the infection of 293 cells in 96-well plates. The cells are analyzed for CPE 10 days after infection. Final titers are determined as plaque-forming units, according the validation method developed by Quantum Biotechnology (Carlsbad, Calif.). Exemplary methods are described in Fueyo et al. (2003). In certain aspects, viral titers will be calculated at 48 and 96 h after infection in a diverse panel of proliferating normal cells and tumor cells (Fueyo et al., 2000). These time points should test the consistency of the ability or inability of the adenoviruses to replicate. Viral titers will be compared between Delta-24-Ang-2, wild-type adenovirus Ad300, and Delta-24 in each cell line.

To Perform U-87 MG and D54 MG Intracranial Implantation.

The implantable guide-screw system of Lal et al. (2000), as described above, for establishing intracranial xenografts in nude mice and for treating engrafted tumors with intratumoral therapies (such as gene or viral therapies) will be used.

Therapeutic Index of Delta-24-Ang-2 Adenovirus.

The inventors will assess the effect of adding Ang-2 on the replication profile of Delta-24 in gliomas in vitro. Studies will be performed in panel of glioma cells (Tie2(+): U-87 MG, D54 MG, LN229 and SNB19; Tie2(−): U251MG) and in quiescent and proliferating normal human astrocytes (NHA).

B. Results

The inventors have constructed a replication-deficient adenoviral vector, AdAng-2 that efficiently transduces Ang-2 into human glioma cells, and produced and secreted Ang-2. Expression of ectopic Ang-2 results in a significant downregulation of VEGF protein and RNA levels in U-87 MG cell line. The data derived under normoxic and hypoxic conditions indicate that this modulation occurs on the transcriptional level, probably by regulating HIF-1α protein levels, and subsequently the DNA-binding activity of this transcription factor. Of interest is the fact that studies revealed that not all of the glioma cell lines tested were as sensitive as U-87 MG to the effect of Ang-2. For example whereas transferring Ang-2 to D-54 MG cells resulted in decreased VEGF and HIF-1 levels, U-251 MG cells were resistant to this effect. Demonstrating the existence of Tie2 in glioma cells, showed that this receptor is present in the two sensitive cell lines but was undetectable in the U-251 MG cell line. The inventors have studied the nature of the transduction signaling that connects the Tie2 receptor to the regulation of HIF-1 activity. Data have shown that Ang-2 downmodulates p42/p44 MAPK activity. In vitro studies showed that Ang-2 interferes with the formation of capillary-like structures by human endothelial cells. Finally, other data show that the effect of Ang-2 on VEGF expression can be augmented by combining AdAng-2 with an adenovirus expressing an antisense VEGF cDNA.

Figure 18:
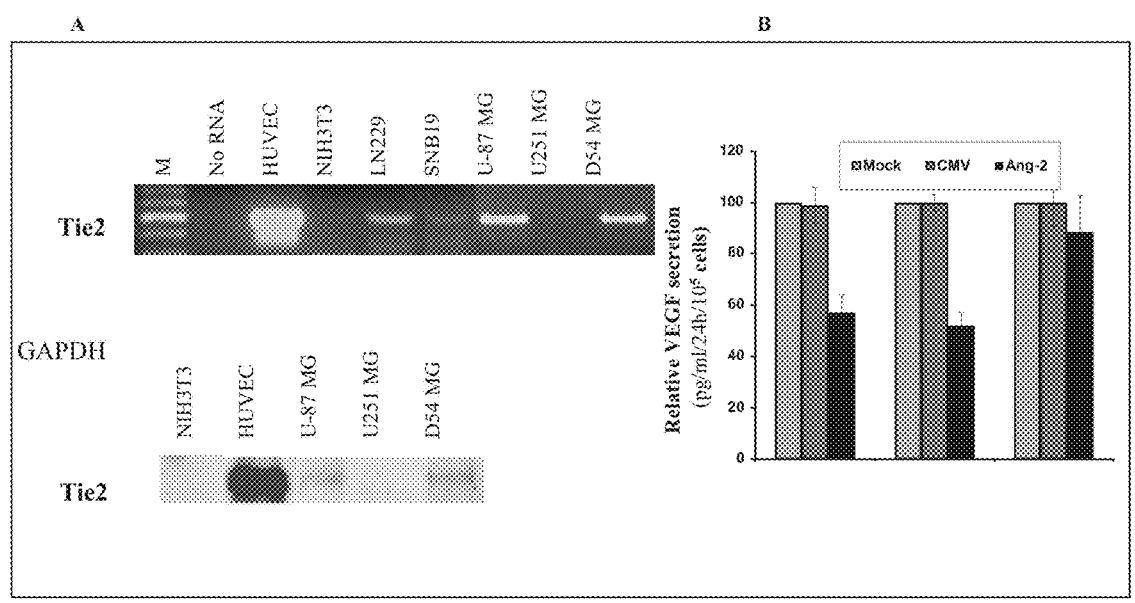
FIGS. 18A-18B.

Tie2 mRNA and protein are expressed in glioma cultures FIG. 18. A 503-bp fragment amplification was obtained from RNA extracted from HU-VEC-C, U-87 MG and D-54 MG cells; however transcript amplification was not detected in U-251 MG cells or NIH3T3 cells (negative control). Anti-human Tie2 antibody recognized a 140-kDa band in the membrane proteins subfraction of HU-VEC-C, U-87 MG and D-54 MG, but not in U-251 MG. Cytosol fraction proteins were negative for Tie2 expression. Immunoprecipitation analysis confirmed these results (data not shown). These data are consistent with the data from mRNA analyses and provide compelling evidence of the effects of Ang-2 in U-87-MG cells. Previous observations suggest that expression of Tie2 is not exclusively in endothelial cells. Valable et al. (2003) have recently reported Tie2 RNA and protein expression in neurons, and Poncet et al. (2003) reported the receptor expression in colon cells, colon carcinoma, and peripheral nervous system. These results are consistent with data showing that Ang-2 affects the regulation of HIF-1α activity in U-87 MG and D-54 MG cells, but not in U-251 MG.

Ang-2-Mediated Modulation of VEGF-A.

ELISA was performed to measure secreted VEGF protein levels in the media from Ang-2-treated U-87 MG, D54 MG and U-251 MG human glioma cell cultures. VEGF levels in Ang-2-treated cells were reduced by 40% in U-87 MG and D54 MG cell lines, compared with mock- and AdCMV-treated cells (P<0.001, t-test, double sided). However, no significant decrease compared to control-treated cells (P>0.5, t-test, double sided) was detected in U-251 MG cells treated with Ang-2, which is correlated with the pattern of Tie2 expression. In addition, transfer of Ang-2 resulted in decreased VEGF RNA expression in U-87 MG cells compared with mock- and AdCMV-treated cells. These studies suggest that Ang-2 decreases the level of secreted VEGF protein at the transcriptional level and points to the existence of a regulatory loop between Ang-2 and VEGF.

Mechanisms of Ang-2-Mediated Downregulation of VEGF.

Because HIF-1α is one of the most important transcriptional regulators of VEGF expression, the inventors examined its expression after transfer of Ang-2. Results showed that the exogenous expression of Ang-2 in U-87 MG or D54 MG decreased HIF-1α at the protein level. However, and consistent with null Tie2 expression, the expression of HIF-1α was not significantly modified when U-251 MG were treated with AdAng-2. In addition, transcription experiments using the luciferase reporter gene driven by the VEGF promoter showed that ectopic Ang-2 decreased promoter activity when the fragment containing the HIF-1α binding site was tested. These data suggest that Ang-2 decreases HIF-1α stimulation of VEGF expression. Northern Blot analyses showed that HIF-1α RNA levels were not significantly changed in AdAng-2-treated U-87 MG cells compared with mock- or AdCMV-treated cells.

Ang-2 Regulation of p53 Expression.

Because p53 is a regulator of VEGF, the inventors determined if the transfer of Ang-2 regulates p53 expression. Western blot analyses of U-87 MG human glioma cell lysates (wild-type p53) three days after treatment with AdAng-2 did not affect the basal levels of p53 (data not shown). A second line of evidence was provided from Luciferase experiments, which showed that the VEGF promoter construct containing an Sp1/p53-binding site is not sensitive to Ang-2.

Figure 19:
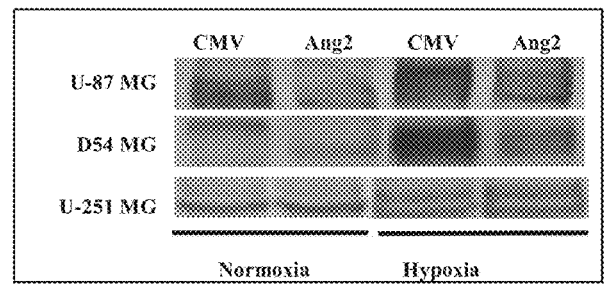
FIG. 19 shows Ang-2 reduced expression of HIF-1α in glioma cells. (Western Blot, Nuclear extracts). Protein nuclear levels of HIF-1α decreased after Ang-2 transfer, compared with control-treated cells in normoxia (21% O2) and hypoxia (1% O2) conditions in U-87 MG and D54 MG cells. Note that the expression of HIF-1α, did not modify after Ang-2 transfer into U-251 MG cells, CMV, AdCMV; Ang-2, AdAng-2.
Figure 20:
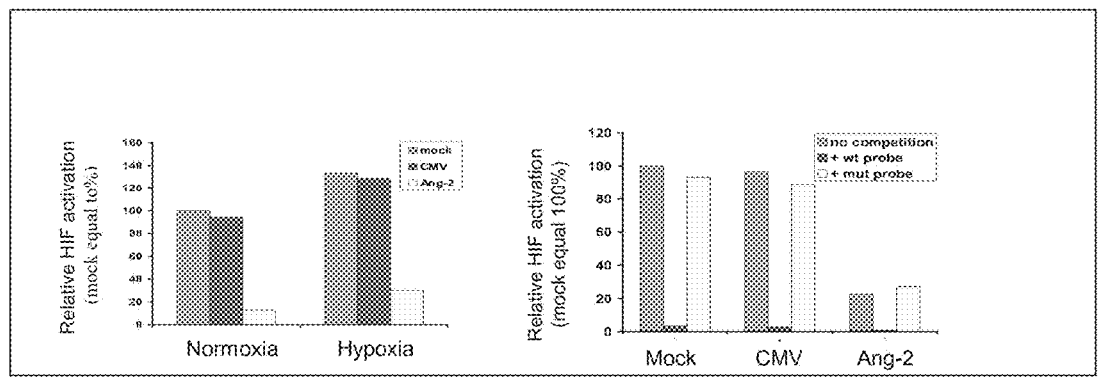
FIG. 20 shows Ang2 downmodulates HIF-DNA binding activity. U-87 MG cells were treated with AdAng2 (Ang2), AdCMV-pA (CMV) or were mock-infected. Equal amounts of nuclear extracts were analyzed for HIF-DNA binding activity in a hypoxic or normoxic setting. Competitive experiments were performed using wild-type (wt) or mutant (mut) oligonucleotides. Data are represented as the mean of three independent experiments (SD was less than 15%).

The inventors investigated the effect of Ang-2 treatment on the DNA-binding activity of HIF-1α using an ELISA-solid phase system. Under hypoxic conditions, the basal activity of HIF-1α increased (FIG. 19). HIF-DNA binding activity was attenuated in the Ang-2-treated samples compared with mock- and AdCMV-pA-treated cultures. The effect was observed under normoxic and hypoxic conditions. For competition experiments, mutant or wild-type oligonucleotides were added to the well prior to the addition of nuclear extract. Wild-type, but not mutant, oligonucleotide modified the activity of HIF in the samples, demonstrating the specificity of the reaction. These data are consistent with and support our previous data, which suggest that Ang-2 downmodulates VEGF levels by regulating HIF-1α.

Ang-2 Inhibits Ang-1-Mediated MEK/ERK Phosphorylation.

Figure 21:
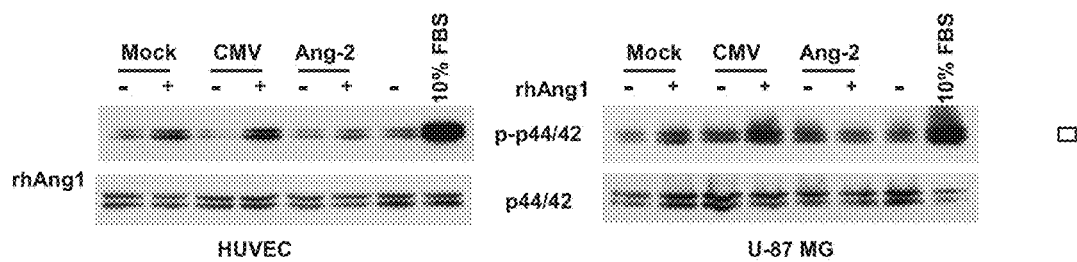
FIG. 21 shows Ang-2 inhibits Ang-1 mediated MEK/ERK phosphorylation of U-87 MG glioma cells. HUVEC and U-87 MG cells were mock-, AdCMV- or AdAng-2-Infected. 24 hours later they were overnights serum-starved, and then stimulated with rhAng-2 for 10 min. Cell lysates were collected and analyzed by Western blotting for expression of phospho- and total p42/p44 MAPK. Ang-1 increased ERK 1/2 phosphorylation what was inhibited by the viral-transduced Ang-2.
Figure 22:
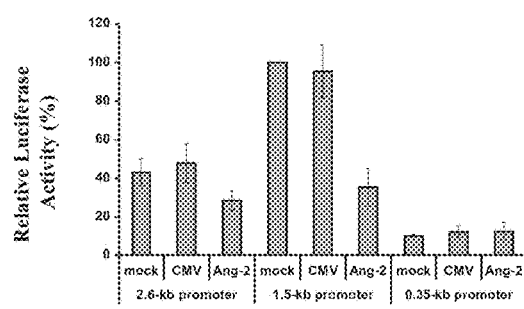
FIG. 22 shows Transcriptional modulation of VEGF by Ang-2 is probably related to the downmodulation of HIF-1α proteins levels (U-87 MG). Luciferase activity is expressed as relative to the VEGF-1.5 kb promoter activity in mock-treated cells (equal to 100%). The result shows that Ang-2 decreased the transcriptional activity of the two constructs that contain the HIF-1α binding site (2.6 and 1.5 kb promoters; Gomez-Manzano et al., 2003), however did not modified the activity of the 0.35-kb promoter, susceptible to p53/VHL regulation.
Figure 23:
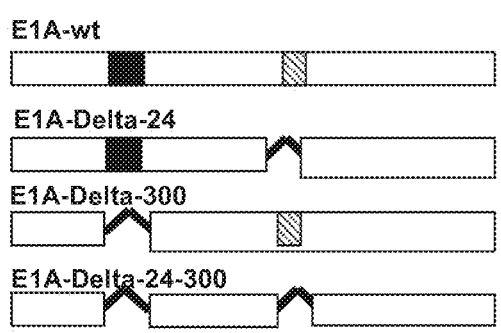
FIG. 23 is a presentation of the E1A region of wild-type (wt), Delta-24, Delta-300 and Delta-24-300 adenoviruses. Solid area: p300 binding area; hatched area: Rb Binding area.
Figure 24:
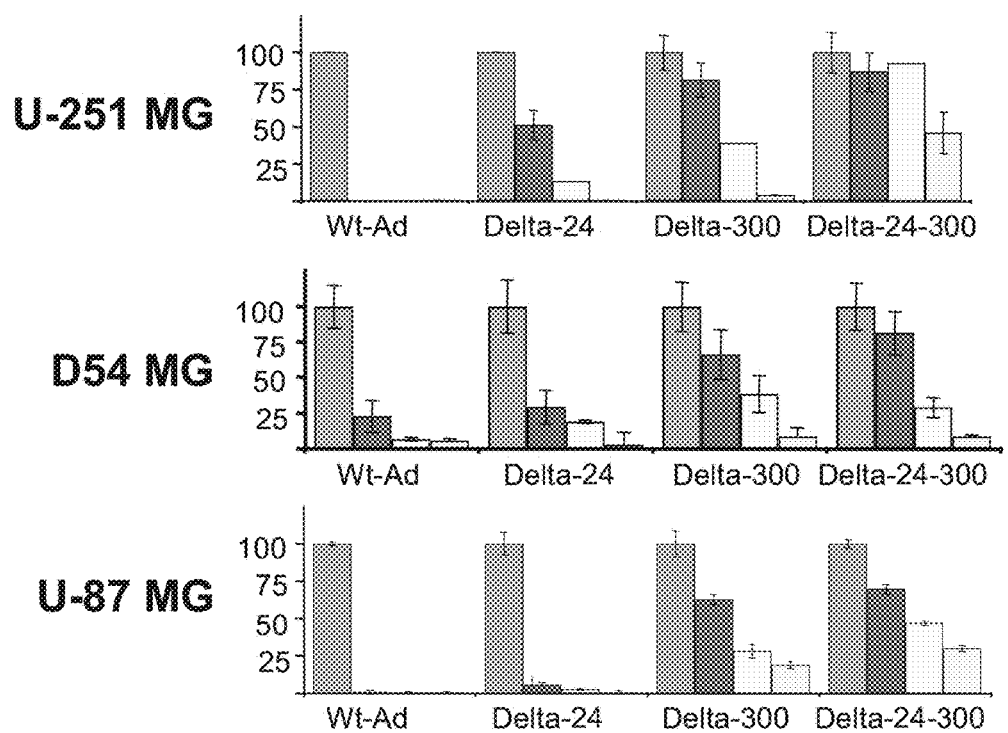
FIG. 24 shows Anti-glioma effect of Delta-24-300, Delta-24, Delta-300 and wt-Ad in vitro. Cells were infected at indicated MOI and viability was assessed ty Trypan blue exclusion. Data shown as the relative percentage of cells alive with UVi-infected cultures equal to 100%
Figure 25:
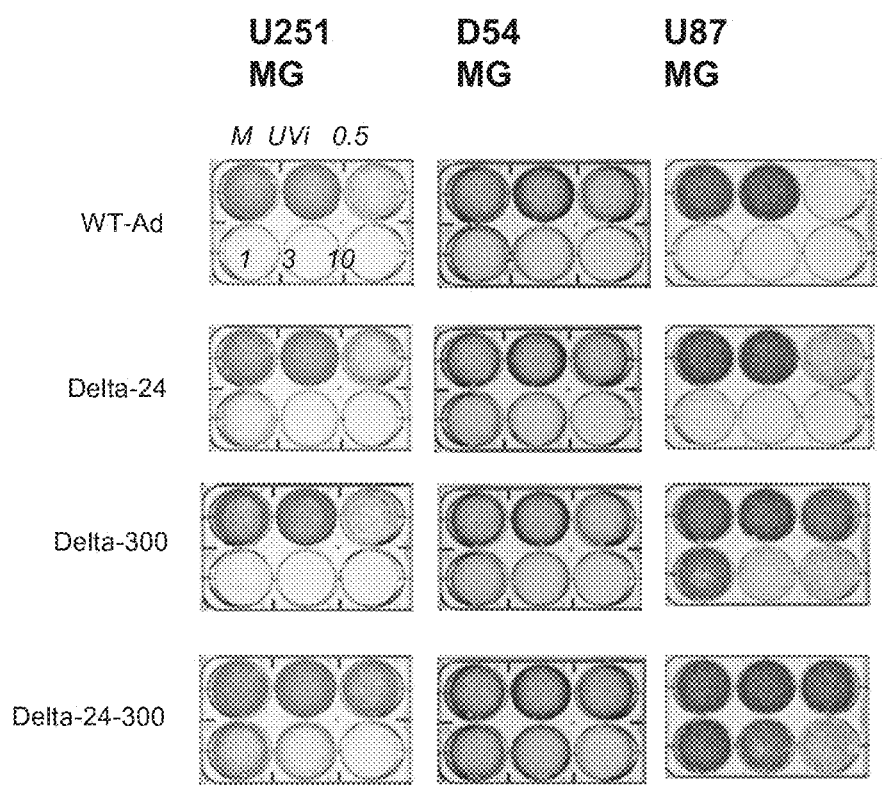
FIG. 25 shows Anti-glioma effect of Delta-24-300, Delta-24, Delta-300 and wt-Ad in vitro. Cell viability was assessed by crystal violet staining after viral infection with a range of MOI, 0.5-10 MOI, as indicated in top left panel. M: mock-infection; UVi. UV-inactivated wt-Ad.
Figure 28:
FIG. 28 shows chimeric fiberprotein. Tail: N-terminal of Ad5 fiber protein (1-83aa); T4 febritin; bacteriophage T4 fibritin helican domain and fold on (233-487 aa); Linker: G4SG4SG4S linker; Ligand: PEPHC1 (HFLIIGFMRRAL-CGA (SEQ ID NO:19).
Figure 29:
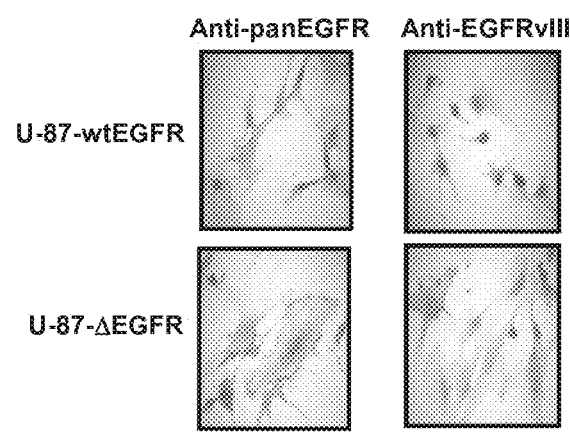
FIG. 29 shows infectivity assay of human mesenchymal stem cells. Light (left) and fluorescence (right) microscopy of the same field of human mesenchymal stem cells at the indicated hours after infection with a replication-deficient adenovirus carrying the GFP cDNA (Ad-GFP) or the tropism-modified Ad-GFP adenovirus (Ad-GFP-RGD) at 100 MOI.

FIG. 21 shows Ang-2 inhibits Ang-1-mediated MEK/ERK phosphorylation in glioma cultures. The Ang-2/Ang-1/Tie2 system has been studied in endothelial cells, and different pathways have been reported as involved in the cascade signaling; these include phosphotidylinositol 2-kinase (PI3-K), focal adhesion kinase, Raf/Ras/mitogen-activated protein kinase (MAPK), and Dok-R/Dok-2/Nck/Pak (Yoon et al., 2003). On the other hand, receptor-mediated HIF-1 regulation has been shown to occur via Ras/MEK/MAPK and PI3K/Akt/FRAP kinase cascades (Bilton and Booker, 2003). These cascades modulate protein synthesis and/or transcriptional activation. Initial results suggest that Ang-1 induces MEK/ERK stimulation in glioma cells. To measure MAPK activity, the inventors measured the degree of phosphorylation of two MAPKs, ERK1 (p44MAPK) and ERK2 (p42MAPK). Consisting with previous reports (Kim et al., 2002), rhAng-1 (100 ng/ml) increased ERK1/2 phosphorylation of HU-VEC-C endothelial cells. Of interest, treatment of U-87 MG with rhAng-1 also increased ERK1/2 phosphorylation. Co-treatment with adenoviral-transduced Ang-2 inhibited the Ang-1 induced ERK1/2 phosphorylation. These data suggest that Ang-2/Ang-1 system exerts its effect through a receptor-mediated mechanism in glioma cells.

Effect of Ang-2 Overexpression on Angiogenesis In Vitro:

These studies were performed to elucidate the role of Ang-2 role in the process of angiogenesis. In these experiments, HU-VEC-C treated with rhAng-2 (400-800 ng/ML) for 18 h, lost their ability to form vascular-like structures was inhibited compared with control (BSA)-treated endothelial cells. These results were not caused by decreased cell viability, as assessed by an endothelial cell growth assay performed under similar conditions. Importantly, tube formation was also compromised when endothelial cells were incubated with conditioned media from AdAng-2-treated U-87 MG cells, (compared to HU-VEC-C cells incubated with conditioned media from AdCMV-treated U-87 MG cells).

Modulation of VEGF Expression by Ang-2 and Antisense VEGF-A.

It has been shown that after U-87 MG malignant glioma cells were infected with AdαVEGF incorporating the cDNA of VEGF in an antisense orientation the level of the endogenous VEGF mRNA was reduced and the production of the targeted secretory form of the VEGF protein was drastically decreased (Im et al., 1999). ELISA experiments were performed to analyze the effect on secreted levels of VEGF-A from a combined treatment combining Ang-2 transfer with antisense VEGF. U-87 MG cell lines were co-infected with AdAng-2 (50 MOIs) and AdαVEGF (50 MOIs), and levels of secreted VEGF-A were quantified in the conditioned media. The combined treatment of Ang-2 and αVEGF resulted in a greater decrease of secreted VEGF (33.1%), compared with the results from a single treatment (Ang-2 or αVEGF alone, 71.4% or 79%, respectively), or control (AdCMV; 100MOIs, equal to 100%).

Characterization of the Modulation of VEGF by Ang-2.

The VEGFs and the angiopoietins seem to play complementary and coordinated roles in vascular development (Yancopoulos, 2000). Tumor cells can initially home in and grow by co-opting host vessels. However, this diversion of the host vessels is sensed as inappropriated and the vessels regress (Holash et al., 1999a and 1999b). As vessels die, the tumor becomes secondarily avascular and hypoxic, resulting in marked induction of tumor-derived VEGF and robust new angiogenesis (Holash et al., 1999a and 1999b). In this setting, Ang-2 expression seems to correlate with vessel destabilization, apparently leading to vessel regression in the absence of VEGF, or robust new angiogenesis following induction of VEGF (Yancopoulos, 2000). Such a coordinated effect of VEGF and Ang-2 in angiogenesis implies certain mechanisms regulating temporally and spatially the expression of both molecules, affording their concurring or subsequential effect on tumorigenesis.

Studies conducted by the inventors indicate that Ang-2 regulates the expression of VEGF through transcriptional mechanisms and data support the fact that downregulation of HIF-1α by Ang-2 is the main factor in the regulation of VEGF (Forsythe et al., 1996, Carmeliet and Jain, 2000). The inventors have demonstrated the existence of the Tie2 receptor in glioma cells, and have collected data suggesting the involvement of transduction signaling in the Ang-2 effect. The existence of different levels of Tie2 in glioma cell lines offers the possibility of 1) testing the effect of Ang-2 in two different scenarios, cells expressing Tie2 (Tie2+) and cells not expressing Tie2 (Tie2−), and 2) the possibility of confirming Ang-2-mediated effects in glioma cell lines not only by adenoviral-transduced Ang-2, but also by treatments using CM from AdAng-2-treated cells and/or direct treatment with rhAng-2.

Study of HIF-1α Protein Levels in Glioma Cells.

Previous results show that Ang-2 downregulates the protein levels of HIF-1α but not the RNA levels in U-87 MG cells. This is consistent with the inventors current understanding that the primary regulation of HIF-1α is posttranscriptional (Semenza, 2002). Preliminary data show that treatment of Tie2 positive cells (U-87 MG and D54 MG) with AdAng-2 decreased HIF-1α nuclear protein levels, but no significant decrease in HIF-1 levels was seen when U-251 MG (undetectable Tie2) was treated. These data will be expanded so that total and nuclear HIF-1α protein levels from several glioma cell lines will be assessed, including U-87 MG, D-54 MG, LN229 and U-251 MG cells, at several time points (24 h, 48 h, and 72 h) after Ang-2 transfer so that consistent results under normoxic and hypoxic conditions (1% $O_2$) can be achieved. The results will be compared to glioma cells treated with vector control (AdCMV), vehicle control (mock), positive control (Adp53), and specificity control (AdGFP); and the results will be confirmed using CM from glioma cells treated with AdAng-2 (or controls as above), or rhAng-2 (with and without previous stimulation of rhAng-1). For the studies using CM from glioma cells the inventors will use transwell cluster plates to maintain co-cultures of Ad-Ang-2-treated glioma cells with untreated glioma cells (Gomez-Manzano et al., 2003). This methods allows continuous exposure of untreated cultures to secreted Ang-2, what is not feasible using rhAng-2. Another variable that will be taken into consideration is the importance of in vitro cell density, even in normoxic conditions (Sheta et al., 2001). For that reason, studies will be performed under similar cell density, and low-density cultures will be used as controls for interpretation of the data. Also, HIF-1α RNA levels will be examined in this panel of glioma cells to confirm previous results showing that Ang-2 dowmodulates HIF-1α at the postrancriptional level.

To obtain a better understanding of the processes involved in HIF-1α inhibition of Ang-2, the effect of Ang-2 on HIF-1α postranscritional regulation will be studied. The Ang-2 effects on HIF-1α protein stability by using the protein translation inhibitor cycloheximide (CHX), as describe previously (Mabjeesh et al., 2003). In the presence of CHX, new protein synthesis is inhibited, so that HIF-1α protein levels predominantly reflect the degradation process of HIF-1α. AdAng-2-treated glioma cells (or treated with control adenoviruses, as above) will be exposed to CHX for 0 to 40 min and HIF-1α protein levels will be analyzed by Western blotting. Densitometry studies of HIF-1α protein levels normalized with actin protein levels will allow us to obtain results on the role of Ang-2 in the stability of HIF-1α protein.

Ang-2 Acceleration of HIF-1α Ubiquitination and Degradation.

AdAng-2-treated U-87 MG cells will be studied in the presence or absence of the proteosome inhibitor (10 µM for 4 hours). It is expected that in AdCMV-treated cells, MG132 will result in enhanced HIF-1α protein levels and multiple higher molecular weight species (poly-ubiquinated HIF-1α protein conjugates). If Ang-2 is involved in HIF-1α protein degradation, MG132 will restore the inhibitory effect of Ang-2 on HIF-1α protein levels.

Ang-2 Effects on HIF-1α Protein Translation.

U-87 MG cells will be labeled with $^{35}S$ methionine when treated with AdAng-2 (or control adenoviruses) for 0 to 120 min. After 15 min of labeling, HIF-1α protein levels will be compared by immunoprecipitation (HIF-1α antibody) and autoradiography. If Ang-2 decreases the synthesis of HIF-1α, the signal will be higher in Ang-2-treated than in the adenovirus control-treated cells.

Analyses of Ang-2-Mediated Modulation of VEGF Promoter Activity.

Initial results indicate that Ang-2 regulates VEGF at the transcriptional level only when VEGF-promoter constructs containing the HIF-1α binding site are present, as demonstrated in U-87 MG cells. Because preliminary data suggest that HIF-1α could be the primary mediator of Ang-2-mediated modulation of VEGF promoter activity, HIF-1α binding site will be inactivated in the VEGF promoter by mutation (Forsythe et al., 1996). A 3-bp substitution in the HIF-1α responsive element should eliminate HIF's mediation of transcription.

Transcriptional Mechanism Involved in the Ang-2-Mediated Regulation of HIF-1α.

The Ang-2/Ang-1/Tie2 system has been studied in endothelial cells, and different pathways have been reported as being involved in the cascade signaling; these include PI3-K/Akt/mTor, FAK, Raf/Ras/MAPK, and Dok-R/Dok-2/Nck/Pak (Yoon et al., 2003). On the other hand, receptor-mediated HIF-1 regulation has been shown to occur via Ras/MEK/MAPK and PI3K/Akt/FRAP kinase cascades (Bilton and Booker, 2003). These cascades modulate protein synthesis and/or transcriptional activation. Initial results suggest the role of Ang-2/Ang-1 to modulate the phosphorylation status of MEK/ERK in glioma cells. To measure PI3-K activity, phosphorylation state of the downstream effector will be assessed, Akt, as previously described (Gomez-Manzano et al., 2003). Studies will be undertaken using adenoviral-transduced Ang-2, and also using rhAng-2 and CM from cells that have been treated with AdAng-2. The inventors use established co-cultures using transwell cluster plates of Ad-Ang-2-treated glioma cells with untreated glioma cells (Gomez-Manzano et al., 2003). This strategy will allow continuous exposure of untreated cultures to secreted Ang-2, which is not feasible using rhAng-2.

Study of the Mechanistic Link Between Tie2 and Ang-2 in Glioma Cells.

Two approaches are proposed to address the importance of Tie2 in the Ang-2/Ang-1 functionality. First, the phosphorylation status of Tie2 receptor in glioma cells will be analyzed after rhAng-2 or CM from cells infected with AdAng-2, with and without previous Ang-1 stimulation. In the second approach, competition studies will be performed using Tie2 neutralizing antibody (R&D Systems). Briefly, human glioma cells (HUV-EC-C as positive control, NIH3T3 as negative control) will be treated with Ang-1, and with Tie2 neutralizing antibody (BSA as control). The phosphorylation status of MEK/ERK will be examined (as well as the phosphorylation of Akt, it plays a role in the glioma system). It is comtemplated that blocking the effect of Tie2 will have a similar result as the effect of Ang-2 on inhibiting the phosphorylation status of MEK/ERK. These data directly connect Ang-1 to MEK/ERK in human glioma cells through Tie2, and indirectly will connect Ang-2 in this system.

Effect of the Overexpression of Ang-2 on Angiogenesis In Vitro.

Studies will be performed on the biologic significance of Ang-2 overexpression in human glioma cells to elucidate the role of Ang-2 in the glioma-mediated process of angiogenesis. Both human glioma and human endothelial cells will be used. Firstly, Ang-2 will be transferred, using AdAng-2, to human glioma cells and collect the conditioned media. Then, endothelial cells will be incubated with this conditioned media, and different assays will be used to analyze their phenotypes. Conditioned media from glioma cells treated with AdCMV, AdGFP, or mock treated, will be used as controls.

Secondly, rhAng-2 will be used to examine the effect of Ang-2 on the dynamic phenotype of endothelial cells (growth, migration, formation of channels) independently from other players in angiogenesis, such as VEGF. For this second approach, vehicle (BSA), rhVEGF (positive control), and rhAng-1 (control for specificity) will be used as controls.

Endothelial Growth, Endothelial Migration, and Channel Formation.

Endothelial cells will be incubated with conditioned media from Ang-2-treated glioma cells to analyze endothelial growth and tube formation assays, their migration towards conditioned media from Ang-2-treated cells will be quantified (migration assay), and the modulation of the effect of Ang-2 will be also assessed by using stimulators of angiogenesis, such as VEGF, or by inhibiting VEGF. rhVEGF protein and anti-human VEGF monoclonal antibody (0 to 1 mg/ml, mouse IgG2B isotype, R&D Systems) will be used as controls. In addition, studies will be performed by pretreating endothelial cells with rhAng-1, prior to the incubation of the cells with conditioned media from glioma-treated with Ang-2. This procedure will allow one to ascertain if Ang-1 rescues the Ang-2-mediated regulation of the endothelial cell phenotype.

Ang-2-Mediated Effect on Endothelial Growth, Migration, and Channel Formation.

Because Ang-2 binds the Tie2 receptor and inhibits pro-angiogenic signals, strategies blocking Tie2 may result in an effect similar to that caused by the overexpression of Ang-2. The inventors will analyze the phosphorylation status of the Tie2 receptor (compared with basal levels) in endothelial cells after incubating them with rhAng-2 or with conditioned media from glioma cells treated with AdAng-2. Because conditioned media from AdAng-2-treated glioma cells should contain low levels of VEGF protein, the phosphorylation status of the VEGFR-2 receptor (compared with basal levels of the protein) on endothelial cells will be assessed after being incubated with conditioned media. rhAng-1 protein will be used as positive control for Tie2, and rhVEGF165 for VEGFR-2 phosphorylation analyses. A dose-dependence study will be conducted using Tie2 blocking antibody (R&D Systems) and examine Tie2's effect on the growth and migration of endothelial cells, and on the ability of endothelial cells to form channels in vitro. Studies will also be performed with Ang-2 and Ang-1 treatment to determine if Ang-1 rescues the Ang-2-mediated regulation of the endothelial cell phenotype.

Construction and Generation of a Regulatable Ang-2 Expression Adenovirus.

To determine the effect of Ang-2 induction during tumor vascularization, a switchable Ang-2 expression system was developed, based on the Adeno-X Expression System from Clontech (Palo Alto, Calif.). A Tet-responsive Ang-2-expression cassette was made by cloning Ang-2 cDNA into pTRE-Shuttle2 (Clontech). Recombinants were identified using restriction analyses and PCR. The Ang-2 expression cassette was excised from pTRE-Shuttle2 and ligated to Adeno-X Viral DNA (the adenoviral genome). When the "Tet-On" expression system was employed, the expression of Ang-2 by tumor cells was induced when doxycycline is added to the culture.

Ang-2 inhibits angiogenesis in vivo (CAM model). The inventors also wanted to know if Ang-2 overexpression interferes with the process of angiogenesis in vivo. For this purpose, CAMs were treated either with rhVEGF (200 ng/ml per egg) or rhAng-2 (200-800 ng/ml per egg). Control CAMs were treated with a 0.5% BSA solution (vehicle for Ang-2). Vascular responses were assessed 72 h later. CAMs treated with BSA displayed the typical vascular pattern of a 12-day-old normal CAM, with thin vessels running parallel to each other in a leaf-like pattern. Ang-2 treatment dramatically decreased newly sprouting angiogenic vessels, with no hemorrhagic areas. As expected, VEGF stimulated a clearly visible angiogenic response in CAMs (data not shown). This study suggests that the overexpression of Ang-2 disrupts the formation of new vessels.

Vascular Development and Growth Kinetics in a Human Glioma Intracranial Animal Model.

The inventors have performed a time point analysis of the evolution of angiogenesis in a U-87 MG animal model and established correlations between histology and growth patterns in the xenografts. The inventors have studied the Ang-2 expression pattern in this intracranial glioma model. After intracranial injection of $5 \times 10^5$ U-87 MG cells into the right basal ganglia of nude mice, the tumors grew from 0.02 mm$^3$ on day 4 to 100 mm$^3$ by day 20. All animals died by day 30 post-implantation. Serial temporal examination of the brains of tumor-bearing animals showed central necrosis of the xenografts within 4 days of implantation. At that time, the vessels surrounding the tumor displayed changes in morphology, including an enlarged diameter and a disorganized structure. There was also evidence of vessel interaction with peripheral tumor cells. These vessels also showed high degree of Ang-2 expression. In addition, glioma cells were also strongly positive for Ang-2 expression in the tumoral rim. After day 4, necrosis was not observed. From days 15 to 20 post-implantation, the tumors were large and hypervascularized, with large vessels. After day 20, the vessels were numerous but thinner.

Markers for endothelial cells and peri-endothelial cells showed that vessels were co-opted by the tumors during the early stages of their development. Smooth muscle actin (SMA) staining was expressed in peritumoral vessels in the early stages of tumor development. However, SMA reactivity was lost in more mature tumors and in intratumoral vessels during later stages of development. Examination of the tumors at the stage of 10-20 days revealed absence of positive vessels around the tumor for Ang-2. The intensity of Ang-2 staining in intratumoral vessels was dramatically decreased, and Ang-2 was expressed in less than 5% of the tumor in glioma cells. Taken together, these data suggest that a high level of Ang-2 is an indicator for incipient formation of vessels, whereas low to null Ang-2 expression is required to maintain tumoral vasculature. Staining for proliferating cell nuclear antigen revealed a high proliferative activity ranging from a few hours after implantation to the end of the experiment. This data indicates that it is possible to delineate a well-characterized in vivo tumor model designed specifically for the study of antiglioma therapy.

Effect of Ang-2 Expression on Glioma Tumorigenicity.

The U-87 MG cell line was infected with AdAng-2 or an adenovirus control, AdCMV, and 3 days later, cells were implanted intracranially in nude mice. These experiments showed that all control-treated U-87 MG cells (n=7) developed into intracranial tumors that ultimately caused the death of the animals by day 35. The tumors were ellipsoid masses that compressed anatomical structures in the ipsilateral and contralateral hemispheres of the brain and were similar to those formed in other experiments using U-87 MG cells (Fuego et al., 2003). Conversely, all but one of the animals bearing U-87 MG cells treated with Ang-2 (n=7) did not show any sign of general toxicity or neurological deficits by day 55 (latest point examined) (P=0.0001; log-rank test). In order to observe if slow-grow tumors are arising from Ang-2-treated U-87 MG cells, the inventors have decided to carry on the study until day 100 after cell implantation. At that moment all survivors will be euthanized and the brains analyzed. Despite the lack of histological information on the brain of the Ang-2 treated animals, these tumorigenicity studies strongly suggest that overexpression of Ang-2 resulted in inhibition of tumor production or markedly interference with the progression of tumor growth.

Characterization of Antisense-VEGF U-87 MG Cell Lines.

The inventors confirmed that the secretion of VEGF is down-modulated in these clones (anti-10: 62.8%, anti-13: 57.3%; anti-17: 71%, with respect to LacZ-transfected U87 MG cells, equal to 100%). Importantly, adenoviral infectivity assays using AdGFP showed that U-87 antisense VEGF clones and U-87 cells transfected with a vector control carrying LacZ, efficiently transduced GFP protein in more than 80% of the cells 3 days after infection with 100 MOI. This experiment showed that these cells have the capacity to be infected by adenoviral vectors.

Effects of Ang-2 on the Growth Kinetics and Angiogenesis in Glioma.

The inventors contemplate that the VEGF blockade stage of tumor development is, at least in part, due to overexpression of Ang-2. The inventors will use the U-87 MG and D54 MG models growing under different conditions of high VEGF expression and low or high Ang-2, and low VEGF expression and low or high Ang-2. Modulation of Ang-2 will be effected by use of isogenic cell lines expressing Ang-2 under a tetracycline regulatable system. For modulation of VEGF levels isogenic U-87 MG cell lines will be used: parental (high VEGF) and stably transfected with antisense VEGF (Cheng et al., 1998), as well as isogenic D-54 MG cell lines: parental (low VEGF) and stably transfected with VEGF165 cDNA. A tetracycline-regulatable system has been utilized in mammalian cells and in transgenic mice. Benjamin and Keshet (1997), among others, have tested a tetracycline-inducible system in gliomas in vivo. Using a tetracycline-regulated VEGF expression system in xenografted C6 glioma cells, they were able to successfully turn on and off VEGF production and VEGF effects. Wang et al. (2001) reported the development and testing of a conditional expression system used to express a reporter gene in human U-87 MG and SNB-19 intracranial xenografts. The xenografts expressed β-gal when the animals were fed drinking water containing Dox, showing that the expression of a target gene in a human intracranial xenograft can be conditionally regulated.

Conditional switching on of Ang-2 correlates with survival. A time point analysis of the evolution of angiogenesis in the U-87 MG animal model has been performed and the findings correlated with the histology and growth patterns of the xenografts. The data showed that it is possible to delineate a well-characterized in vivo tumor model that is designed specifically for the study of antiglioma therapy. Furthermore, specific expression of different angiogenesis-related markers at different stages of tumor growth can be used as a guide for assessing the modulation of angiogenesis by Ang-2.

Regulatable-Ang-2 expressing U-87 MG cells will be injected intracranially in nude mice. Three groups of animals will be established for every cell line, in which Ang-2 will be turned on by administration of Dox (antibiotic dissolved in the drinking water) through different periods. The particular time points selected for examining the timing of Ang-2 expression were derived from results obtained in the study of the intracranial U-87 MG xenograft. Thus, three group of animals will be analyzed in which the expression of Ang-2 will be turn on at different times: (A) the same day of cell implantation (tumorigenicity study); (B) 4 days after cell implantation (angiogenesis switching; early vasculature); or (C) 10 days after cell implantation (establishment of intratumoral vasculature). Animals will be sacrificed if and when they demonstrate signs of general toxicity, or neurological signs or, in the case of long survivors, animals will be sacrificed 60 days post-implantation, and brains will be extracted. Similar experiments will be performed in the D54 MG cell line.

Several reports have shown that Ang-2 promoted blood vessel destabilization and regression in the absence of the VEGF or bFGF survival factors. To examine if the effect of Ang-2 in this glioma system is dependent on a VEGF background, in vivo studies will be performed using regulatable-Ang-2 expressing clones from two isogenic U-87 MG cell lines that express different levels of VEGF (A) parental U-87 MG, and U-87 MG with low VEGF expression (stably transfected with antisense VEGF), as well as with two isogenic D54 MG cell lines expressing different levels of VEGF or (B) parental D54 MG, and D54 MG with a high expression of VEGF165 (stably transfected with VEGF165 cDNA, (Ke et al., 2000). Statistical analyses will analyze if changes in VEGF expression modified the effect of Ang-2 on the survival of U-87- or D54 MG tumor-bearing animals. Tumors will be examined using H/E staining and immunohistochemistry, as described herein.

Modulation of Tumor Angiogenesis by Ang-2.

In each treatment group tumor cells will be analyzed for PCNA (proliferation marker), apoptosis (TUNEL), VEGF, and Ang-2. The expression of CD34, % TUNEL (ratio CD34/TUNEL-positive cells), SMA (pericytes) will also be determined. After exogenous Ang-2 is expressed, it is anticipated that the production of smaller tumors as compared to the control group. In these Ang-2-overexpressing tumors, an inverse correlation is expected between proliferation and apoptosis index. It is predicted that tumor cell production of VEGF will be significantly reduced and that microvascular density (MVD) (measured by staining with antibodies against CD34) will be inversely proportional to the expression of Ang-2 and directly proportional to the expression of VEGF. The microvessel pericyte coverage index (vessels positive for both endothelial and pericyte markers) will be inversely related to Ang-2 expression, indicating that overexpression of Ang-2 destabilized vessel formation. The endpoints are to correlate overexpression of Ang-2 with (a) decreased production of tumor angiogenesis; (b) decreased tumor proliferation; (c) increased tumor and endothelial cell apoptosis; (d) decreased formation of mature vessels; and (e) reduced tumor production of VEGF. Quantification of the data obtained will be by three-color immunofluorescence analysis of CD31 and TUNEL quantified by LSC (CompuCyte Corporation, Cambridge, Mass.) (Davis et al., 2004). The LSC is an instrument designed to enable fluorescence-based quantitative measurements on cellular preparations at the single cell level.

The objectives include the collection of data on the timing of Ang-2 overexpression and the response to that (survival) in each cell line. The studies will be performed to analyze survival in glioma-bearing nude mice with and without Dox treatment. Two isogenic U-87 MG cell lines will be used for these studies that have been stable transfected with the regulatable Ang-2 system. Survival curves will be estimated using the Kaplan-Meier method. Cox proportional hazards regression analysis will be used to estimate the hazard ratio between groups along with a 95% confidence interval for this ratio and a likelihood ratio p-value for testing if the ratio is different from 1 (the value of the ratio if the groups have the same survival distributions). The hazard ratio quantifies the relative rates of death between the groups. Based on historic data it is expected that the control animals will have a median survival of 20 days. One aspect of these data is that there is a guaranteed time during which animals have an extremely low risk of death. Based on historic data, a good estimate for this guaranteed time is about 15 days. For a one-sided alpha of 5% and a power of 90% we need 10 animals for each treatment group (10 animals×2 isogenic cell lines×2 different treatments (dox)=40 animals).

Ang-2 and/or VEGF-Based Antiangiogenesis Therapy.

In addition to mechanistic obstacles, the efficiency of gene therapy in general, has been halted by the inability of the replication-deficient adenovirus to transduce a sufficient number of cells to induce a significant anticancer effect in vivo. Adenovirus typically delivers a functional p53 protein in the vicinity of the injection site, but that the majority of the tumor remains uninfected (Lang et al., 2003). For that reason, replication-competent adenoviral system will be used as a delivery tool, preferably Delta-24 adenovirus, which replicates efficiently in human glioma cells but does not replicate in normal cells (Fueyo et al., 2000).

Although the selectively and safety of the oncolytic system in vitro and in vivo have been demonstrated by our laboratory (Fueyo et al., 2000, Suzuki et al., 2001), the oncolytic adenovirus by itself has been unable to suppress tumor growth in most of the animals. For that reason, an oncolytic adenovirus that will deliver high levels of Ang-2 to the tumor. A pilot study showed that the new construct also replicates and expresses Ang-2 at high levels in an in vivo intracranial glioma animal model. The results of that experiment also suggested that Delta-24-Ang-2 has an anticancer effect. Finally, data show the effect of other antiangiogenic agents that are in clinical trials or are being planned for testing in clinical trials for patients with malignant gliomas.

Transfer of Antisense-VEGF Inhibits Tumor Growth In Vivo.

VEGF is potentially an optimal target for therapeutic strategies because it is essential for tumor growth and progression. The recombinant adenoviral vector Ad5CMV-αVEGF incorporates the coding sequence of wild-type VEGF165 cDNA in an antisense orientation. Infection of U-87 MG malignant glioma cells with AdαVEGF reduced the amount of endogenous VEGF mRNA and drastically decreased the production of the targeted secretory form of the VEGF protein. Subcutaneous human glioma tumors established in nude mice were treated with an intralesional injection of AdαVEGF, resulting in inhibited tumor growth (P=0.004). Taken together, these findings indicated that the efficient downregulation of VEGF produced by tumoral cells using antisense strategies produces an antitumor effect in vivo.

Transfer of Ang-2 Improves Survival of Intracranial U-87 MG Tumor-Bearing Mice.

Intratumoral treatment with Ang-2 was assessed for modification of the survival of mice bearing U-87 MG intracranial tumors. The inventors implanted $5 \times 10^5$ U-87 MG human glioma cells intracranially into nude mice. Three days later, treatment with 1.5×10⁸ p.f.u. of AdAng-2 or AdCMV was injected into the tumor using a guide-screw system. Treatment was repeated twice weekly until mice, whose tumors were treated with AdCMV, died (day 32). In contrast, 50 days after cell implantation, 70% of the animals whose tumors were treated with AdAng-2 were still alive, without showing any signs of general or local toxicity. These experiments demonstrated a significantly improved survival of animals treated with AdAng-2 compared with AdCMV-treated animals (P=0.0001, log-rank test). A second experiment performed with a decrease in the number of intratumoral injections administered (until day 20 post-cell implantation) also resulted in a significant increased in survival (P=0.012; log-rank test). However, the fact that a comparative study between both treatments showed a significant difference in the improvement in the median survival vs. control for the experiment with longer period of treatment compared with the three-weeks period treatment (P=0.026; log-logistic distribution), lead to the thought that the continuous expression of Ang-2 is necessary to obtain an anticancer effect. For that reason, the combination of oncolytic adenovirus continuously expressing the Ang-2 transgene is especially interesting.

Armed Delta-24-Ang-2 Efficiently Transduces Ang-2 In Vitro.

Initial results support the use of the replication-selective oncolytic adenovirus Delta-24 as an expression vector. U-87 MG cell were infected with the replication-deficient AdAng-2 or with the virus control AdCMV-pA at 5 MOIs, or the new construct Delta-24-Ang-2 at 0.1 MOIs. Cell lysates were collected 2 and 4 days after infection and equal amount of proteins were analyzed by Western Blotting for expression of Ang-2. The replication-competent adenovirus Delta-24-Ang-2 transduced higher levels of Ang-2 than its replication deficient counterpart AdAng-2.

Anticancer Effect of Delta-24-Ang-2 In Vitro.

In this study U-87 MG human glioma cells were infected with Delta-24-Ang-2, or UV-inactivated adenovirus (at doses of 0, 0.1, 1, 5, and 10 MOIs). Crystal violet viability assays showed that Delta-24-Ang-2 exhibited an increasing CPE with increasing MOIs. The oncolytic effect was noticeable with a 1-MOI dose and was higher than 100% with a dose of 10 MOIs on the 8th day after infection. To ascertain if the CPE was due to adenovirus replication, TCID50 replication assay was performed. Three days after the infection of glioma cells with 1 MOI of Delta-24-Ang-2, media and cell lysates were collected and the titer of adenovirus was measured in 293 cells. No new viral progeny were detected in cells infected with UV-inactivated adenovirus. Two independent experiments showed that Delta-24-Ang-2 replicated in U-87 MG cells (3.1×10⁶ pfu/ml, and 7.9×10⁶ pfu/ml). Studies are in progress to compare replication and CPE induced by Delta-24-Ang-2 to Delta-24 and wild-type adenoviruses. Of importance, the above studies suggested that Delta-24-Ang-2 maintains its replication phenotype and is able to transduce Ang-2, at higher levels that a replication deficient vector.

Delta-24 Expresses Ang-2 and Replicates In Vivo.

5×10⁵ U-87 MG human glioma cells were injected intracranially into nude mice. Three days later 1.5×10⁸ pfu of Delta-24-Ang-2 (2 mice) or UV-inactivated-Delta-24-Ang-2 (2 mice) were injected into the tumor using a guide-screw system. Animals were sacrificed 11 days after implantation and brains were collected. Fresh sections were stained with H&E, and permanent paraffin sections were deparaffinized and stained to detect the expression of Ang-2. Optical microscopy of the UV-inactivated Delta-24-Ang-2 treated tumors showed a tumoral mass (>20 mm3) that was highly vascularized and that had no areas of necrosis. In contrast, Delta-24-Ang-2 tumors were significantly smaller (<0.5 mm³), and showed necrotic areas. Immunohistochemical staining of Ang-2 in U-87 MG human tumor xenografts treated with Delta-24-Ang-2, demonstrated high levels of transduced protein compared with the control-treated xenograft. Of importance, staining with anti-hexon protein (structural viral protein) was positive in xenograft treated with Delta-24-Ang-2, suggesting adenoviral replication. These studied suggest that the Ang-2-armed Delta-24 adenovirus transduces high levels of Ang-2 and induces an important suppression of glioma growth in vivo.

Co-Infection with Delta-24 Enhances the Potency of Replication Deficient Vectors.

U-87 MG cell line was infected with Delta-24 (10 MOIs) or UV-inactivated Delta-24 (10 MOIs), and the replication-deficient AdGFP (25 MOIs) or the control AdCMV (no exogenous cDNA). Three days later cultures were imaged under a fluorescence microscope. Preliminary data showed an increase of positive-green cells when AdGFP co-existed with Delta-24, suggesting that Delta-24 acts as a facilitator for the delivery of replication-deficient E1-deleted adenovirus vectors (Steinwaerder et al., 2002; Bernt et al.; 2002, Carlson et al., 2002; Alemany et al., 1999).

LN229 and SNB19 Human Cell Lines Exhibit Invasive Phenotype In Vivo.

To complement the U-87 MG in vivo system, several human glioma cell lines have been tested that will have more clinical significance. In this regard, LN229 and SNB19 human glioma cell lines are tumorgenic when injected intracranially and exhibit an invasive phenotype in vivo. Furthermore, both cell lines expressed Tie2, which makes them likely candidates for an Ang-2-based strategy.

Testing the effect of antiangiogenic compounds on the survival of human glioma xenograft mouse model. Comparative survival analysis of the anticancer effect of different antiangiogenic treatments have been performed using the U-87 MG xenograft mouse model). PTK787/ZK 222584 was evaluated as a VEGFR inhibitor (Thomas et al., 2003); and imatinib/Glivec as a potent PDGFRβ inhibitor (Manley et al., 2002). Briefly, human glioma cells (5×10⁵ U-87 MG) were engrafted into the caudate nucleus of athymic mice using a guide-screw system as previously described (Fueyo et al., 2003). PTK787 or Imatinib was administered at a dose of 25 mg/kg/ip/day or 20 mg/kg/ip/twice/day, respectively, until the animals showed signs of general or local toxicity. Treatment with these drugs did not significantly improve the survival of these animals (P>0.5, logrank test) compared with control-treated animals (vehicle). Neither group treatment had long-term survivors.

The Antiglioma Effect of Combined Therapies Based on the Transfer of Angiopoietin-2, Using Oncolytic Adenoviruses, and Antisense VEGF.

The inventors have designed an Ang-2/VEGF-based antiangiogenesis therapy with tumor selectivity and efficient delivery. In addition to mechanistic obstacles, the efficiency of gene therapy is abrogated by the inability of replication-deficient adenoviruses to transduce a number of cells in vivo sufficient to induce a significant anticancer effect. This limitation is underscored by results obtained in a clinical trial using Ad-p53 in gliomas. This trial demonstrated that the adenovirus delivered a functional p53 protein in the vicinity of the injection site, with the majority of tumor cells remaining uninfected (Lang et al., 2003). Because of that finding, we will utilize a replication-competent adenoviral system as a delivery tool in this competitive renewal. The system is based on a replication-selective Delta-24 (Fueyo et al., 2000).

Role of the Rb Pathway in Controlling the Oncolytic Effect of Delta-24-Ang-2.

Since Delta-24 and Delta-24-Ang-2 encompass a similar E1A deletion, it is expected that oncolysis can be controlled by restoring the Rb pathway. To demonstrate this the ability of Delta-24-Ang-2 to replicate in cancer cells expressing null or restored Rb function will be assessed (Fuego et al., 2000).

The Effect of Delta-24 on HIF-1α Activity.

Zoltan et al. (1996) reported that in response to hypoxia, E1A inhibits HIF-1 activity by specifically targeting p300. That phenomenon could have synergistic/additive effects when Delta-24 is combined with the expression of Ang-2. From a mechanistic point of view the effect of E1A could interfere with interpreting the effect of Ang-2 on the activity of HIF-1α. The inventors will assess the effect of oncolytic replication competent adenoviruses on two different systems. The first approach will involve the use of normal rodent cells, NIH3T3 (ATCC), which do not support the replication of the adenovirus but allow for the expression of E1A. This cellular context will allow the dissection of the effect of E1A on HIF-1α activity, independently from other adenoviral proteins and from adenovirus replication. The second approach will involve the use of glioma cultures (U-87 MG), which have constitutively high levels of HIF-1. After infecting both cultures with Ang-2 under hypoxic conditions (Zoltan et al., 1996), HIF activity will be assessed by detection of luciferase to quantify the transcriptional activity of HIF-1 and its DNA-binding capacity. If Delta-24 downregulates HIF-1 activity, additional oncolytic adenovirus will be studied. One of these oncolytic adenovirus incorporates a deletion that encompasses the p300-binding region of E1A (Delta-39; aa. $D_{48}LDVTAPEDPNEE_{60}$) (SEQ ID NO:18). The other adenoviral construct has a combination of the E1A deletions present in both Delta-24 and Delta-39 (Delta-24/39) constructs. If the mutant Delta-39 does not have any effect on HIF-1α activity, an expression cassette of Ang-2 will be inserted in the E3 region of the Delta-24/39. Thus, the tumor selectivity produced by the 24-bp deletion will be preserved and will have impaired the ability of E1A to interact with p300.

Delta-24-Ang-2 Replication In Vivo and Modification of the Angiogenic Process.

$5 \times 10^5$ human glioma cells (U-87 MG and LN229) will be injected intracranially into 5 nude mice. Three days later, $1.5 \times 10^8$ plaque-forming units of Delta-24-Ang-2 or UV-inactivated-Delta-24-Ang-2 will be injected into the tumor using a guide-screw system. Animals will be sacrificed 20 days after treatment to examine the spread of the Delta-24-Ang-2 adenovirus within the tumor. Fresh sections will be stained with H&E. Permanent paraffin sections from the brain will be deparaffinized and stained for the detection of viral proteins such as hexon and E1A. Angiogenesis analyses will be performed. Tumor size, necrosis areas, MVD, PCI, endothelial or tumor apoptosis, and expression and localization of Ang-2 and VEGF will be determined.

AdαVEGF Replicative Properties when it Co-Exists with Delta-24.

Infection of Delta-24 with AdGFP (has a similar structure as AdαVEGF, but with GFP cDNA) (Fuego et al., 2000) will allow us to indirectly analyze the replication of the adenoviral vector. U-87 MG, D54 MG, and LN229 cells will be infected with Delta-24 at an MOI of 10 (UV-inactivated Delta-24 as control) and AdGFP (AdCMV as control) at an MOI of 25 or 50. Two and four days later GFP-positive cells will be scored in a total of 500 cells.

Infection of Delta-24 with AdαVEGF will allow one to directly analyze the replication of the adenoviral vector. U-87 MG, D54 MG, and LN229 cells will be infected with Delta-24 at an MOI of 10 (UV-inactivated Delta-24 as control) and AdαVEGF (AdCMV as control) at an MOI of 25 or 50. Two, four, and six days later, quantitative PCR amplification of a fragment of the AdαVEGF containing the insert will be performed.

In Vivo Anticancer Effect of Combining Delta-24-Ang-2 with AdαVEGF.

Studies will be performed in U-87 MG, D54 MG, and LN229-based intracranial xenografts in nude mice. Treatments will consist of intratumoral administration of Delta-24-Ang-2 with AdαVEGF, Delta-24-Ang-2 with AdCMV, UV-inactivated Delta-24-Ang-2 with AdαVEGF, UV-inactivated Delta-24-Ang-2 with AdCMV, wild-type Ad300 with AdαVEGF, and Ad300 with AdCMV. Results from our preliminary experiments show that an empirically chosen dose of $1.5 \times 10^8$ pfu (administered 3 times) significantly improves survival. For that reason, we selected this as the initial dose to test in the animal model.

Although the primary studies will be focused on survival, at the moment of death (cancer-induced or sacrificed), all of the brain tissue will be extracted. The tumors will then be examined using H&E staining and immunohistochemistry for viral proteins and angiogenesis. Since there will be only one time point, the pathologic examination will be utilized for a descriptive analysis.

Although treating U-87 MG intracranial xenografts with Delta-24 results in an increased survival, 80% of the animals died from mass effect of the tumor growth. Since tumor growth is, at least in part, related to increased angiogenesis, the inventors expect that after combining Delta-24 with the delivery of Ang-2, along with a decrease in VEGF levels, the percentage of long-term survivors will increase. Delta-24-Ang-2 may be used in combination with other antiangiogenic agents to abolished mature, preexisting vasculature in established tumors.

Example 8

Tropism of Delta-24 Adenovirus to Human Glioma Cells

A. Material and Methods

Delta-24-300.

pXC1-D24 containing the D-24 deletion (Fuego et al., 2000) was used as the template DNA. Two 5' phosphorylated primers consisting of sequences of 20 nucleotides on either side of the deletion (sequence DLDVTAPEDPNEE, 48-60 aa of E1A protein (SEQ ID NO:18)) were used for linear mutagenesis primer-incorporating PCR. The template was linearized and the PCR product was recircularized by ligation and transformed into *E. coli* to produce the vector pXC1-D24/300 encompassing deletions disabling binding of E1A protein with both Rb and p300. pXC1-D24/300 and pBHG10 (Microbix Biosystem, Inc.) were co-transfected by liposome-mediated method into 293 cells for homologous recombination and individual plaques were isolated and amplified.

Anti-Glioma Effect of Delta-24-300

U-87 MG, U-251 MG and D54 MG Human glioma cells were infected with Delta-24-300, Ad300 (wild-type adenovirus), Delta-300, Delta-24, or UV-inactivated Ad300 and assessed cell viability by crystal violet assay and then quantified with MTT tests. Both analyses showed a consistent dose-response effect of Delta-24-300 on the three human glioma cell lines. MTT analyses further showed that the decreased viability observed in the crystal violet assays was highly reproducible and dose dependent in the three cell lines tested. Delta-24-300 is able to induce cell death in glioma cells in vitro at a dose of less than 10 MOI and causes a 50% decrease is cell viability.

Differential Expression of Viral Proteins in Glioma and Normal Astrocytes

Expression of early (E1A) and late (hexon) genes were evaluated in U-251 MG and normal human astrocytes prepared 16 hours after infection with Delta-24-300, Delta-24 or Delta-300. Expression of E1A and fiber protein was significantly down-regulated in the Delta-24-300-treated NHA as compared to the Delta-24-300-treated U-251 MG glioma cells.

Replication Profile of Delta-24-300 in NHA Cultures

Delta-24 has been shown to replicate inefficiently and wild-type adenovirus replicates efficiently in quiescent normal cultures (Fueyo et al., 2000, 2003). An E2F-1-promoter construct driving the reported luciferase gene (Johnson et al., 1994) is used to determine if adenoviral-mediated S-phase induction would be impaired following infection of proliferating NHA with Delta-24-300 while wild-type adenovirus would efficiently induce S phase. E2F-1-activity in NHA cultures infected with Delta-24-300 was similar to the mock-treated cultures and lower than that induced by Delta-24. As expected, the highest E2F-1 promoter activity was observed in cultures infected with the wild-type adenovirus. The data suggest that Delta-24-300 is unable to elicit an S-phase like response in normal cells and suggest that its toxicity will be lower than that of Delta-24.

To confirm the selectivity of Delta-24-300, the replication phenotypes in glioma cultures and actively-dividing NHA infected with Delta-24-300, Delta-24, Delta-300, wild-type or UV-inactivated wild-type adenovirus were compared. Analysis of viral titers 3 days after infection revealed that the replicative ability of Delta-24-300 is greatly attenuated in the dividing normal cell population and that the ability of Delta-24-300 to acquire a replication phenotype in normal dividing cells is impaired compared to Delta-24 or Delta-300.

Construction of Delta-24-vIII.

Delta 24-vIII contains Delta-24 deletion and the chimeric fiber targeting EGFR vIII. The chimeric fiber was designed having the N-terminal of Ad5 fiber protein (1-83aa), T4 febritin (bacteriophage T4 fibritin halican domain and fold (233-487 aa), linker (e.g., G4SG4SG4S linker), and PEPHC1 ligand (HFLIIGFMRRALCGA (SEQ ID NO:19)) (Krasnykh et al. 2001; Campa et al. 2000). The tail and T4 fibritin moieties ensure the formation of the trimeric structure of the fiber as well as the correct insertion of the fiber into the virion particle through the tail. The linker joins the fiber and the anti-EGFR vIII ligand.

To construct the chimeric fiber, oligonucleotides of cDNAs for the linker and ligand (PEPHC1) were synthesized according to their amino acid sequences. Complementary oligonucleotides were annealed and inserted into plasmids. The pQE-trisystem (Qiagen, Valencia, Calif.) was used to construct the chimeric fiber so that the protein can ultimately be expressed in E. coli or mammalian cells to verify fiber trimerization. Trimerization was assessed by expression in E. coli M15 (pREP4) (Qiagen) and human cancer cells. The proteins collected from the E. coli or human cancer cells were denatured or not denatured, and then separated by SDS-PAGE and immunoblotted with anti-Ad fiber tail MAb 4D2 (NeoMarkers, Fremont, Calif.). The protein was successfully able to trimerize, showing a shift in the non-denatured sample to approximately threefold the size of the denatured sample (data not shown).

Generation of D24-300 vIII.

The whole fiber cDNA (1745 bp) has been deleted from pAB26 (Microbix Biosystem, Ontario, Canada) and created a Pac I site at the position where the chimeric fiber will be inserted. Three deletions (fiber, Delta-24 and p300) will be made within the Bst BI/Xba I fragment of the pFG173 plasmid (Microbix Biosystem, Ontario, Canada). In particular, these deletions will be made in a pBluescript KS+ backbone and the Bst BI/Xba I fragment containing the deletions will be ligated back to the remaining of pFG173 to obtain pFGΔfΔ24-300. At the same time, an expression minicassette for Enhanced Green Fluorescence Protein (EGFP) will be inserted into the deleted E3 region of the adenovirus and will be used as a reporter of adenoviral infection ability. The EGFP expression cassette will also be inserted into multiple cloning sites of the plasmids pAB26 and pABΔf to yield pAB-EGFP and pABΔf-EGFP.

Construction of the Shuttle Plasmid Containing the Chimeric Fiber.

The chimeric fiber FFL, which contains the peptide targeting EGFRvIII, will be inserted into pABΔf or pABΔf-EGFP in the same direction as the original fiber to obtain pAB-FFL or pAB-FFL-EGFP. Similarly, FF6H (a chimeric fiber containing a peptide control) will also be cloned into pABΔf or pABΔf-EGFP to yield pAB-FF6H or pAB-FF6H-EGFP.

The shuttle plasmids and pFGΔfΔ24 will be co-transfected into 211B cells which constitutively express fiber protein to allow homologous recombination. The media from the co-transfected 211B cells suspected of demonstrating cytopathic effect will be collected and tested via a PCR assay to verify the recombinant viral genomic region for the specific virus. The confirmed recombinant virus from the cell lysates will be plagued and each individual plaque will be amplified and verified in 211B cells. At this stage, the virions will have both the Ad5 fiber and chimeric fiber. The modified adenoviruses will be propagated in A549 cells (ATCC) where the virions should have only chimeric fibers. Since A549 cells do not express adenoviral genes, the production of wild-type adenovirus is highly unlikely. PCR amplification of E1A followed by enzyme digestion (Fuego et al., 2000) will be performed to detect the E1A mutation for each batch of the virus.

EGFR and EGFRvIII Expression in U87MG.wtEGFR and U87 MG.ΔEGFR Cells

To test the ability of the new virus to target EGFRvIII, U87 MG.wtEGFR and U87MG.ΔEGFR cell lines were obtained (Nishikawa et al. 1994; Mishima et al. 2001). These cell lines stably over-express either wild-type EGFR (U87MG.wtEGFR) or EGFR vIII (U87MG.ΔEGFR). EGFRs were detected by immunoblotting and immunohistochemistry. The anti-EGFR antibody (Cell Signaling, Beverly, Mass.) recognizes both EGFR and EGFRvIII and the anti-EGFRvIII antibody (Zymed Laboratories Inc., San Francisco, Calif.) specifically recognizes EGFRvIII. These cell lines represent a bona fide system to test selectivity of the targeted adenovirus infectivity and will be used for in vitro and in vivo studies.

Expression of EGFR and EGFRvIII in Heterotransplants from Tumors.

Heterotransplants of human gliomas expressing EGFR or EGFRvIII will be used to study the targeting of the adenoviral constructs. Immunohistochemical analyses detected expression of EGFR and EGFRvIII. Interestingly, the heterotransplants exhibited an invasive pattern when injected intracranially in nude mice.

Infectivity of Mesenchymal Stem Cells.

The ability of adenovirus to infect human stem cells, will be assessed using human mesenchymal stem cells and two GFP-adenoviral vectors. One of the vectors was redirected to infect through a CAR-independent pathway. Studies showed that adenovirus poorly infects mesenchymal stem cells. Flow cytometry was used to quantify infected cells (GFP-positive cells). Cells were plated to a density of $10^4$ and 24 hours later were infected with AdGFP or AdGFP-RGD at an MOI of 10. 72 hours after infection, cells were examined for green fluorescence by flow cytometry. Cultures infected with Ad-GFP showed 13.5+/−5.4% positive cells and cultures infected with Ad-GFP-RGD showed 30.1+/−7.2% positive cells. Low infectivity of mesenchymal stem cells with the virus of unmodified tropism is consistent with the low expression of CAR.

Delta-24-300 Replication In Vivo.

Figure 30:
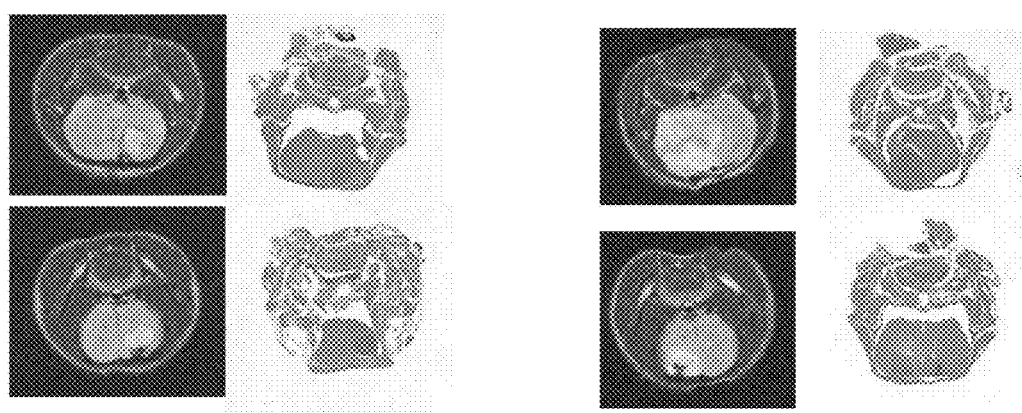
FIG. 30 shows MRI studies nude mice bearing intracranial U-87 MG xenografts. Animals were imaged 7 and 14 days after cell implantation. Shown are T2 images (left) and gross morphologic features (right, H&E) of the brains of tumors treated with UV-inactivated Delta-24-300 or Delta-24-300. Note that Delta-24-300 treatment resulted in inhibition of the tumoral growth as seen simultaneously in both pathological and imaging studies.
Figure 31:
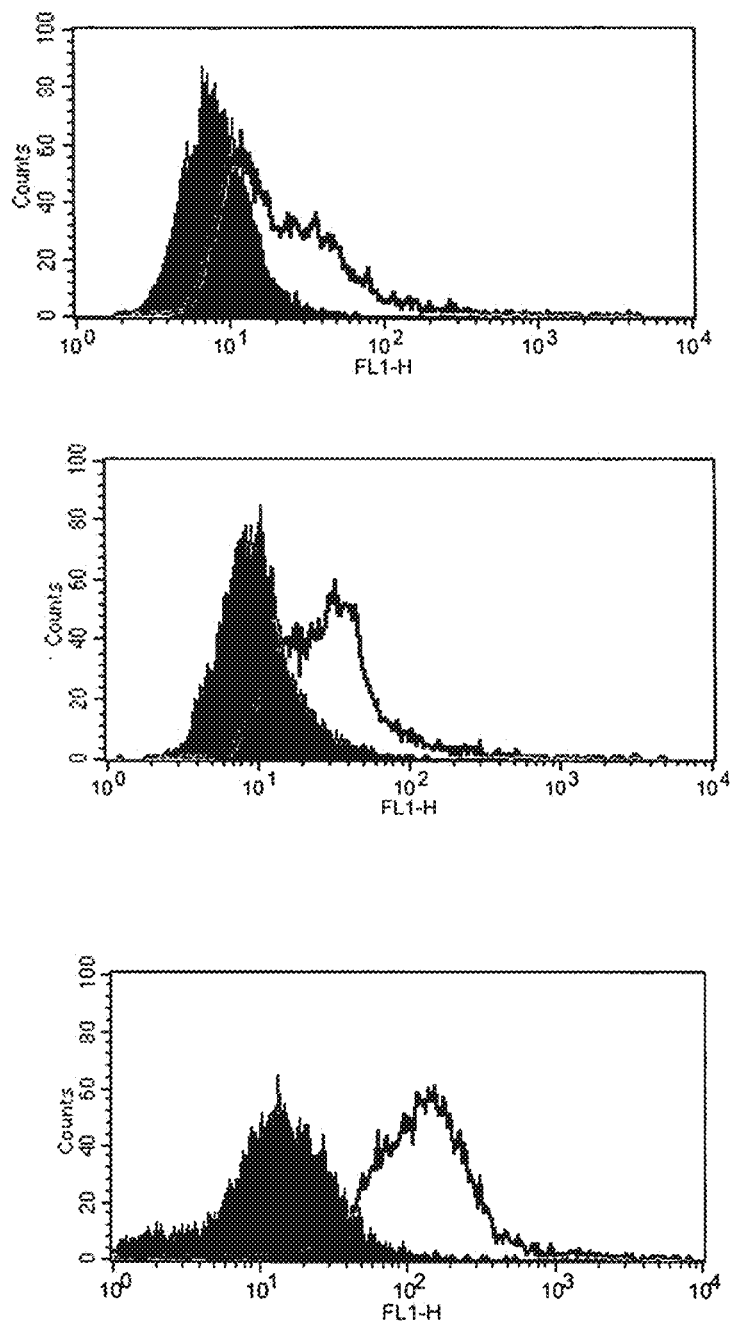
FIG. 31 shows specific binding of EGFRvIII-peptide (PEPCH1) to EGFRvIII-expressing cells. Briefly, the inventors performed membrane fluorescence staining of single-cell suspensions after incubating U-87 MG, U87.wtEGFR, and U-87.ΔEGFRvIII (Nishikawa et al., 1994) with the anti-EGFRvIII peptide (PEPCH1)-FITC (1 μM) (Campa et al., 2000) for 30 min. The cells were then washed twice with PBS and then analyzed for fluorescence with an EPICS XL-MCL flow cytometer (Beckman-Coulter Inc., Miami, Fla.) using a 488 nm argon laser for excitation. Fluorescence was detected with a 520 nm band-pass filter, and all cytometric data was analyzed with the System II software (Beckman-Coulter Inc.). Data are shown as the percentages of FICT-positive cells (empty graph) compared to mock-treated cells (solid graphs) from a representative experiment.
Figure 32:
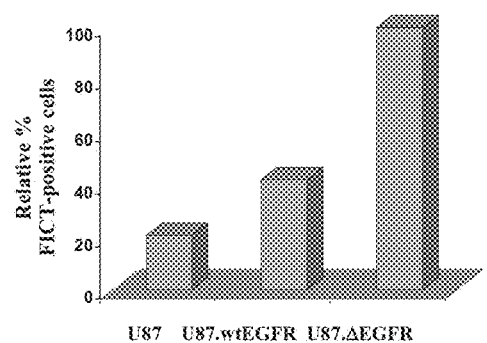
FIG. 32 shows data are shown after normalization of the binding value, as FITC-positive U87.ΔEGFR cells equal to 100%.
Figure 33:
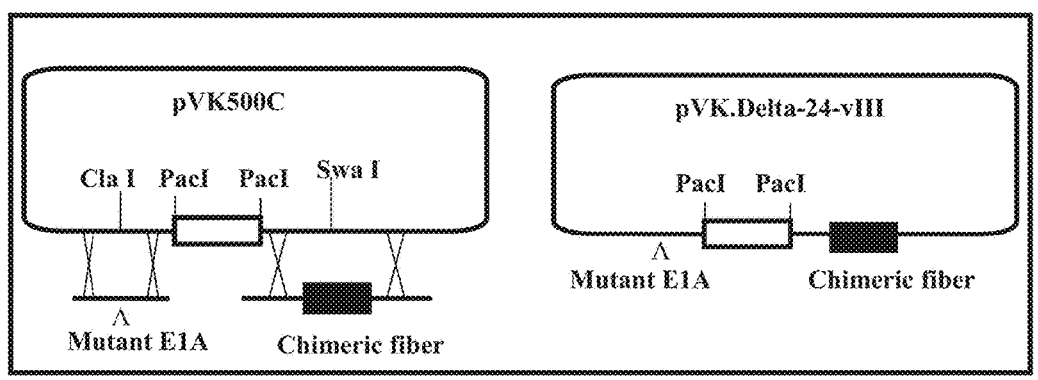
FIG. 33 shows construction of pVK.Delta-24-vIII. Schema showing key information of the adenoviral vector pVK500C and accomplished homologous recombinations. E1A adenoviral gene containing a 24 base-pair deletion that encompasses an area responsible for binding Rb protein (nucleotides 923 to 946), corresponding to the amino acids $L_{122}TCHEAGF_{129}$ (as Delta-24, Fueyo et al., 2000), was transfected into *E. coli* BJ5183, together with pVK500C, previously linearalized with ClaI enzyme. The resultant plasmid, this time linearilized with SwaI, and the recombinant DNA for the fiber-fibritin-ligand (FFL=DNA sequence for PEPHC1) chimera was cotransfected into *E. coli* BJ5183, obtaining pVK.Delta-24-vIII.

In order to determine if Delta-24-300 replicates in vivo, a study was performed in two animals bearing intracranial U-87 MG xenografts ($5 \times 10^5$ cells inoculum) infected with Delta-24-300 or UV-inactivated Delta-24-300 (control) as a single dose of $10^8$ pfu/tumor. Brain MRI was performed on Days 7 and 14 after cell implantation and then sacrificed. The MRI scans, shown in FIG. 30, showed growth progression in the control tumors, but no growth progression in the tumors infected with Delta-24-300. These results were consistent with histopathologic examination of the brains collected at sacrifice, which showed inclusion bodies around areas of necrosis in the tumors infected with Delta-24-300, suggesting the presence of new adenoviral progeny. There was no evidence of necrosis in the tumors infected with control UV-inactivated Delta-24-300 virus. The replication property of the Delta-24-300 virus was confirmed by expression of late structural genes (hexon). In addition, the inclusion bodies were positive for adenoviral proteins. Together, these data indicate that Delta-24-300 replicates in vivo and suggest that infection of tumors with this agent may result in therapeutic effect.

Analysis of Infectivity of Subventricular Area.

To assess infection in the subventricular zone, a series of archived U-87 MG tumors were analyzed and included (A) 10 brains with tumors treated with Delta-24, (B) 5 brains with tumors treated with Delta-24-RGD, (C) 2 brains with tumors treated with Delta-300, and (D) 2 brains with tumors treated with Delta-24-300 as described above. Cases in which the tumor showed high level of viral infection throughout the tumor and inclusion bodies were observed near the edge of the tumor tissue were selected. Immunohistochemical analysis of viral proteins did not reveal any adenoviral-positive cells in the subventricular zone in any of the examined brains. Therefore, the inventors believe that there is no spreading of adenoviral infection from the tumor to the subventricular zone.

Human Glioma Cell Lines

To test the effect of D24-300 and D24-300vIII in vitro, glioma cell lines have been selected that have 80-100% transduction efficiency with replication-competent adenoviral vectors (U-87 MG, U-251 MG, D-54 MG) (Fueyo et al., 1996a), and where Delta-24-mediated anti-cancer effect has been already tested. The U-87 MG cell line (ATCC) was developed by Nikshikawa et al. (1994). Briefly, U-87 MG cells have been stably transfected with wt-EGFR (U-87 MGwtEGFR) or mutant EGFR (U-87 MGΔEGFR), expressing wt EGFR or EGFRvIII, respectively.

Other Cancer Cell Lines and Normal Human Cell Cultures.

The following cell lines from the ATCC will be used: Saos-2 and U-2 Os (human osteogenic sarcomas); NCI-H446, NCI-H209 and NCI-H146 (human small cell carcinoma of lung); PC-3 and DU141 (human prostate carcinoma); MDA-MB-157, MDA-MB-231, and MDA-MB-361 (breast carcinoma). Normal cell cultures from ATCC that will be tested for infectivity and for the effect of the adenoviral construct include Normal Astrocytes (Clonetics), CDD-29Lu and CDD-33Lu (human lung fibroblasts); CDD-33Co, CDD-18Co, and CDD-112Co N (human colon fibroblasts), BUD-8 (human skin fibroblasts); HU-VEC-C (human endothelial cells). Human stem cultures will be represented in the in vitro experiments by mesenchymal stem cells and neural progenitors cultures (Cambrex, Walkersville, Md.). Culture conditions will be performed as recommended by manufacturers.

Cell Synchronization.

Cells will be serum-starved for 3 days by culturing in MCDB-105 serum-free medium (Sigma St. Louis, Mo.). To stimulate synchronous cell cycling progression, medium will be replaced with DMEM containing 10% fetal calf serum.

Infection Conditions.

Infection of cell lines will be carried out by dilution of viral stock to particular concentrations, addition of viral solutions to cell monolayers (0.5 mL per 60 mm dish) and incubation at 37° C. for 30 min with brief agitation every 5 min. The infected cells will be returned to the 37° C. incubator.

PCR Analysis.

This test will be used to detect the presence of wild-type adenoviruses, adenoviruses carrying wild-type E1A (Fuego et al., 2000).

BrdU Analysis.

Cells will be pulse-labeled with BrdU for 2 h before collection. After BrdU labeling, adherent and nonadherent cells will be combined, resuspended in 0.5 mL PBS, and fixed in 5 mL 70% ethanol, 50 mM glycine (pH 2.0). Samples will be subjected to denaturation in 0.5 mL 4M HCl for 20 min and then incubated at 37° C. for 1 h in 0.1 mL PBS containing 0.5% BSA, 0.1% Tween and 20 µL FITC-conjugated anti-BrdU antibody (clone BMG 6H8, Roche Molecular Biochemicals, Indianapolis, Ind.). After incubation, samples will be centrifuged and resuspended in a 0.5 mL solution containing 500 µg/mL RNase A and 10 µg/mL propidium iodide in PBS. Cells will be analyzed by two-color flow cytometry for BrdU incorporation and DNA content.

Immunofluorescence.

Cells will be seeded at $10^5$ cells per well in two-well chamber slides, allowed to grow for 20 hours and then infected with Delta-24-300. 24 hours later, cells will be fixed with methanol for 4 minutes at −20° C. The slides will be incubated for 10 minutes with DAKO protein block serum-free and then incubated with primary antibodies (anti-E1A, Santa Cruz Inc., Santa Cruz, Calif.; anti-BrdU (Biogenics, San Ramon, Calif.). Cells will be pulse-labeled with BrdU for 2 hours before collection. The slides will be washed twice for 5 min with PBS and fluorescent antibody (FICT and Rho) will be added. Slides will be covered with mounted media and fluorescence detected under a fluorescent microscope.

CPE Assays.

As described above, see Fueyo et al., 2000.

Viral Replication.

Viral production will be quantified by plaque-forming assay. 36 hours after infection, cells will be scraped into culture medium and lysed by three cycles of freezing and thawing. Cell lysates will be clarified by centrifugation and the supernatant will be serially diluted in medium for infection of 293 cells in 6-well dishes. After 1 hour of incubation at 37° C., the infected cells will be overlaid with 3 mL 1.25% SeaPlaque agarose (FMC, Rockland, Me.) in DMEM/F12 with 10% fetal bovine serum. Additional agarose will be added to each dish 4 days later. Plaques will be visualized 7 days after infection.

Immunohistochemistry.

The presence of adenoviral E1A and hexon proteins in the treated xenografts will be assessed by immunohistochemistry. Paraffin-embedded sections from tumors will be de-paraffinized and rehydrated through xylene and ethanol into PBS. Endogenous peroxidase activity will be quenched by incubation for 30 minutes in 0.3% $H_2O_2$ in methanol. Sections will be treated with goat anti-hexon (Chemicon Inc., Temecula, Calif.) or goat anti-E1A (Santa Cruz Inc., Santa Cruz, Calif.). Immunohistochemical staining will be performed according to the manufacturer's instructions with diaminobenzidine by using Vector Laboratories ABC kits (Amersham).

Selective Infectivity of the vIII-Adenoviral Constructs

To ascertain whether the insertion of the EGFRvIII-chimeric fiber motif is responsible for selective infectivity, two different studies will be performed with an established system where U-87 MG cells have been stably transfected with either EGFRvIII or wild-type EGFR.

Infectivity Analyses (GFP Detection):

Briefly, 48 hrs after infection, cells will be collected by trypsinization, washed with PBS, and stained with 50 mg/mL propidium iodide and 20 mg/mL RNAse for 15 min at room temperature. Samples will be analyzed with an EPICS XL-MCL flow cytometer (Beckman-Coulter, Inc., Miami, Fla.) by using a 488-nm argon laser for excitation. Fluorescence will be detected through 520 band pass filter. All cytometric data will be analyzed with the System II software (Beckman-Coulter, Inc.).

Competitive Inhibition Assay:

PEPHC1 peptide and 6H (control) peptide will be produced synthetically. Cells will be cultured in 96-well plates. 20-24 hours later, PEPHC1 peptide (1 mg/ml) will be added to the culture. Ten minutes later, cultures will be treated with D24-300vIII-EGFP, D24-300-FF6H-EGFP, or D24-300-EGFP. 48 hours later, a direct examination of the cells with fluorescence microscopy will take place, followed by determination of the percentage of green cells (fluorescence) after scoring 500 cells using phase contrast.

Detection of EGFR or EGFR vIII (Immunohistochemistry):

An anti-EGFR antibody (Cell Signaling, Beverly, Mass.) will be used that recognizes both EGFR and EGFRvIII and an anti-EGFRvIII antibody (Zymed Laboratories Inc., San Francisco, Calif.) that specifically recognizes EGFRvIII.

Intracranial Implantation and Treatment of the Tumors.

The implantable guide-screw method described above (Lal et al., 2000) will be used. PET scan will be used to determine the antiglioma efficiency of the oncolytic system targeting EGFRvIII.

Correlation of EGFRvIII Expression with Survival.

The inventors plan to perform in vivo studies with 3 cell lines expressing different levels of EGFRvIII and wild-type EGFR: parental U-87 MG, U-87 MG-DEGFR (high expression levels of EGFRvIII), and U-87 MG-wtEGFR (high expression levels of wild-type EGFR). The studies with the U-87 MG system (very low CAR expression) address the question of the relevance of EGFRvIII on the anti-cancer effect in a system in which all other factors are similar in both cell lines and can therefore be subtracted in the interpretation of the results.

Besides the study of viral replication inside the tumor, the histopathological examination of the brains will allow the examination of other interesting aspects involving adenoviral distribution in vivo. Viral particles will be detected by immunostaining for viral proteins as hexon and E1A, as well, as detection of viral inclusions. Because the proliferative potential of precursors cells, and thus, the possibility of supporting viral replication, the subventricular zone, the subgranular zone, the hippocampus and cortex (Gage, 2000) will be examined systematically for the expression of adenoviral proteins. Double immunofluorescence for E1A/hexon and nestin will be performed to elucidate the existence of viral particles in precursor cells.

Engrafting Human Glioma Cells and Intratumoral Injections $5 \times 10^5$ U-87 MG cells will be engrafted into the caudate nucleus of athymic mice, using a guide-screw system as previously described (Lal et al., 2000). The animals showing general or local symptoms of toxicity will be sacrificed. The surviving animals 100 days after engraftment. Brains will be fixed in 4% formaldehyde for 24 h and then embed them in paraffin. Animal studies will be performed in the veterinary facilities of M. D. Anderson Cancer Center in accordance with institutional guidelines.

Heterotransplants

Tumor specimens from tumor lines already established will be obtained and will used to generate tumor lines. Heterotransplants will be minced and injected subcutaneously into the right flank of nude mice in a volume of less than 1.0 ml using a 16-gauge needle. Treated and control tumors will be measured once or twice weekly with calipers, and the volumes will be calibrated according to the formula a2Xb/2, were a=width and b=length. For tumor passage, the animals will be euthanized, tumors will be removed under sterile conditions, and, after appropriate material will be obtained for histological analysis, the tumors will be passed in a modified tissue press through 30/40 mesh cytosieves. Volumes of 50-200 µl of this processed tissue will then be implanted into the right flank of the recipient animals. Serially passed tumors will be followed until a volume of at least 1000 $mm^3$ is achieved. Volume doubling times will be calculated from sequential measurements once exponential growth begins. A volume of 500 $mm^3$ will be tacked as a measure of successful growth as volumes will probably fluctuate somewhat below this level, and progressive growth is expected to occur 500 $mm^3$ will be on the linear portion of the growth curve in all instances. To assess tumor morphology portions of subcutaneous lesions from all mice that die spontaneously or will be killed will be fixed for at least 48 hours in 10% buffered formalin, embedded in paraffin, cut into 5/7 micron sections, and stained with H&E. These slides will be coded and evaluated for the presence of neoplastic cells.

B. Results

The Delta-24 oncolytic system will be modified to improve the ability of the adenovirus to identify cancer cells. In order to improve the selectivity of current gene therapy strategies, the inventors will target the oncolytic adenoviruses to specific cell-surface receptors. Compared to wild-type adenovirus, the proposed adenoviral constructs are designed to infect through a mutant form of EGFR, known as variant III or EGFRvIII (Kuan et al., 2001). This mutant receptor has been found expressed only in cancer cells, including approximately 30% of glioblastoma multiforme, which is the most frequent and most common form of gliomas. EGFRvIII encompasses an in-frame deletion of exons 2 through 7 (amino acid residues 6-273) in the extracellular domain. Due to the presence of this deletion, peptides can be designed to bind specifically to EGFRvIII, but not to any of the wild type forms of EGFR. Since malignant gliomas express low levels of adenoviral receptors, redirection of adenoviruses to cancer-related receptors, such as EGFRvIII, should result in a high therapeutic index through the improvement of efficiency in the infection of cancer cells and inability of infection of normal cells.

The inventors will replace the wild-type fiber structure of the protein with a chimeric fiber that has been constructed using a commercially available T4 fibritin DNA (Krasnykh et al., 2001), a DNA linker, and finally, the binding peptide. The peptide will be the "contact area" with the host cell. An adenovirus, which has been modified to express a chimeric fiber to bind the EGFRvIII receptor, will be able to bind and internalize exclusively into human glioma cells. In addition, an adenovirus directed to bind EGFRvIII should be able to infect human glioma cells more efficiently than a wild-type adenovirus because glioma cells express low levels of the natural, main receptor for adenovirus (CAR). EGFRvIII was selected because it is one of the best-examined systems in gliomas. Also, at least one peptide has already been described that is able to bind EGFRvIII. To test the ability of Delta-24-300vIII and Delta-24-300 to infect cells exhibiting low CAR expression and differing levels of EGFRvIII expression, a system will be used that limits the differences between cells in regards to EGFRvIII expression. This system consists of a human glioma cell line, U-87 MG, which expresses low levels of CAR and EGFRvIII and has been genetically modified to constitutively express high levels of EGFRvIII (U-87 MG-ΔEGFR) or EGFR (U-87 MGwtEGFR) (Nikshikawa et al. 1994). Comparisons between the wild-type fiber and fiber-modified adenoviruses in this system should yield clear information about the infectivity capability of both constructs.

Targeting oncolytic adenovirus to either of EGFRvIII or EGFR should result in adenovirus that preferentially infects cancer cells. These two receptors have been selected because both have been well characterized and defined in human glioma cells. The urokinase plasminogen activator receptor, uPAR, protein has been targeted using peptides that allow the internalization of adenoviral vectors (Drapkin et al., 2000). It has been demonstrated that urokinase plasminogen activator, or a 7-residue peptide derived from this protein (u7-peptide), binds the receptor and stimulates apical endocytosis. Both ligands enhanced gene transfer by nonspecifically binding adenovirus and adeno-associated viral vectors as well as a modified adenoviral vector that was coupled to the u7-peptide. These data provide strong evidence that the uPA/uPAR system may offer significant advantages for targeted oncolytic systems. The increased expression of certain fibroblast growth factor (FGF) family members, including basic and acidic FGF, has already been strongly associated with malignancy in human astrocytic tumors. Glioblastomas also express an alternatively spliced form of FGFR1 containing two immunoglobulin-like disulfide loops (FGFR1 beta), whereas normal human adult and fetal brain tissues express a form of the receptor containing three immunoglobulin-like disulfide loops (FGFR1 alpha) (Yamaguchi et al., 1994). The selective expression of FGFR in malignant gliomas and the presence of alternative spliced forms make FGFR (Jin et al., 2000) a desirable target for oncolytic adenoviral targeted anchorage in human malignant gliomas.

Selectivity and Efficacy of Glioma-Targeted-Delta-24 In Vivo.

The intracranial model of human glioma xenografts implanted in nude mice is one of the most representative procedures for the exploration of novel therapies for brain tumors. The inventor will check the pathology of the tumors, the expression of viral proteins, and the spread of the virus throughout the tumor at several time points in every experiment. The study is designed to ascertain whether or not there is a correlation between the kinetics of the viral spread, the tumor suppression and the improvement of survival. Survival data and pathological observations support the hypothesis that one can efficiently examine the adenovirally-mediated anti-cancer effect in vivo. Furthermore, these data are consistent with the prediction that tropism-modified adenoviruses are more powerful than wild-type fiber adenoviruses, such as Delta 24, in a cell line expressing low levels of CAR.

The inventors will perform studies with two different animal models. First, the inventors shall use the U-87 MG system. Glioma cells will be injected intracranially into nude mice. In the second study, the inventors shall use heterotransplants of human gliomas expressing EGFR or EGFRvIII implanted subcutaneously in nude mice. This model is required because the expression of EGFRvIII is generally lost in human glioma cell lines (Bigner et al. 1990). In addition, data from this model will complement those obtained from the U-87 MG model which is both more accurate to analyze the dependence on the expression of EGFRvIII for adenoviral infection, but more artificial than the heterotransplant system. The U-87 system and the heterotransplants are two complementary models in the way that in the U-87 MG system, all cells have a similar genetic makeup with the exception of the artificial expression of EGFR or EGFRvIII. In the heterotransplant model, the common characteristic between all the tumors should be the abnormal expression of EGFR or EGFRvIII with most probably different genetic abnormalities. The cell line model will be used to examine in detail adenoviral mediated anti-cancer effect. The second model will be used to determine the specificity in a more realistic setting closer to the clinical scenario. Heterotransplants are also useful to examine the degree of homogeneity in the ability of the targeted adenovirus to infect tumors with different degrees of EGFRvIII expression.

Example 9

Tie2 Expression in Gliomas and its Involvement in Tumor Formation

To examine the relationship of Tie2 expression in gliomas and the possibility of Tie2 of being involved in tumor formation, the inventors are applying two different and complementary approaches. One approach consists of the isolation of Tie2+ cells from established human glioma cultures, and then characterize these populations for tumor stem-cell like and/or tumorigenic properties. A second approach is based on the isolation of tumor spheroids (stem-like cultures) from human glioma specimens, and subsequent analysis of the expression of Tie2, and the tumorigenic properties of Tie2+ populations in these tumor neuro-spheroids. Alternatively, the information can be obtained from the stable cell lines.

Functional Characterization of the Tie2-Positive Tumor Cell Population and its Significance in Glioma Tumor Formation In Vivo.

The inventors have collected convincing data on the expression of the tyrosine receptor Tie2 in human glioma cells in culture, in glioma culture-derived intracranial xenograft, and importantly in malignant glioma human specimens. Tie2 expression was not detectable in human normal brain. Tie2 transcript was present in tumor neurospheres derived from human glioma tumors in co-existence with CD133 (stem cell marker). Furthermore, a small population of partially differentiated neural precursors was positive for Tie2 expression. To determine the role of Tie2 in gliomas, A172 glioma cell line was divided into two populations: Tie2+ and Tie2−.

Expression of Tie2 in human malignant gliomas is shown in FIG. 18. RT-PCR analysis was performed on mRNA extracted from human glioma cell lines and cultures. Primers and conditions for the PCR reaction were published previously (Poncet et al., 2003). A 503-bp fragment amplification was obtained from RNA extracted from the majority of the cell lines and high Tie2 RNA levels were present in A172, U-87 MG, and D54 MG. Sequencing of the amplified product in these cell lines confirmed the presence of the Tie2 transcript. Furthermore, Tie2 expression was detected by western blotting using the membrane subfraction lysates from different cell lines. Anti-human Tie2 antibody recognized a 140-kDa band in the membrane proteins subfraction of HU-VEC-C, U-87 MG and D-54 MG, A172, but not in U-251 MG.

Cytosol fraction proteins were negative for Tie2 expression. Because expression of RTKs have been reported being different in vitro than in vivo, U-87 MG cells were implanted in the brain of nude mice and Tie2 expression was assessed in sections of those xenografts. Tie2 levels were analyzed using two different antibodies (Santa Cruz, R&D), and competitive inhibition of the epitope/antibody reaction, was obtained with Tie2 peptide. Tie2 expression was in the endothelial cells of some tumoral vessels and peritumoral vessels, as well as in the glioma compartment. To determine whether the expression of Tie2 in human glioma cell lines was an artifact originated by clonal selection or in vitro culture, a series of human gliomas and normal brain tissues were examined using a microtissue array (Wang et al., 2004). These experiments showed that Tie2 is frequently expressed in Grade III and Grade IV gliomas, but is not expressed in normal brain. As expected, Tie2 was present in most tumoral vessels in every tumor grade.

Data shows that Tie2 is present in primary tumor neurosphere culture. Cultures were established from 3 GBMs tumors, which were acutely dissociated into individual cells. Culture conditions were used that favored stem cell growth, established previously for isolation of neural stem cells as neurospheres (Galli et al., 2004). SFM allows for the maintenance of an undifferentiated stem cell state, and the addition of bFGF and EGF induced the proliferation of multipotent, self-renewing, and expandable neural stem cells (Reynolds et al., 1996). Within 7-14 days of primary culture a subset of the GBMs tumors (3 out of 5) yielded a minority fraction of cells that demonstrated growth into neurosphere-like clusters, or tumor neurospheres. Analysis of primary and secondary tumor neurospheres generated from the three specimens showed expression of nestin transcript (an intermediate filament protein found in undifferentiated central nervous system cells and a characteristic neural stem cell marker), CD133 transcript, a novel putative neural stem cell marker (Singh et al., 2003 and 2004), and Bmi1, a molecule necessary for neural stem cell renewal and early neural progenitors (Valk-Lingbeek et al., 2004). The tumor spheres did express Tie2 (please note that tumor should contain glial and endothelial Tie2). Furthermore, RT-PCR was used to detect the presence of CD133 and nestin transcript in A172 and U-87 MG glioma cells lines (Tie2+ cancer cells). As control, cultures of cortical mouse astrocytes were tested (McCarthy et al., 1980), which were negative for CD133, and Tie2, but positive for GFAP, showing that Tie2 expression is not the result of tissue culture-originated artifact. Glioma sphere have been tested for self-renewal activity by the ability to form secondary and tertiary spheres. The morphology and expression of several stem-like cell markers did not varied or increased in those consecutive populations, showing positive expression of Tie2, CD133, and Brm1.

Next, conditions used for normal neurosphere differentiation were applied to primary tumor spheres to determine whether Tie2 expression was present in partially differentiated cells. After differentiation with 10% FBS for 1 day, immunocytochemistry was performed on tumor stem cells using GFAP (for astrocytes), and Tie2 antibodies. Strikingly, dissociated tumor spheres from the specimen tested grown adherently and in serum expressed GFAP, recapitulating the astrocytic lineage of the tumor. Interestingly, Tie2 expression was present in some of the partially differentiated cells.

Tie2+ populations were isolated from A172 human glioma cell line. To better define the significance of Tie2 expression on glioma cells, the expression of Tie2 was analyzed using flow cytometry, and Tie2 positive and negative cell populations were sorted. Flow cytometric quantification of Tie2 expression in A172 glioma cultures was 11.2%. When tumor cell cultures were sorted for Tie2 expression, Tie2 positive (1.2% total population) and negative (16.5%) cell populations were collected and cultured separately in serum-free neural stem cell medium. Tie2− and Tie2+A172 cells were cultured in suspension in this media. Although some cells died in this culture condition, approximately 50% of the Tie2+ cells remained viable showing with morphological signs of active mitosis, at the moment of that submission.

Growth Kinetics in a Human Glioma Intracranial Animal Model.

After intracranial injection of $5\times10^5$ U-87 MG cells into the right basal ganglia of nude mice (day 0), the tumors grew from 0.02 mm$^3$ on day 4 to 100 mm$^3$ bp day 20. All animals died by day 30. Serial temporal examination of the brains of tumor-bearing animals showed central necrosis of the xenografts within 4 days. At that time, the vessels surrounding the tumor displayed changes in morphology, including an enlarged diameter and a disorganized structure. After day 4, necrosis was not observed. From days 15 to 20, the tumors were large (41.2±6.3 mm$^3$) and hypervascularized with large vessels (36.7±3.4 and 53.1±12.9 vessels/0.5 mm$^2$). After day 20 and (104.66±7.1 mm$^3$) the vessels were numerous (53.1±12.9 vessels/0.5 mm$^2$). Staining for proliferating cell nuclear antigen revealed a high proliferative activity ranging from a few hours after implantation (>80% cells).

Characterization of the Tie2 Transduction Signaling in Glioma Cells and its Impact in the Glioma Phenotype In Vitro.

The inventors have generated data in support of a connection between the Ang1/Tie2 pathway and the Ras/p42/p44 MAPK signaling pathway. In addition, modulation of Tie2 signaling seems to be related to proliferation, adhesion and migration of human glioma cells. Of importance, Ang- 2-mediated blockade of this pathway blockade results in a prolonged survival of U87 MG-bearing animals.

To explore the regulation of Tie2 signaling by Angs in U-87 MG cells, Tie2 was immunoprecipitated from membrane fractions of U-87 MG cells treated with rAng1 (500 ng/ml) for 10 min, and phosphorylation of Tie2 was addressed using anti-phosphotyrosine antibody. Interestingly, treatment of Ang1 induced phosphorylation of Tie2 in U-87 MG cells, suggesting that Tie2 receptor is functional in U-87 MG cells. Therefore, the antagonizing effects of rAng-2 on Ang1-induced signaling pathway in U-87 MG cells was investigated Inhibition of Tie2 phosphorylation by Ang1 treatment in rAng-2 treated U-87 MG cells was observed.

The Ang-2/Ang1/Tie2 system has been studied in endothelial cells, and different pathways have been reported as involved in the cascade signaling. The inventors have obtained results that suggest that Ang1 induces MEK/ERK stimulation in glioma cells. MAPK activity was measured by the degree of phosphorylation of two MAPKs, ERK1 ($p44^{MAPK}$) and ERK2 ($p42^{MAPK}$). Consistant with previous reports (Kim et al., 2002; Tournaire et al., 2004), rhAng1 (100 ng/ml) increased ERK1/2 phosphorylation of HUVEC-C endothelial cells. Of interest, treatment of U-87 MG with rhAng1 also increased ERK1/2 phosphorylation. Co-treatment with Ad-transduced Ang-2 inhibited the Ang1 induced ERK1/2 phosphorylation. Of importance for establishing a definitive link between Tie2 and MAPKs, the presence of soluble Tie2, partially inhibited ERK1/2 phosphorylation.

In addition, the inventors have obtained data regarding the upstream effector of p42/p44 MAPK, Ras, by analyzing Ras activity in Ang1-estimulated U-87 MG cells. Ras activity, which detects active GTP-bound Ras, was performed by immunoprecipitation of Ras-Raf complexes (contains only active Ras), and consequent western blotting detection of Ras-GTP molecule. The inventors results show that Ras activity increases after Ang1-stimulation, suggesting the idea of Ang1/Tie2 signalling through Ras/MAPK in gliomas.

Consistant with previous reports, Ang-1/Tie signaling in endothelial cells in vitro involves PI3K/Akt activation (DeBusk et al., 2004; Papapetropoulos et al., 2000). Similar experiments were performed by the inventors confirming the Ang1 effect on Akt phosphorylation in HUVEC (endothelial cells); however, treatment of U-87 MG glioma cells with rhAng1 (100-500 ng/ml) did not modify the pattern of phosphorylation of the Akt molecule.

Tie2 can also recruit additional signaling molecules that participate in cellular pathways that affect the shape and migratory properties of cells. In this regard, the Tie2-associated docking protein Dok-R can potentiate NCK-dependent endothelial cell migration in response to Ang1 (Master et al., 2001; Jones et al., 2003). Our preliminary results performed in stable transfected Tie2–U-251 MG showed that stimulation of Tie2 with Ang1 results in Tie2 association with Dok-R protein.

In order to generate a cell system suitable for the analyses of the Tie2's effect in cell growth, cell invasion, and tumorigenicity, the inventors have constructed an isogenic U-251 MG that constitutively expresses Tie-2. The generation of the cell line involved the stable transfection of Tie-2 cDNA (Audero et al., 2004). Transfected cells have been characterized by immunoblotting for basal and p-Tie2 expression, as well as flow cytometry studies.

In addition and as a complementary system, the inventors planned to modify the Tie2-positive U-87 MG (ATCC). For that purpose, Tie2 siRNA has been used (Santa Cruz Biotechnology) (Niu et al., 2004). Since both U-251 MG and U-87 MG express a mutant PTEN and therefore are characterized by high levels of p-AKT, a LNN29 isogenic cell line expressing Tie2 will be generated. This cell line will be used to examine the effect of the Tie-2 pathway in a glioma cell line expressing a wild type PTEN protein.

Modulation of Glioma Phenotype by Angs/Tie2.

Modulation of Tie2 signaling was investigated in relation to the proliferative and survival signals on U-87 MG glioma cells. First, the viability of sustained Ang-2-treated U-87 MG cells were analyzed. Cell growth followed by 7 d indicated a decreased in viability of 20% of the culture ($P<0.001$), with a representation of 10% of apoptotic cells by TUNNEL assay (data no shown).

It was reported that Ang1 promotes adhesion of Tie2+ hematopoietic stem cells to fibronectin and collagen and also promotes the interaction of endothelial cells with surrounding mesenchymal cells and the extracellular matrix (Davis et al., 1996; Suri et al., 1996; Arai et al., 2004). Therefore, the inventors analyzed the effects of Ang1/Tie2 signalling on glioma adhesion. Briefly, 96-well dishes were coated for 2 hr at room temperature (RT) with rAng1 diluted in PBS. Wells were then blocked for 30 min at RT with 0.5% heat-inactivated BSA in PBS (80° C. for 10 min) and washed three times with PBS before adding cells. U-87 MG cells were harvested and resuspended. 30,000 cells were seeded/well, and the plate was incubated at 37° C. for 1 hr. Nonadherent cells were removed and attached cells were fixed in 4% paraformaldehyde and stained with 0.2% crystal violet. Cells were solubilized in DMSO and absorbance of each well was read at 570 nm. The data suggest that Ang1/Tie2 pathway functions increasing adhesion properties of U-87 glioma cells ($P<0.0001$, double sided t-test). Moreover, addition of sTie2-Fc, in this culture, decreased the proportion of U-87 cells adhering to the Ang1-coated well, probably by blocking Ang1/Tie binding ($P<0.003$ vs. Ang1-treated cultures, double sided t-test). Similar results were obtained when Tie2– and Tie2+U-251 MG were used. In addition, the possibility of Ang1-induced adhesion has been assessed. For that study, the wells were coated with several ECM and then, U-87 MG cells that were previously stimulated with Ang1 (BSA control), were plated on those wells. An increased in the adhesion capabilities of Ang1-stimulated U-87 MG cells to collagen I, fibronectin (both, $P<0.0004$), collagen IV and vitronectin (both, $P<0.01$) has been observed. No modifications were observed with laminin or BSA-coated dishes (both, $P>0.1$), suggesting a indirect role for Tie2 in that experiment, what could be consistent with the reported Tie2-mediated upregulation of integrins.

Chemotactic Migration.

Witzenbichler et al. (1998) have reported the chemotactic properties of Ang1 for Tie2-endothelial cells. A chemotaxis assay was performed in the presence or absence of Ang1. Incubation with various concentrations of Ang1 enhanced chemotactic migration of U-87 MG cells. Migration assay was performed as described previously (Gomez-Manzano, 2003). Briefly, the lower surface of the filter was coated with gelatin. 600 µl of DMEM/F-12 (1:1) containing rAng1 and 0.1% BSA was added into lower compartment of the Transwell chamber, and 100 µl of cell suspension was added in the upper chamber. After 24 h of incubation, the filters were fixed, stained with H/E, and the cells on the lower surface of the filters were counted at 400× with Zeiss microscope. Assays were performed in triplicate. Ang1 led to a significant increase in directed migration of U-87 MG cells (P=0.028, double-sided t-test). To distinguish between chemotactic and chemokinetics effect of Ang1 on U-87 MG, an analysis was performed where similar doses of Ang1 were present above and below the filter. Significant migration was observed only when a concentration gradient of Ang1 was established, a finding typical of factors inducing chemotaxis. In contrast, adding equivalent concentrations of Ang1 to both sides of the filter did not enhance cell movement (P=0.28), thereby excluding a significant chemokinetic effect of Ang1. Counterpart experiments using similar doses of Ang-2, showed that Ang-2 is not a chemotactic for U-87 MG human glioma cells.

Effect of Ang-2 expression on glioma tumorigenicity. Overexpression of Ang-2 modifies intracranial tumorigenicity properties in the U-87 MG cell line. In this study, the U-87 MG cell line was infected with AdAng-2 or an adenovirus control, AdCMV, and 3 days later, cells were implanted intracranially in nude mice. These experiments showed that all control-treated U-87 MG cells (n=17) developed into intracranial tumors that ultimately caused the death of the animals by day 38. The tumors were ellipsoid masses that compressed anatomical structures in the ipsilateral and contralateral hemispheres of the brain and were similar to those formed in other experiments using U-87 MG cells (Fuego et al., 2003). Conversely, animals bearing intracranial Ang-2-treated U-87 MG cells had a longer survival (P<0.0001, log-rank test); and importantly, 3 of them (3/17; in controls: 0/17) longer than 100 days without signs of neurological disease. These studies showed sustained expression of Ang-2 lead to significant increased on survival. Examination of the brains of long-term survivor animals did not revealed residual tumor. Time point analyses were performed were animals were sacrificed 36 h and 10 days after cell implantation. Analyses of Ang-2-U-87 MG derived tumors within 36 hrs of implantation showed enhanced expression of Ang-2. 10 d after cell implantation, Ang-2-U-87 MG derived tumors showed big areas of necrosis and fibrinoid necrosis of tumoral vessels. These tumorigenicity studies strongly show that overexpression of Ang-2 resulted in inhibition of tumor production or markedly interference with the progression of tumor growth, and suggest a relationship between Tie2 signalling and glioma development.

NLLMAAS (SEQ ID NO:20) Peptide Specifically Interacts with Tie2.

In an attempt to identify peptides that specifically interact with and block the Tie2 pathway, Tournaire et al. (2004) screened a phage-displayed peptide on a recombinant Tie2 receptor. One peptide, NLLMAAS (T4), completely abolished by binding to the Tie2 receptor, the binding of both Ang1 and Ang-2. Testing the binding of the proposed Tie2-ligand, T4, the inventors synthesized the peptide linked to FAM signal that was suitable for flow cytometric detection. Peptide was synthesized by automatic solid phase chemistry using Fmoc strategy. The N-terminal aminohexanoic acid was labeled by coupling 5(6)-carboxyfluorescein. Peptides were purified to >98% purity by reverse phase HPLC. The inventors have obtained data confirming by flow cytometric methods, that the peptide T4 binds preferentially to the membrane of cells overexpressing Tie2, using U-251 MG isogenic system, and A172.

Tie2+ Populations Derived from Cell Lines.

The inventors have isolated Tie2+ and Tie2− populations from A172 human glioma cell line by flow cytometric softening. Similarly, Tie2+ and Tie2− populations will be isolated from U-87 MG cell line. Sorted Tie2+ and Tie2− aliquots from each cell line will be examined by flow cytometry to evaluate the efficiency of sorting and purity of both populations will be analyzed. Parallel studies will be performed by immunohistochemistry analysis of Tie2 expression.

Tie2 Expression in Tumor Spheres Derived from Human Glioma Tumors.

Cultures have been established from 3 glioblastoma multiforme tumors, which were acutely dissociated into individual cells, and cultured. Each brain tumor yielded a minority fraction of cells that demonstrated growth into neurosphere-like clusters, termed tumor spheres. These tumor neurospheres showed some properties related with stem cell populations, as self-renewal (formation of secondary and tertiary neurospheres) and were positive for stem-cell markers. Of interest, Tie2 expression was positive in these cultures.

Frequency of stem cells populations within every tumor will be determined by primary sphere formation assay. Limited dilutions will be performed as described previously (Singh et al., 2003). Spheres will be dissociated and plated in 96-well microwell plates in 0.2 ml volume of serum-stem cell line medium. Cultures will be fed 0.025 ml of this media every 2 days until day 7, when the percentages of wells not containing spheres for each plating density will be calculated and plotted against the number of cells per well. For primary sphere formation assays, this analysis will be performed on the entire acutely dissociated tumor cell population on day 0 to quantify stem cell frequency within the tumor.

Purity of Brain Tumor Stem Cell Population.

Because normal stem cells can migrate to sites of injury, and brain tumor cultures may potentially be contaminated with some normal neural stem cell, a conventional cytogenetic analysis will be conducted to demonstrate that the glioma tumor stem cells being isolated are indeed transformed and are not normal brain cells.

Identification of Double Tie2/CD133 Population.

The co-existence of Tie2+ and CD133+ cells will be analyzed by using double immunostaining and flow cytometric analysis to detect these markers in the membrane of the isolated population from both, Tie2+ cells from glioma cell cultures, and tumor neurospheres from GBMs specimens.

Study of the Potential of Tie2+ Cell Populations for Self-Renewal and Proliferation.

Neurosphere-initiating cells will be assessed for self-renewal activity by examining the replating activity of single viable cells from the Tie2+-sorted/expanded neurosphere cells. Cells derived from neurosphere cultures (single neurospheres in 96-well dishes) initiated from Tie2+-sorted cells should consistently reinitiate the formation of secondary neurospheres. The morphology of secondary tumor spheres and the maintenance of expression of the neural stem cell markers nestin, CD133, Brm1, will be assessed, as well as maintenance of Tie2 expression. Proliferation ability of Tie2+ cells will be assessed by plating 1000 cells/well, and quantifying the number of viable cells on days 0, 3, 5, and 7 after plating using a colometric assay. In addition, MIB-1 index will be analyzed for the tumor neropheres.

Tumorigenicity in the Initial Tumor.

Tie2 expression in human glioma cell lines: correlation with tumor formation. The main question for this experiment is the importance of Tie2+ populations in tumorigenesis or glioma initiation. A time point analysis of the evolution of the histology and growth patterns of intracranial U-87 MG-derived xenografts has been performed. Tie2+ and Tie2− U-87 MG cells will be injected intracranially in nude mice. Two weeks after cell implantation animals will be sacrificed and brains collected and analyzed for incorporation of transplanted cells into the brain. Analysis will be based on the formation of tumor. In the case of tumor formation the inventors will examine if tumors maintain similar characteristics of U-87 MG parental-derived tumors, such as vascular proliferation (factor VIII, CD31), MIB index, and/or Tie2 expression.

Statistical Methods.

Fisher's exact test will be used to assess differences between the Tie2+ and the Tie2− groups. The inventors contemplate that at least 90% of the Tie2+ mice will have tumor 2 weeks post intra-cranial injection while no more than 20% of the mice in the Tie2− group will have tumor at this time.

To determine if there is a dose-response relationship within the Tie2− and Tie2+ cell lines a Bayesian generalized linear model will be used to assess the dose response relationship for the Tie2− and Tie2+ cell lines. In this study mice will be randomized to a combination of one of three cell concentrations and also to Tie2− or Tie2+ cell lines. Note that the cell lines are derived from specific patient's tumors thus the inventors have included a cell line source random effect in this model. The response variable for this model is the presence or absence of tumor within a given mouse. This methodology models association between pairs of responses for a given patient with log odds ratios.

The inventors contemplate using 2 mice per treatment group/cell line/cell source combination (total mice=2 mice×6 trt grps/Cell line combinations×10 cell sources=120 mice). With a total of 20 mice receiving $10^3$ Tie2− cells and 20 mice receiving $10^5$ Tie2− cells, the Fisher's Exact test will have 97% power to detect a difference of 70% tumorigenesis rate in the $10^5$ Tie2− cells group vs. a 10% tumorigenesis rate in the $10^3$ Tie2− cells group.

To analyze the survival data, survival curves will be estimated using the Kaplan-Meier method. The inventors will use Cox proportional hazards regression analysis to estimate the hazard ratio between groups along with a 95% confidence interval for this ratio and a likelihood ratio p-value for testing if the ratio is different from 1 (the value of the ratio if the groups have the same survival distributions). The hazard ratio quantifies the relative rates of death between the groups. Based on historic data the inventors expect the control animals to have a median survival of 20 days.

A second group of experiments will be focused in analyze the anticancer effect with viral spread (Fueyo et al., 2003). The inventors will perform similar studies as above, however animals will be sacrificed at different time points after cell implantation: 10 and 20 days, and brains will be extracted and analyzed for: (a) tumor size, (b) areas of necrosis, (c) viral spread, and (d) localization of the virus around necrosis/microcystic areas, and compare with U-87 parental-derived tumors. The study will reflect adenoviral infection and replication within tumor cells.

For each measure, Spearman rank correlation analysis, which is sensitive to general monotonic relationships and is robust to outliers in the data, will be performed.

Tie2+ Population in Tumor-Stem Cell Like Populations.

To determine if the Tie2+ populations from human glioma specimens are related to the human brain tumor initiating cells, the inventors will transplant Tie2+ sorted/expanded neurosphere cells into nude mice. Briefly, expanded Tie2+ and Tie2− sorted neurosphere cells at passage 6-10 will be harvested and gently dissociated with collagenase. $10^3$, $10^4$, $10^5$ cells will be transplanted from every group (Tie2+ and Tie2−) into the brain of nude mice. Three weeks after cell implantation animals will be scarified and brains collected and analyzed for incorporation of transplanted cells into the brain. Analysis will be based on the formation of tumor. In the case of tumor formation all the key WHO defining features of GBMs will be assessed by H&E staining of the glioblastoma xenograft (mitotic figures, vascular proliferation, nuclear atypia, and pseudopallisading necrosis). In addition, the in situ expression of neuronal (β-tubuline 3) and glial (GFAP) cells will be examined, as well as precursor markers (Nestin, CD133), and Tie2 expression. The results will be compared to the original sample from the tumor (cryostat section from original tumor). Finally, proliferation properties by expression analysis of Ki-67, will be quantify and compared to the original tumor.

Modulation of Tie2 Pathway.

Modulation of Tie2 pathway will be studied using two different approaches. First, acute stimulation using recombinant protein Ang1 (rAng1) will be studied using time-dependent and dose-dependent studies. Counterpart experiments will consist on competitive inhibition by treatment with rAng-2, soluble Tie2 receptor (Tie2-Fc), or T4 peptide (as Tournaire et al., 2004).

Second, effect of sustained Tie2 stimulation will be also studied, as it is a more similar to the in vivo scenario, where Ang1 and Ang-2 are secreted continuously in the tumor environment. For that purpose adenoviral vectors expressing Ang1 will be used (Genetech, CA), and competitive inhibition will be performed by the use of an adenovirus expressing Ang-2.

Development of a Differential Tie2 Expression System.

The inventors have tested the expression of endogenous Tie2 in a panel of glioma cell lines cell lines. Two Tie2-positive glioma cell lines, U-87 MG, D54 MG, and two Tie2-negative glioma cell lines, U-251 MG and LN229 have been chosen for further study. The inventors have generated an isogenic system consisting of parental U-251 MG and Tie2-expressing U251. Similarly, U-87 MG cell line has been cloned and several clones have been isolated that differ in the levels of Tie2 transcript expression. The inventors have demonstrated that siRNA-Tie2 can inhibited more than 80% of the Tie2 transcript. This strategy will be extended to the Tie2-positive cell line D54 MG and the Tie2-negative cell line LN229.

Ang1/Tie-2 Signaling Pathway in Glioma Cells.

Ang1/Tie2 system in endothelial cells has been related with migration, sprouting, and survival. In these cell lines, several groups have demonstrated that these processes are mediated through pathways that include PI3K/Akt, FAK, Raf/Ras/MAPK, and Dok-R/Dok-2/Nck/Pak. Although the significance of Ang1 and Tie2 in vasculogenesis is well established, the signal transduction cascades initiated by the binding of Ang1 to the Tie2 receptor have not been completely characterized. In addition, the transduction signal trigger by Ang1-mediated activation of Tie2 is unknown in glioma cells. The inventors have found that Ang1/Tie2 is involved in MAPK activation, and no Akt activation, in U-87 MG cell line. In addition, active Tie2 recruits Dok-R in glioma cells, leading to the hypothesis of Tie2 regulating glioma migration.

The Role of Ang1/Tie2 in the Activation of the Ras/MAPK Pathway.

Ang1 had been previously shown to activate the MAPK signaling cascade in HUVECs. The inventors have data suggesting the presence of an active Tie2/Ras/MAPK pathway in U-87 MG glioma cells. Studies will be performed using a panel of glioma cells, including Tie2+/− isogenic system. For these studies the inventors will determine whether Ang1-triggered p42/p44 phosphorylation can be completely abolished by recombinant soluble Tie2 receptor (sTie2), by the presence or absence of a series of concentrations of the Tie2-binding peptide T4, and by Ang-2. The inventors will also study the role of Ras, an intermediary signaling mediator between receptors and ERK1/2. Ras-Raf complexes (containing only active Ras) will be immunoprecipitated, and consequent western blotting detection of Ras-GTP molecule. The inventors have shown that Ras activity increases after Ang1-stimulation, suggesting that Ang1/Tie2 signaling through Ras/MAPK in gliomas. Studies will involve pre-treatments with Tie2 blockers, as well as inhibitors of Ras (FTIs) and MAPK (PD98059) to ascertain whether there is a concatenation of signaling from Ang1/Tie2 to Ras/MAPK.

The Role of Ang1/Tie2 in the Activation of the PI3k/AKT Pathway.

A recent study indicates that Tie2 activates PI 3'-kinase through an association with the p85 regulatory unit (Jones et al., 1999; Kontos et al., 1998). Although these findings have been observed without Ang1 stimulation, this result suggests that Ang1 can activate PI 3'-kinase through Tie2 binding. Data produced by the inventors suggest that Ang1/Tie2 does not regulate PI3/AKT activation in U-87 MG human glioma cells. Studies will be directed to ascertain whether Ang1 induced phosphorylation of the Tie2 receptor results in the activation of the p85 subunit of PI 3'-kinase and increased the activity of PI 3'-kinase in the above isogenic cell lines. Cells will be seeded and grown for 24 hours. Then, the medium will be change to medium containing wortmannin. Two hours later, rAng1 will be added to the cells at the indicated amounts, and the cells will be incubated for the indicated times. Then a phosphorylation assay of the Tie2 or p85 subunit of PI 3'-kinase will be performed with anti-Tie2 antibody (Santa Cruz Biotechnology) or anti-p85 subunit of PI 3'-kinase (Upstate Biotechnology, Inc) according to the method described by Maisonpierre and collaborators (1997) and Hu and coworkers (1996). In addition, the phosphorylation of AKT will be assessed comparing basal and phosphorylated levels. If PI3K/Akt pathway is activated in glioma cell lines upon Tie2 activation, complementary studies to confirm the cellular responses to that pathway will involve blockade of that signaling by LY294002, and PTEN expression (Gomez-Manzano et al., 2003).

The Role of Ang1/Tie2 in the Activation of the Dok-R Pathway.

Addition of PI 3' kinase inhibitors in cell motility assays blocks Ang1-stimulated migration of both endothelial and nonendothelial cells expressing Tie2 as well as Ang-2-stimulated chemotaxis of endothelial cells. Interestingly, however, inhibition of PI 3' kinase activity can only partially inhibit the chemotactic effect of Ang1 on endothelial cells (Jones et al., 1999; Fujikawa et al., 1999), thereby implying that additional Tie2 binding partners may also contribute to Ang1-mediated endothelial cell migration. Phosphorylation of Tie2 further results in its association with a docking protein related to downstream of kinase Dok-R (Jones and Dumont, 1998). The inventors will perform studies to ascertain whether the Ang1/Tie2 signaling in human glioma cells involves the activation of Dok-R. The most straightforward approach is the performance of Tie2 and DokR co-immunoprecipitation in the presence of Ang1 or Tie2-blocking agents in isogenic cell lines and in A172 human glioma cell line (Tie2+). Recruitment of Dok-R to the activated Tie2 receptor via its PTB domain results in the phosphorylation of Dok-R on multiple tyrosine residues. Dok-R will be immunoprecipitated after Ang1 stimulation followed by immunoblotting the precipitates for phosphotyrosine to establish whether Ang1-mediated activation of Tie2 results in the phosphorylation of Dok-R. Phosphorylation of DokR establishes binding sites for the Ras GTPase-activating protein and the adaptor protein Nck, both of which have been implicated in cell motility and actin rearrangement (Jones et al., 2003). Coimmunoprecipitation studies will then be performed to ascertain whether Ang1 triggering induces significant association of Dok-1 with PAK and Nck. To ascertain that Ang1/Tie2 stimulates the activation of PAK kinase in glioma cells, the inventors will stimulate Tie2 positive glioma cells with mock, Ang1 or EGF, and PAK immunoprecipitates will be subjected to an in vitro kinase assay to measure the ability of PAK to phosphorylate MBP (myelin basic protein). If the experiments show that Ang1 stimulates PAK activity, relationship between PAK and migration can easily tested by overexpressing PAK and then, analyzing migration abilities of glioma cells.

Cellular Responses Elicited by Activation of the Ang1/Tie2 Pathway.

Studies will be performed to analyze the impact of Ang1/Tie12 signaling in the glioma phenotype. For specificity purpose sTie2, T4 peptide, and Ang-2, will be used, as well as integrin-blocking agents (RGD; see Fueyo et al., 2003). Signaling pathways will be modulated by specific inhibitors (wortmannin or LY294002 for PI3K pathway; PD98059 for MAPK activity) to correlate signal pathways with cellular responses.

Survival.

Although Ang1 does not stimulate the proliferation of endothelial cells, it promotes survival of those cells (Koblizek et al., 1998; Kim et al., 2000). The inventors have shown that blockade of Tie2 by sustained expression of Ang-2, leads to a decrease of viability in U-87 MG cell line. Studies will be performed using isogenic cell lines exposed to Ang-2, sTie2 and T4, with or without Ang1 treatment. Population doubling time, cell cycle analysis, and BrdU incorporation will be assessed for the Ang1-treated isogenic systems and then compared. Involvement of signaling pathways will be studied by analysis of Tie2 phosphorylation, activation of MEK or Akt (western blotting), and the use of specific inhibitors.

Colony Forming Assay.

The effect of Ang-1 on colony formation ability under anchorage independent conditions in the above glioma isogenic cell lines will be assessed. The inventors contemplate an enhanced ability to form colonies in the isogenic cell lines expressing Tie2 and a reduction in the number and the size of the colonies in cells treated with soluble Tie2-Fc, Ang-2. It is also contemplated that exogenous Ang-1 will support colony formation in a dose-dependent manner.

Tie2/Ang1 Pathway in Adhesion.

In vitro experiments have shown that Ang1 has little effect on proliferation, but that it potently stimulates endothelial cell adhesion (Carlson et al., 2001; Xu et al., 2001). It was reported that Ang1 promotes adhesion of Tie2+ hematopoeitic stem cells to fibronectin and collagen (Sato et al., 1998; Takakura et al., 1998), and also promotes the interaction of endothelial cells with surrounding mesenchymal cells and the extracellular matrix (Davis et al., 1996; Suri et al., 1996). Arai and collaborators (2004), demonstrated that Ang1 enhances through Tie2 the adhesion of HSCs to be adhered to the bone. Since Tie2 is expressed in human glioma cells, the inventors contemplate that Tie2 is critical for maintenance of the neoplastic phenotype via cell adhesion to the ECM of the tumor. Therefore, the effects of Tie2/Ang-1 signaling on cell adhesion will be analyzed.

First Tie2+ cell lines (U-87 MG and A172) will be plated onto wells of a tissue culture dish that had been precoated with either Ang-1 or Ang-2 or various other known ECM proteins. These experiments will be performed also with isogenic cell lines that differ only in their Tie2 status (U-251 MG). The requirement of Tie2 for adhesion will be assessed by blocking the positive reactions with sTie2 and or T4 peptide. Because it has been recently demonstrated that Tie2/Ang-1 interaction enhances adhesion of HSC via β1-integrin (Arai et al., 2004), the effect of the Ang1-treatment of Tie-2+ human glioma cells U-87 MG, A172, and Tie2-expressing U-251 MG in the expression of β1-integrin will be studied using Western blot. If β1-integrin is upregulated upon Tie2 activation, adhesion studies will be performed using RGD peptide as blocker. In a parallel set of studies, pharmacological inhibition of ERK1/2 activation (PD98059) will be induced and assessed for Ang1-induced adhesion, suggesting that intracellular activation of MAPK is required for Ang1-induced adhesion.

Another study is based on the reported capability of Ang1 to be incorporated into the ECM (Xu et al. 2001). To understand the impact of that phenomena in glioma phenotype, ECM-associated Ang1 will be studied in glioma adhesion. Glioma cells will be seeded onto plastic dishes with or without Ang1 or the culture dish containing the ECM components deposited by confluent U-87MG expressing Ang1 (infected with AdAng1). Adherence of glioma cells to ECM-associated Ang1, as well as the activation of Tie2 receptor in their surfaces will be assessed by western blot. Competitive experiments will include the blockade of the Tie2 receptor binding (sTie2, T4), as well as integrin binding (RGD).

The Role of Tie2/Ang1 in the Migration of Glioma Cells.

Several reports have shown data on the chemotactic properties of Ang1 for endothelial cells (Witzenbichler et al, 1998), as well as eosinophils (Feistritzer et al., 2004). An isogenic system (U-87parental and siTie2–U87 MG; U-251 MG parental and Tie2-expressing U-251 MG) will be used to test chemotactic properties of Ang1 in cancer cells, particularly gliomas. Using chemotaxis Boyden chambers, the chemotactic response of those cell lines to increasing amounts of Ang1 and Ang-2 will be assessed and compared to that FBS. To establish specificity, Ang1 will be applied at different doses with and without a 10-fold excess to reach maximal saturated concentration of either sTie2 or T4 to the lower chambers. To distinguish between chemotactic and chemokinetics effects of Ang1 on glioma cells, a modified checkerboard analysis will be performed in which the concentration of the chemoattractant above and below the filter will vary. If Ang1 is a chemoattractant factor, glioma cells only will migrate when a concentration gradient is present.

Generation of an Oncolytic Adenovirus Retargeted to Infect Tie2+ Cells.

For uptake-related studies, the inventors have constructed isogenic cell lines that only differ in their Tie2 status. The inventors also contemplate the introduction of GFP cDNA in a retargeted Tie2 construct to easily monitor the adenoviral infectivity. In order to examine the selective replication of the proposed construct, the MAPK activity of several cell lines (Ahmed et al., 2003) have been tested and will use MAPK inhibitors for specificity questions.

Generation of Ad-E1A-COX-Tie2.

To study uptake of a retargeted adenovirus, the inventors will construct an adenovirus carrying the GFP cDNA in the E3 deleted region, driven by the CMV promoter. T4 (Tie2 ligand) coding sequence will be inserted in the HI loop of the fiber protein. The modified adenoviruses will be propagated in A549 cells (ATCC) where the virions should have only chimeric fibers. Since A549 cells do not express adenoviral genes, the production of wild-type adenovirus is highly unlikely. PCR amplification of E1A, and knob fiber-encoding sequence, followed by enzyme digestion (Fueyo et al., 2000) will be performed for each batch of the virus (See Fueyo et al., 2003). An Ad-E1A-cTie2 will be generated as a control, having a similar backbone structure than Ad-E1A-Tie2 but having a random peptide in the HI loop. Both adenoviruses will carry a minicassette of expression for the GFP gene (CMV-GFP-SV40 polyadenylation signal) that will be cloned in the deleted E3 region. The strategy will consist of introducing the Tie2 ligand into the HI loop of the fiber protein. pXKdeltaHI is a fiber shuttle vector designed to introduce the ligands into the HI loop of the fiber protein and will be used in the construction of retargeted adenoviruses of the invention. The T4 peptide encoding sequence will be cloned into the EcoRV site of the vector. In addition to the ligand-encoding sequence DNA fragment to be cloned should contain two Thr codons upstream from the ligand and a CC sequence downstream of it (Thr-Thr-ligand-CC). This way, the ligand will be positioned between the Thr-546 and Pro-547 residues of the fiber protein, that is—within the HI loop sequence. For CAR-binding ablation the approach by Alemany et al. (2001) will followed, mutating the residue Y477 in the loop of the fiber, which is critical for binding.

Replication-Selective Tie2 Targeted Adenovirus.

In a second step the inventor will construct the Ad-E1A-COX-Tie2. Ad-E1A-COX-Tie2 will contain the adenovirus E1A gene fused with the PTGS2 3' UTR, as Ahmed et al., 2003. For this construct the inventors will repeat several of the in vitro experiments performed with Ad-E1A-Tie2, and then it will be tested for anti-cancer effect in vivo. Adenoviral constructs used as controls will include adenovirus with a mutant peptide (cTie2) in the HI loop (Ad-E1A-Cox-cTie2), Ad-E1A-Cox (non-retargeted virus), Adwt, Adwt-Tie2, and PBS. For the in vivo experiments isogenic systems from high-MAPK activity cell lines (U-87 MG and U-251 MG) will be used, as well as low-MAPK activity cell line (U-118 MG). The pathologic examination of the infected xenografts should reveal the characteristics of the adenoviral spread, the timing of the spread and the pathologic basis of the anti-glioma effect.

Selective Infectivity of the CAR-Ablated Tie2-Targeted Adenoviruses.

In order to ascertain whether the insertion of the Tie2 fiber motif is responsible for selective infectivity, two studies will be performed with an established system where U-251 MG cells have been stably transfected with Tie2 cDNA. In addition, infectivity experiments will be performed in a set of cell lines that express different levels of Tie2 and CAR: HUVEC, U-87 MG, A172 (low CAR/high Tie2), LN229, SNB19 (high CAR, low Tie2).

CAR-Ablated Ad-E1A-Tie2 Infection Via Tie2.

The inventors will use GFP (cell quantification) and E1A expression (cell quantification by immunohistochemistry) to quantified the infectivity of the different constructs. The inventors contemplate that the Tie2-targeted vector will infect high-Tie2 expressing cell lines more efficiently, independently of their CAR expression. The Ad-cTie2 construct, which is expressing in the HI loop of the fiber the control peptide, should infect all these cultures poorly.

Mechanisms of Ad-Tie2 Uptake.

Competitive inhibition of Ad-mediated gene delivery by the T4 peptide (Tie2) will be studied using test and control adenoviruses in assays based on the competitive inhibition of Ad-mediated gene delivery by the targeted Tie2 peptide (T4)(see Fueyo et al., 2003 for methods). These studies will address the specificity of the Tie2-adenovirus construct. Consequently, cells will be treated with either T4 or a control peptide, cT4, and then infected with Ad-GFP-Tie2, Ad-GFP-cTie2, or wild-type adenoviruses. Since Tie2 is used only by the Ad-Tie2 construct for internalization, the inventors contemplate a decrease in the infectivity of this vector in the U-251-Tie2 cells pretreated with the T4 peptide. On the contrary, pretreatment with this peptide should not result in a modification of the infectivity of the control adenoviruses.

Viral Production.

Ad-GFP-Tie2 and Ad-GFP-cTie2 possess similar replication systems but the insertion of the Tie2-targeted peptide and ablation of the CAR binding enhances the selectivity of the former to infect Tie2 expressing glioma cells. Since the ability to replicate is inherently related to the ability of the virus to infect, the inventors are interested in determining whether Ad-GFP-Tie2 infection leads to an increased viral production in Tie2-expressing cancer cells. For viral production analysis the inventors will use TCID50 methodology and an hexon-expressing quantitative assay (BD Bioscience).

Oncolytic power of Ad-E1A-Cox-Tie2. Studies will be performed to compare the oncolytic effects of Ad-E1A-Cox-Tie2, Ad-E1A-Cox-cTie2, Ad-E1A-Cox (non-retargeted virus), Adwt, Adwt-Tie2 in normal (toxicity) and cancer cell cultures. These studies will be design to demonstrate that the new construct enhances oncolytic effect in the cultures with Tie2 and low CAR expression (U-87 MG and HUVEC).

Cell Viability Analyses.

Crystal Violet and Trypan Blue Exclusion Test will be performed in the panel of glioma cells described above after infection with Ad-E1A-Cox-Tie2, and the explained controls. Dose dependence experiments will be performed (Gomez-Manzano et al., 2004).

Toxicity in Normal Cultures.

The expression of Tie2 and CAR in Normal Human astrocytes and Neuronal Precursors will be assessed by RT-PCR, Western blot and Immunohistochemical analyses. Transduction will be assessed by GFP detection analyzed after infection with the GFP-constructs (Ad-GFP-Tie2, Ad-GFP-cTie2, and Ad-GFP). Cell viability will be assessed by trypan blue exclusion test after viral infection. The inventors contemplate that although neuronal precursors express Tie2, these cells would not support a efficient viral replication due to low levels of MAPK activity.

MAPK-Dependent Replication.

Although the correlation between MAPK activity and Ad-E1A-COX ability to replicate has been shown (Ahmed et al., 2003), the inventors have designed studies to assess the ability of retargeted constructs to replicate in glioma cells with high or low MAPK activity. To characterize the effects of the insertion of the 3' UTR on E1A expression, inhibitors of kinases signaling, PD98059 (p42/p44 MAPK inhibitor), and for specificity testing: SB203580 (p38 MAPK inhibitor) and LY294002 (PI3K inhibitor) will be used. The inventors will use an isogenic U-87 MG system, containing a stably integrated, IPTG-inducible activated Ha-rasVal12 cDNA (Sheng et al., 2000). This model system is based in cells that only differ in the expression of an activated variant of the Hras oncogene, Ha-rasVal12 (Sheng et al., 2000). The will assess whether PTGS2 3' UTR-mediated Ad-E1A-COX-Tie2 depends on the P-MAPK pathway. The inventors have shown that PD98059 effectively inhibited P-MAPK expression in U-87 MG cells. The replication capability of Ad-E1A-COX-Tie2 in U87-MG cells untreated and treated with PD98059 (and the control inhibitors) will be assessed. The inventors contemplate that inhibition of P-MAPK activity by PD98059 will greatly reduce the ability Ad-E1A-COX-Tie2 to replicate even with high expression of Ha-rasVal12 induced by IPTG in the isogenic U-87 MG. To further assess the selectivity of the Ad-E1A-COX-Tie2 virus, the inventors will use histologically closely matched glioma tumor lines that differ in P-MAPK activity (Ahmed et al., 2003).

Correlation of Tie2 Targeted Therapy and Survival.

The implantable guide-screw method, as described herein will be used in these studies (Lal et al., 2000). In vivo experiments will be performed with 3 isogenic cell line-based systems expressing different levels of Tie2: (a) parental U-87 MG (high expression levels of Tie2 and high MAPK activity) and siTie2-transfected U-87 MG cells (low Tie2 expression); (b) U-251 MG parental (undetectable levels of Tie2 and high MAPK activity) and U-251 MG-Tie2 (high expression levels of Tie2 and high MAPK activity); and (c) U-118 MG parental (low MAPK, Tie2) and U-118 isogenic cell line (low MAPK, Tie2). The studies with the U-87 MG system (very low CAR expression) address the question of the relevance of Tie2 on the anti-cancer effect. U-87 MG parental cells will be implanted into the brain of nude mice animals (Lal et al., 2000), and then treated with Ad-E1A-Cox-Tie2 (T4 peptide), Ad-E1A-Cox-cTie2 (control peptide), Ad-E1A-Cox (non-retargeted virus), Adwt, Adwt-Tie2, and PBS (to examine the effect of the technique in survival). A similar strategy will be used with the isogenic cell line U-87 MG.siTie2 cells. Results from preliminary studies show that an empirically chosen dose of $1.5 \times 10^8$ (administered three times) of a non-targeted and retargeted construct significantly improves survival time (Fuego et al., 2003; Gomez-Manzano et al., 2004). Animals will be sacrificed if and when they demonstrate signs of general toxicity, or neurological signs or, in the case of long survivors, animals will be euthanized 90 days post-implantation, and brains will be extracted. Tumors will be examined using H/E staining and immunohistochemistry for Tie2 and p42/p44 MAPK (basal and phosphorylated levels) expression. Similar experiments will be performed with the three above described pair of isogenic cell lines.

One of skill in the art readily appreciates that the present invention is well adapted to carry out the objectives and obtain the ends and advantages mentioned as well as those inherent therein. Methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437

U.S. Pat. No. 4,366,241
U.S. Pat. No. 4,472,509
U.S. Pat. No. 4,554,101
U.S. Pat. No. 4,683,195
U.S. Pat. No. 4,683,202
U.S. Pat. No. 4,800,159
U.S. Pat. No. 4,883,750
U.S. Pat. No. 4,938,948
U.S. Pat. No. 4,946,773
U.S. Pat. No. 5,021,236
U.S. Pat. No. 5,196,066
U.S. Pat. No. 5,279,721
U.S. Pat. No. 5,545,548
U.S. Pat. No. 5,665,567
U.S. Pat. No. 5,840,873
U.S. Pat. No. 5,843,640
U.S. Pat. No. 5,843,650
U.S. Pat. No. 5,843,651
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,483
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,882,864
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,630
U.S. Pat. No. 5,922,574
U.S. Pat. No. 5,925,517
U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 6,586,411
U.S. Patent Appln. 20030138405

Abbondanzo et al., *Breast Cancer Res. Treat.*, 16:182(#151), 1990.
Ahmed et al., *Nat. Biotechnol.*, 21(7):771-777, 2003.
Aiello, *Proc. Natl. Acad. Sci. USA*, 92:10457, 1995.
Alemany et al., *Cancer Gene Ther.*, 6:21-5, 1999.
Alemany et al., *Neurologia.*, 16(3):122-127, 2001.
Allred et al., *Arch. Surg.*, 125(1):107-113, 1990.
Andreanski et al., *Cancer Res.*, 57:1502-1509, 1997.
Arai et al., *Cell*, 118(2):149-161, 2004.
Atherton et al., *Biol. Reprod.*, 32(1):155-171, 1985.
Audero et al., *J. Biol. Chem.*, 279(13):13224-13233, 2004.
Bellus, *J. Macromol. Sci. Pure Appl. Chem.*, A31(1): 1355-1376, 1994.
Bemt et al., *J Virol.*, 76:10994-1002, 2002.
Bigner et al. *Cancer Res.*, 50(24):8017-8022, 1990.
Bilton and Booker, *Eur. J. Biochem.*, 270:791-798, 2003.
Bischoff et al., *Science*, 274:373-376, 1996.
Brooks et al., *Methods Mol Biol.*, 129:257-69, 1999.
Brown et al. *Immunol. Ser.*, 53:69-82, 1990.
Brown et al., *Am. J. Pathol.*, 156: 2179-2183, 2000.
Cameliet and Jain, *Nature*, 407:249-57, 2000.
Campa et al., *Biochem. Biophys. Res. Commun.*, 275(2): 631-636, 2000.
Carlson et al., *J. Biol. Chem.*, 276(28):26516-26525, 2001.
Carlson et al., *Mol. Ther.*, 6:99-105, 2002.
Chase et al., *Nat. Biotechnol.*, 16, 444-448, 1998.
Cheng et al., *Proc. Natl. Acad. Sci. USA*, 93:8502-8507, 1996.
Chintala et al., *Oncogene*, 15(17):2049-2057, 1997.
Cho et al., *Gene Ther.*, 7(9):740-749, 2000.
Cho et al., *Gene Ther.*, 9(17):1139-1145, 2002.
Coffey et al., *Science*, 282:1332-1334, 1998.
Collins and James, *FASEB J.*, 7:926-930, 1993.
Costello et al., *Cancer Res.*, 56:2405-2410, 1996.
Costello et al., *Cancer Res.*, 57:1250-1254, 1997.
Dai et al., *Nature*, 379:458-460, 1996.
Davis et al., *Cell*, 87:1161-116, 1996.
Davis et al., *Clin. Cancer Res.*, 10:33-42, 2004.
De Jager et al., *Semin. Nucl. Med.*, 23(2):165-179, 1993.
DeBusk et al., *Exp. Cell. Res.*, 298(1):167-177, 2004.
Dholakia et al., *J. Biol. Chem.*, 264(34):20638-20642, 1989.
Doolittle and Ben-Zeev, *Methods Mol Biol*, 109:215-237, 1999.
Drapkin et al., *J. Clin. Invest.*, 105(5):589-596, 2000.
Dyson and Harlow, *Cancer Surv.*, 12:161-195, 1992.
Ekstrand et al., *Proc. Natl. Acad. Sci. USA*, 89(10):4309-4313, 1992.
Eskandar et al., *Anat, Rec.*, 230(2):169-174, 1991.
European Appln. 320308
European Appln. 329 822
Feistritzer et al., *J Allergy Clin Immunol.*, 114(5):1077-1084, 2004.
Ferrara and Alitalo, *Nature Medicine*, 5:1359-1364, 1999.
Ferrara, *Nat. Rev. Cancer*, 2:795-803, 2002.
Fine et al., *J. Clin. Oncol.*, 18:708-715, 2000.
Flint and Shenk, *Annu. Rev. Genet.*, 31:177-212, 1997.
Forsythe et al., *Mol. Cell Biol.*, 16:4604-4613, 1996.
Frederick et al., *Neuro-oncol.*, 2(3):159-163, 2000.
Freytag et al., *Hum. Gene Ther.*, 9:1323-1333, 1998.
Frohman, In: *PCR Protocols: A Guide To Methods And Applications*, Academic Press, N.Y., 1990.
Fueyo et al., *Archives of Neurology*, 56(4):445-448, 1999.
Fueyo et al., *J. Natl. Cancer Inst.*, 95:652-60, 2003.
Fueyo et al., *Nat. Med.*, 4:685-690, 1998b.
Fueyo et al., *Nature Medicine*, 4(6):685-690, 1998.
Fueyo et al., *Neurology*, 50:1307-1315, 1998c.
Fueyo et al., *Neurology*, 51:1250-1255, 1998a.

Fueyo et al., *Oncogene*, 12:103-110, 1996a.
Fueyo et al., *Oncogene*, 13:1615-1619, 1996b.
Fueyo et al., *Oncogene*, 19:2-12, 2000.
Fueyo et al., *Oncogene*, 19:2-12, 2000.
Fujikawa et al., *J. Vasc. Res.*, 36(4):272-281, 1999.
Furnari et al., *Cancer Surv.*, 25, 233-275, 1995.
Gage, *Obstet. Gynecol.*, 96(6):879-885, 2000.
Galli et al., 2004
GB Appln. 2 202 328
Geoerger et al., *Cancer Res.*, 62(3):764-772, 2002.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gomez-Manzano et al., *Ann. Neurol.*, 53:109-17, 2003.
Gomez-Manzano et al., *Cancer Res.*, 56:694-9, 1996.
Gomez-Manzano et al., In: *Gene Transfer and Therapy for Neurological Disorders*, Chiocca and Breakefield (Eds.), Human Press Inc.: NJ, 201-225, 1998.
Gomez-Manzano et al., *Int. J. Oncol.*, 19(2):359-365, 2001.
Gomez-Manzano et al., *Oncogene*, 23(10):1821-1828, 2004.
Graham and Prevec, In: *Methods in Molecular Biology: Gene Transfer and Expression Protocol*, Murray (Ed.), Humana Press, Clifton, N.J., 7:109-128, 1991.
Grunhaus and Horwitz, *Seminar in Virology*, 3:237-252, 1992.
Gulbis and Galand, *Hum. Pathol.*, 24(12):1271-1285, 1993.
Haberkorn and Altmann, *Curr. Gene Ther.*, 1(2):163-182, 2001.
Haberkorn and Altmann, *J. Cell Biochem. Suppl.*, 39:1-10, 2002.
Haberkorn et al., *Eur. J. Nucl. Med.*, 28(5):633-638, 2001.
Haberkorn et al., *J. Nucl. Med.*, 42(2):317-325, 2001.
Haberkorn, *Exp. Clin. Endocrinol. Diabetes*, 109(1):60-62, 2001.
Hamel et al., *J. Neurooncol.*, 16:159-165, 1993.
Hamstra et al., *Hum. Gene Ther.*, 10:1993-2003, 1999.
Harlow and Lane, In: *Antibodies: A Laboratory Manual*, Cold Spring Harbor Laboratory, Cold Spring Harbor, NY, 346-348, 1988.
Heise et al., *Nat. Med.*, 3:639-645, 1997.
Heise et al., *Nat. Med.*, 6:1134-9, 2000.
Hemminki et al. *Cancer Res.*, 61(17):6377-6381, 2001.
Henson et al., *Ann. Neurol.*, 36:714-721, 1994.
Hermiston, *J. Clin. Invest.*, 105:1169-1172, 2000.
Hess et al., *Neuro-Oncol.*, 1(4):282-288, 1999.
Hirvonen et al., *Br. J. Cancer*, 69:16-25, 1994.
Holash et al., *Oncogene*, 18:5356-62, 1999b.
Holash et al., *Science*, 284:1994-8, 1999a.
Im et al., *Br. J. Cancer*, 84:1252-1252, 2001.
Im et al., *Cancer Res.*, 1999, 59:895-900, 1999.
Innis et al., *PCR Protocols*, Academic Press, Inc., San Diego Calif., 1990.
Ipata et al., *Biochemistry*, 10(23):4270-4276, 1971.
Ipata et al., *Methods Enzymol.*, 51:394-400, 1978.
Jacotot, *Acad. Sci. Hebd. Seances Acad. Sci.*, 264(22):2602-2603, 1967.
Jen et al., *Cancer Res.*, 54:6353-6358, 1994.
Jin et al., *Cancer Res.*, 60(5):1221-1224, 2000.
Johnson et al., 1994
Jones and Dumont, *Oncogene*, 17(9):1097-1108, 1998.
Jones et al., *Mol. Cell Biol.*, 23(8):2658-2668, 2003.
Kaelin, *Bioessays*, 21(11):950-8, 1999.
Karlsson et al., *EMBO J.*, 5:2377-2385, 1986.
Katsuragi et al., *Appl. Biochem. Biotechnol.*, 16:61-69, 1987.
Katsuragi et al., *Exp. Pathol.*, 29(3):129-142, 1986.
Ke et al., *Cancer Res.*, 62:1854-1861, 2002.
Ke et al., *Clin. Cancer Res.*, 6: 2562-2562, 2000b.
Ke et al., *Mol. Cell Probes*, 14:127-135, 2000a.
Khatoon et al., *Ann. Neurol.*, 26(2):210-5, 1989.
Kievit et al., *Cancer Res.*, 59:1417-1421, 1999.
Kim et al., *FASEB J.*, 16:1126-1128, 2002.
Kim et al., *Proc. Natl. Acad. Sci. USA*, 99:11399-11404, 2002.
King et al., *J. Biol. Chem.*, 264(17):10210-10218, 1989.
Kirn et al., *Nat. Med.*, 4, 1341-1342, 1998.
Kirn, *Expert Opin. Biol. Ther.*, 1(3):525-538, 2001.
Koblizek et al., *Curr Biol.*, 8(9):529-532, 1998.
Kohrle, *Z rztl Fortbild Qualitatssich*, 93(1):17-22, 1999.
Kontos et al., *Mol. Cell Biol.*, 18(7):4131-4140, 1998.
Krasnykh et al., *J. Virol.*, 75(9):4176-83, 2001.
Kruse et al., *J. Neuro-Oncol.*, 19:161-168, 1994.
Kuan et al., *Endocr. Relat. Cancer*, 8(2):83-96, 2001.
Kuan et al., *Endocr. Relat. Cancer*, 8(2):83-96, 2001.
Kwoh et al., *Proc. Natl. Acad. Sci. USA*, 86:1173, 1989.
Kyritsis and Yung, *Baillieres Clinical Neurology*, 5(2):295-305, 1996.
Kyritsis et al., *Mol. Carcinog.*, 15:1-4, 1996b.
Kyritsis et al., *Oncogene*, 12:63-67, 1996a.
Kyte and Doolittle, *J. Mol. Biol.*, 157(1):105-132, 1982.
La Perle et al., *Prostate*, 50(3):170-178, 2002.
Lal et al., *J. Neurosurg.*, 92:326-333, 2000.
Lal et al., *J. Neurosurgery*, 92:326-333, 2000.
Lang et al., *J. Clin. Oncol.*; 21:2508-2518, 2003.
Levine, *JAMA*, 273(7):592, 1995.
Levy et al., *J. Bioenerg. Biomembr.*, 30(2):195-206, 1998b.
Levy et al., *J. Biol. Chem.*, 273(35):22657-22663, 1998a.
Lin et al., *Proc. Natl. Acad. Sci. USA*, 95:8829-34, 1998.
Lorimer et al., *Proc. Natl. Acad. Sci. USA*, 93(25):14815-14820, 1996.
Mabjeesh et al., *Cancer Cell*, 3:363-75, 2003.
Macejak and Sarnow, *Nature*, 353:90-94, 1991.
Maisonpierre et al., *Science*, 277:55-60, 1997.
Manley et al., *Eur. J. Cancer*, 38(5):S19-27, 2002.
Martuza et al., *Science*, 10:854-856, 1991.
Master et al., 2001
McCarthy et al., *J. Cell Biol.*, 85(3):890-902, 1980.
Millauer et al., *Nature*, 367:576-9, 1994.
Miller et al., *Cancer Res.* 62:773-780, 2002.
Mineta et al., *Nat. Med.*, 9:938-943, 1995.
Mishima et al., *Cancer Res.*, 61(14):5349-5354, 2001.
Nakamura et al., In: *Handbook of Experimental Immunology* (4th Ed.), Weir et al. (Eds), 1:27, Blackwell Scientific Publ., Oxford, 1987.
Nevins, *Science*, 258:424-429, 1992.
Nishikawa et al. *Proc. Natl. Acad. Sci. USA*, 91(16):7727-7731, 1994.
Nishiyama et al., *Cancer Res.*, 45(4):1753-1761, 1985.
Niu et al., *J. Biol. Chem.*, 277(35):31768-31773, 2004.
O'Shannessy et al., *Anal Biochem*, 163(1):204-209, 1987.
O'Donovan and Neuhard, *Bacteriol. Rev.*, 34(3):278-343, 1970.
Ohara et al., *Proc. Natl. Acad. Sci. USA*, 86:5673-5677, 1989.
Owens and Haley, *Biochem. Biophys. Res. Commun.*, 142(3):964-971, 1987.
Papapetropoulos et al., *J. Biol. Chem.*, 275(13):9102-91025, 2000.
PCT Appln. PCT/US87/00880
PCT Appln. PCT/US89/01025
PCT Appln. WO 88/10315
PCT Appln. WO 89/06700
PCT Appln. WO 95/27071
PCT Appln. WO 96/12406

PCT Appln. WO 96/33280
PCT Appln. WO 90/07641
Pelletier and Sonenberg, *Nature*, 334(6180):320-325, 1988.
Petrich et al., *Eur. J. Nucl. Med. Mol. Imaging*, 29(7):842-854, 2002.
Plate et al. 1992
Pollack et al., *J. Neurosurg.*, 73(1):106-112, 1990.
Poncet et al., *Neuropathol. Appl. Neurobiol.*, 29:361-9, 2003.
Potter and Haley, *Methods Enzymol*, 91:613-633, 1983.
Puumalainen et al., *Hum. Gene Ther.*, 9:1769-1774, 1998.
Racher et al., *Biotechnology Techniques*, 9:169-174, 1995.
Remington's Pharmaceutical Sciences, 15$^{th}$ ed., 33:624-652, Mack Publishing Company, Easton, Pa., 1980.
Reynolds et al., 1996
Roth and Cristiano. *J. Natl. Cancer Inst.*, 89:21-39, 1997.
Rouslahti and Rajotte, *Annu. Rev. Immunol.*, 18, 813-827, 2000.
Sambrook et al., In: *Molecular cloning*, Cold Spring Harbor Laboratory Press, Cold Spring Harbor, NY, 2001.
Sato et al., *Int. Immunol.*, 10(8):1217-1227, 1998.
Sato et al., *Nature*, 376:70-74, 1995.
Schiffer, *Forum*, 8(3):244-255, 1998.
Schmidt et al., *Cancer Res.*, 54:6321-6324, 1994.
Sehgal, *Seminars in Surgical Oncology*, 14(1): 3-12, 1998.
Semenza, *Biochem. Pharmacol.*, 64:993-8, 2002.
Senter et al., *Bioconjug. Chem.*, 2(6):447-451, 1991.
Shapiro and Shapiro, *Oncology*, 12(2):233-240, 1998.
Sheng et al., *Oncogene*, 19(42):4847-4854, 2000.
Sheta et al., *Oncogene*, 20:7624-34, 2001.
Sidransky et al., *Nature*, 355:846-847, 1992.
Singh 2004
Singh et al., 2003
Smanik et al., *Biochem. Biophys. Res. Commun.*, 226:339-345, 1996.
Springer et al., *Mol Ther.*, 1(1):82-87, 2000.
Steinwaerder et al., *Nat. Med.*, 7:240-3, 2001.
Sugawa et al. *Proc. Natl. Acad. Sci. USA*, 87(21):8602-5606, 1990.
Suri et al., *Cell*, 87:1171-80, 1996.
Suri et al., *Science*, 282:468-71, 1998.
Suzuki et al., *Clin. Cancer Res.*, 7:120-126, 2001.
Suzuki et al., *Clin. Cancer Res.*, 7:120-6, 2001.
Takakura et al., *Immunity*, 9(5):677-686, 1998.
Thomas et al., *Semin. Oncol.*, 30:32-8, 2003.
Tournaire et al., *EMBO Rep.*, 5(3):262-267, 2004.
Ueki et al., *Cancer Res.*, 56:150-153, 1996.
Valable et al., *FASEB J.*, 17:443-5, 2003.
Valk-Lingbeek et al., *Cell*, 118(4):409-418, 2004.
Vile, *Cancer Gene Ther.*, 9(12):1062-1067, 2002.
Wang et al., 2004
Wang et al., *Biotechniques*, 31:196-202, 2001.
Wei et al., *Clin. Cancer Res.*, 1(10):1171-1177, 1995.
West et al., *J Bacteriol.*, 149(3):1171-1174, 1982.
Whyte et al., *Cell*, 56:67-75, 1989.
Whyte et al., *Cell*, 62:257-265, 1988.
Wildner et al., *Cancer Res.*, 59:410-413, 1999.
Witzenbichler et al., *J. Biol. Chem.*, 273(29):18514-18521, 1998.
Xu et al., 2001
Yamaguchi et al., 1994
Yan et al., *J. Virol.*, 77(4):2640-2650, 2003.
Yancopoulos et al., *Nature*, 407: 242-8, 2000.
Yergatian et al., *Experientia*, 33(12):1570-1571, 1977.
Yoon et al., *Biochem. Biophys. Res. Commun.*, 308:101-5, 2003.
Zadeh et al., *Am. J. Pathol.*, 164:467-76, 2004.
Zagzag et al., *Lab. Invest.*, 80:837-49, 2000.
Zoltan et al., 1996

What is claimed is:

1. A method of treating brain cancer in a patient comprising:
   a) administering to said patient an effective amount of a pro-drug, wherein the pro-drug is metabolized to a cytotoxic drug by a yeast cytosine deaminase; and
   b) administering to said patient a composition comprising an oncolytic adenovirus encoding (i) an adenovirus E1A polypeptide that lacks amino acids 122-129 of wild-type E1A polypeptide, and (ii) a polynucleotide encoding a yeast cytosine deaminase, wherein said yeast cytosine deaminase is expressed by said oncolytic adenovirus at a level sufficient to produce cytotoxic level of said prodrug at 14 days post-infection; and
wherein administering comprises direct administration of the vector to a tumor site, whereby said brain cancer is treated by oncolysis from said oncolytic adenovirus and cytotoxicity from said cytotoxic drug.

2. The method of claim 1, wherein the oncolytic adenovirus is a Delta 24 adenovirus.

3. The method of claim 1, wherein the yeast cytosine deaminase is a humanized yeast cytosine deaminase.

4. The method of claim 3, wherein the brain cancer is a astrocytoma, oligodendroglioma, anaplastic glioma, glioblastoma, ependymoma, meningioma, pineal region tumor, choroid plexus tumor, neuroepithelial tumor, embryonal tumor, peripheral neuroblastic tumor, tumor of cranial nerves, tumor of the hemopoietic system, germ cell tumors, or tumor of the sellar region.

5. The method of claim 1, wherein the oncolytic adenovirus comprises a targeting moiety.

6. The method of claim 5, wherein the targeting moiety is a chimeric adenoviral fiber protein.

7. The method of claim 5, wherein the chimeric adenoviral fiber protein comprises an RGD amino acid sequence, a vIII amino acid sequence, or a PEPHC1 amino acid sequence.

8. The method of claim 1, wherein the oncolytic adenovirus is suitably dispersed in a pharmacologically acceptable formulation.

9. The method of claim 1, wherein the administration occurs more than once.

10. The method of claim 1, further comprising administering to the patient an anti-angiogenic therapy, chemotherapy, immunotherapy, surgery, radiotherapy, an immunosuppressive agent, or gene therapy with a therapeutic polynucleotide.

11. The method of claim 10, wherein the chemotherapy comprises an alkylating agent, mitotic inhibitor, antibiotic, antimetabolite, CPT-11, temozolomide, or a platin compound.

12. The method of claim 10, wherein radiotherapy comprises X-ray irradiation, UV-irradiation, γ-irradiation, or microwaves.

13. The method of claim 1, wherein from about $10^3$ to about $10^{15}$ viral particles are administered to the patient.

* * * * *